(12) United States Patent
Prabhakar et al.

(10) Patent No.: US 8,338,119 B2
(45) Date of Patent: Dec. 25, 2012

(54) CHONDROITINASE ABC I AND METHODS OF DEGRADING THEREWITH

(75) Inventors: Vikas Prabhakar, Cambridge, MA (US); Ishan Capila, Ashland, MA (US); Rahul Raman, Arlington, MA (US); Carlos Bosques, Cambridge, MA (US); Kevin Pojasek, Cambridge, MA (US); Ram Sasisekharan, Bedford, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 871 days.

(21) Appl. No.: 11/638,318

(22) Filed: Dec. 13, 2006

(65) Prior Publication Data

US 2007/0148740 A1    Jun. 28, 2007

Related U.S. Application Data

(62) Division of application No. 11/078,915, filed on Mar. 10, 2005.

(60) Provisional application No. 60/552,232, filed on Mar. 10, 2004, provisional application No. 60/578,917, filed on Jun. 10, 2004, provisional application No. 60/625,052, filed on Nov. 3, 2004.

(51) Int. Cl.
C12Q 1/34 (2006.01)
C12N 9/24 (2006.01)
C12P 19/28 (2006.01)
C07H 21/04 (2006.01)

(52) U.S. Cl. ............ 435/18; 435/200; 435/85; 536/23.2

(58) Field of Classification Search .................. None
See application file for complete search history.

(56) References Cited

U.S. PATENT DOCUMENTS

| | | |
|---|---|---|
| 5,198,855 A | 3/1993 | Iwai |
| 5,292,509 A | 3/1994 | Hageman |
| 5,496,718 A | 3/1996 | Hashimoto et al. |
| 5,498,536 A | 3/1996 | Khandke |
| 5,525,500 A | 6/1996 | Khandke et al. |
| 5,578,480 A | 11/1996 | Khandke |
| 5,716,617 A | 2/1998 | Khandke et al. |
| 5,741,692 A | 4/1998 | Khandke et al. |
| 5,763,205 A | 6/1998 | Hashimoto et al. |
| 5,773,277 A | 6/1998 | Hashimoto et al. |
| 5,888,798 A | 3/1999 | Lotvin et al. |
| 5,997,863 A | 12/1999 | Zimmermann et al. |
| 6,001,630 A | 12/1999 | Ichikawa et al. |
| 6,007,810 A | 12/1999 | Ishikawa et al. |
| 6,054,569 A | 4/2000 | Bennett et al. |
| 6,093,563 A | 7/2000 | Bennett et al. |
| 6,184,023 B1 | 2/2001 | Hashimoto et al. |
| 6,217,863 B1 | 4/2001 | Godavarti et al. |
| 6,597,996 B1 | 7/2003 | Venkataraman et al. |
| 6,869,789 B2 | 3/2005 | Liu et al. |
| 6,962,699 B2 | 11/2005 | Pojasek et al. |
| 7,056,504 B1 | 6/2006 | Sasisekharan et al. |
| 7,083,937 B2 | 8/2006 | Sasisekharan et al. |
| 7,105,334 B2 | 9/2006 | Pojasek et al. |
| 7,110,889 B2 | 9/2006 | Venkataraman et al. |
| 7,117,100 B2 | 10/2006 | Venkataraman et al. |
| 7,129,335 B2 | 10/2006 | Pojasek et al. |
| 7,139,666 B2 | 11/2006 | Venkataraman |
| 7,247,445 B2 | 7/2007 | Sasisekharan et al. |
| 7,270,815 B2 | 9/2007 | Sasisekharan et al. |
| 7,390,633 B2 | 6/2008 | Liu et al. |
| 7,396,824 B2 | 7/2008 | Sasisekharan et al. |
| 7,399,604 B2 | 7/2008 | Sasisekharan et al. |
| 7,412,332 B1 | 8/2008 | Venkataraman et al. |
| 7,429,474 B2 | 9/2008 | Sasisekharan et al. |
| 7,455,986 B2 | 11/2008 | Liu et al. |
| 7,504,247 B2 | 3/2009 | Sasisekharan et al. |
| 7,507,570 B2 | 3/2009 | Prabhakar et al. |
| 7,508,206 B2 | 3/2009 | Sasisekharan et al. |
| 7,553,950 B2 | 6/2009 | Prabhakar et al. |
| 7,560,106 B2 | 7/2009 | Sasisekharan et al. |
| 7,585,642 B2 | 9/2009 | Sasisekharan et al. |
| 7,592,152 B2 | 9/2009 | Prabhakar et al. |
| 7,662,604 B2 | 2/2010 | Prabhakar et al. |
| 7,687,479 B2 | 3/2010 | Sasisekharan et al. |
| 7,695,711 B2 | 4/2010 | Myette et al. |

(Continued)

FOREIGN PATENT DOCUMENTS

EP    0 576 294    12/1993

(Continued)

OTHER PUBLICATIONS

Yoshida et al. Cloning, sequencing, and expression of the gene from *Bacillus circulans* that codes for a heparinase that degrades both heparin and heparan sulfate, Biosci Biotechnol Biochem. Sep. 2002;66(9):1873-9.*
[No Author Listed] NCBI database, Protein 1DBOA Chain A. Crystal Structure of Chondroitinase B, Accession No. 6980642. BCT Nov. 3, 1999, 4 pages.
[No Author Listed] NCBI database, Structure Summary 1DBO, Crystal Structure of Chondroitinase B, MMMDB No. 12452. Deposition date Nov. 3, 1999, 1page.
[No Author Listed] Protein Data Bank, Structure Explorer—1DBO, "Crystal Structure of Chondroitinase B" http://www.rcsb.org/pdb/cgi/explore.cgi/ex;ore.cgi?pdbId=1DBO, Deposition date Nov. 3, 1999; Release date Jan. 12, 2000; printed Feb. 23, 2005, 1 page.
[No Author Listed] Structure Summary Printout for 1dbo, http://pdbbeta.rcsb.org/pdb/explore.do?structureId=1dbo, Deposition date Nov. 3, 1999; Release date Jan. 12, 2000; printed Feb. 23, 2005, 1 page.

(Continued)

*Primary Examiner* — Anand Desai
*Assistant Examiner* — Iqbal H Chowdhury
(74) *Attorney, Agent, or Firm* — Wolf, Greenfield & Sacks, P.C.

(57) ABSTRACT

The invention relates to chondroitinase ABC I and uses thereof. In particular, the invention relates to recombinant and modified chondroitinase ABC I, their production and their uses. The chondroitinase ABC I enzymes of the invention are useful for a variety of purposes, including degrading and analyzing polysaccharides such as glycosaminoglycans (GAGs). These GAGs can include chondroitin sulfate, dermatan sulfate, unsulfated chondroitin and hyaluronan. The chondroitinase ABC I enzymes can also be used in therapeutic methods such as promoting nerve regeneration, promoting stroke recovery, treating spinal cord injury, treating epithelial disease, treating infections and treating cancer.

35 Claims, 27 Drawing Sheets

| U.S. PATENT DOCUMENTS | | |
|---|---|---|
| 7,709,461 B2 | 5/2010 | Liu et al. |
| 7,728,589 B2 | 6/2010 | Sasisekharan et al. |
| 7,737,692 B2 | 6/2010 | Sasisekharan et al. |
| 7,842,492 B2 | 11/2010 | Myette et al. |
| 7,939,292 B2 | 5/2011 | Liu et al. |
| 7,951,560 B2 | 5/2011 | Myette et al. |
| 8,018,231 B2 | 9/2011 | Sasisekharan et al. |
| 8,173,384 B2 | 5/2012 | Sasisekharan et al. |
| 2002/0122793 A1 | 9/2002 | Liu et al. |
| 2002/0128225 A1 | 9/2002 | Liu et al. |
| 2002/0169143 A1 | 11/2002 | Sasisekharan et al. |
| 2003/0008820 A1 | 1/2003 | Kwan et al. |
| 2003/0099628 A1 | 5/2003 | Liu et al. |
| 2003/0191587 A1 | 10/2003 | Venkataraman et al. |
| 2004/0091471 A1 | 5/2004 | Myette et al. |
| 2004/0091472 A1 | 5/2004 | Pojasek et al. |
| 2004/0092037 A1 | 5/2004 | Sasisekharan et al. |
| 2004/0197933 A1 | 10/2004 | Venkataraman et al. |
| 2004/0204869 A1 | 10/2004 | Venkataraman et al. |
| 2005/0037376 A1 | 2/2005 | Sasisekharan et al. |
| 2005/0118157 A1 | 6/2005 | McMahon et al. |
| 2005/0214276 A9 | 9/2005 | Myette et al. |
| 2005/0227320 A1 | 10/2005 | Pojasek et al. |
| 2005/0233402 A1 | 10/2005 | Liu et al. |
| 2005/0233419 A1 | 10/2005 | Pojasek et al. |
| 2006/0024664 A1 | 2/2006 | Sasisekharan et al. |
| 2006/0057638 A1 | 3/2006 | Bosques et al. |
| 2006/0067927 A1 | 3/2006 | Chandrasekaran et al. |
| 2006/0067928 A1 | 3/2006 | Liu et al. |
| 2006/0078959 A1 | 4/2006 | Prabhakar et al. |
| 2006/0083711 A1 | 4/2006 | Berry et al. |
| 2006/0105430 A1 | 5/2006 | Sasisekharan et al. |
| 2006/0127950 A1 | 6/2006 | Bosques et al. |
| 2006/0154337 A1 | 7/2006 | Sato et al. |
| 2006/0154894 A1 | 7/2006 | Berry et al. |
| 2006/0177885 A1 | 8/2006 | Myette et al. |
| 2006/0177910 A1 | 8/2006 | Myette et al. |
| 2006/0177911 A1 | 8/2006 | Myette et al. |
| 2006/0182734 A1 | 8/2006 | Liu et al. |
| 2006/0183713 A1 | 8/2006 | Liu et al. |
| 2006/0183891 A1 | 8/2006 | Myette et al. |
| 2006/0233782 A1 | 10/2006 | Gruskin et al. |
| 2006/0292130 A1 | 12/2006 | Sasisekharan et al. |
| 2006/0292655 A1 | 12/2006 | Sasisekharan et al. |
| 2006/0292673 A1 | 12/2006 | Sasisekharan et al. |
| 2007/0004012 A1 | 1/2007 | Sasisekharan et al. |
| 2007/0020243 A1 | 1/2007 | Sengupta et al. |
| 2007/0065424 A1 | 3/2007 | Pojasek et al. |
| 2007/0065921 A1 | 3/2007 | Sasisekharan et al. |
| 2007/0066769 A1 | 3/2007 | Venkataraman et al. |
| 2007/0148157 A1 | 6/2007 | Prabhakar et al. |
| 2007/0148158 A1 | 6/2007 | Sasisekharan et al. |
| 2007/0148740 A1 | 6/2007 | Prabhakar et al. |
| 2007/0161073 A1 | 7/2007 | Sasisekharan et al. |
| 2007/0202563 A1 | 8/2007 | Prabhakar et al. |
| 2007/0224670 A1 | 9/2007 | Prabhakar et al. |
| 2008/0071148 A1 | 3/2008 | Bosques et al. |
| 2008/0278164 A1 | 11/2008 | Sasisekharan et al. |
| 2008/0301178 A1 | 12/2008 | Venkataraman et al. |
| 2009/0045811 A1 | 2/2009 | Sasisekharan et al. |
| 2009/0081635 A1 | 3/2009 | Liu et al. |
| 2009/0105463 A1 | 4/2009 | Berry et al. |
| 2009/0119027 A1 | 5/2009 | Venkataraman et al. |
| 2009/0156477 A1 | 6/2009 | Berry et al. |
| 2009/0269326 A1 | 10/2009 | Myette et al. |
| 2010/0062468 A1 | 3/2010 | Sasisekharan et al. |
| 2010/0119494 A1 | 5/2010 | Sengupta et al. |
| 2010/0129868 A1 | 5/2010 | Myette et al. |
| 2010/0216176 A1 | 8/2010 | Sasisekharan et al. |
| 2011/0033901 A1 | 2/2011 | Myette et al. |
| 2012/0027744 A1 | 2/2012 | Liu et al. |
| 2012/0045425 A1 | 2/2012 | Myette et al. |

| FOREIGN PATENT DOCUMENTS | | |
|---|---|---|
| EP | 0 613 949 A2 | 9/1994 |
| JP | 2000044601 A | 2/2000 |
| WO | WO 94/25567 A1 | 11/1994 |
| WO | WO-95/29232 * | 11/1995 |
| WO | WO 95/29232 A1 | 11/1995 |
| WO | WO 96/01894 A1 | 1/1996 |
| WO | WO 97/16556 A1 | 5/1997 |
| WO | WO 00/12726 A2 | 3/2000 |
| WO | WO 00/65521 A2 | 11/2000 |
| WO | WO 01/35977 A2 | 5/2001 |
| WO | WO 01/66772 A2 | 9/2001 |
| WO | WO 02/23190 A2 | 3/2002 |
| WO | WO 02/32406 A2 | 4/2002 |
| WO | WO 02/077199 A2 | 10/2002 |
| WO | WO 03/074080 | 9/2003 |
| WO | WO 03/102160 A2 | 12/2003 |
| WO | WO 2004/055491 A2 | 7/2004 |
| WO | WO 2004/062592 A2 | 7/2004 |
| WO | WO 2004/069152 A2 | 8/2004 |
| WO | WO 2004/110360 A2 | 12/2004 |
| WO | WO 2005/087920 A2 | 9/2005 |
| WO | WO 2005/110438 A2 | 11/2005 |
| WO | WO 2005/111627 A2 | 11/2005 |
| WO | WO 2006/076627 A2 | 7/2006 |
| WO | WO 2006/083328 A2 | 8/2006 |
| WO | WO 2006/088491 A2 | 8/2006 |
| WO | WO 2006/105313 A2 | 10/2006 |
| WO | WO 2006/105315 A2 | 10/2006 |
| WO | WO 2007/044471 A2 | 4/2007 |
| WO | WO 2007/120478 A2 | 10/2007 |

OTHER PUBLICATIONS

[No Author Listed] MMDB Summary Printout for 1HM2, http://pdbbeta.rcsb.org/pdb/explore.do?structureId=1hm2, Deposition date Dec. 4, 2000; Release date May 2, 2001; printed Feb. 23, 2005, 1 pages.

[No Author Listed] Protein Data Bank, Structure Explorer—1HM2, "Active Site of Chondroitinase Ac Lyase Revealed by The Structure of Enzyme-Oligosaccharide Complexes and Mutagenesis", http://www.rcsb.org/pdb/cgi/explore.cgi?pdbId=1HM2, Deposition date Dec. 4, 2000; Release date May 2, 2001; printed Feb. 23, 2005, 1 page.

[No Author Listed] NCBI Database, Structure Summary for 1HM2, *Crystal Structure of Chondroitinase B*, MMDB No. 16157. Deposition date Dec. 4, 2000; 1 page.

[No Author Listed] MMDB Summary Printout for 1plu, "Pectate Lyase C From Erwinia Chrysanthemi With 1 LU+3 Ion in the Putative Calcium Binding Site", http://pdbbeta.rcsb.org/pdb/explore.do?structureld=1plu, Deposition date Jun. 4, 1999; Release date Jul. 13, 1999; printed Feb. 23, 2005, 1 page.

[No Author Listed] NCBI database, Structure Summary for 1DBG, Crystal Structure of Chondroitinase B, MMDB No. 12451. Deposition date Nov. 2, 1999, 1 page.

[No Author Listed] Structure Summary Printout for 1dbg, http://pdbbeta.rcsb.org/pdb/explore.do?structureId=1dbg, Deposition date Nov. 2, 1999; Release date Jan. 12, 2000; printed Feb. 23, 2005, 1 page.

[No Author Listed] Protein Data Bank, Structure Explorer—1DBG, "Crystal Structure of Chondroitinase B", http://www.rcsb.org/pdb/cgi/explore.cgi?pdbId=1DBG, Deposition date Nov. 2, 1999; Release date Jan. 12, 2000; printed Feb. 23, 2005, 1 page.

[No Author Listed] NCBI database, Protein 1HN0A Chain A. Crystal Structure of Chondroitinase Abc Lyase I From Proteus Vulgaris At 1.9 Angstroms Resolution, gi: 30749254. BTC Oct. 1, 2007, 6 pages.

[No Author Listed] NCBI database, "Pedobacter Heparinus Chondroitinase B Precursor (cs1B) gene Complete cds", Accession No. U27584.1 GI:1002526. BCT Jan. 6, 2000, 2 pages.

[No Author Listed] NCB databse, "Sequence 2 from patent US 5578480", Accession No. AAB43331; PAT Feb. 7, 1997, 1 page.

Genbank Submission; NIH/NCBI, Accession No. 129953; Khandke; Pat Feb. 6, 2007, 2 pages.

Genbank Submission; NIH/NCBI, Accession No. P59807; Sato et al.; BCT Feb. 5, 2008, 9 pages.

Genbank Submission; NIH/NCBI, Accession No. E08025; Sato et al.; PAT Nov. 4, 2005 2 pages.

IUBMB Enzyme Nomenclature. EC 4.2.2.21. http://www.chem.qmul.ac.uk/iubmb/enzyme/EC2/2/2/21.html, created 2006, 2 pages.

IUBMB Enzyme Nomenclature. EC 4.2.2.20. http://www.chem.qmul.ac.uk/iubmb/enzyme/EC4/2/2/20.html, created 2006, 2 pages.
IUBMB Enzyme Nomenclature. EC 4.2.2.4. http://www.chem.qmul.ac.uk/iubmb/enzyme/EC4/2/2/4.html, created 1972, 1 page.
IUBMB Enzyme Nomenclature. EC 4.2.2.5. http://www.chem.qmul.ac.uk/iubmb/enzyme/EC4/2/2/5.html, created 1972, 2 pages.
Achur et al., Characterization of proteoglycans of human placenta and identification of unique chondroitin sulfate proteoglycans of the intervillous spaces that mediate the adherence of Plasmodium falciparum-infected erythrocytes to the placenta. J Biol Chem. Dec. 22, 2000;275(51):40344-56.
Alkhalil et al., Structural requirements for the adherence of Plasmodium falciparum-infected erythrocytes to chondroitin sulfate proteoglycans of human placenta. J Biol Chem. Dec. 22, 2000;275(51):40357-64.
Bao et al., Chondroitin sulfate/dermatan sulfate hybrid chains from embryonic pig brain, which contain a higher proportion of L-iduronic acid than those from adult pig brain, exhibit neuritogenic and growth factor binding activities. J Biol Chem. Mar. 12, 2004;279(11):9765-76. Epub Dec. 29, 2003.
Baumann et al., Three-dimensional structure of the alkaline protease of *Pseudomonas aeruginosa*: a two-domain protein with a calcium binding parallel beta roll motif. EMBO J. Sep. 1993;12(9):3357-64.
Bernfield et al., Functions of cell surface heparan sulfate proteoglycans. Annu Rev Biochem. 1999;68:729-77.
Binari et al., Genetic evidence that heparin-like glycosaminoglycans are involved in wingless signaling. Development. Jul. 1997;124(13):2623-32.
Bradbury et al., Chondroitinase ABC promotes regeneration and functional recovery following spinal cord injury. Society for Neuroscience Abstracts. 2001;27(2):1835. Abstract.
Bradbury et al., Chondroitinase ABC promotes functional recovery after spinal cord injury. Nature. Apr. 11, 2002;416(6881):636-40.
Bruce et al., Flavobacterium heparinum 6-O-sulphatase for N-substituted glucosamine 6-O-sulphate. Eur J Biochem. Oct. 1, 1985;152(1):75-82.
Cohen, The parallel beta helix of pectate lyase C: something to sneeze at. Science. Jun. 4, 1993;260(5113):1444-5.
Daidouji et al., Neoplastic changes in saccharide sequence of dermatan sulfate chains derived from human colon cancer. Dig Dis Sci. Feb. 2002;47(2):331-7.
Denholm et al., Anti-tumor activities of chondroitinase AC and chondroitinase B: inhibition of angiogenesis, proliferation and invasion. Eur J Pharmacol. Mar. 30, 2001;416(3):213-21.
Desai et al., Specificity studies on the heparin lyases from Flavobacterium heparinum. Biochemistry. Aug. 17, 1993;32(32):8140-5.
Dietrich et al., Sequential degradation of heparin in Flavobacterium heparinum. Purification and properties of five enzymes involved in heparin degradation. J Biol Chem. Sep. 25, 1973;248(18):6408-15.
Dietrich et al., Enzymic degradation of heparin. A glucosaminidase and a glycuronidase from Flavobacterium heparinum. Biochemistry. May 1969;8(5):2089-94.
Ernst et al., Expression in *Escherichia coli*, purification and characterization of heparinase I from Flavobacterium heparinum. Biochem J. Apr. 15, 1996;315 ( Pt 2):589-97.
Ernst et al., Enzymatic degradation of glycosaminoglycans. Crit Rev Biochem Mol Biol. 1995;30(5):387-444.
Feingold et al., Conformational aspects of the reaction mechanisms of polysaccharide lyases and epimerases. FEBS Lett. Nov. 2, 1987;223(2):207-11. Review.
Fernandez et al., Dermatan sulfate and LMW heparin enhance the anticoagulant action of activated protein C. Thromb Haemost. Nov. 1999;82(5):1462-8.
Fethiere et al., Crystal structure of chondroitin AC lyase, a representative of a family of glycosaminoglycan degrading enzymes. J Mol Biol. May 14, 1999;288(4):635-47.
Franklin et al., *Pseudomonas aeruginosa* AIgG is a polymer level alginate C5-mannuronan epimerase. J Bacteriol. Apr. 1994;176(7):1821-30.
Gacesa, Alginate-modifying enzymes: a proposed unified mechanism of action for the lyases and epimerases. FEBS Letters. 1987;212(2):199-202.
Gandra et al., Anticoagulant sulfated glycosaminoglycans in the tissues of the primitive chordate Styela plicata (Tunicata). Glycobiology. Dec. 2000;10(12):1333-40.
Gerlt et al., Understanding the rates of certain enzyme-catalyzed reactions: proton abstraction from carbon acids, acyl-transfer reactions, and displacement reactions of phosphodiesters. Biochemistry. Nov. 16, 1993;32(45):11943-52.
Gioldassi et al., Determination of phosphorylated and sulfated linkage-region oligosaccharides in chondroitin / dermatan and heparan sulfate proteoglycans by high performance liquid chromatography. J Liq Chrom Rel Technol. 1999;22(13):1997-2007.
Godavarti et al., Heparinase III from Flavobacterium heparinum: cloning and recombinant expression in *Escherichia coli*. Biochem Biophys Res Commun. Aug. 23, 1996;225(3):751-8.
Grimpe et al., A novel DNA enzyme reduces glycosaminoglycan chains in the glial scar and allows microtransplanted dorsal root ganglia axons to regenerate beyond lesions in the spinal cord. J Neurosci. Feb. 11, 2004;24(6):1393-7.
Gu et al., Purification, characterization and specificity of chondroitin lyases and glycuronidase from Flavobacterium heparinwn. Biochem J. Dec. 1, 1995;312 ( Pt 2):569-77.
Habuchi et al., Diversity and functions of glycosaminoglycan sulfotransferases. Biochim Biophys Acta. Apr. 6, 2000;1474(2):115-27.
Hamai et al., Two distinct chondroitin sulfate ABC lyases. An endoeliminase yielding tetrasaccharides and an exoeliminase preferentially acting on oligosaccharides. J Biol Chem. Apr. 4, 1997;272(14):9123-30.
Harrisson et al., On the presence of proteolytic activity in glycosaminoglycan-degrading enzyme preparations. J Histochem Cytochem. Sep. 1986;34(9):1231-5.
Hildebrand et al., Interaction of the small interstitial proteoglycans biglycan, decorin and fibromodulin with transforming growth factor beta. Biochem J. Sep. 1, 1994;302 ( Pt 2):527-34.
Hovingh et al., Specificity of flavobacterial glycuronidases acting on disaccharides derived from glycosaminoglycans. Biochem J. Aug. 1, 1977;165(2):287-93.
Huang et al., Crystal structure of Proteus vulgaris chondroitin sulfate ABC lyase I at 1.9A resolution. J Mol Biol. May 2, 2003;328(3):623-34.
Huang et al., Crystal structure of chondroitinase B from Flavobacterium heparinum and its complex with a disaccharide product at 1.7 a resolution. J Mol Biol. Dec. 17, 1999;294(5):1257-69.
Huang et al., Active site of chondroitin AC lyase revealed by the structure of enzyme-oligosaccharide complexes and mutagenesis. Biochemistry. Feb. 27, 2001;40(8):2359-72.
Iozzo et al., The family of the small leucine-rich proteoglycans: key regulators of matrix assembly and cellular growth. Crit Rev Biochem Mol Biol. 1997;32(2):141-74.
Iozzo et al., Altered proteoglycan gene expression and the tumor stroma. Experientia. May 15, 1993;49(5):447-55.
Jandik et al., Action pattern of polysaccharide lyases on glycosaminoglycans. Glycobiology. Jun. 1994;4(3):289-96.
Jedrzejas et al., Structural and functional comparison of polysaccharide-degrading enzymes. Crit Rev Biochem Mol Biol. 2000;35(3):221-51.
Kretsinger et al., Structure and evolution of calcium-modulated proteins. CRC Crit Rev Biochem. 1980;8(2):119-74. Review.
Liaw et al., Comparison of heparin- and dermatan sulfate-mediated catalysis of thrombin inactivation by heparin cofactor II. J Biol Chem. Sep. 24, 1999;274(39):27597-604.
Linhardt et al., Examination of the substrate specificity of heparin and heparan sulfate lyases. Biochemistry. Mar. 13, 1990;29(10):2611-7.
Linhardt et al., Polysaccharide lyases. Appl Biochem Biotechnol. Apr. 1986;12(2):135-76.
Linker et al., The enzymatic degradation of heparin and heparitin sulfate. I. The fractionation of a crude heparinase from flavobacteria. J Biol Chem. Oct. 1965;240(10):3724-8.
Liu et al., Tumor cell surface heparan sulfate as cryptic promoters or inhibitors of tumor growth and metastasis. Proc Natl Acad Sci U S A. Jan. 22, 2002;99(2):568-73.

Lohse et al., Purification and characterization of heparin lyases from Flavobacterium heparinum. J Biol Chem. Dec. 5, 1992;267(34):24347-55.

Lunin et al., High-resolution crystal structure of Arthrobacter aurescens chondroitin AC lyase: an enzyme-substrate complex defines the catalytic mechanism. J Mol Biol. Mar. 19, 2004;337(2):36786.

Lyon et al., Hepatocyte growth factor/scatter factor binds with high affinity to dermatan sulfate. J Biol Chem. Jan. 2, 1998;273(1):271-8.

Lyon et al., The mode of action of heparan and dermatan sulfates in the regulation of hepatocyte growth factor/scatter factor. J Biol Chem. Jan. 11, 2002;277(2):1040-6. Epub Oct. 31, 2001.

Maimone et al., Structure of a dermatan sulfate hexasaccharide that binds to heparin cofactor II with high affinity. J Biol Chem. Oct. 25, 1990;265(30):18263-71. Erratum in: J Biol Chem Aug. 5, 1991;266(22):14830.

Makatsori et al., Large matrix proteoglycans, versican and perlecan, are expressed and secreted by human leukemic monocytes. Anticancer Res. Jul.-Aug. 2003;23(4):3303-9.

Mascellani et al., Structure and contribution to the heparin cofactor II-mediated inhibition of thrombin of naturally oversulphated sequences of dermatan sulphate. Biochem J. Dec. 15, 1993;296 ( Pt 3):639-48.

McLean et al., Flavobacterium heparinum 2-O-sulphatase for 2-O-sulphato-delta 4,5-glycuronate-terminated oligosaccharides from heparin. Eur J Biochem. Dec. 17, 1984;145(3):607-15.

Michel et al., The structure of chondroitin B lyase complexed with glycosaminoglycan oligosaccharides unravels a calcium-dependent catalytic machinery. J Biol Chem. Jul. 30, 2004;279(31):32882-96. Epub May 21, 2004.

Monagle et al., Covalent heparin cofactor II-heparin and heparin cofactor II-dermatan sulfate complexes. Characterization of novel anticoagulants. J Biol Chem. Dec. 11, 1998;273(50):33566-71.

Morgenstern et al., Chondroitin sulphate proteoglycans in the CNS injury response. Prog Brain Res. 2002;137:313-32.

Myette et al., Molecular cloning of the heparin/heparan sulfate delta 4,5 unsaturated glycuronidase from Flavobacterium heparinum, its recombinant expression in Escherichia coli, and biochemical determination of its unique substrate specificity. Biochemistry. Jun. 11, 2002;41(23):7424-34.

Oike et al., Proteinase activity in chondroitin lyase (chondroitinase) and endo-beta-D-galactosidase (keratanase) preparations and a method to abolish their proteolytic effect on proteoglycan. Biochem J. Oct. 1, 1980;191(1):203-7.

Papadas et al., Alterations in the content and composition of glycosaminoglycans in human laryngeal carcinoma. Acta Otolaryngol. Apr. 2002;122(3):330-7.

Plaas et al., Glycosaminoglycan sulfation in human osteoarthritis. Disease-related alterations at the non-reducing termini of chondroitin and dermatan sulfate. J Biol Chem. May 15, 1998;273(20):12642-9.

Pojasek et al., Recombinant expression, purification, and kinetic characterization of chondroitinase AC and chondroitinase B from Flavobacterium heparinum. Biochem Biophys Res Commun. Aug. 17, 2001;286(2):343-51.

Pojasek et al., Biochemical characterization of the chondroitinase B active site. J Biol Chem. Aug. 23, 2002;277(34):31179-86. Epub Jun. 12, 2002.

Prabhakar et al., Biochemical characterization of the chondroitinase ABC I active site. Biochem J. Sep. 1, 2005;390(Pt 2):395-405.

Prabhakar et al., Chondroitinase ABC I from Proteus vulgaris: cloning, recombinant expression and active site identification. Biochem J. Feb. 15, 2005;386(Pt 1):103-12.

Prabhakar et al., The catalytic machinery of chondroitinase ABC I utilizes a calcium coordination strategy to optimally process dermatan sulfate. Biochemistry. Sep. 19, 2006;45(37):11130-9.

Rhomberg et al., Mass spectrometric and capillary electrophoretic investigation of the enzymatic degradation of heparin-like glycosaminoglycans. Proc Natl Acad Sci U S A. Apr. 14, 1998;95(8):4176-81.

Rice et al., A potential virulence gene, hylEfm, predominates in Enterococcus faecium of clinical origin. J Infect Dis. Feb. 1, 2003;187(3):508-12. Epub Jan. 8, 2003.

Sasisekharan et al., Cloning and expression of heparinase I gene from Flavobacterium heparinum. Proc Natl Acad Sci U S A. Apr. 15, 1993;90(8):3660-4.

Sato et al., Cloning and expression in *Escherichia coli* of the gene encoding the Proteus vulgaris chondroitin ABC lyase. Appl Microbiol Biotechnol. Mar. 1994;41(1):39-46.

Schmidt et al., Interaction of small dermatan sulfate proteoglycan from fibroblasts with fibronectin. J Cell Biol. Jun. 1987;104(6):1683-91.

Shriver et al., Emerging views of heparan sulfate glycosaminoglycan structure/activity relationships modulating dynamic biological functions. Trends Cardiovasc Med. Feb. 2002;12(2):71-7.

Sugahara et al., Novel sulfated oligosaccharides containing 3-O-sulfated glucuronic acid from king crab cartilage chondroitin sulfate K. Unexpected degradation by chondroitinase ABC. J Biol Chem. Oct. 25, 1996;271(43):26745-54.

Sugahara et al., Recent advances in the structural biology of chondroitin sulfate and dermatan sulfate. Curr Opin Struct Biol. Oct. 2003;13(5):612-20.

Tkalec et al., Isolation and expression in *Escherichia coli* of cslA and cs1B, genes coding for the chondroitin sulfate-degrading enzymes chondroitinase AC and chondroitinase B, respectively, from Flavobacterium heparinum. Appl Environ Microbiol. Jan. 2000;66(1):29-35.

Trowbridge et al., Dermatan sulfate binds and potentiates activity of keratinocyte growth factor (FGF-7). J Biol Chem. Nov. 8, 2002;277(45):42815-20. Epub Sep. 4, 2002.

Trowbridge et al., Dermatan sulfate: new functions from an old glycosaminoglycan. Glycobiology. Sep. 2002;12(9):117R-25R.

Tumova et al., Heparan sulfate proteoglycans on the cell surface: versatile coordinators of cellular functions. Int J Biochem Cell Biol. Mar. 2000;32(3):269-88.

Venkataraman et al., Sequencing complex polysaccharides. Science. Oct. 15, 1999;286(5439):537-42.

Vicente et al., Unbalanced effects of dermatan sulfates with different sulfation patterns on coagulation, thrombosis and bleeding. Thromb Haemost. Nov. 2001;86(5):1215-20.

Vlodavsky et al., Mammalian heparanase: gene cloning, expression and function in tumor progression and metastasis. Nat Med. Jul. 1999;5(7):793-802.

Warnick et al., Purification of an unusual—glycuronidase from flavobacteria. Biochemistry. Feb. 15, 1972;11(4):568-72.

Wishart et al., A single mutation converts a novel phosphotyrosine binding domain into a dual-specificity phosphatase. J Biol Chem. Nov. 10, 1995;270(45):26782-5.

Witkowski et al., Conversion of a beta-ketoacyl synthase to a malonyl decarboxylase by replacement of the active-site cysteine with glutamine. Biochemistry. Sep. 7, 1999;38(36):11643-50.

Yamaguchi et al., Negative regulation of transforming growth factor-beta by the proteoglycan decorin. Nature. Jul. 19, 1990;346(6281):281-4.

Yang et al., Purification and characterization of heparinase from Flavobacterium heparinum. J Biol Chem. Feb. 10, 1985;260(3):1849-57.

Yoder et al., Unusual structural features in the parallel beta-helix in pectate lyases. Structure. Dec. 15, 1993;1(4):241-51.

Yoder et al., New domain motif: the structure of pectate lyase C, a secreted plant virulence factor. Science. 1993;260:1503-1506.

Sato et al., Subunit structure of chondroitinase abc from proteus vulgaris. Agricultural and Biological Chemistry. Japan Soc for Bioscience, Biotechnology and Agrochem. Tokyo, Japan. 1986;50(4):1057-1059.

Branden et al., Introduction to protein structure, Garland Publishing Inc., New York, 1991, p. 247.

Seffernick et al., Melamine deaminase and atrazine chlorohydrolase: 98 percent identical but functionally different. J Bacteriol. Apr. 2001;183(8):2405-10.

Whisstock et al., Prediction of protein function from protein sequence and structure. Q Rev Biophys. Aug. 2003;36(3):307-40.

Yoshida et al., Cloning, sequencing, and expression of the gene from *Bacillus circulans* that codes for a heparinase that degrades both heparin and heparan sulfate. Biosci Biotechnol Biochem. Sep. 2002;66(9):1873-9.

\* cited by examiner

Figure 7

Chondroitin 4-Sulfate

Chondroitin 6-Sulfate

R= SO3⁻  Dermatan Sulfate

Biochemical Characterization of Proposed Active Site

- Alanine Knockouts of Catalytic Residues
  - H501A, Y508A, R560A, E653A

Product Profile

Activity

|        | C6S | DS |
|--------|-----|-----|
| cABC I | +   | +   |
| H501A  | -   | -   |
| E653A  | -   | -   |
| Y508A  | -   | -   |
| R560A  | -   | -   | cABC I Glu653

| cABC I Glu653 Mutant | Kinetics | | End-point | |
|---|---|---|---|---|
| | C6S | DS | C6S | DS |
| Glu653Ala | - | - | - | - |
| Glu653Asp | - | - | + | + |
| Glu653Gln | + | + | + | + |

Figure 22 cABC I Tyr508

- Tyr508Ala
  - Knockout: no activity against any GalAG substrate
- Tyr508Phe
  - Conservation of Aromatic Ring, loss of Hydroxyl group Chondroitin-6-Sulfate

|       | Km  | Kcat  | Eff.  |
|-------|-----|-------|-------|
| MOJO  | 1.2 | 37361 | 32162 |
| Y508F | 36.4 | 31.2 | 0.9  |

Dermatan Sulfate

|       | Km  | Kcat  | Eff.  |
|-------|-----|-------|-------|
| MOJO  | 2.5 | 27102 | 10727 |
| Y508F | 48.9 | 104.8 | 2.11 |

Figure 24 cABC I Glu653 Mutagenesis

Chondroitin-6-Sulfate

| | Km | Kcat | Eff. |
|---|---|---|---|
| MOJO | 1.2 | 37361 | 32162 |
| E653Q | 6.1 | 1608 | 262 |

Dermatan Sulfate

| | Km | Kcat | Eff. |
|---|---|---|---|
| MOJO | 2.5 | 27102 | 10727 |
| E653Q | 4.2 | 5175 | 1245 |

Glu  $-CH_2-CH_2-COO^-$

Ala  $-CH_3$

Asp  $-CH_2-COO^-$

Gln  $-CH_2-CH_2-CONH_2$

Figure 25

CHONDROITINASE ABC I AND METHODS OF DEGRADING THEREWITH

RELATED APPLICATIONS

This application is a divisional application of U.S. application Ser. No. 11/078,915, filed Mar. 10, 2005, pending, which claims priority under 35 U.S.C. §119 to U.S. provisional application No. 60/552,232, filed Mar. 10, 2004, U.S. provisional application No. 60/578,917, filed Jun. 10, 2004, and U.S. provisional application No. 60/625,052, filed Nov. 3, 2004, each of which is incorporated herein by reference in its entirety.

GOVERNMENT SUPPORT

Aspects of the invention may have been made using finding from National Institutes of Health Grant number GM57073. Accordingly, the Government may have rights in the invention.

FIELD OF THE INVENTION

The invention relates to chondroitinase ABC I and uses thereof. In particular, the invention relates to recombinantly produced and/or purified chondroitinase ABC I as well as to modified versions of the enzyme. Also provided are methods of producing and uses for the enzymes, which include cleaving and analyzing polysaccharides, such as glycosaminoglycans, particularly galactosaminoglycans (GalAGs). The invention further relates to polysaccharides that are produced as a result of their interaction with the enzymes provided. These polysaccharides or the enzymes provided, alone or in combination, can be used in methods of treatment, such as, promoting nerve regeneration, promoting stroke recovery, treating spinal cord injury, treating epithelial disease, treating infections and treating cancer.

BACKGROUND OF THE INVENTION

Glycosaminoglycans (GAGs) are linear, acidic polysaccharides that exist ubiquitously in nature as residents of the extracellular matrix (ECM) and at the cell surface, as constituents of proteoglycans, of many different organisms of divergent phylogeny (Habuchi, O. (2000) *Biochim Biophys Acta* 1474, 115-27; Sasisekharan, R., Bulmer, M., Moremen, K. W., Cooney, C. L., and Langer, R. (1993) *Proc Natl Acad Sci USA* 90, 3660-4). Glycosaminoglycans consist of a disaccharide repeat unit of a hexosamine linked to an uronic acid. These sugars, apart from having important structural roles in the ECM, are also fundamental modulators of many biological processes like development, cell proliferation, signaling and inflammation (Bemfield, M., Gotte, M., Park, P. W., Reizes, O., Fitzgerald, M. L., Lincecum, J. and Zako, M. (1999) Functions of cell surface heparan sulfate proteoglycans. Annu Rev Biochem 68, 729-777; Sugahara, K., Mikami, T., Uyama, T., Mizuguchi, S., Nomura, K. and Kitagawa, H. (2003) Recent advances in the structural biology of chondroitin sulfate and dermatan sulfate. Curr Opin Struct Biol 13, 612-620.) GAGs act as critical modulators of a number of biochemical signaling events (Tumova, S., Woods, A., and Couchman, J. R. (2000) *Int J Biochem Cell Biol* 32, 269-88) requisite for cell growth and differentiation, cell adhesion and migration, and tissue morphogenesis. Chondroitin sulfate (CS)/dermatan sulfate (DS) polysaccharides have been implicated in a variety of biological phenomena ranging from anticoagulation to osteoarthritis (Mascellani, G., Liverani, L., Bianchini, P., Parma, B., Torri, G., Bisio, A., Guerrini, M., and Casu, B. (1993) *Biochem. J.* 296, 639-48; Achur, R. N., Valiyaveettil, M., Alkhalil, A., Ockenhouse, C. F., and Gowda, D. C. (2000) *J. Biol. Chem.* 275, 40344-56; and Plaas, A. H., West, L. A., Wong-Palms, S., and Nelson, F. R. (1998) *J. Biol. Chem.* 273, 12642-9). In addition, modification of existing GAG sequences by chondroitinase ABC and chondroitinase AC may inhibit angiogenesis and tumor metastasis (Denholm, E. M. et al. (2001) *Eur. J. Pharmacol.* 416, 213-21).

The chemical heterogeneity of GAGs is responsible for their wide-ranging biological influence. Each GAG disaccharide repeat unit can be customized through a variety of biosynthetic modifications that include epimerization of the uronic acid and variable sulfation. The specific sequence of chemical modifications on GAG chains imparts a potential for interaction with other biological agents, including growth factors, cytokines, and other signal transducers. Even more, specific sequences within the oligosaccharide chain have been shown to be activating, and others inhibitory, with regard to specific biological processes (Bao, X., Nishimura, S., Mikami, T., Yamada, S., Itoh, N. and Sugahara, K. (2004) Chondroitin sulfate/dermatan sulfate hybrid chains from embryonic pig brain, which contain a higher proportion of L-iduronic acid than those from adult pig brain, exhibit neuritogenic and growth factor binding activities. J Biol Chem 279, 9765-9776.) This emerging paradigm of structure-function glycobiology promises to create new strategies for the crafting of medical interventions.

The development of complementary biochemical tools that cleave GAGs in a sequence-specific fashion has enabled progress in the polysaccharide sequencing field. Many microorganisms express GAG-degrading enzymes for the purpose of facile invasion of host tissue and to acquire nutrition from decaying animal tissues (Ernst, S., Langer, R., Cooney, C. L. and Sasisekharan, R. (1995) Enzymatic degradation of glycosaminoglycans. Crit Rev Biochem Mol Biol 30, 387-444.) A number of these enzymes have been cloned and sequenced and are being developed in polysaccharide sequencing methodologies and other industrial applications. These include heparinases I, II, and III and chondroitinases AC and B (cAC and cB, respectively) from *Flavobacterium heparinum* (Venkataraman, G., Shriver, Z., Raman, R. and Sasisekharan, R. (1999) Sequencing complex polysaccharides. Science 286, 537-54; Sasisekharan, R., Bulmer, M., Moremen, K. W., Cooney, C. L. and Langer, R. (1993) Cloning and expression of heparinase I gene from *Flavobacterium heparinum*. Proc Natl Acad Sci U S A 90, 3660-3664; Godavarti, R., Davis, M., Venkataraman, G., Cooney, C., Langer, R. and Sasisekharan, R. (1996) Heparinase III from *Flavobacterium heparinum*: cloning and recombinant expression in *Escherichia coli*. Biochem Biophys Res Commun 225, 751-758; Pojasek, K., Shriver, Z., Kiley, P., Venkataraman, G. and Sasisekharan, R. (2001) Recombinant expression, purification, and kinetic characterization of chondroitinase AC and chondroitinase B from *Flavobacterium heparinum*. Biochem Biophys Res Commun 286, 343-351.) Overall, the role of GAGs as specific mediators of tumorigenesis and other biological events is an emerging field that offers the potential for the development of novel therapeutics (Shriver, Z. et al. (2002) *Trends. Cardiovasc. Med.* 12, 71-7; and Liu, D. et al. (2002) *Proc. Natl. Acad. Sci. USA* 99, 568-73).

SUMMARY OF THE INVENTION

The invention provided relates, in part, to chondroitinase ABC I (cABC I) enzymes and methods for their production and use. In one aspect of the invention a cABC I enzyme that has the amino acid sequence of SEQ ID NO: 2 is provided. In another aspect of the invention a polypeptide comprising the amino acid sequence of SEQ ID NO: 2 or a fragment thereof is provided. The fragment, for example, can be any portion of the amino acid sequence of SEQ ID NO: 2 up to the full length of the sequence provided that the fragment is at least 8 amino acids in length. In some embodiments the fragment is at least 10, 15, 20, 30, 50, 75, 125, 100, 150, 200, 250, 300, 350, 400, 450, 500, 600, 700, 800, 900, 950, 975, 990 or more amino acids in length.

The enzymes provided, in some aspects, include modified versions of native chondroitinase ABC I enzymes. Therefore, in one aspect, a modified chondroitinase ABC is provided. In one embodiment the modified chondroitinase ABC I enzymes have the amino acid sequence of a native cABC I enzyme with amino acid substitutions of conserved residues, potential general bases, and/or residues in close proximity to potential general bases and which seem to protrude into the catalytic cleft. The modified chondroitinase ABC I enzymes, in one embodiment, has the amino acid sequence of the peptide (mature or immature) of a native chondroitinase ABC I, wherein at least one residue, such as at position 105, 131, 154, 218, 219, 221, 222, 253, 276, 286, 309, 312, 322, 388, 389, 392, 439, 442, 444, 490, 500, 501, 508, 560, 561, 587, 653, 678, 694 or 712, has been substituted with a different amino acid than in the native chondroitinase ABC I. The residue numbering provided herein is consistent with that found in the literature. Namely the numbering is based on the numbering of the immature sequence (with the signal peptide), such as, for example, the numbering of the native chondroitinase ABC I sequence given by GenBank Accession Number P59807. In one embodiment the amino acid sequence of the modified chondroitinase ABC I is not the amino acid sequence of any of SEQ ID NOs: 3-24.

The chondroitinase ABC I enzymes and polypeptides provided herein can in some embodiments include the signal sequence. In other embodiments they do not include the signal sequence.

Modified chondroitinase ABC I enzymes can be produced using conservative substitutions, non-conservative substitutions, deletions or multiple mutant combinations of any of the residues provided herein. In some embodiments the modified chondroitinase ABC I enzymes are produced by substituting 1, 2, 3, 4, 5, 6, 7, 8, 9, 10, 15, 20, 25, 30, 35, 40, 50 or more residues of a native chondroitinase ABC I enzyme with a different amino acid than that found in the native enzyme. In some embodiments the nucleic acid molecule encoding the modified chondroitinase ABC I enzyme is at least 80%, 85%, 90%, 91%, 92%, 93%, 94%, 95%, 96%, 97%, 98%, 99% homologous to the nucleic acid that encodes the native enzyme. The enzymes encoded by such nucleic acids are also provided herein.

In one embodiment the modified chondroitinase ABC I is produced by substituting at least one of the residues described herein with an amino acid such as alanine, histidine, cysteine, phenylalanine, isoleucine, leucine, methionine, lysine, proline, arginine, tyrosine, aspartic acid, glutamic acid, glutamine or serine provided that the substituting amino acid is different from the residue found in the native enzyme. In another embodiment the residue is substituted with alanine. In still another embodiment the residue is substituted with an amino acid residue that is not alanine. In one embodiment the residue substituted is the residue at position 501 and/or 508 and the residue is substituted with an amino-acid other than alanine. In another embodiment the residue substituted is the residue at position 154 and the residue is substituted with an amino acid other than alanine.

In one embodiment the modified chondroitinase ABC I is produced by substituting the residue at position 154 with alanine. In another embodiment the modified chondroitinase ABC I is produced by substituting the residue at position 221 with alanine, lysine, methionine or glutamine. In still another embodiment the modified chondroitinase ABC I is produced by substituting the residue at position 309 with isoleucine. In still a further embodiment the modified chondroitinase ABC I is produced by substituting the residue at position 322 with leucine. In yet another embodiment the modified chondroitinase ABC I is produced by substituting the residue at position 388 with alanine, lysine or arginine. In still another embodiment the modified chondroitinase ABC I is produced by substituting the residue at position 389 with alanine, lysine or arginine. In yet another embodiment the modified chondroitinase ABC I is produced by substituting the residue at position 392 with alanine or phenylalanine. In still a further embodiment the modified chondroitinase ABC I is produced by substituting the residue at position 439 with alanine. In yet another embodiment the modified chondroitinase ABC I is produced by substituting the residue at position 442, 444, and/or 490 with alanine. In still a further embodiment the modified chondroitinase ABC I is produced by substituting the residue at position 493 with alanine. In still another embodiment the modified chondroitinase ABC I is one where the residue at position 500 is substituted with alanine, methionine, cysteine, glutamine or lysine. In still another embodiment the modified chondroitinase ABC I is produced by substituting the residue at position 501 with alanine, lysine or arginine. In still another embodiment the modified chondroitinase ABC I is produced by substituting the residue at position 508 with phenylalanine. In yet another embodiment the modified chondroitinase ABC I is one where the residue at position 560 is substituted with alanine, methionine, glutamine or lysine. In a further embodiment the modified chondroitinase ABC I is one where the residue at position 561 is substituted with alanine. In still a further embodiment the modified chondroitinase ABC I is produced by substituting the residue at position 653 with alanine, aspartic acid or glutamine. In another embodiment the residue at position 694 is substituted with proline or glutamine. In another embodiment the residue at position 712 is substituted with alanine.

In another aspect of the invention a modified chondroitinase ABC I which has the amino acid sequence of the peptide of a native chondroitinase ABC I, and the amino acid sequence contains at least one residue at position 105, 131, 154, 218, 219, 221, 222, 253, 276, 286, 309, 312, 322, 388, 389, 392, 439, 442, 444, 490, 500, 501, 508, 560, 561, 587, 653, 678, 694 or 712 of native chondroitinase ABC I and at least one amino acid substitution is provided. The at least one amino acid substitution refers to one or more substitutions of one or more residues other than the residues or set of residues that are maintained from the native enzyme. The at least one amino acid substitution can be a substitution of at least one of the residues recited above provided that the residue(s) is/are not of the set to be maintained in the enzyme. The at least one amino acid substitution can be a substitution of a residue that is not one of the residues recited above. The residue, in one embodiment, can be remote from the catalytic, substrate binding and/or calcium coordination motif sites of cABC I. In another embodiment the amino acid sequence of the modified chondroitinase ABC I is not the amino acid sequence of any of SEQ ID NOs: 3-24. In one embodiment the modified chondroitinase ABC I enzyme maintains at least the residue at position 501 of the native enzyme and further includes at least one amino acid substitution of some other residue. In still another embodiment the modified chondroitinase ABC I enzyme maintains at least one of the residues at positions 501, 508, 560, or 653 or some combination thereof of the native enzyme and further includes at least one amino acid substitution of some other residue than those maintained. The modified chondroitinase ABC I enzymes of this aspect of the invention can contain any of the residues provided herein or combinations thereof which are found in a native chondroitinase ABC I enzyme and at least one amino acid substitution. In one embodiment the modified chondroitinase ABC I has an amino acid sequence that contains the residues at positions 501, 508, 560 and 653 of a native chondroitinase ABC I and at least one amino acid substitution.

Modified chondroitinase ABC I enzymes that have altered $K_m$ or $K_{cat}$ values as compared to a native cABC I enzyme are also provided. In some embodiments the modified chondroitinase ABC I enzymes have a $K_m$ that is at least 2-, 3-, 4-, 5-, 6-, 7-, 8-, 9-, 10-, 11-, 12-, 13-, 14-, 15-, 16-, 17-, 18-, 19-, 20-, 25-, or 30-fold or more higher or lower than the $K_m$ of the native enzyme. In other embodiments the modified chondroitinase ABC I enzymes have a $K_{cat}$ that is at least 2-, 3-, 4-, 5-, 6-, 7-, 8-, 9-, 10 15-, 20-, 25-, 30-, 50-, 75-, 100-, 150-, 200-, 300-, 500-, 750-, 1000-, 1500-, 2000-, 3000-fold or more higher or lower than the $K_{cat}$ of the native enzyme.

Therefore, the modified chondroitinase ABC I enzymes provided herein can have increased or decreased activity when acting on a particular substrate. In one embodiment the modified enzymes has a $k_{cat}$ or $K_M$ value for a substrate that is at least 5%, 10%, 20%, 30%, 40%, 50%, 60%, 70%, 80% or 90% different from a $k_{cat}$ or $K_M$ value of a native enzyme. In another embodiment the modified chondroitinase ABC I has a $k_{cat}$ or $K_M$ value for a substrate that is at least 10% different than a native chondroitinase ABC I $k_{cat}$ or $K_M$ value. In yet another embodiment the modified chondroitinase ABC I has a $k_{cat}$ or $K_M$ value that is at least 20% different than a native chondroitinase ABC I $k_{cat}$ or $K_M$ value. In still another embodiment the modified chondroitinase ABC I has a $k_{cat}$ or $K_M$ value that is at least 50% different than a native chondroitinase ABC I $k_{cat}$ or $K_M$ value.

As provided above, the modified chondroitinase ABC I enzymes provided herein can have altered activity when compared to a native chondroitinase ABC I enzyme. In one embodiment the modified chondroitinase ABC I enzymes produce a modified product profile that is different from the native product profile. In one embodiment the modified product profile is at least 5%, 10%, 20%, 30%, 40%, 50%, 60%, 70%, 80% or 90% different from a product profile of a native cABC I enzyme. In one embodiment the modified product profile can be at least 10% different than a native product profile of a native chondroitinase ABC I. In another embodiment the modified product profile is at least 20% different than a native product profile of a native chondroitinase ABC I. In yet another embodiment the modified product profile is at least 50% different than a native cABC I product profile. In one embodiment the modified chondroitinase ABC I has the amino acid sequence of a native chondroitinase ABC I and has a residue at position 508 that is substituted with phenylalanine. In another embodiment the modified chondroitinase ABC I has the amino acid sequence of a native chondroitinase ABC I and has a residue at position 560 that is substituted. In another embodiment the amino acid of the modified chondroitinase ABC I enzyme is not the amino acid sequence of any of SEQ ID NOs: 3-24.

The substrates on which a native or modified cABC I enzyme provided herein can act include any polysaccharide. In one embodiment the polysaccharide is a glycosaminoglycan. In another embodiment the polysaccharide is a galactosaminoglycan.

In still another embodiment the polysaccharide is chondroitin, chondroitin sulfate, dermatan sulfate, chondroitin 4-sulfate, chondroitin 6-sulfate, chondroitin D (CSD), chondroitin E (CSE), hyaluronan or some combination thereof.

Provided herein are chondroitinase ABC I enzymes that selectively degrade a particular substrate and/or have altered substrate specificity. In one embodiment the substrate is chondroitin sulfate, and a modified chondroitinase ABC I that selectively degrades chondroitin sulfate is provided. In one embodiment the modified chondroitinase ABC I has the amino acid sequence of a native chondroitinase ABC I and has a residue at position 388 or 389 or a combination thereof that is substituted with alanine, lysine or arginine. In another embodiment the modified chondroitinase ABC I has the amino acid sequence of a native chondroitinase ABC I and has a residue at position 500 that is substituted with alanine. In still another embodiment the modified chondroitinase ABC I has the amino acid sequence of a native chondroitinase ABC I and has a residue at position 653 that is substituted with alanine, lysine or arginine.

In another embodiment a chondroitinase ABC I that selectively degrades dermatan sulfate is provided. In one embodiment the chondroitinase ABC I has the amino acid sequence of a native chondroitinase ABC I and has a residue at position 560 that is substituted with alanine or lysine.

In yet another embodiment a chondroitinase ABC I that selectively degrades chondroitin 6-sulfate is provided. In one embodiment the chondroitinase ABC I has the amino acid sequence of a native chondroitinase ABC I and has a residue at position 500 that is substituted with cysteine or lysine.

In still a further embodiment a chondroitinase ABC I that selectively degrades chondroitin 4-sulfate is provided. In one embodiment the chondroitinase ABC I has the amino acid sequence of a native chondroitinase ABC I and has a residue at position 221 that is substituted with alanine. In another embodiment the chondroitinase ABC I has the amino acid sequence of a native chondroitinase ABC I and a residue at position 500 that is substituted with glutamine.

Also provided herein are chondroitinase ABC I enzymes that are DS-exclusive enzymes or CS-exclusive enzymes. In one embodiment the chondroitinase ABC I enzyme is one where the residue at position 105, 312, and/or 388 has been substituted with a different amino acid than that found in a native cABC I enzyme. cABC I enzymes with chondroitinase AC(cAC)-like activity include modified chondroitinase ABC I enzymes that have the amino acid sequence of a native chondroitinase ABC I and a residue at position 388 and/or 389 that is substituted with alanine, lysine or arginine. Another cABC I enzyme with cAC-like activity is a modified chondroitinase ABC I that has the amino acid sequence of a native chondroitinase ABC I and a residue at position 500 that is substituted with alanine. cABC I enzymes with chondroitinase B(cB)-like activity are also provided. In one embodiment the chondroitinase ABC I with cB-like activity has the amino acid sequence of a native chondroitinase ABC I and has a residue at position 560 that is substituted with alanine or lysine. In other embodiments chondroitinase ABC I enzymes that are specific for hyaluronan-based GAGs are also provided. cABC I enzymes that have such specificity for certain GAGs engineered out of the enzymes are also provided.

Chondroitinase ABC I enzymes with an altered calcium coordination motif are also provided. It has now been found that the residues at positions 442, 444 and 490 coordinate calcium ion and helps with the processing of substrates, such as dermatan sulfate, by the enzyme. Therefore, these residues can be manipulated to control enzyme activity. In one embodiment the activity is the processing of iduronic acid-containing glycosaminoglycans. In another embodiment the activity is the processing of dermatan sulfate or heparin sulfate. In one embodiment, therefore, a modified chondroitinase ABC I enzyme is provided where a residue at position 442, 444 and/or 490 or some combination thereof is substituted. In another embodiment the substitution(s) is with alanine. In yet another embodiment a modified chondroitinase ABC I enzyme is provided where the residue at position 442, 444 and 490 are substituted. In another embodiment the residues are each substituted with alanine.

In still a further embodiment the modified chondroitinase ABC I enzyme is one where the residue at 218, 219, 222, 312, 561 or 712 or some combination thereof is substituted with alanine. In another embodiment the modified chondroitinase ABC I enzyme is one where the residue at 309 is substituted with valine. Modified chondroitinase ABC I enzymes are provided where one or more of the residues described herein are substituted.

In another aspect of the invention polypeptides comprising the amino acid sequence of the enzymes described herein or fragments thereof are provided. Nucleic acids encoding such polypeptides are also provided. In one aspect of the invention nucleic acids that encode the chondroitinase ABC I enzymes or polypeptides described herein are provided. In one embodiment the nucleic acid is the nucleic acid as provided by SEQ ID NO: 1. In another embodiment the nucleic acid is a degenerate or complement of the nucleic acid sequence of SEQ ID NO: 1. Also provided herein, therefore, are vectors containing the nucleic acids described as are methods of producing chondroitinase ABC I enzymes using such vectors. Therefore, in another embodiment the chondroitinase ABC I enzymes provided are in recombinant form, and preferably, in a substantially purified recombinant form.

In another aspect of the invention compositions comprising the chondroitinase ABC I enzymes, polypeptides, nucleic acids, etc. described herein are provided. In one embodiment the compositions further comprise a pharmaceutically acceptable carrier. In another embodiment the compositions provided further comprise a physiologically acceptable carrier.

In one aspect of the invention a composition is provided that comprises a chondroitinase and a divalent ion. The ion can be any ion including, but not limited, to calcium ion, manganese ion, copper ion, iron ion, barium ion, magnesium ion, zinc ion and lanthanides. In one embodiment the ion is not zinc ion. In another embodiment the ion is a lanthanide, such as, terbium or lutetium. In yet another embodiment the calcium ion is in the form of $CaCl_2$. The $CaCl_2$ can be at any concentration. In some embodiments, the $CaCl_2$ is at a concentration of at least 1, 2, 3, 4, 5, 6, 7, 8, 9, or 10 mM or more in a composition. In one embodiment the $CaCl_2$ is at a concentration of at least 5 mM. In another embodiment the $CaCl_2$ is at a concentration of at least 10 mM. In still another embodiment the $CaCl_2$ is at a concentration of 10 mM. In other embodiments the chondroitinase can be chondroitinase B, chondroitinase AC, chondroitinase ABC I or chondroitinase ABC II. Also provided in another aspect of the invention are compositions that include the chondroitinase enzyme, divalent ion and a pharmaceutically or physiologically acceptable carrier.

Compositions of a galactoaminoglycan-degrading enzyme and an enzyme stabilizer are also provided. In one embodiment the enzyme stabilizer is a protease inhibitor. Protease inhibitors include, but are not limited to, AEBSF, bestatin, E64 protease inhibitor, pepstatin A or phosphoramidon. In another embodiment the enzyme stabilizer is a water mimic, such as, for example, glycerol or dextran. In one embodiment the galactosaminoglycan-degrading enzyme is chondroitinase AC, chondroitinase B, chondroitinase ABC I, chondroitinase ABC II, chondro-4-sulfatase, chondroi-6-sulfatase or hyaluronidase or some combination thereof. In another aspect of the invention compositions that include a galactosaminoglycan-degrading enzyme, an enzyme stabilizer and a pharmaceutically or physiologically acceptable carrier are also provided.

The compositions and enzymes provided herein can be used for a variety of purposes. In one aspect a method of degrading a polysaccharide, such as a glycosaminoglycan, by contacting the glycosaminoglycan with any of the enzymes or compositions provided herein in an amount effective to degrade the glycosaminoglycan is provided. In one embodiment the method can further include contacting the glycosaminoglycan with at least one other polysaccharide-degrading enzyme, such as a glycosaminoglycan-degrading enzyme or galactosaminoglycan-degrading enzyme. Other glycosaminoglycan-degrading enzymes include heparinases, glycuronidases, sulfatases, etc. In one embodiment the methods for degrading a polysaccharide can be carried out in the presence of a divalent ion. Ions (e.g., zinc) can be inhibitory to enzyme function. Therefore, in one embodiment, methods and compositions are provided where zinc is not included. In another embodiment calcium is present while other ions, such as zinc, are not. In another embodiment the methods can further include the step of contacting the glycosaminoglycan and/or the glycosaminoglycan-degrading enzyme, such as a chondroitinase, with zinc ion. The introduction of zinc ion can inhibit the degradation reaction and can serve as a way to control the enzymatic reaction. In some instances the presence of zinc may be desired to control the reaction of substrate and enzyme. Therefore methods of degrading polysaccharides are provided whereby two or more divalent ions can be introduced to the enzymatic reaction at the same or at different points of the reaction process. In one embodiment one of the ions is zinc ion. In another embodiment the zinc ion is introduced after the introduction of another divalent ion to the reaction. The divalent ions can include any such ions known in the art including those described herein.

As another way to control polysaccharide degradation reactions, chelators may be used. Therefore, in one embodiment the methods provided can further include the step of introducing a chelator to the enzymatic reaction. In one embodiment the chelator is EDTA or EGTA.

Methods and compositions are also provided herein where a polysaccharide, such as, for example, dermatan sulfate, is processed in the presence of calcium. A novel calcium-coordination site in proximity to the enzyme active site has been found. The residues at positions 490, 442, and 444 are important components of this calcium-coordination site. Modulating this site, as well as regulating calcium levels in reaction, are important parts of controlling activity. Therefore compositions and methods are provided whereby the presence of calcium is controlled. In one embodiment of such compositions and methods alterations of one or more of the calcium coordination motif residues of a cABC I enzyme can also be included.

In another aspect of the invention methods of degrading a polysaccharide, such as a glycosaminoglycan, that include the step of contacting a polysaccharide, such as a glycosaminoglycan, with a polysaccharide-degrading enzyme, such as a galactosaminoglycan-degrading enzyme in the presence of an enzyme stabilizer. In one embodiment the enzyme stabilizer is a protease inhibitor, such as AEBSF, bestatin, E64 protease inhibitor, pepstatin A or phosphoramidon. In another embodiment the enzyme stabilizer is a water mimic, such as glycerol or dextran.

cABC I enzymes have been analyzed in a variety of reaction conditions. Enzyme-substrate reaction parameters can be chosen to control substrate specificity, the mechanism of action, and/or the product profile. These reaction parameters include salt (e.g., NaCl, NaAC), temperature, pH, buffer (Tris buffer, or phosphate buffer), and reaction volume. Therefore compositions and methods are provided whereby these reaction parameters or some combination thereof are controlled. In one aspect methods of degrading a polysaccharide are provided whereby the pH is controlled. In one embodiment a polysaccharide, such as a glycosaminoglycan, is contacted with a degrading enzyme in a solution with a pH greater than 7 but less than 8. In another embodiment the pH of the solution is altered after the polysaccharide is contacted with the degrading enzyme. In another embodiment the pH for acting on the polysaccharide is less than 9.0. In another embodiment the pH is 8.0. In still another embodiment the pH is 7.0. In yet another embodiment the pH is between 6.0 and 9.0. In still a further embodiment the pH is between 7.0 and 8.0. In one embodiment when a phosphate buffer is used and the substrate on which the enzyme acts is chondroitin sulfate, the pH is 7.0.

In another embodiment of the invention methods are provided whereby the buffer is controlled. In some embodiments the buffer is Tris buffer or phosphate buffer.

In another embodiment the ionic strength (salt concentration) is controlled. In one embodiment the salt concentration is less than 500 mM. In another embodiment the salt concentration is less than 400 mM. In still another embodiment the salt concentration is less than 250 mM. In one embodiment the salt concentration is between 50-500 mM. In still another embodiment the salt concentration is greater than 50 mM. In yet another embodiment the salt concentration is between 60-125 mM. In still another embodiment the salt concentration is between 125-150 mM. In another embodiment the salt concentration is between 50-400, 150-400 or 150-500 mM. In yet another embodiment the salt concentration is between 50-125 mM. In still another embodiment the salt concentration when the substrate is chondroitin sulfate is 62.5 mM. In a further embodiment the salt concentration is between 250-500 mM. In still another embodiment the salt concentration is between 100-250 mM. In one embodiment the salt concentration is 100, 125 or 250 mM. The salt can be any of those known in the art and include sodium chloride, sodium acetate, sodium sulfate or ammonium sulfate. In one embodiment of the invention a method is provided whereby dermatan sulfate is contacted with an enzyme provided herein in the presence of salt.

In another embodiment of the invention methods are provided whereby the concentration of sodium acetate is controlled. In one embodiment sodium acetate is present at 25-150 mM. In another embodiment 50-100 mM sodium acetate is present. In yet another embodiment the sodium acetate is present at a concentration of 50 mM. In another embodiment the sodium acetate is present at a concentration of 100 mM. In another aspect where chondroitin sulfate is the substrate, sodium acetate is included in the composition or method.

In yet another embodiment of the invention the temperature is controlled. In one embodiment the temperature is less than 40° C. In another embodiment the temperature is between 25-45° C. In still another embodiment the temperature is between 30-40° C. In yet another embodiment the temperature is between 25-40° C. In still another embodiment the temperature is between 30-37° C. In another embodiment the temperature is between 38-45° C. or 38-50° C. In a further embodiment the temperature is 40° C. In still another embodiment the temperature is 37° C.

In other aspects of the invention methods and compositions are provided whereby more than one of the reaction parameters are controlled.

In another aspect of the invention the degraded glycosaminoglycans produced by the methods described herein are also provided. Also provided are compositions that include the degraded glycosaminoglycans and a pharmaceutically or physiologically acceptable carrier.

In another aspect of the invention methods for selectively degrading a polysaccharide are also provided. In one aspect a method of selectively degrading chondroitin sulfate is given. In another aspect the method is a method of selectively degrading dermatan sulfate. In another aspect the method is a method of selectively degrading chondroitin 6-sulfate. In still a further aspect the method is a method of selectively degrading chondroitin 4-sulfate.

In another aspect of the invention a method of analyzing a sample of polysaccharides by contacting the sample with any of the enzymes or compositions described herein is provided. In one embodiment the polysaccharides are glycosaminoglycans. In another embodiment the glycosaminoglycans are galactosaminoglycans. In one aspect of the invention the method of analysis is a method for sequencing. In another aspect the method is a method for identifying the presence of a particular polysaccharide in a sample. In still a further aspect of the invention the method is a method for determining the purity of a sample of polysaccharides. In yet another aspect of the invention the method is a method for determining the composition of a sample of polysaccharides.

The enzymes and compositions provided can further be used in various treatment methods. For instance, in one aspect of the invention a method for promoting nerve regeneration is provided. In one embodiment the nerve regeneration is axon regeneration. In one embodiment the method is directed to the treatment of a subject that has had a central nervous system injury. In another embodiment the subject has had a spinal cord injury. In another embodiment the subject has a neurodegenerative disorder. In yet a further embodiment the subject has had a stroke.

In another aspect of the invention the enzymes and compositions provided can be used in methods for treating cancer. In still another aspect of the invention methods for inhibiting angiogenesis are provided. In yet another aspect of the invention methods for inhibiting coagulation are provided. In still another aspect of the invention methods for treating psoriasis are provided. In yet another aspect of the invention methods for treating osteoarthritis are provided. In still another aspect methods for treating a microbial infection, such as maternal malarial infection, are provided. In yet another aspect of the invention methods for treating epithelial disease (e.g., cystic fibrosis) are provided. In still another aspect of the invention methods for treating viral, bacterial or pathogenic infection or provided. In these aspects the methods for treatment include administering to a subject in need thereof an effective amount of a pharmaceutical preparation of the enzymes or compositions provided herein or a polysaccharide or group of polysaccharides that result from contact with the enzymes provided alone or in combination with other polysaccharide-degrading enzymes or both.

In another aspect pharmaceutical preparations are provided. The pharmaceutical preparation in one aspect includes the chondroitinase ABC I enzymes provided and a pharmaceutically acceptable carrier. In another aspect the pharmaceutical preparation includes a degraded polysaccharide, such as a glycosaminoglycan, and a pharmaceutically acceptable carrier. In some aspects the pharmaceutical preparations include both the enzyme and the degraded glycosaminoglycan. In preferred embodiments the pharmaceutical preparations include sterile formulations of the enzymes or degraded polysaccharides or both. Steriled formulations of any of the compositions described are also provided herein.

In another aspect of the invention a method for recombinantly expressing a chondroitinase ABC I polypeptide is provided. In still another aspect of the invention a method for preparing purified chondroitinase ABC I is also provided. In still other another aspect a method for recombinantly expressing and preparing a purified chondroitinase ABC I is provided. In one aspect of the invention a method for producing chondroitinase ABC I is provided which includes the steps of harvesting cells that express chondroitinase ABC I, lysing the cells, obtaining supernatant, and in some way purifying or filtering the supernatant (e.g., applying the supernatant to a column and eluting the chondroitinase ABC I from the column). In one embodiment the method also includes putting the cells, supernatant, filtered supernatant or eluate on ice as part of one or more of the steps. The method also can include putting the cells, supernatant, filtered supernatant or eluate on ice between any of the steps (e.g., between 2, 3, 4 or more steps). In one embodiment the cells, supernatant, filtered supernatant or eluate are put on ice at least twice during the method for the production of chondroitinase ABC I. The methods provided can also be used for the production/purification of other polysaccharide-degrading enzymes, such as glycosaminoglycan-degrading enzymes, galactosaminoglycan-degrading enzymes, chondroitinases, etc. In another aspect of the invention a method for producing chondroitinase ABC I is provided which includes the steps of harvesting cells that express chondroitinase ABC I, lysing the cells, obtaining supernatant, and in some way purifying or filtering the supernatant (e.g., applying the supernatant to a column and eluting the chondroitinase ABC I from the column), wherein one or more of the steps include the use of one or more protease inhibitors. In one embodiment the methods can also include filtering the supernatant, or purifying the enzyme with a $Ni^{+2}$ column. The methods can further include the use of 6x-His tags that can be cleaved off. The 6x-His tags bind $Ni^{+2}$ column and allows enzyme purification from crude extract (e.g., as one chromatography step). In still another embodiment the methods include centrifugation to obtain a cell pellet. In one embodiment the pellet is not stored prior to further processing.

In another aspect of the invention the methods of production/purification are performed rapidly. In one embodiment the methods are performed in about 4 hours or less. In another embodiment the methods are performed in about 5 hours or less.

In still another aspect methods for producing the enzyme where the signal sequence is removed are provided.

In another aspect of the invention the chondroitinase ABC I or modified forms thereof are in a substantially purified recombinant form.

In one aspect of the invention a chondroitinase ABC I with a specific activity of 20 mU/μg or more is provided. In one embodiment the specific activity is at least 30, 40, 50, 60, 70, 80, 90, 100, 125, 150, 175, 200 mU/μg or more. In still another embodiment the specific activity is at least 164 mU/μg. In another embodiment the specific activity is at least 197.9 or 230.6 mU/μg. In another aspect of the invention a chondroitinase ABC I enzyme is provided that has a specific activity that is 2-, 3-, 4-, 5-, 6-, 7-, 8-, 9-, 10-, 15-, 20-, 30, 40-, 50-fold or more greater than the activity of the enzyme obtained from a crude lysate.

In a further aspect of the invention an immobilized chondroitinase ABC I which includes at least one of the chondroitinase ABC I enzymes provided herein and a solid support membrane, wherein the chondroitinase ABC I is immobilized on the solid support membrane, is provided.

Also provided herein are drug delivery strategies of cABC I and its modified counterparts. These include fusion proteins, where the cABC I enzyme is conjugated to a targeting molecule, such as a cancer antigen, pathogen toxin or portion thereof, or a molecule that targets the glial scar. Therefore, the cABC I enzymes delivered with the aid of a targeting molecule that has facile and specific localization to a physiological target(s) can be used in the methods of treatment provided.

The compositions and methods provided can further include the use of other glycosaminoglycan-degrading enzymes, such as galactosaminoglycan-degrading enzymes. In some embodiments, such enzymes can include chondroitinase AC, chondroitinase B, chondroitinase ABC II, hyaluronidase, chondro-4-sulfatase, chondro-6-sulfatase, mutant versions, functional equivalents or some combination thereof.

Each of the limitations of the invention can encompass various embodiments of the invention. It is, therefore, anticipated that each of the limitations of the invention involving any one element or combinations of elements can be included in each aspect of the invention.

These and other aspects of the invention will be described in further detail in connection with the detailed description of the invention.

BRIEF DESCRIPTION OF THE FIGURES

Figure 7:
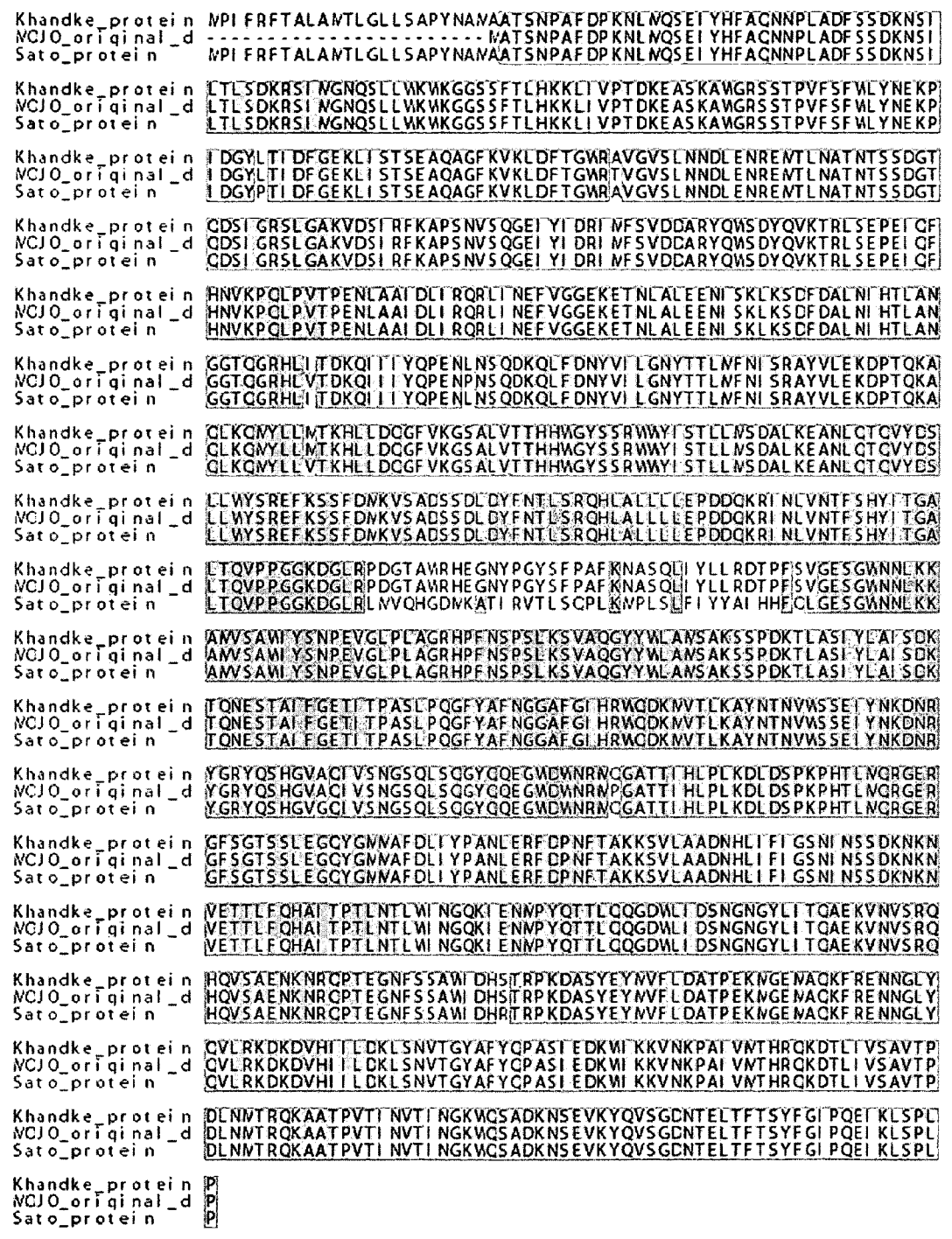

FIG. 7 depicts the comparison of three amino acid sequences of chondroitinase ABC I protein. The sequences of Sato et al. (SEQ ID NO: 4) and Khandke/Ryan (SEQ ID NO: 3) et al. [13 and 14, Example 1] were compared to the sequence from the original truncated clone described in the Examples below.

FIG. 22 shows the activity of various Glu653 mutants acting on the substrates C6S and DS.

FIG. 24 provides the results from the kinetic analysis of a Tyr508 mutant as compared to cABC I against two substrates, C6S and DS.

FIG. 25 provides the results from the kinetic analysis of a Glu653 mutant as compared to cABC I against two substrates, C6S and DS.

DETAILED DESCRIPTION

Members of the glycosaminoglycan (GAG) family of complex polysaccharides includes dermatan sulfate (DS), chondroitin sulfate (CS), heparin/heparan sulfate (HSGAG), keratan sulfate, and hyaluronic acid. Chondroitin sulfate and dermatan sulfate glycosaminoglycan polysaccharides, have been implicated in biological processes ranging from osteoarthritis to anticoagulation. Dermatan sulfate is emerging as an important regulator of cellular signaling processes. An oversulfated hexasaccharide found in DS that binds heparin cofactor II and promotes a 1000-fold increase in anticoagulation is the most characterized biological paradigm for DS (Maimone, M. M., and Tollefsen, D. M. (1991) J Biol Chem 266, 14830; Mascellani, G., Liverani, L., Bianchini, P., Parma, B., Torri, G., Bisio, A., Guerrini, M., and Casu, B. (1993) Biochem J 296, 639-48). Several recent studies have implicated DS in promoting FGF-7 mitogenic activity (Trowbridge, J. M., Rudisill, J. A., Ron, D., and Gallo, R. L. (2002) J Biol Chem 277, 42815-20) and enhancing the activity of hepatocyte growth factor/scatter factor (Lyon, M., Deakin, J. A., Rahmoune, H., Femig, D. G., Nakamura, T., and Gallagher, J. T. (1998) J Biol Chem 273, 271-8; Lyon, M., Deakin, J. A., and Gallagher, J. T. (2002) J Biol Chem 277, 1040-6), suggesting an important role for DS in mediating cell signaling.

Figure 8:
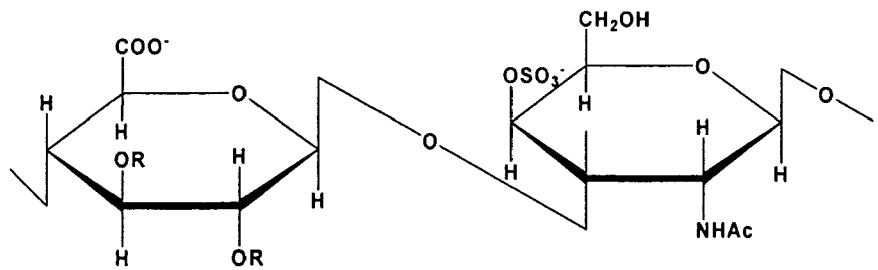
FIG. 8 provides GalAG disaccharide chemical structures. GAGs are polymers of repeated disaccharide units consisting of an uronic acid and a hexosamine. In the case of GalAGs, the hexosamine moiety is a galactosamine.
Figure 8:
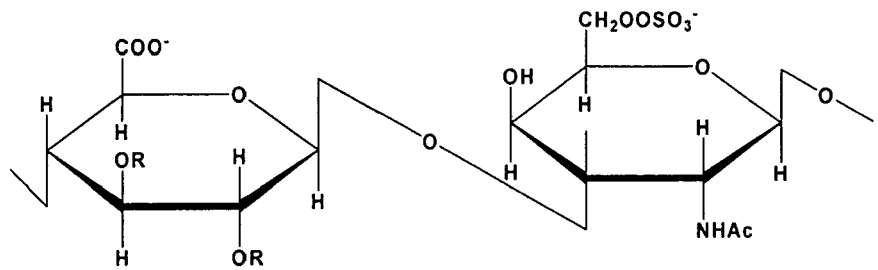
Figure 8:
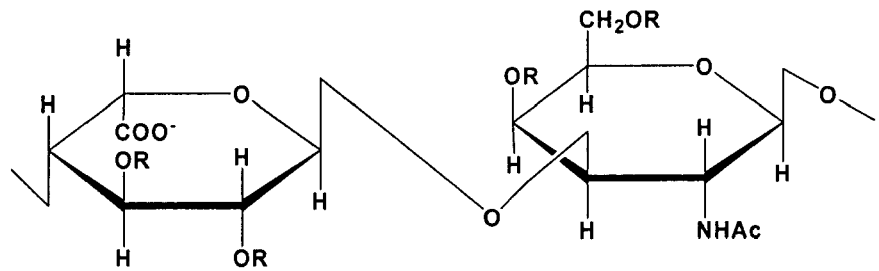

Dermatan sulfate is just one member of a subset of the glycosaminoglycan (GAG) family of chemically heterogeneous polysaccharides that are involved in a wide range of biological processes. This subset is referred to as galactosaminoglycans (GalAGs). GalAGs are one of four classes of GAGs (Ernst, S., Langer, R., Cooney, C. L. and Sasisekharan, R. (1995) Enzymatic degradation of glycosaminoglycans. Crit Rev Biochem Mol Biol 30, 387-444.) Galactosaminoglycans are composed of a disaccharide repeat unit of uronic acid [α-L-iduronic (IdoA) or β-D-glucuronic (GlcA)] (1→3) linked to N-acetyl-D-galactosamine (GalNAc). These basic disaccharide units (FIG. 8) are linearly associated via β(1→4) linkages to form polymers of chondroitin sulfate (CS) or dermatan sulfate (DS). The uronic acids of CS are exclusively GlcA; with DS, epimerization at the C-5 position of the uronic acid moiety during biosynthesis results in a mixture of IdoA and GlcA epimers. Chondroitin sulfate can be O-sulfated at the C-4 of the galactosamine (chondroitin-4-sulfate, C4S or CSA) or the C6 of the galactosamine (chondroitin-6-sulfate, C6S or CSC). For DS, C-4 sulfation of the galactosamine is a common modification and O-sulfation at C-2 of the IdoA moiety may also occur. Other rare modifications in CS, such as 2-O or 3-O sulfation of the GlcA moiety, have also been reported (Nadanaka, S. and Sugahara, K. (1997) The unusual tetrasaccharide sequence GlcA beta 1-3GalNAc(4-sulfate)beta 1-4GlcA(2-sulfate)beta 1-3GalNAc(6-sulfate) found in the hexasaccharides prepared by testicular hyaluronidase digestion of shark cartilage chondroitin sulfate D. Glycobiology 7, 253-263; Sugahara, K., Tanaka, Y., Yamada, S., Seno, N., Kitagawa, H., Haslam, S. M., Morris, H. R. and Dell, A. (1996) Novel sulfated oligosaccharides containing 3-O-sulfated glucuronic acid from king crab cartilage chondroitin sulfate K. Unexpected degradation by chondroitinase ABC. J Biol Chem 271, 26745-26754.) GalAGs include chondroitin and dermatan sulfate GAGs, such as C4S, C6S, DS, chondroitin, chondroitin D, chondroitin E and hyaluronan. These complex biomacromolecules are believed to be responsible for the inhibition of nerve regeneration following injury to the central nervous system. The enzymatic degradation of GAG chains in damaged nervous tissue by chondroitinase ABC I (cABC I), a broad specificity lyase that degrades GalAGs, promotes neural recovery.

Several studies have implicated GalAGs as key modulators of fundamental biological processes. Galactosaminoglycans interact with a wide variety of proteins such as growth factors, chemokines, lipoproteins and enzymes in the extracellular environment. These interactions play critical roles in modulating the function of the protein (Trowbridge, J. M. and Gallo, R. L. (2002) Dermatan sulfate: new functions from an old glycosaminoglycan. Glycobiology 12, 117R-125R; Sugahara, K., Mikami, T., Uyama, T., Mizuguchi, S., Nomura, K. and Kitagawa, H. (2003) Recent advances in the structural biology of chondroitin sulfate and dermatan sulfate. Curr Opin Struct Biol 13, 612-620.) Dermatan sulfate is known to bind with thrombin (Liaw, P. C., Austin, R. C., Fredenburgh, J. C., Stafford, A. R. and Weitz, J. I. (1999) Comparison of heparin- and dermatan sulfate-mediated catalysis of thrombin inactivation by heparin cofactor II. J Biol Chem 274, 27597-27604) and activated protein C (Fernandez, J. A., Petaja, J. and Griffin, J. H. (1999) Dermatan sulfate and LMW heparin enhance the anticoagulant action of activated protein C. Thromb Haemost 82, 1462-1468) to influence anticoagulation; collagen (Iozzo, R. V. (1997) The family of the small leucine-rich proteoglycans: key regulators of matrix assembly and cellular growth. Crit Rev Biochem Mol Biol 32, 141-174), fibronectin (Tumova, S., Woods, A. and Couchman, J. R. (2000) Heparan sulfate chains from glypican and syndecans bind the Hep II domain of fibronectin similarly despite minor structural differences. J Biol Chem 275, 9410-9417; Schmidt, G., Robenek, H., Harrach, B., Glossl, J., Nolte, V., Hormann, H., Richter, H. and Kresse, H. (1987) Interaction of small dermatan sulfate proteoglycan from fibroblasts with fibronectin. J Cell Biol 104, 1683-1691; Walker, A. and Gallagher, J. T. (1996) Structural domains of heparan sulphate for specific recognition of the C-terminal heparin-binding domain of human plasma fibronectin (HEPII). Biochem J 317 (Pt 3), 871-877), and tenascin-X (Elefteriou, F., Exposito, J. Y., Garrone, R. and Lethias, C. (2001) Binding of tenascin-X to decorin. FEBS Lett 495, 44-47) to stabilize the extracellular matrix; transforming growth factor-β (Yamaguchi, Y., Mann, D. M. and Ruoslahti, E. (1990) Negative regulation of transforming growth factor-beta by the proteoglycan decorin. Nature 346, 281-284; Hildebrand, A., Romaris, M., Rasmussen, L. M., Heinegard, D., Twardzik, D. R., Border, W. A. and Ruoslahti, E. (1994) Interaction of the small interstitial proteoglycans biglycan, decorin and fibromodulin with transforming growth factor beta. Biochem J 302 (Pt 2), 527-534) to regulate growth; and hepatocyte growth factor/scatter factor (Lyon, M., Deakin, J. A., Mizuno, K., Nakamura, T. and Gallagher, J. T. (1994) Interaction of hepatocyte growth factor with heparan sulfate. Elucidation of the major heparan sulfate structural determinants. J Biol Chem 269, 11216-11223; Lyon, M., Deakin, J. A., Rahmoune, H., Femig, D. G., Nakamura, T. and Gallagher, J. T. (1998) Hepatocyte growth factor/scatter factor binds with high affinity to dermatan sulfate. J Biol Chem 273, 271-278) to spur cellular proliferation and organogenesis. In a growing number of instances, it has also been established that there is sequence-specificity in GalAG-protein interactions in terms of the precise modifications in the chemical structure of GalAGs that bind with high affinity to a given protein (Mascellani, G., Liverani, L., Bianchini, P., Parma, B., Torri, G., Bisio, A., Guerrini, M. and Casu, B. (1993) Structure and contribution to the heparin cofactor 11-mediated inhibition of thrombin of naturally oversulphated sequences of dermatan sulphate. Biochem J 296 (Pt 3), 639-648; Maimone, M. M. and Tollefsen, D. M. (1991) Structure of a dermatan sulfate hexasaccharide that binds to heparin cofactor II with high affinity. J Biol Chem 266, 14830.) Further, manipulation of GAG chemical structure has been shown to promote anti-tumor activities, inhibiting angiogenesis and tumor metastasis (Denholm, E. M., Lin, Y. Q. and Silver, P. J. (2001) Anti-tumor activities of chondroitinase AC and chondroitinase B: inhibition of angiogenesis, proliferation and invasion. Eur J Pharmacol 416, 213-221.) Modification of CS-containing proteoglycans has been observed in a variety of human cancers including those of the colon (Iozzo, R. V. and Cohen, I. (1993) Altered proteoglycan gene expression and the tumor stroma. Experientia 49, 447-455; Makatsori, E., Lamari, F. N., Theocharis, A. D., Anagnostides, S., Hjerpe, A., Tsegenidis, T. and Karamanos, N. K. (2003) Large matrix proteoglycans, versican and perlecan, are expressed and secreted by human leukemic monocytes. Anticancer Res 23, 3303-3309), blood (Makatsori, E., Lamari, F. N., Theocharis, A. D., Anagnostides, S., Hjerpe, A., Tsegenidis, T. and Karamanos, N. K. (2003) Large matrix proteoglycans, versican and perlecan, are expressed and secreted by human leukemic monocytes. Anticancer Res 23, 3303-3309), and larynx (Papadas, T. A., Stylianou, M., Mastronikolis, N. S., Papageorgakopoulou, N., Skandalis, S., Goumas, P., Theocharis, D. A. and Vynios, D. H. (2002) Alterations in the content and composition of glycosaminoglycans in human laryngeal carcinoma. Acta Otolaryngol 122, 330-337.) Defined GalAG oligosaccharides are also being developed as therapeutics for blood coagulation disorders (Vicente, C. P., Zancan, P., Peixoto, L. L., Alves-Sa, R., Araujo, F. S., Mourao, P. A. and Pavao, M. S. (2001) Unbalanced effects of dermatan sulfates with different sulfation patterns on coagulation, thrombosis and bleeding. Thromb Haemost 86, 1215-1220; Gandra, M., Cavalcante, M. and Pavao, M. Styela plicata (Tunicata). Glycobiology 10, 1333-1340.) Thus, the characterization of structure-function relationships involving GalAGs helps with the understanding of their biological roles.

The structural characterization of complex acidic polysaccharides, like GAGs, is a challenging task. Due to their complex non-template based biosynthesis, it has been difficult to develop methodologies to obtain sufficient material containing pure GAG oligosaccharides. Further, the chemical heterogeneity and highly acidic nature of GAGs have complicated their analysis. Significant advances have been made in the development of enzymatic tools to depolymerize GAGs at specific linkages. Analytical tools such as mass spectrometry (Rhomberg, A. J., Ernst, S., Sasisekharan, R. and Biemann, K. (1998) Mass spectrometric and capillary electrophoretic investigation of the enzymatic degradation of heparin-like glycosaminoglycans. Proc Natl Acad Sci U S A 95, 4176-4181), capillary electrophoresis (Rhomberg, A. J., Ernst, S., Sasisekharan, R. and Biemann, K. (1998) Mass spectrometric and capillary electrophoretic investigation of the enzymatic degradation of heparin-like glycosaminoglycans. Proc Natl Acad Sci U S A 95, 4176-4181) and NMR (Guerrini, M., Raman, R., Venkataraman, G., Torri, G., Sasisekharan, R. and Casu, B. (2002) A novel computational approach to integrate NMR spectroscopy and capillary electrophoresis for structure assignment of heparin and heparan sulfate oligosaccharides. Glycobiology 12, 713-719) have also been useful for accurate structural characterization of GAGs using very small amounts of material that are typically isolated from tissues. Enzymatic tools, when used in conjunction with analytical methods, have allowed for the rapid and precise sequencing of biologically relevant GAGs (Venkataraman, G., Shriver, Z., Raman, R. and Sasisekharan, R. (1999) Sequencing complex polysaccharides. Science 286, 537-542.) Various microorganisms express GAG-degrading polysaccharide lyases. Mechanistically, these lyases degrade their substrates via a β-elimination reaction that generates products with an unsaturated 4, 5 bond on the uronic acid at the site of cleavage. Extensive biochemical characterization of the activity and substrate specificity of some of these enzymes, such as the heparinases, have successfully enabled their utilization as tools for structural characterization of heparin and heparan sulfate GAGs (HSGAGs) (Venkataraman, G., Shriver, Z., Raman, R. and Sasisekharan, R. (1999) Sequencing complex polysaccharides. Science 286, 537-542; Ernst, S., Rhomberg, A. J., Biemann, K. and Sasisekharan, R. (1998) Direct evidence for a predominantly exolytic processive mechanism for depolymerization of heparin-like glycosaminoglycans by heparinase I. Proc Natl Acad Sci U S A 95, 4182-4187.) The GalAG-processing (also referred to as GalAG-degrading enzymes) enzymes include chondroitinase AC (cAC, EC 4.2.2.5) chondroitinase B (cB) from *Flavobacterium heparinum* (now known as *Pedobacter heparinus*), chondroitinase ABC I (cABC I), ABC II (cABC II, EC 4.2.2.4) from *Proteus vulgaris* and hyaluronidase. Chondroitinase AC shows activity against C4S and C6S, while chondroitinase B cleaves DS as its sole substrate. Chondroitinase ABC I and cABC II process a variety of substrates including C4S, C6S, DS, and hyaluronan. Particularly striking is the ability of these broad substrate specificity enzymes (cABC I and II) to process GalAGs containing either uronic acid epimer.

As introduced above, chondroitinase ABC I is a glycosaminoglycan (GAG) degrading enzyme that selectively depolymerizes chondroitin sulfate (CS) and dermatan sulfate (DS) substrates, as well as unsulfated chondroitin and hyaluronan, albeit at lower rates. Chondroitinase ABC I has been demonstrated to have utility in the analysis of CS/DS and hyaluronan oligosaccharides both from commercial sources and from biologically relevant cell and tissue model systems. In addition, it has been suggested that chondroitinase ABC I may play a direct role as a therapeutic in various clinical conditions. Specifically, chondroitinase ABC I has shown promise in promoting functional recovery through neuro-regenerative activities. In fact, chondroitinase ABC I has recently been employed as a potential nerve regeneration therapeutic for spinal cord injury (Bradbury, E. J., Moon, L. D., Popat, R. J., King, V. R., Bennett, G. S., Patel, P. N., Fawcett, J. W. and McMahon, S. B. (2002) Chondroitinase ABC promotes functional recovery after spinal cord injury. Nature 416, 636-640.) Additionally, it was reported that chondroitin sulfate chains are inhibitory to axon regeneration, providing a physical obstacle for this healing process (Morgenstern, D. A., Asher, R. A. and Fawcett, J. W. (2002) Chondroitin sulphate proteoglycans in the CNS injury response. Prog Brain Res 137, 313-332.) Furthermore, degradation of these inhibitory GalAG chains present in the glial scar was shown to impart some level of restoration of physical function in an in vivo mouse model. Understanding the mechanism of action of cABC I, therefore, improve its use as biochemical tool for studying GalAG structure and advance its therapeutic potential in treatment of medical conditions.

Chondroitinase ABC I and chondroitinase ABC II (EC 4.2.2.4) (Hamai, A., Hashimoto, N., Mochizuki, H., Kato, F., Makiguchi, Y., Horie, K. and Suzuki, S. (1997) Two distinct chondroitin sulfate ABC lyases. An endoeliminase yielding tetrasaccharides and an exoeliminase preferentially acting on oligosaccharides. J Biol Chem 272, 9123-9130) are two related enzymes with broad substrate specificity produced by the bacterium *Proteus vulgaris*. These enzymes depolymerize a variety of GAG substrates, including chondroitin-4-sulfate (C4S), dermatan sulfate (DS), chondroitin-6-sulfate (C6S), and hyaluronic acid. These enzymes have previously been purified and studied (Hamai, A., Hashimoto, N., Mochizuki, H., Kato, F., Makiguchi, Y., Horie, K. and Suzuki, S. (1997) Two distinct chondroitin sulfate ABC lyases. An endoeliminase yielding tetrasaccharides and an exoeliminase preferentially acting on oligosaccharides. J Biol Chem 272, 9123-9130.) Chondroitinase ABC I is a 997 amino acid residue endocytic enzyme that cleaves GAG substrates to tetrasaccharides and disaccharides. It degrades GalAGs regardless of the C5 epimerization state of the uronic acid. This is particularly notable, as cABC I processes DS despite having little sequence or structural homology when compared with chondroitinase B (cB) (Huang, W., Matte, A., Li, Y., Kim, Y. S., Linhardt, R. J., Su, H. and Cygler, M. (1999) Crystal structure of chondroitinase B from *Flavobacterium heparinum* and its complex with a disaccharide product at 1.7 A resolution. J Mol Biol 294, 1257-1269.) The crystal structure of cABC I (Huang, W., Lunin, V. V., Li, Y., Suzuki, S., Sugiura, N., Miyazono, H. and Cygler, M. (2003) Crystal structure of *Proteus vulgaris* chondroitin sulfate ABC lyase I at 1.9A resolution. J Mol Biol 328, 623-634) reveals that it has three major domains and indicates that this enzyme shares considerable structural homology with *F. heparinum* chondroitinase AC (cAC) (Fethiere, J., Eggimann, B. and Cygler, M. (1999) Crystal structure of chondroitin AC lyase, a representative of a family of glycosaminoglycan-degrading enzymes. J Mol Biol 288, 635-647), although there is little sequence identity between the enzymes.

Discrepancies in past cloned sequences of cABC I have augmented confusion in studying this enzyme (Sato, N., Shimada, M., Nakajima, H., Oda, H. and Kimura, S. (1994) Cloning and expression in *Escherichia coli* of the gene encoding the *Proteus vulgaris* chondroitin ABC lyase. Appl Microbiol Biotechnol 41, 39-46; Ryan, M. J., Khandke, K. M., Tilley, B. C. and Lotvin, J. A. (1994), (international application published under the patent cooperation treaty) WO 94/25567.) Moreover, the cloning and expression of cABC I is challenging because of its size, stability and solubility. In addition to the difficulty of obtaining a pure recombinant protein, the broad substrate specificity complicates elucidation of mechanism as it is unclear how this GAG lyase is able to process such a broad range of substrates. Provided herein is the sub-cloning of cABC I from *Proteus vulgaris* and a facile methodology for the recombinant expression and purification of this enzyme (a one-step purification of the pure protein). Namely the use of a 6x-His tag and a $Ni^{2+}$ affinity column that allows enzyme purification from crude extract in one chromatography step. The originally expressed cABC I clone resulted in an enzyme with low activity against a variety of GalAG substrates. Sequencing of the cABC I clone revealed four point mutations at issue with the electron density data of the cABC I crystal structure. Site-directed mutagenesis produced a clone with restored GalAG-degrading function. The enzyme was characterized biochemically, including an analysis of its substrate specificity, an activity assessment and a product profile determination of the recombinant enzyme against a spectrum of GAG substrates. By coupling structural inspections of cABC I and an evaluation of sequence homology against other GAG-degrading lyases, a set of amino acids was chosen for further study. Mutagenesis studies of these residues resulted in the first experimental evidence of cABC I's active site as well as the residues that are important for catalytic activity.

Chondroitinase ABC I was sub-cloned from *Proteus vulgaris* into an *E. coli*-based recombinant expression system without its N-terminal leader sequence, expressed and purified to homogeneity using the N-terminal 6X His tag. Sequence analysis of the cloned gene revealed four point mutations (Thr154Ala, Val309Ile, Pro322Leu, and Pro694Glu) in the DNA sequence that led to significantly diminished enzymatic activity. These mutations were restored using PCR site-direct mutagenesis (SDM) leading to a fully functional, highly active recombinant chondroitinase ABC I. This enzyme was then characterized in terms of its structural stability, substrate specificity, product profile, and kinetics of action on a variety of GAG substrates. Understanding the mode of action of cABC I and its engineered variants will facilitate the structure-function characterization of biomedically-relevant GAGs/GalAGs and provide for the development of therapeutics, including therapeutics for nerve regeneration, cancer, etc. Provided herein, therefore, is the recombinant expression of chondroitinase ABC I and a variety of engineered mutants thereof for the treatment of various pathologies.

It has been determined that on opposing sides of the catalytic cleft are substrate specific residues. His388 and His389 (residue numbering is consistent with the numbering prevalently used in the literature) are important for dermatan sulfate (DS) processing, and when mutated (to alanine, lysine or arginine) has activity against chondroitin-6-sulfate (C6S) and chondroitin-4-sulfate (C4S), and not DS (like chondroitinase AC). On the opposing cleft, Arg560 is important for C4S and C6S processivity; modification of this residue (such as to alanine or lysine) results in a DS-exclusive enzyme (like chondroitinase B). Further mutagenesis, in the form (for example) of a double or triple mutant, may also result in modified cABC I enzymes that have a different set substrate specificities, or an altered product profile. Additionally, specificity for hylauronan-based GAGs could be conserved in cABC I mutants; alternatively, activity against these GAGs could be engineered out, so as to provide a means to selectively alter specific parts of the extracellular matrix (cABC I processes galactosaminoglycans including C4S, C6S, dermatan sulfate, and modified GalAGs such as chondroitin D and chondroitin E; cABC I also processes the glucosaminoglycan hyaluronan). There are a number of other residues which play some role in regulating substrate specificity. Tyr392 is important in this way. His561 and Asn587 interact with the 4-O-sulfate of GalNAC4S. Arg500Lys and Arg221Ala provide C6S selective enzymes; Arg500Gln provides a C4S selective enzyme. Tyr508Phe and Arg560-based mutants provide altered product profiles, including yielding higher order products. Therefore the mutants provided can be selected for the regulation of substrate specificity and the generation of unique, novel, or difficult-to-attain product profiles.

In one aspect of the invention a method of recombinantly expressing chondroitinase ABC I is provided. In another aspect of the invention a method for purifying a recombinantly expressed chondroitinase ABC I is provided. Also provided are the chondroitinase ABC I enzymes themselves. The nucleic acid and amino acid sequence of a cABC I enzyme provided herein is provided as SEQ ID NO: 1 and SEQ ID NO: 2, respectively. Additionally, also provided are polypeptides that comprise the amino acid sequence of SEQ ID NO: 2 and fragments thereof. The fragment can be of any size greater than 7 amino acids in length. In some embodiments the fragment is at least 10, 15, 20, 30, 50, 75, 125, 100, 150, 200, 250, 300, 350, 400, 450, 500, 600, 700, 800, 900, 950, 975, 990 or more amino acids in length.

The chondroitinase ABC I enzymes provided also include modified chondroitinase ABC I enzymes. Such enzymes include those that can contain amino acid substitutions (e.g., at one or more of the important amino acid residues) of native chondroitinase ABC I as provided herein. The chondroitinase ABC I enzymes provided can have altered enzymatic activity and/or substrate specificity as compared to a native chondroitinase ABC I. In some embodiments, the chondroitinase ABC I enzymes have increased enzymatic activity. In others, the chondroitinase ABC I enzymes have diminished enzymatic activity.

As used herein a "native chondroitinase ABC I" refers to a chondroitinase ABC I enzyme that would be found in nature. Examples of native chondroitinase ABC I enzymes, therefore, include, chondroitinase ABC I enzymes with an amino acid sequence of any of SEQ ID NOs: 1-10, 14, 15 and 22-24. Native cABC I also include the enzymes represented by, for example, those sequences found in the following: GenBank Accession Numbers 1HN0_A, I29953, P59807 and gi:30749254; SEQ ID NOs: 2 and 6 of U.S. Pat. No. 5,578, 480; SEQ ID NOs: 2 and 5 of PCT/US94/04495; and Sato et al., Appl. Microbiol. Biotechnol. (1994) 41:39-46. Sequences derived from proteins extracted from cultures of, for example native *Proteus vulgaris* are considered within the definition of native cABC I, including those sequences that were derived from native cultures but contain sequencing errors.

Native chondroitinase ABC I enzymes, therefore, differ from "modified chondroitinase ABC I enzymes", which are chondroitinase ABC I enzymes that are not as they would be found in nature and are somehow altered or modified. As used herein the "sequence of a modified chondroitinase ABC I" is intended to include the sequences of the modified enzymes provided with conservative substitutions therein and functional equivalents thereof, including, but not limited to fragments of the enzymes. These sequences in some embodiment include the signal sequence. In other embodiments the signal sequence is not included. In one embodiment, the cABC I enzymes provided, such as the modified chondroitinase ABC I enzymes, do not include those with an amino acid sequence as provided in any of SEQ ID NOs: 3-24. In instances where the term "chondroitinase ABC I" is used without the terms "native" or "modified" the term is intended to refer to both native and modified cABC I enzymes. Modified chondroitinase ABC I enzymes can be produced using conservative substitutions, nonconservative substitutions, deletions, additions or a multiple mutant combination.

In some embodiments, the modified chondroitinase ABC I enzymes have a modified product profile. A "modified product profile" is the set of products that results from the interaction of the modified chondroitinase ABC I enzymes with a polysaccharide or group of polysaccharides in a sample. The "set of products" is the number and kind of resulting reaction products. The modified product profile differs from a "native product profile" in that the native product profile is the set of products that results from the interaction of native chondroitinase ABC I enzyme with a polysaccharide or group of polysaccharides. In order to compare a native product profile with a modified product profile, the number and kind of resulting reaction products are compared under the same experimental conditions with the same polysaccharide or group of polysaccharides.

Therefore, in some aspects of the invention modified chondroitinase ABC I enzymes are provided that have a modified product profile that is at least 10% different than the modified product profile of a native chondroitinase ABC I. In some embodiments the product profile differs from that of the native enzyme by at least 20%, 30%, 40%, 50%, 60%, 70%, 80%, 90% or more. The difference between two product profiles can be quantitated in a variety of ways. For example, the number of a particular saccharide reaction product can be compared, the number of all reaction products can be compared, the number of kinds of reactions products can be compared, or some combinations of these values, etc. In one embodiment the product profiles are determined from the interaction of the enzymes on a galactosaminoglycan, such as chondroitin sulfate. In other embodiments the product profiles are determined from the interaction of the enzymes on dermatan sulfate. In one embodiment the product profiles are determined with capillary electrophoresis. In other embodiments the product profiles are determined with a combination of capillary electrophoresis and mass spectrometry, e.g., MALDI-MS. Other ways to compare the product profiles are known to those of ordinary skill in the art.

A published crystal structure of chondroitinase ABC I was used as a template for the design of active site mutants. The properties of the resulting enzymes were studied in an attempt to determine the importance of individual amino acid residues for enzymatic activity. His501, Tyr508, Arg560 and Glu653 were all mutated to alanine using SDM, recombinantly expressed and characterized. The inactivity of all of these mutants confirmed their role in the catalytic activity of chondroitinase ABC I. Therefore, in one aspect of the invention modified chondroitinase ABC I enzymes are provided which contain His501, Tyr508, Arg560 or Glu653 or some combination thereof and at least one amino acid substitution. The at least one amino acid substitution is, in one embodiment, a substitution of a residue other than the residue or set of residues chosen from His501, Tyr508, Arg560 and Glu653 to be maintained. In another aspect of the invention a modified chondroitinase ABC I is provided wherein the amino acid sequence of the modified enzyme contains at least one amino acid residue that has been substituted with a different amino acid residue than in native chondroitinase ABC I and wherein the residue that is substituted is His501, Tyr508, Arg560 or Glu653. In some embodiments the different amino acid is not alanine.

In addition to these residues, another set of amino acids that were potentially important in substrate binding, substrate positioning, catalysis, and product release were identified. Mutating His388 and His389 to alanine, lysine, or arginine resulted in an enzyme that can process chondroitin 4-sulfate and 6-sulfate, but not DS. Mutating Arg560 to alanine or lysine resulted in an enzyme that exclusively degrades DS. Mutating Arg500 to lysine resulted in an enzyme that degrades chondroitin 6-sulfate as its sole substrate, similar to chondroitinase C. Finally, mutating Arg500 to glutamine resulted in an enzyme that selectively degrades chondroitin 4-sulfate, an enzymatic specificity that has not been previously described. Therefore, a diversity of rationally site-directed mutants of chondroitinase ABC I were created that demonstrate significantly altered substrate specificity and reaction kinetics. These mutant enzymes will be valuable as both tools for studying structure-function relationships of GAGs as well as therapeutics for tailoring the GAG profile in specific diseases, such as nerve injury; stroke; epithelial disease; viral, bacterial and pathogenic infection; and cancer.

Therefore, in one aspect of the invention chondroitinase ABC I enzymes are provided that have altered substrate specificity. These chondroitinase ABC I enzymes can be used to selectively degrade certain polysaccharides. As used herein, "degrade" refers to any action of an enzyme on a polysaccharide that results in its modification or cleavage. "Polysaccharide-degrading enzymes", therefore, refer to any enzyme that degrades a polysaccharide. Such enzymes include glycosaminoglycan-degrading enzymes. "Glycosaminoglycan-degrading enzymes" refer to enzymes that degrade a glycosaminoglycan and include, for example, heparinase I, heparinase II, heparinase III, Δ4,5 glycuronidase, 2-O sulfatase, 3-O sulfatase, 6-O sulfatase, N-sulfatase, chondroitinase, hyaluronidase, etc. as well as mutant versions and functional equivalents thereof. "Galactosaminoglycan-degrading enzymes" refer to enzymes that degrade a galactosaminoglycan and include chondroitinase B, chondroitinase AC, chondroitinase ABC I, chondroitianse ABC II, chondro-4 sulfatase, chondro-6 sulfatase, hyaluronidase, etc. as well as mutant versions and functional equivalents thereof. The chondroitinase ABC I enzymes and compositions provided can be used to degrade a polysaccharide (e.g., glycosaminoglycan(s) and/or galactosaminoglycan(s)) in vitro or in vivo. The degradation can be a result of the use of a chondroitinase ABC I or composition thereof provided herein alone or in combination with at least one other polysaccharide-degrading enzyme. For instance, the at least one other polysaccharide-degrading enzyme can be native or modified versions of any of the enzymes provided herein, which include chondroitinase ABC I, chondroitinase AC, chondroitinase B, chondroitinase ABC II, etc.

Provided herein is a chondroitinase ABC I that processes chondroitin sulfate and not dermatan sulfate. In another aspect of the invention a chondroitinase ABC I that selectively degrades dermatan sulfate is provided. In still other aspects of the invention a chondroitinase ABC I that selectively degrades chondroitin 6-sulfate is provided. In yet other aspects of the invention a chondroitinase ABC I that selectively degrades chondroitin 4-sulfate is provided. Therefore, modified chondroitinase ABC I enzymes are provided which include any combination of the amino acid substitutions provided herein. As used herein, "selectively degrades" refers to the enzymes action toward a particular substrate. Selectively degrade is meant to encompass circumstances where an enzyme that acts upon a particular substrate does so at an increased rate as compared to the rate of action on another substrate. The term is also meant to encompass circumstances where an enzymes degrades one particular substrate or set of substrates exclusively. The term is also intended to encompass situations whereby the enzymes act upon a particular substrate in a way such that one of ordinary skill in the art can observe a preference of action. Therefore, provided herein are cABC I enzymes that exhibit "cAC-like" or "cB-like" activity. Chondroitinase ABC I enzymes that cleave C4S and C6S preferentially are referred to herein as chondroitinase ABC I enzymes with cAC-like activity. Similarly, cABC I enzymes that preferentially cleave DS are referred to herein as chondroitinase ABC I enzymes with cB-like activity.

One of ordinary skill in the art is enabled, in light of the present disclosure, to produce chondroitinase ABC I enzymes by standard technology, including recombinant technology, direct synthesis, mutagenesis, etc. A number of native sequences of chondroitinase ABC I are provided herein (e.g., SEQ ID NOs: 1 and 2; GenBank Accession number P59807, which provides the amino acid sequence for chondroitin ABC lyase I precursor (the mature chain is given as amino acids 25-1021 of the precursor sequence), See also Ryan et al. (Ryan, M. J., Khandke, K. M., Tilley, B. C. and Lotvin, J. A. (1994), WO 94/25567.) One may produce a modified chondroitinase ABC I having an amino acid sequence of the peptide of a native chondroitinase ABC I, wherein at least one residue at position 105, 131, 154, 218, 219, 221, 222, 253, 276, 286, 309, 312, 322, 388, 389, 392, 439, 442, 444, 490, 500, 501, 508, 560, 561, 587, 653, 678, 694 or 712 has been substituted or deleted.

One of skill in the art may also substitute appropriate codons to produce the desired amino acid substitutions by standard site-directed mutagenesis techniques. It is possible to use any sequence which differs from the nucleic acid equivalents of the sequences of chondroitinase ABC I only due to the degeneracy of the genetic code as the starting point for site directed mutagenesis. The mutated nucleic acid sequence may then be ligated into an appropriate expression vector and expressed in a host such as F. heparinum or E. coli. The resultant chondroitinase ABC I may then be purified by techniques provided herein and/or known by those of ordinary skill in the art. One of ordinary skill in the art is also enabled in light of the present disclosure to produce modified chondroitinase ABC enzymes having an amino acid sequence of native chondroitinase ABC or conservative substitutions thereof, wherein at least one of the residues at a position selected from 105, 131, 154, 218, 219, 221, 222, 253, 276, 286, 309, 312, 322, 388, 389, 392, 439, 442, 444, 490, 500, 501, 508, 560, 561, 587, 653, 678, 694 or 712 is maintained. These modified chondroitinase ABC I enzymes further contain at least one amino acid substitution. In some embodiments these amino acid substitutions are in portions of the enzymes that have not been shown to be important to catalysis, substrate binding, calcium coordination, etc. In other embodiments the at least one amino acid substitution is of one of the residues listed above provided that it is not a substitution of the residue or residues that are maintained. In some embodiments, the modified chondroitinase ABC enzymes contain 1, 2, 3, 4, 5, 6, 7, 8, 9, 10, 11, 12, 13, 14, 15, 16, 17, 18, 19, 20, 21, 22, 23, 24, 25, 30, 40, 50 or more substitutions.

Mutations can be made by selecting an amino acid substitution, or by random mutagenesis of a selected site in a nucleic acid which encodes the polypeptide. Modified polypeptides are then expressed and tested for one or more activities to determine which mutation provides a modified polypeptide with the desired properties.

Methods for making amino acid substitutions, additions or deletions are well known in the art. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions, and properties of amino acids which lead to their definition as polar, non-polar or acidic.

One type of amino acid substitution is referred to as a "conservative substitution." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants.

Additionally, some of the amino acid substitutions are non-conservative substitutions. Non-conservative substitutions, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain.

The modified chondroitinase ABC I can have specific substitutions in specified portions of the peptide. In addition to these substitutions which may be conservative or non-conservative, other regions of the peptide may include substitutions that do not impact the activity of the modified chondroitinase ABC I. Therefore, in some embodiments, the nonconservative or conservative substitutions are introduced at residues that are remote from, for instance, the catalytic, substrate binding and/or calcium coordination motif residues as provided herein. One skilled in the art will appreciate that the effect of a particular substitution can be evaluated by routine screening assays, preferably the biological assays described herein.

In some embodiments the chondroitinase ABC I is in substantially pure form. As used herein, the term "substantially pure" means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations. Polypeptides can be isolated from biological samples, and can also be expressed recombinantly in a variety of prokaryotic and eukaryotic expression systems by constructing an expression vector appropriate to the expression system, introducing the expression vector into the expression system, and isolating the recombinantly expressed protein. Polypeptides can also be synthesized chemically using well-established methods of peptide synthesis. In some embodiments, chondroitinase ABC I in a substantially purified recombinant form is a preparation of chondroitinase ABC I which has been recombinantly synthesized and which is greater then 90% free of contaminants. Preferably, the material is greater than 91%, 92%, 93%, 94%, 95%, 96%, 97%, 98%, or even greater then 99% free of contaminants. The degree of purity may be assessed by means known in the art.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, i.e., isolated from other proteins.

A "modified chondroitinase ABC I polypeptide" is a polypeptide which contains one or more modifications to the primary amino acid sequence of a chondroitinase ABC I polypeptide. The modified chondroitinase ABC I polypeptide can contain 1, 2, 3, 4, 5, 6, 7, 8, 9, 10, 15, 20, 25, 30 or more modifications. Modifications which create a modified chondroitinase ABC I polypeptide may be made recombinantly to the nucleic acid which encodes the modified chondroitinase ABC I polypeptide, and can include deletions, point mutations, truncations, amino acid substitutions and addition of amino acids or non-amino acid moieties to (as described herein): 1) alter enzymatic activity; 2) provide a novel activity or property to a chondroitinase ABC I polypeptide, such as addition of a detectable moiety; or 3) to provide equivalent, greater or lesser interaction with other molecules (e.g., chondroitin sulfate and dermatan sulfate). Alternatively, modifications can be made directly to the polypeptide, such as by cleavage, and the like. Modifications also embrace fusion proteins comprising all or part of the chondroitinase ABC I amino acid sequence.

Fusion proteins are also provided in which a chondroitinase ABC I is in a conjugate form with, for example, a targeting molecule. Fusion proteins provide a strategy for the efficacious delivery of an enzyme, e.g., cABC I, and would entail its coupling, via recombinant molecular biotechnology, to a peptide that could deliver the enzyme-targeting molecule unit to a therapeutic target. For example, a peptide fragment responsible for transport to a site within the central nervous system could be developed from a clostridial neurotoxin, such as tetanus toxin. The coupling of this fragment, without its pathogenic portion, to an enzyme would result in the efficacious therapy of, for example, stroke or spinal cord injury. Additionally, an enzyme could be delivered along with another molecule to provide a joint therapy. For example, the administration of a growth factor from the FGF family along with a chondroitinase agent could provide additional benefit in the treatment of spinal cord injury or stroke. Targeting molecules, therefore, include cancer antigens or portions thereof and pathogen toxins or portions thereof (e.g., tetanus toxin fragment, $H_c$), and conjugates of targeting molecules with cABC I are also provided.

According to the invention, isolated nucleic acid molecules that code for a chondroitinase ABC I polypeptide are provided and include: (a) nucleic acid molecules which hybridize under stringent conditions to the nucleic acid equivalent which codes for a chondroitinase ABC I polypeptide as described herein or, parts thereof, (b) deletions, additions and substitutions of (a) which code for a respective chondroitinase ABC I polypeptide or parts thereof, (c) nucleic acid molecules that differ from the nucleic acid molecules of (a) or (b) in codon sequence due to the degeneracy of the genetic code, and (d) complements of (a), (b) or (c).

In certain embodiments, the nucleic acid molecule that codes for a chondroitinase ABC I is highly homologous to the nucleic acid molecules described herein. Preferably the homologous nucleic acid molecule comprises a nucleotide sequence that is at least about 90% identical to the nucleotide sequence provided herein. More preferably, the nucleotide sequence is at least about 95% identical, at least about 97% identical, at least about 98% identical, or at least about 99% identical to the nucleotide sequence provided herein. The homology can be calculated using various, publicly available software tools well known to one of ordinary skill in the art. Exemplary tools include the BLAST system available from the website of the National Center for Biotechnology Information (NCBI) at the National Institutes of Health.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

Optionally the chondroitinase ABC I is recombinantly produced. Such molecules may be recombinantly produced using a vector including a coding sequence operably joined to one or more regulatory sequences. As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The term "high stringency conditions" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM NaH$_2$PO$_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C. There are other conditions, reagents, and so forth which can be used, which result in the same degree of stringency. A skilled artisan will be familiar with such conditions, and thus they are not given here.

The skilled artisan also is familiar with the methodology for screening cells for expression of such molecules, which then are routinely isolated, followed by isolation of the pertinent nucleic acid. Thus, homologs and alleles of the chondroitinase ABC I, as well as nucleic acids encoding the same, may be obtained routinely, and the invention is not intended to be limited to the specific sequences disclosed.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAMneo, pKRC and the like. Preferably, the selected vector of the present invention has the capacity to autonomously replicate in the selected host cell. Useful prokaryotic hosts include bacteria such as *E. coli, Flavobacterium heparinum, Bacillus, Streptomyces, Pseudomonas, Salmonella, Serratia*, and the like.

To express the chondroitinase ABC I in a prokaryotic cell, it is desirable to operably join the nucleic acid sequence of a chondroitinase ABC I to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ (P$_L$ and P$_R$), the trp, recA, lacZ, lacI, and gal promoters of *E. coli*, the α-amylase (Ulmanen et al., *J Bacteriol.* 162:176-182 (1985)) and the ζ-28-specific promoters of *B. subtilis* (Gilman et al., *Gene sequence* 32:11-20 (1984)), the promoters of the bacteriophages of *Bacillus* (Gryczan, In: *The Molecular Biology of the Bacilli*, Academic Press, Inc., NY (1982)), and *Streptomyces* promoters (Ward et al., *Mol. Gen. Genet.* 203:468-478 (1986)).

Prokaryotic promoters are reviewed by Glick (*J. Ind. Microbiol.* 1:277-282 (1987)); Cenatiempo (*Biochimie* 68:505-516 (1986)); and Gottesman (*Ann. Rev. Genet.* 18:415-442 (1984)).

Proper expression in a prokaryotic cell also requires the presence of a ribosome binding site upstream of the encoding sequence. Such ribosome binding sites are disclosed, for example, by Gold et al. (*Ann. Rev. Microbiol.* 35:365-404 (1981)).

Because prokaryotic cells may not produce the chondroitinase ABC I with normal eukaryotic glycosylation, expression of the chondroitinase ABC I in eukaryotic hosts is useful when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO—K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in *Drosophila* larvae. Using insect cells as hosts, the *Drosophila* alcohol dehydrogenase promoter can be used (Rubin, *Science* 240:1453-1459 (1988)). Alternatively, baculovirus vectors can be engineered to express large amounts of the chondroitinase ABC I in insect cells (Jasny, *Science* 238:1653 (1987); Miller et al., In: *Genetic Engineering* (1986), Setlow, J. K., et al., eds., Plenum, Vol. 8, pp. 277-297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or which are subject to chemical (such as metabolite) regulation.

Chondroitinase ABC I enzymes are useful as an enzymatic tool due to substrate specificity and specific activity. The enzymes are also useful for degrading polysaccharides. The chondroitinase ABC I enzymes may be used to specifically cleave a polysaccharide by contacting the polysaccharide substrate with the chondroitinase ABC I. In some embodiments the chondroitinase ABC I enzymes degrade particular polysaccharide exclusively. The invention is useful in a variety of in vitro, in vivo and ex vivo methods in which it is useful to degrade polysaccharides.

Compositions with agents in addition to a polysaccharide-degrading enzyme are also useful for degrading polysaccharides, such as glycosaminoglycans. For instance, it has been found that the addition of divalent ions can alter the function of a polysaccharide-degrading enzymes, such as cABC I. The divalent ions can be, but are not limited to, calcium ion, manganese ion, copper ion, iron ion, barium ion, magnesium ion, zinc ion and lanthanides, such as, terbium or lutetium. In one embodiment where it is desirable to inhibit the function of the enzyme the composition can include zinc ion. The compositions are also meant to encompass combinations of divalent ions. Where enzyme processivity is desirable, calcium ion, such as in the form of $CaCl_2$, can be included with the enzyme. The $CaCl_2$ can be at any concentration, for instance, the $CaCl_2$ can be at a concentration of at least 1, 2, 3, 4, 5, 6, 7, 8, 9, or 10 mM or more in a composition. Compositions are also provided wherein the compositions contain enzyme, divalent ion and a pharmaceutically or physiologically acceptable carrier.

Compositions are also provided whereby the composition contains an enzyme and an enzyme stabilizer. The enzyme stabilizer can be, for example, a protease inhibitor, such as, AEBSF, bestatin, E64 protease inhibitor, pepstatin A or phosphoramidon. A number of commercially available protease inhibitors and protease inhibitor cocktails are known in the art (e.g., Benzamidine, Protease Arrest™ Reagent, Protease Inhibitor Cocktail Set II, Protease Inhibitor Cocktail Set III (Calbiochem)). The enzyme stabilizer can also be a water mimic, such as, for example, glycerol or dextran. Compositions are also provided that include an enzyme, enzyme stabilizer and a pharmaceutically or physiologically acceptable carrier.

The compositions and enzymes provided herein can be used for a variety of purposes. Methods of degrading a polysaccharide, such as a glycosaminoglycan, by contacting the glycosaminoglycan with any of the enzymes or compositions provided herein in an amount effective to degrade the glycosaminoglycan, therefore is provided. As used herein "an amount effective" is one in which one particular agent or a set of agents in a composition produces the desired effect. For example, an amount effective of a composition that contains two enzymes, refers to the amount necessary to obtain a desired effect as a result of the action of one enzyme or the other, or the amount of the two enzymes in combination whereby it is the combination that provides the desired effect. The methods for degrading (i.e., cleaving or modifying the polysaccharide in some way) can include the use of one or more polysaccharide-degrading enzymes that can be placed in contact with one or more polysaccharides. The enzymes that are used can be placed in contact with the polysaccharide at the same time or at different times. Depending on the action of the enzymes, a specific order of enzymes may be desired. Encompassed herein is the use of two or more enzymes in any order to degrade a polysaccharide.

Methods for degrading a polysaccharide are also provided whereby the polysaccharide is cleaved by the action of an enzyme in the presence of a divalent ion. The divalent ion can be introduced to the reaction at any point before, concomitantly with or after contacting a polysaccharide with a polysaccharide-degrading enzyme. Divalent ions can result in better processing of a substrate or can result in the inhibition of the processing of a substrate. Therefore, different divalent ions may be used in the method of degrading a polysaccharide. The ions can be used at the same time or can be used at different times to modulate the enzymatic reaction. For instance, a divalent ion, such as calcium may be used to facilitate the reaction, and at some point after, zinc ion may be introduced to the reaction (ions such as zinc can be inhibitory to enzyme function). In some embodiments it is desirable not to use a divalent ion, such as zinc. The divalent ions can be introduced to the enzymatic reaction in any way such that the reaction is altered in some way. The divalent ions can be placed in contact with the polysaccharide, the polysaccharide-degrading enzyme or both. The divalent ions can include any such ions known in the art including those described herein.

As another way to control polysaccharide degradation reactions, chelators may be used. Therefore, the methods provided can further include the step of introducing a chelator to the enzymatic reaction. Chelators can be introduced to any of the compositions and methods provided. For example, the chelator can be introduced before, concomitantly with or after the introduction of a divalent ion to the reaction. In one embodiment the chelator is EDTA or EGTA.

Methods and compositions are also provided herein where a polysaccharide is processed in the presence of calcium. In one embodiment the cABC I enzyme used in these methods and compositions are those that have had the calcium coordination motif modified in some way. A novel calcium-coordination site in proximity to the enzyme active site has been found. The residues at positions 490, 442, and 444 are important components of this calcium-coordination site. Modulating this site, as well as regulating calcium levels in reaction, are important parts of controlling activity. Therefore, methods are provided whereby a polysaccharide is degraded with a modified cABC I, that has had a modification of one or more of these calcium coordination motif residues. The method can also include the modulation of calcium levels to control the enzymatic reaction driven by the modified cABC I. Compositions are also provided that contain such modified cABC I enzymes as well as varying levels of calcium (e.g., calcium ion in the form of $CaCl_2$).

Methods are also provided for the degradation of a polysaccharide using the enzymes and compositions provided herein in the presence of an enzyme stabilizer. In one embodiment the enzyme stabilizer is a protease inhibitor, such as AEBSF, bestatin, E64 protease inhibitor, pepstatin A or phosphoramidon. In another embodiment the enzyme stabilizer is a water mimic, such as glycerol or dextran.

There are a number of other ways in which the enzymatic reaction can be controlled. Therefore, compositions and methods are also provided which incorporate the following other agents and their use, respectively. Any of the conditions can be used in any combination to produce the desired enzymatic effect in the methods provided herein. Likewise any combination of agents that control these conditions (e.g., pH modifying agents, salts, buffer, etc.) can be incorporated in any of the compositions provided. Therefore, combinations of divalent ions and/or enzyme stabilizers with one or more of the following are also specifically contemplated for the methods and compositions provided herein. cABC I enzymes have been analyzed in a variety of reaction conditions. Enzyme-substrate reaction parameters can be chosen to control substrate specificity, the mechanism of action, and/or the product profile. These reaction parameters include salt (e.g., NaCl, NaAC), temperature, pH, buffer (Tris buffer, or phosphate buffer), and reaction volume. Therefore compositions and methods are provided whereby these reaction parameters or some combination thereof are controlled. For example, the pH can be controlled. The pH for a reaction or in a composition can be, for example, greater than 7 but less than 8. In other examples, the pH can be less than 9. The pH can also be 7 or 8. In other examples, the pH can be between 6 and 9 or between 7 and 8. In one embodiment when a phosphate buffer is used and the substrate on which the enzyme acts is chondroitin sulfate, the pH is 7. The pH can be controlled with a pH modifying agent, such agents are well known to those of skill in the art. Such agents can be added to any of the compositions provided herein, such that the composition has a resulting pH that is desired.

Methods and compositions are also provided whereby the buffer is controlled. In some embodiments the buffer is Tris buffer or phosphate buffer.

Methods and compositions where the ionic strength (e.g., salt concentration) is controlled or of a certain concentration are also provided. The salt concentration can be less than 500 mM, less than 400 mM or less than 250 mM. The salt concentration can also be between 50-500 mM, 50-125 mM, 60-125 mM, 125-150 mM, 100-250 mM, 50-400 mM, 150-400 mM, 100-500 mM or 150-500 mM. The salt concentration can also be greater than 50 mM, 62.5 mM, 100 mM, 125 mM or 250 mM. The salt can be any of those known in the art and include sodium chloride, sodium acetate, sodium sulfate or ammonium sulfate.

Methods are also provided that include the control of the temperature of the reaction. The temperature can be less than 40° C. The temperature can also be between 25-45° C., between 30-40° C., between 25-40° C., between 30-37° C., between 38-45° C. or between 38-50° C. The temperature can also be 37° C. or 40° C.

Analyses of polysaccharides as described in the present disclosure are possible using chondroitinase ABC I alone or in conjunction with other enzymes as well as the compositions provided. Other polysaccharide-degrading enzymes include but are not limited to other chondroitinases (e.g. chondroitinase AC, chondroitinase B, C, ABC II), lyases (e.g., the two classes of GAG lyases based on structural folds; barrel-like, $\alpha 5$-$6$/$\alpha 5$-$6$ topology and right-handed parallel $\beta$-helix fold), hydrolases, chondro-4-sulfatase, chondro-6-sulfatase, hyaluronate lyase, hyaluronidase, heparin hydrolase, heparinase-I, heparinase-II, heparinase-III, keratanase, D-glucuronidase, Delta 4,5-glycuronidase and L-iduronidase, 2-O sulfatase, pectin lyase, pectate lyase, modified versions of these enzymes, variants and functionally active fragments thereof or combinations thereof. As used herein a "polysaccharide-degrading enzyme" is any enzyme which cleaves or somehow modifies a polysaccharide. The chondroitinase ABC I enzymes provided, when used in conjunction with one or more other enzymes, can be used prior to, subsequent to or concurrent with the use of the one or more other enzymes.

The methods that may be used to test the specific activity of chondroitinase ABC I include those known in the art. The term "specific activity" as used herein refers to the enzymatic activity of a preparation of chondroitinase ABC I. These methods may also be used to assess the function of variants and functionally active fragments of chondroitinase ABC I. The $k_{cat}$ value may be determined using any enzymatic activity assay to assess the activity of a modified chondroitinase ABC I enzyme. Several such assays are well-known in the art. For instance, an assay for measuring $k_{cat}$ is described in (Ernst, S. E., Venkataraman, G., Winkler, S., Godavarti, R., Langer, R., Cooney, C. and Sasisekharan. R. (1996) Biochem. J. 315, 589-597). The "native chondroitinase ABC I $k_{cat}$ value" is the measure of enzymatic activity of a native chondroitinase ABC I. The native chondroitinase ABC I can be obtained from cell lysates of *P. vulgaris*.

Due to the activity of chondroitinase ABC I on polysaccharides, the product profile produced by a chondroitinase ABC I may be determined by any method known in the art for examining the type or quantity of degradation product produced by chondroitinase ABC I alone or in combination with other enzymes. One of skill in the art will also recognize that the chondroitinase ABC I may also be used to assess the purity of polysaccharides in a sample.

One preferred method for determining the type and quantity of product is described in Rhomberg, A. J. et al., *PNAS*, v. 95, p. 4176-4181 (April 1998), which is hereby incorporated in its entirety by reference. The method disclosed in the Rhomberg reference utilizes a combination of mass spectrometry and capillary electrophoretic techniques to identify the enzymatic products produced by heparinase. The Rhomberg study utilizes heparinase to degrade HLGAGs (heparin-like glycosaminoglycans) to produce HLGAG oligosaccharides. MALDI (Matrix-Assisted Laser Desorption Ionization) mass spectrometry can be used for the identification and semiquantitative measurement of substrates, enzymes, and end products in the enzymatic reaction. The capillary electrophoresis technique separates the products to resolve even small differences amongst the products and is applied in combination with mass spectrometry to quantitate the products produced. Capillary electrophoresis may even resolve the difference between a disaccharide and its semicarbazone derivative.

The chondroitinase ABC I enzymes may also be used as a tool to sequence polysaccharides. Detailed methods for sequencing polysaccharides and other polymers are disclosed in co-pending U.S. patent applications Ser. Nos. 09/557,997 and 09/558,137, both filed on Apr. 24, 2000 and having common inventorship. The entire contents of both applications are hereby incorporated by reference. Briefly, the method is performed by enzymatic digestion, followed by mass spectrometry and capillary electrophoresis. In the example described in the Rhomberg reference, enzymatic reactions are performed by adding 1 microliter of enzyme solution to 5 microliter of substrate solution. The digestion is then carried out at room temperature (22° C.), and the reaction is stopped at various time points by removing 0.5 microliter of the reaction mixture and adding it to 4.5 microliter of a MALDI matrix solution, such as caffeic acid (approximately 12 mg/mL) and 70% acetonitrile/water. The reaction mixture is then subjected to MALDI mass spectrometry. The MALDI surface is prepared by the method of Xiang and Beavis (Xiang and Beavis (1994) *Rapid. Commun. Mass. Spectrom.* 8, 199-204). A two-fold lower access of basic peptide $(Arg/Gly)_{15}$ is premixed with matrix before being added to the oligosaccharide solution. A 1 microliter aliquot of sample/matrix mixture containing 1-3 picomoles of oligosaccharide is deposited on the surface. After crystallization occurs (typically within 60 seconds), excess liquid is rinsed off with water. MALDI mass spectrometry spectra is then acquired in the linear mode by using a PerSeptive Biosystems (Framingham, Mass.) Voyager Elite reflectron time-of-flight instrument fitted with a 337 nanometer nitrogen laser. Delayed extraction is used to increase resolution (22 kV, grid at 93%, guidewire at 0.15%, pulse delay 150 ns, low mass gate at 1,000, 128 shots averaged). Mass spectra are calibrated externally by using the signals for proteinated $(Arg/Gly)_{15}$ and its complex with the oligosaccharide.

Capillary electrophoresis may then be performed on a Hewlett-Packard$^{3D}$ CE unit by using uncoated fused silica capillaries (internal diameter 75 micrometers, outer diameter 363 micrometers, $1_{det}$ 72.1 cm, and $1_{tot}$ 85 cm). Analytes are monitored by using UV detection at 233 nm and an extended light path cell (Hewlett-Packard). The electrolyte is a solution of 10 microliter dextran sulfate and 50 millimolar Tris/phosphoric acid (pH 2.5). Dextran sulfate is used to suppress nonspecific interactions of the glycosaminoglycan oligosaccharides with a silica wall. Separations are carried out at 30 kV with the anode at the detector side (reversed polarity). A mixture of a ⅕-naphtalenedisulfonic acid and 2-naphtalenesulfonic acid (10 micromolar each) is used as an internal standard.

Additionally, the coupling of CE and MALDI-MS with enzymes and a bioinformatics-based, property-encoded nomenclature (PEN) have led to a sequencing strategy (PEN-MALDI) described in (Venkataraman, G., Shriver, Z., Raman, R., and Sasisekharan, R. (1999) Science 286, 537-42).

Other methods for assessing the product profile may also be utilized. For instance, other methods include methods which rely on parameters such as viscosity (Jandik, K. A., Gu, K. and Linhardt, R. J., (1994), *Glycobiology,* 4:284-296) or total UV absorbance (Ernst, S. et al., (1996), *Biochem. J,* 315:589-597) or mass spectrometry or capillary electrophoresis alone.

The enzymes and compositions provided herein can also be used in methods for analyzing the purity of a sample of polysaccharides, methods for determining the presence of a polysaccharide in a sample, methods for determining the composition of a polysaccharide in a sample and the like. As used herein a "method for determining the composition of a polysaccharide in a sample" is intended to encompass methods whereby one or more of the polysaccharides in the sample are identified. In some instances the method is one in which all of the polysaccharides in the sample are identified. In other instances the method encompasses the quantity as well as the identity of one or more of the polysaccharides in the sample.

As used herein, a "polysaccharide" is a polymer composed of monosaccharides linked to one another. In many polysaccharides the basic building block of the polysaccharide is actually a disaccharide unit, which can be repeating or non-repeating. Thus, a unit when used with respect to a polysaccharide refers to a basic building block of a polysaccharide and can include a monomeric building block (monosaccharide) or a dimeric building block (disaccharide). The term polysaccharide is also intended to embrace an oligosaccharide. Polysaccharides include but are not limited to glycosaminoglycans such as chondroitin, chondroitin sulfate, dermatan sulfate, chondroitin-6 sulfate, chondroitin-4 sulfate, chondroitin D, chondroitin E, heparin, heparin-like glycosaminoglycans (HLGAGs), heparan sulfate, hyaluronic acid, keratan sulfate, and derivatives or analogs thereof, chitin in derivatives and analogs thereof. In some embodiments the GAGs are in the form of chains associated with core protein, such as proteoglycans.

In addition to polysaccharides from natural sources, the polysaccharides of the invention also include molecules that are biotechnologically prepared, chemically modified and synthetic. The term "biotechnological prepared" encompasses polysaccharides that are prepared from natural sources of polysaccharides which have been chemically modified. This is described for example in Razi et al., Bioche. J. 1995 Jul. 15; 309 (Pt 2): 465-72 and in Yates et al., Carbohydrate Res 1996 Nov. 20; 294:15-27, and is known to those of skill in the art. Synthetic polysaccharides are also well known to those of skill in the art and is described in Petitou, M. et al., Bioorg Med Chem Lett. 1999 Apr. 19; 9(8):1161-6.

As used herein a "sample" of polysaccharides is meant to include any sample which has one or more polysaccharides contained therein.

One of ordinary skill in the art, in light of the present disclosure, is enabled to produce preparations of polysaccharide, e.g. glycosaminoglycan (GAG) or galactosaminoglycan (GalAG) fragment compositions utilizing the chondroitinase ABC I molecules alone or in conjunction with other enzymes as well as with the compositions provided herein. GAG or GalAG fragments have many therapeutic utilities. The GAG or GalAG fragment preparations are prepared from polysaccharide sources. A "polysaccharide source" as used herein refers to glycosaminoglycan composition which can be manipulated to produce GAG or GalAG fragments. As described above, GAG or GalAG include but are not limited to isolated chondroitin sulfate, dermatan sulfate as well as chemically modified, biotechnology prepared and synthetic versions of such polysaccharides. Thus GAG or GalAG can be isolated from natural sources, prepared by direct synthesis.

The terms "polysaccharide fragment" and "GAG or GalAG fragment" as used herein refers to the resultant product(s) from the activity, respectively, of a polysaccharide-degrading or GAG or GalAG degrading enzyme on a polysaccharide or GAG or GalAG. The GAG or GalAG fragments can include portions of the original GAG or GalAG (prior to the action of the enzyme) or a modified version of the original GAG or GalAG (e.g., desulfated version). The GAG or GalAG fragment, in some embodiments, has therapeutic activity.

For instance, the GAG or GalAG fragment can promote nerve regeneration, promote stroke recovery or prevent the proliferation and/or metastasis of a tumor cell. The GAG or GalAG fragment can also be used to inhibit or treat microbial infection, to treat a coagulation disorder, to stabilize the extracellular matrix, to promote cell proliferation or to promote organogenesis. The GAG or GalAG fragment can also treat epithelial diseases, such as cystic fibrosis or viral, bacterial or pathogen infection. The use of the GAG or GalAG fragments for other desired therapeutic activities are described below. Such compounds may be generated using chondroitinase ABC I to produce therapeutic fragments or they may be synthesized de novo based on information derived from the use of chondroitinase ABC I. GAG or GalAG fragments can be tested for therapeutic activity using any of the assays described herein or known in the art. Thus the therapeutic GAG or GalAG fragment may be a synthetic GAG or GalAG fragment generated based on the sequence of the GAG or GalAG fragment identified when a polysaccharide source is contacted with chondroitinase ABC I, or having minor variations which do not interfere with the activity of the compound. Alternatively the therapeutic GAG or GalAG fragment may be an isolated GAG or GalAG fragment produced when the polysaccharide source is contacted with chondroitinase ABC I.

Thus, the methods of the invention enable one of skill in the art to prepare or identify an appropriate composition of GAG or GalAG fragments, depending on the subject and the disorder being treated. These compositions of GAG or GalAG fragments may be used alone or in combination with other GAG or GalAG fragments, chondroitinase ABC I and/or other enzymes. Likewise chondroitinase ABC I may also be used to produce GAG or GalAG fragments in vivo alone or in conjunction with other enzymes.

The chondroitinase ABC I molecules and/or GAG or GalAG fragments produced using the chondroitinase ABC I or composition described herein can be used for the treatment of any type of condition or circumstance in which chondroitinase ABC I therapy and/or GAG or GalAG fragment therapy has been identified as a useful therapy, e.g., promoting nerve regeneration, such as after spinal cord injury, promoting stroke recovery, preventing coagulation, treating a coagulation disorder, inhibiting angiogenesis, inhibiting proliferation, inhibiting cancer cell growth and metastasis, preventing angiogenesis, preventing neovascularization, treating neurodegenerative disorders, treating psoriasis, inhibiting or treating microbial infection, to stabilize the extracellular matrix, to spur cell proliferation, to promote organogenesis, etc. The chondroitinase ABC I and/or GAG or GalAG fragments can also be used for mediating cell signaling. Thus, the invention is useful in a variety of in vitro, in vivo and ex vivo methods in which therapies are useful. Chondroitinase ABC I is also useful in the treatment of osteoarthritis and maternal malarial infection. The GAG or GalAG fragment compositions may also be used in in vitro assays, such as a quality control sample.

The disorders provided herein are known in the art and/or are described in, for instance, *Harrison's Principles of Internal Medicine* (McGraw Hill, Inc., New York), which is incorporated by reference.

In one embodiment the preparations of the invention are used for promoting nerve regeneration. An effective amount for promoting nerve regeneration of the GAG or GalAG fragment preparation and/or chondroitinase ABC I or other composition provided herein is administered to a subject in need of treatment thereof. The subject in need of treatment thereof includes subjects that suffer from nerve disorders, such as diseases associated with neurodegeneration and injuries that result in nerve damage, in which nerve regeneration is desirable. In some embodiments the subject suffers from a central nervous system injury, such as a spinal cord injury, a brain injury, has suffered a stroke, a neurodegenerative disease, multiple sclerosis or any other disease or condition that causes or results in a loss of neurons or neuronal connections. "Central nervous system" as used herein is intended to include the brain, the spinal cord and neurons whose cell bodies lie within or have a primary synapse in the brain or spinal cord. Examples of such neurons include neurons of the cranial nerves (damage to which can cause, for example, Bell's palsy) and motor neurons that innervate the musculature and whose cell bodies are in the ventral horn of the spinal cord. "Spinal cord injury" as used herein includes, but is not limited to, injury cause by assault, accident, tumor, intervertebral disc or bone abnormality, or surgery. The methods and compositions provided herein, however, are also directed to treatment of central nervous system damage other than spinal cord injury. Central nervous system damage includes, for example, stroke, brain injury, multiple sclerosis and neurodegenerative disease, such as Alzheimer's.

The terms "treat" and "treating" as used herein refer to partially or completely promoting nerve cell regeneration and/or motility or migration of a nerve cell. The terms also refer to partially or completely restoring motor/physical function. The term also encompasses axon regeneration. Axon regeneration, for example, includes sensory and motor axon regeneration.

The nerve cells may be treated in vivo, in vitro, or ex vivo. Thus, the cells may be in an intact subject or isolated from a subject or alternatively may be an in vitro cell line.

Thus the invention contemplates the treatment of subjects having or at risk of developing neurodegenerative disease or suffering an injury to nerve cells. Neuronal cells are predominantly categorized based on their local/regional synaptic connections (e.g., local circuit interneurons vs. longrange projection neurons) and receptor sets, and associated second messenger systems. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, proprioceptive neurons (in the trigeminal mesencephalic nucleus), ciliary ganglion neurons (in the parasympathetic nervous system), etc. A person of ordinary skill in the art will be able to easily identify neuronal cells and distinguish them from non-neuronal cells such as glial cells, typically utilizing cell-morphological characteristics, expression of cell-specific markers, secretion of certain molecules, etc.

"Neurodegenerative disorder" is defined herein as a disorder in which progressive loss of neurons occurs either in the peripheral nervous system or in the central nervous system. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor). and Wernicke-Korsakoff's related dementia. Neurodegenerative diseases affecting sensory neurons include Friedreich's ataxia, diabetes, peripheral neuropathy, and retinal neuronal degeneration. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

The compositions provided herein can be combined with other treatments used to promote nerve regeneration or treat neurodegenerative disease.

For example, antiparkinsonian agents include but are not limited to Benztropine Mesylate; Biperiden; Biperiden Hydrochloride; Biperiden Lactate; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinelorane Hydrochloride; Ropinirole Hydrochloride; Selegiline Hydrochloride; Tolcapone; Trihexyphenidyl Hydrochloride. Drugs for the treatment of amyotrophic lateral sclerosis include but are not limited to Riluzole. Drugs for the treatment of Paget's disease include but are not limited to Tiludronate Disodium.

Therefore, compositions and methods are provided for treating spinal cord injury. Spinal cord injury currently affects 3-5 out of every 100,000 Americans. 11,000 new cases occur each year in the United States, approximately 80% of which are men. Most of the people who suffer from spinal cord injury are completely or partially paralyzed, and such paralysis usually lasts throughout the injured individual's lifetime and is generally though to be incurable. The consequences to the injured, their friends and family can be devastating, and, therefore, any treatment would have a profound impact on the quality of life of injured patients.

Administration can be by any conventional route, including any route capable of delivering the chondroitinase ABC I enzymes and/or GAG or GalAG fragments provided herein across the blood brain barrier. The route of administration can be by direct administration to the central nervous system, e.g., by infusion via cannula or injection. The administration can be directly to the site of injury, neighboring tissues or into the cerebrospinal fluid. Administration can be effected by any of the other ways that are known in the art. In some embodiments the method of administration can include targeting to chondroitinase ABC I enzyme and/or GAG or GalAG fragment to the site in need of treatment. Therefore, in some embodiments the chondroitinase ABC I enzyme and/or GAG fragment is targeted to the site through the use of a targeting molecule. Targeting molecules for delivery to the central nervous system include, for example, tetanus neurotoxin fragments (e.g., $H_c$).

Therefore, chondroitinase ABC I enzymes and/or GAG or GalAG fragments provided can be conjugated to a targeting molecule and compositions thereof are also provided.

The chondroitinase ABC I molecules and GAG or GalAG fragment preparations are useful for treating or preventing disorders associated with coagulation. A "disease associated with coagulation" as used herein refers to a condition characterized by inflammation resulting from an interruption in the blood supply to a tissue, which may occur due to a blockage of the blood vessel responsible for supplying blood to the tissue such as is seen for myocardial, cerebral infarction, or peripheral vascular disease, or as a result of embolism formation associated with conditions such as atrial fibrillation or deep venous thrombosis. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The chondroitinase ABC I or the GAG or GalAG fragments generated therewith may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulants include, but are not limited to, heparin, warfarin, coumadin, dicumarol, phenprocoumon, acenocoumarol, ethyl biscoumacetate, and indandione derivatives.

Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents include, but are not limited to, plasminogen, $a_2$-antiplasmin, streptokinase, antistreplase, tissue plasminogen activator (tPA), and urokinase.

In one embodiment the preparations of the invention are used for inhibiting angiogenesis. An effective amount for inhibiting angiogenesis of the GAG or GalAG fragment preparation or chondroitinase ABC I is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. The inhibition of angiogenesis can cause tumor regression in animal models, suggesting a use as a therapeutic anticancer agent. An effective amount for inhibiting angiogenesis is an amount of GAG or GalAG fragment preparation and/or a chondroitinase ABC I which is sufficient to diminish the number of blood vessels growing into a tumor. This amount can be assessed in an animal model of tumors and angiogenesis, many of which are known in the art.

The compositions of the invention are useful for treating and preventing cancer cell proliferation and metastasis. Thus, according to another aspect of the invention, there is provided methods for treating subjects having or at risk of having cancer. The terms "treat" and "treating" tumor cell proliferation as used herein refer to inhibiting completely or partially the proliferation or metastasis of a cancer or tumor cell, as well as inhibiting any increase in the proliferation or metastasis of a cancer or tumor cell.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. Cancers also include cancer of the blood and larynx.

A "subject at risk of having a cancer" as used herein is a subject who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with a chondroitinase ABC I or degradation product thereof the subject may be able to kill the cancer cells as they develop.

When administered to a patient undergoing cancer treatment, the chondroitinase ABC I and/or GAG or GalAG fragment may be administered in cocktails containing other anticancer agents. The compounds may also be administered in cocktails containing agents that treat the side-effects of radiation therapy, such as anti-emetics, radiation protectants, etc.

Anti-cancer agents also can include cytotoxic agents and agents that act on tumor neovasculature. Cytotoxic agents include cytotoxic radionuclides, chemical toxins and protein toxins. The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, 188Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Toxins also include poisonous lectins, plant toxins such as ricin, abrin, modeccin, botulina and diphtheria toxins. Of course, combinations of the various toxins are also provided thereby accommodating variable cytotoxicity. Other chemotherapeutic agents are known to those skilled in the art.

Agents that act on the tumor vasculature can include tubulin-binding agents such as combrestatin A4 (Griggs et al., Lancet Oncol. 2:82, 2001), angiostatin and endostatin (reviewed in Rosen, Oncologist 5:20, 2000, incorporated by reference herein), interferon inducible protein 10 (U.S. Pat. No. 5,994,292), and the like. Anticancer agents also include immunomodulators such as α-interferon, γ-interferon, and tumor necrosis factor alpha (TNFα).

The invention also encompasses screening assays for identifying therapeutic GAG or GalAG fragments for the treatment of any of the conditions/disorders provided herein, such as the treatment of a tumor, for preventing metastasis or other treatment endpoints. The assays may be accomplished, for instance, by treating a tumor or isolated tumor cells with chondroitinase ABC I alone or in some combination with other native or modified GAG or GalAG degrading enzymes, such as heparinases, and isolating the resultant GAG or GalAG fragments. The isolated GAG or GalAG fragments may then be tested for therapeutic activity in the prevention of tumor cell proliferation and metastasis. Thus the invention encompasses individualized therapies, in which a tumor or portion of a tumor is isolated from a subject and used to prepare the therapeutic GAG or GalAG fragments. These therapeutic fragments can be re-administered to the subject to protect the subject from further tumor cell proliferation or metastasis or from the initiation of metastasis if the tumor is not yet metastatic. Alternatively the fragments can be used in a different subject having the same type or tumor or a different type of tumor.

Effective amounts of the chondroitinase ABC I and/or GAG or GalAG fragments, or compositions that contain them, of the invention are administered to subjects in need of such treatment. Effective amounts are those amounts which will result in a desired improvement in the condition or symptoms of the condition, e.g., for cancer this is a reduction in cellular proliferation or metastasis, while for neurodegenerative disease or damage this is the regeneration of nerve cells, the prolonged survival of nerve cells, the migration of nerve cells or the restoration of nerve function. The amount effective can be the amount of a single agent that produces a desired result or can be the amount of two or more agents in combination. Such amounts can be determined with no more than routine experimentation.

It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In some aspects of the invention the effective amount of chondroitinase ABC I and/or GAG or GalAG fragment is that amount effective to prevent invasion of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327-336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the chondroitinase ABC I compositions or degradation products thereof can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378-383. Matrigel is a reconstituted basement membrane containing type IV collagen, laminin, heparan sulfate proteoglycans such as perlecan, which bind to and localize bFGF, vitronectin as well as transforming growth factor-β(TGF-β), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

The chondroitinase ABC I and/or GAG or GalAG fragments may also be linked to a targeting molecule. A targeting molecule is any molecule or compound which is specific for a particular cell or tissue and which can be used to direct the chondroitinase ABC I and/or GAG or GalAG to the cell or tissue. Preferably the targeting molecule is a molecule which specifically interacts with a cancer cell or a tumor. For instance, the targeting molecule may be a protein or other type of molecule that recognizes and specifically interacts with a tumor antigen.

Tumor-antigens include Melan-A/MART-1, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, Imp-1, EBV-encoded nuclear antigen (EBNA)-1, and c-erbB-2.

The preparations of the present invention may also be used to inhibit or treat infections, such as viral, bacterial, pathogenic or microbial infections. For instance, the preparations provided can be used to inhibit binding to CS/DS proteoglycans that act as cell adhesion molecules, particularly during infection (e.g. malarial infection). It has been found that in pregnant women infected with Plasmodium falciparum infected red blood cells (IRBCs) accumulate in the placenta. The accumulation of IRBCs is believed to be due to the adhesion of IRBC membrane proteins to molecules found in the intervillous space in the placenta such as chondroitin 4-sulfate (Achur et. al., 2000, The Journal of Biological Chemistry, Vol. 275, No. 51 and Alkhalil, et. al., 2000, The Journal of Biological Chemistry, Vol. 275, No. 51). One aspect of the present invention, therefore, is a method for inhibiting maternal malarial infection. An effective amount for treating malarial infection is that amount that leads to a decrease in the number of infected red blood cells in the placenta sufficient that eliminate or decrease the undesirable effects of malarial infection during pregnancy. These effects include: low birth weight, still birth, abortion, premature delivery and maternal morbidity and mortality (Achur et. al., 2000, The Journal of Biological Chemistry, Vol. 275, No. 51).

The preparations provided herein can be used for the treatment of osteoarthritis or psoriasis. Treatment of osteoarthritis refers to any reduction of the subject's symptoms associated with osteoarthritis or controlling the progression of the disease. Generally treatment of osteoarthritis includes reducing pain and/or improving joint movement. Treatment of psoriasis includes the reduction of symptoms of the disease, such as reducing the shedding of skin, or controlling the progression of the disease. Treatment includes, therefore, methods for reducing inflammation associated with psoriasis. As used herein "controlling the progression of the disease" refers to any reduction in the rate of the progression of the disease. The term also includes halting disease progression.

The methods and compositions provided herein can also include other treatments used in osteoarthritis or psoriatic subjects. Other osteoarthritic treatments include NSAIDS and corticosteroids. Other psoriatic treatments include steroids, such as cortisone; scalp treatment with coal tar or cortisone (at times in combination with salicylic and lactic acid); anthralin; vitamin D (synthetic vitamin D analogue (calcipotriene)); retinoids (prescription vitamin A-related gels, creams (tazarotene), and oral medications (isotrentinoin, acitretin)); coal tar; Goeckerman Treatment (coal tar dressings and ultraviolet light); light therapy (Ultraviolet light B (UVB)); psoralen and UVA (PUVA); methotrexate; cyclosporine; alefacept; etancercept; infliximab; adalimumab; and efalizumab.

The methods provided also include methods of using the chondroitinase ABC I enzymes, polysaccharide fragments and compositions provided herein to modulate the extracellular matrix and/or to target specific cell-surface architecture for the diagnosis and treatment of disease.

The methods provided also include methods of promoting cellular proliferation or organogenesis with the preparations provided.

The chondroitinase ABC I is, in some embodiments, immobilized on a support. The chondroitinase ABC I may be immobilized to any type of support but if the support is to be used in vivo or ex vivo it is desired that the support is sterile and biocompatible. A biocompatible support is one which would not cause an immune or other type of damaging reaction when used in a subject. The chondroitinase ABC I may be immobilized by any method known in the art. Many methods are known for immobilizing proteins to supports. A "solid support" as used herein refers to any solid material to which a polypeptide can be immobilized.

Solid supports, for example, include but are not limited to membranes, e.g., natural and modified celluloses such as nitrocellulose or nylon, Sepharose, Agarose, glass, polystyrene, polypropylene, polyethylene, dextran, amylases, polyacrylamides, polyvinylidene difluoride, other agaroses, and magnetite, including magnetic beads. The carrier can be totally insoluble or partially soluble and may have any possible structural configuration. Thus, the support may be spherical, as in a bead, or cylindrical, as in the inside surface of a test tube or microplate well, or the external surface of a rod. Alternatively, the surface may be flat such as a sheet, test strip, bottom surface of a microplate well, etc.

The chondroitinase ABC I may also be used to remove active GAGs or GalAGs from a GAG or GalAG containing fluid. A GAG or GalAG containing fluid is contacted with the chondroitinase ABC I of the invention to degrade the GAG or GalAG. The method is particularly useful for the ex vivo removal of GAGs or GalAGs from blood. In one embodiment the chondroitinase ABC I may be immobilized on a solid support as is conventional in the art. The solid support containing the immobilized chondroitinase ABC I may be used in extracorporeal medical devices (e.g. hemodialyzer, pump-oxygenator) to prevent the blood in the device from clotting. The support membrane containing immobilized chondroitinase ABC I is positioned at the end of the device to neutralize the GAG or GalAG before the blood is returned to the body.

Compositions comprising the chondroitinase ABC I enzymes are also provided. Such compositions can be used in any of the methods provided herein.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, which comprise chondroitinase ABC I and/or GAG or GalAG fragments together with one or more pharmaceutically acceptable carriers and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the chondroitinase ABC I and/or GAG or GalAG fragments, and with each other, in a manner such that there is no interaction which would substantially impair the desired pharmaceutical efficiency.

The enzymes, fragments and compositions provided herein can be combined with a physiologically acceptable carrier. The term "physiologically-acceptable" refers to a non-toxic material that is compatible with the biological systems such of a tissue or organism. The physiologically acceptable carrier must be sterile for in vivo administration. The characteristics of the carrier will depend on the route of administration.

A variety of administration routes are available. The particular mode selected will depend, of course, upon the particular active agent selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. A preferred mode of administration is a parenteral route. The term "parenteral" includes subcutaneous injections, intravenous, intramuscular, intraperitoneal, intrasternal injection or infusion techniques. Other modes of administration include oral, mucosal, rectal, vaginal, sublingual, intranasal, intratracheal, inhalation, ocular, transdermal, etc.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The compositions may conveniently be presented in unit dosage form and may be prepared by any of the methods well known in the art of pharmacy.

Other delivery systems can include time-release, delayed release or sustained release delivery systems. Such systems can avoid repeated administrations of the compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

Controlled release of chondroitinase ABC I or GAG or GalAG fragments can also be achieved with appropriate excipient materials that are biocompatible and biodegradable. These polymeric materials which effect slow release of the chondroitinase ABC I or GAG or GalAG fragments may be any suitable polymeric material for generating particles, including, but not limited to, nonbioerodable/non-biodegradable and bioerodable/biodegradable polymers. Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride polystyrene, polyvinylpryrrolidone, hyaluronic acid, and chondroitin sulfate.

Examples of preferred non-biodegradable polymers include ethylene vinyl acetate, poly(meth) acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

A subject is any human or non-human vertebrate, e.g., monkey, dog, cat, horse, cow, pig, mouse, rat.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Materials and Methods

Subcloning of Chondroitinase ABC I from *Proteus vulgaris*

Genomic DNA was isolated from cultures of *Proteus vulgaris* (ATCC #6896) using a DNeasy purification kit from Qiagen (Valencia, Calif.). Primers were designed based on the previously published sequence of the gene (NCBI nucleotide accession: E08025) [13]. It has been previously reported that the active form of chondroitinase ABC I isolated from *P. vulgaris* is missing the N-terminal signal sequence [9]. Therefore, two 5' end primers were designed so as to generate a full length clone and a truncated version of the gene by omitting 72 bases encoding the signal sequence. In order to facilitate cloning into a pET-28a vector (Novagen, Madison, Wis.), the forward primer was constructed so as to incorporate an Nde I restriction site, and the reverse primer had a BamHI and a Xho I restriction site built in. The primers for cloning cABC I have the sequences: 5'-CATATGC-CGATATTTCGTTTTACTGCA-3' (SEQ ID NO: 25) (forward primer for full length gene), 5'-CATATGCCCACCAG-CAATCCTGCATTTG-3' (SEQ ID NO: 26) (forward primer for truncated gene) and 5'-GGATCCTCGAGTCAAGG-GAGTGGCGAGAGTTTG-3' (SEQ ID NO: 27) (reverse primer). PCR was run using *P. vulgaris* genomic DNA as the template and a slightly longer extension time (3 min.) was used to account for the length of the gene (2994 bp) being amplified.

The PCR product was initially ligated into the pCR® 4-TOPO vector using the TOPO TA Cloning Kit (Invitrogen, Carlsbad, Calif.) and transformed into TOP10 *E. coli* cells. Plasmid DNA was isolated from positive colonies and the cABC I gene was excised from the TOPO vector using the previously engineered Nde I and Xho I restriction sites. The excised gene was ligated into pET-28a that had been digested with the same restriction enzymes. The ligation products were then transformed into DH5α *E. coli* cells and plasmid DNA isolated from the colonies was screened by restriction digestion for incorporation of the cABC I gene. Plasmid DNA isolated from the positive colonies was also sequenced to confirm incorporation of the gene.

Site-Directed Mutagenesis Studies

The QuikChange Site-Directed Mutagenesis Kit (Stratagene, La Jolla, Calif.) was used with plasmid DNA template to produce mutants of cABC I. Briefly, mutants were produced by plasmid denaturation and annealing of complementary oligonucleotide primers containing the desired mutation. This was followed by extension of the primers with a temperature cycler and PfuTurbo DNA polymerase, resulting in a mutated plasmid with staggered nicks. Digestion of hemimethylated DNA of the parental template with Dpn I endonuclease selects for the mutation-containing synthesized DNA. Primer sequences for mutagenesis studies are presented in Table 1. The mutated plasmids were transformed into XL1-Blue supercompetent cells. The plasmids were prepared using a miniprep kit (Qiagen). Each clone was sequenced to confirm the presence of the desired mutation. Plasmid DNA was used to transform BL21 (DE3) *E. coli*.

TABLE 1

Summary of Primer Sequences for Site-Directed Mutagenesis Studies

| Mutant | Primer Pair Sequences[a] | |
|---|---|---|
| Thr154Ala | 5'-ACTGGCTGGCGTGCTGTGGGAGTCTCT-3' | (SEQ ID NO: 28) |
| | 5'-AGAGACTCCCACAGCACGCCAGCCAGT-3' | (SEQ ID NO: 29) |
| Val309Ile | 5'-GGAACGCAAGGCAGACATCTGATCACTGATAAACAAATC-3' | (SEQ ID NO: 30) |
| | 5'-GATTTGTTTATCAGTGATCAGATGTCTGCCTTGCGTTCC-3' | (SEQ ID NO: 31) |
| Pro322Leu | 5'-CAACCAGAGAATCTTAACTCTCAAGATAAACAACTATTTG-3' | (SEQ ID NO: 32) |
| | 5'-CAAATAGTTGTTTATCTTGAGAGTTAAGATTCTCTGGTTG-3' | (SEQ ID NO: 33) |
| Pro694Gln | 5'-GGTTGGGATTGGAATAGAATGCAAGGGGCAACCACT-3' | (SEQ ID NO: 34) |
| | 5'-AGTGGTTGCCCCTTGCATTCTATTCCAATCCCAACC-3' | (SEQ ID NO: 35) |
| His501Ala | 5'-TGATGGTACAGCATGGCGAGCTGAAGGCAACTATCCGGGCTA-3' | (SEQ ID NO: 36) |
| | 5'-TAGCCCGGATAGTTGCCTTCAGCTCGCCATGCTGTACCATCA-3' | (SEQ ID NO: 37) |

TABLE 1-continued

Summary of Primer Sequences for Site-Directed Mutagenesis Studies

| Mutant | Primer Pair Sequences[a] | |
|---|---|---|
| Tyr508Ala | 5'-GGCAACTATCCGGGCGCCTCTTTCCCAGCC-3' | (SEQ ID NO: 38) |
|  | 5'-GGCTGGGAAAGAGGCGCCCGGATAGTTGCC-3' | (SEQ ID NO: 39) |
| Arg560Ala | 5'-CCGCTTGCAGGAGCACACCCTTTTAACTCACCTTCG-3' | (SEQ ID NO: 40) |
|  | 5'-CGAAGGTGAGTTAAAAGGGTGTGCTCCTGCAAGCGG-3' | (SEQ ID NO: 41) |
| Glu653Ala | 5'-CACCAATGTTTGGTCATCTGCAATTTATAACAAAGATAACCGT-3' | (SEQ ID NO: 42) |
|  | 5'-ACGGTTATCTTTGTTATAAATTGCAGATGACCAAACATTGGTG-3' | (SEQ ID NO: 43) |
| His561Ala | 5'-CCGCTTGCAGGAAGAGCCCCTTTTAACTCACCTTCG-3' | (SEQ ID NO: 44) |
|  | 5'-CGAAGGTGAGTTAAAAGGGGCTCTTCCTGCAAGCGG-3' | (SEQ ID NO: 45) |
| His712Ala | 5'-GACAGTCCTAAACCTGCTACCTTAATGCAACGTGGAGAG-3' | (SEQ ID NO: 46) |
|  | 5'-CTCTCCACGTTGCATTAAGGTAGCAGGTTTAGGACTGTC-3' | (SEQ ID NO: 47) |
| Arg500Ala | 5'-CCTGATGGTACAGCATGGGCACATGAAGGCAACTATGCGGGC-3' | (SEQ ID NO: 48) |
|  | 5'-GCCCGGATAGTTGCCTTCATGTGCCCATGCTGTACCATCAGG-3' | (SEQ ID NO: 49) |

[a]Mutation codons are indicated in bold; bases modified in order to create the desired point mutations are underscored. Forward primers for each mutant are listed first.

Recombinant Expression and Protein Purification of Chondroitinase ABC I and Mutants Recombinant cABC I and the site-directed mutants were expressed in *E. coli* and purified essentially as previously described [8]. Cultures for expression contained 40 µg/ml kanamycin. The presence and purity of the proteins were assessed by SDS-polyacrylamide gel electrophoresis analysis using precast Invitrogen NuPAGE 12% Bis-Tris gels, the XCell SureLock Mini-Cell, and Simply Blue SafeStain (Invitrogen). A relative protein concentration was calculated using the Bradford assay (Bio-Rad Laboratories, Hercules, Calif.) with bovine serum albumin (Sigma, St. Louis, Mo.) as a standard. The 6× His tag was cleaved using the Thrombin Capture Kit (Novagen, San Diego, Calif.) as previously described [17].

Structural Characterization

Circular dichroism (CD) spectra were recorded at 25° C. on an Aviv 202 CD spectrophotometer using Quartz cuvettes with optical path length of 0.1 cm. Scans were collected between 300 and 195 nm with a 1.0-nm bandwidth and a scan rate of 1 nm/min. Three scans were averaged for each protein. For melting experiments, spectra were collected at 5° C. intervals from 5° C. to 80° C. Recombinant proteins were concentrated and buffer-exchanged into 50 mM sodium phosphate pH 7.5 using Centricon 10 filters (Millipore, Billerica, Mass.). Protein content was quantified by standard methods using the Bio-Rad Protein Assay Kit (Bio-Rad Laboratories). All spectra were collected using a protein concentration of 0.2 mg/ml. The buffer contribution was accounted for in all spectra. The signal was normalized to molar ellipticity, $\theta M$, in degrees·cm$^2$·dmol$^{-1}$.

Determination of Optimal Biochemical Conditions for Recombinant Chondroitinase ABC I Activity For these studies C6S and DS were dissolved at a 1 mg/mL concentration in various buffers in an attempt to determine the relative effects of pH, temperature, ionic strength and sodium acetate concentration on enzyme activity. The activity of a fixed amount of recombinant active cABC I (0.2 µg) was assessed based on the change in absorbance at 232 nm per minute ($\Delta A_{232}$/min) as reaction conditions were varied. The effect of pH was investigated by using 2 different buffer systems: (1) 50 mM sodium phosphate pH 6.5, 7.0, 7.5, 8.0, 8.5, 9.0 and (2) 50 mM Tris pH 7.5, 8.0, 8.5, 9.0. Activity at various temperatures (25° C.-45° C.) was also investigated.

To determine the relative effect of ionic strength, the NaCl concentration was varied from 0-1.0 M in 50 mM Tris buffer (pH 8.0). Previous studies have suggested that addition of sodium acetate to the buffer enhances the activity of cABC I [9]. To confirm this we varied the sodium acetate concentration from 0-0.5 M in 50 mM Tris buffer (pH 8.0).

The temperature study was carried out using a temperature-controlled UV spectrophotometer (DU 800, Beckman Coulter, Fullerton, Calif.) in a quartz cuvette at a 1 mL final reaction volume. The other optimization experiments were carried out on a SpectraMax 190 (Molecular Devices, Sunnyvale, Calif.) using a 96-well quartz plate. Eight enzyme reactions (i.e. 1 column of the plate) could be initiated and monitored simultaneously using our setup. This semi-high throughput approach enabled us to sample multiple reaction conditions in an easily repeatable manner. The temperature on the SpectraMax was set to 37° C. for these experiments. Absorbance at 232 nm was monitored for 2-4 min, and activity was calculated based on the initial rate of product formation.

Product Profile Analysis

Capillary electrophoresis (CE) was performed using similar conditions to those developed for the separation of heparan sulfate GAG disaccharides [18]. Briefly, 100 µl of 100 µg/ml substrate was placed in a reaction vial with 1 µg of enzyme and incubated at 37° C. overnight. Substrates used included C6S from shark cartilage (Sigma), DS from porcine intestinal mucosa (Sigma), and C4S from sturgeon notochord (Seikagaku, Tokyo, Japan). Uncoated fused silica capillaries (i.d. of 75 µm and $1_{tot}$ of 80.5 cm) coupled with an extended path detection cell were used on a Hewlett-Packard $^{3D}$CE unit. Di- and oligosaccharides were detected at 232 nm using an electrolyte solution of 50 mM Tris/phosphoric acid, pH 2.5. Dextran sulfate was added to the buffer to suppress nonspecific interactions with the fused silica wall of the capillaries. Electrophoretic separation was performed using reverse polarity at a voltage of −30 kV. Peak identities were confirmed by co-migration with known standards.

Chondroitinase ABC I Activity Analysis

Two µl of enzyme were placed in 248 µl of 50 mM Tris-HCl, 50 mM sodium acetate, pH 8.0 with 1 mg/ml of substrate (0.25 mg/ml for hyaluronan) at 37° C. Product formation was monitored as an increase in absorbance at 232 nm as a function of time in our semi-high throughput format. Initial rates represent <10% substrate turnover. Chondroitinase ABC (protease free) was purchased from Seikagaku. Substrates used in these studies are described above and additionally include chondroitin from shark cartilage (Seikagaku), hyaluronan from human umbilical cord (Sigma), heparin (Celsus, Cincinnati, Ohio), and heparan sulfate (Celsus). The quantity of enzyme used in each reaction was measured using the Bio-Rad protein assay kit. A kinetic analysis of cABC I employed our semi-high throughput spectrophotometric approach and is essentially as previously described [19]. One µl of 0.2 µg/µl cABC I was added to 249 µl of a solution containing different concentrations of GalAG substrates (C4S, C6S and DS) in 50 mM Tris-HCl, 50 mM sodium acetate, pH 8.0. Each well contained different substrate concentrations ranging from 0.1 to 5 mg/ml. Product formation was monitored by measuring the absorbance at 232 nm every 2 seconds.

To evaluate the kinetic data, the initial reaction rate ($v_o$) was first determined from the value of the slope from the plot of product formation as a function of time. The values of $V_{max}$ and $K_m$ were extracted from the slope and y-intercept of the Hanes plot generated by monitoring the product formation and using Equation 1 below:

$$\frac{[subs]}{v_o} = \left(\frac{1}{V_{max}}\right)[subs] + \left(\frac{K_m}{V_{max}}\right), \quad \text{Equation 1}$$

the substrate concentration.

The $k_{cat}$ was calculated by dividing $V_{max}$ by the concentration of enzyme in the reaction. A molar absorptivity coefficient ($\epsilon$) for the product of the enzymatic reaction of 3,800 $M^{-1} \cdot cm^{-1}$ was used. The calculated value for the path length of the well using 250 µl volume for the reaction was 0.904 cm. The analyses were performed in triplicate.

Results

Cloning of the Chondroitinase ABC I Gene from the *Proteus vulgaris* Genome

The gene for cABC I was cloned from *P. vulgaris* genomic DNA as a full-length version and the mature enzyme, without its putative leader sequence. The PCR product of approximately 3 kb was subcloned into pET-28a, via an intermediate TOPO cloning step, to facilitate its incorporation and expression in *E. coli*. Chondroitinase ABC I was expressed in *E. coli* as previously described, with an N-terminal 6x histidine tag. The histidine tag enabled quick purification of the enzyme over a charged $Ni^{+2}$ column. Expression of the initial clone resulted in an enzyme with low activity against GalAG substrates.

DNA sequencing analysis revealed a number of differences between our sequence and the previously published sequence of the gene by Sato et al (NCBI nucleotide accession: E08025) [13]. The major irregularity was observed in the resulting amino acid sequence between residues 494-530, which can be attributed to a pair of frame-shift errors in the published DNA sequence [13]. After position 1771 there should be an additional cytosine (C) base in the published sequence (CGC CCT G instead of CGC CTG), that would result in a proline instead of a leucine at position 494. At position 1870 there is an additional thymidine (T) base which should be removed (TCA GTG GGT instead of CAG TTG GGT), thereby resulting in a better alignment between the published sequence and our cloned sequence. Other errors in the Sato et al sequence [13] produce differences in amino acids at positions 125 (Pro instead of Leu), 369 (Val instead of Met), 670 (Gly instead of Ala) and 865 (Arg instead of Ser). These errors in the previously published sequence have also been observed by Huang et al [11].

The clone produced was in close agreement to the Ryan et al. sequence. However, there were four point mutations present in the clone at variance with the sequence suggested by Ryan et al [14]. At amino acid position 154, an ACT codon produces a threonine residue instead of an alanine residue (GCT). At position 309, our clone contains a GTC codon yielding a valine residue, instead of isoleucine (ATC). At position 322, a CCT codon gives proline instead of a leucine (CTT) residue. And, at position 694, a CCA codon generates a proline residue instead of glutamine (CAA). Since expression of the initial clone resulted in a low activity enzyme, these point mutations were "repaired" using site-directed mutagenesis techniques. All four point mutations were corrected sequentially so as to conform precisely with the protein sequences reported in the crystal structure [11] and by Ryan et al [14].

Recombinant Expression and Purification of Chondroitinase ABC I

Figure 1:
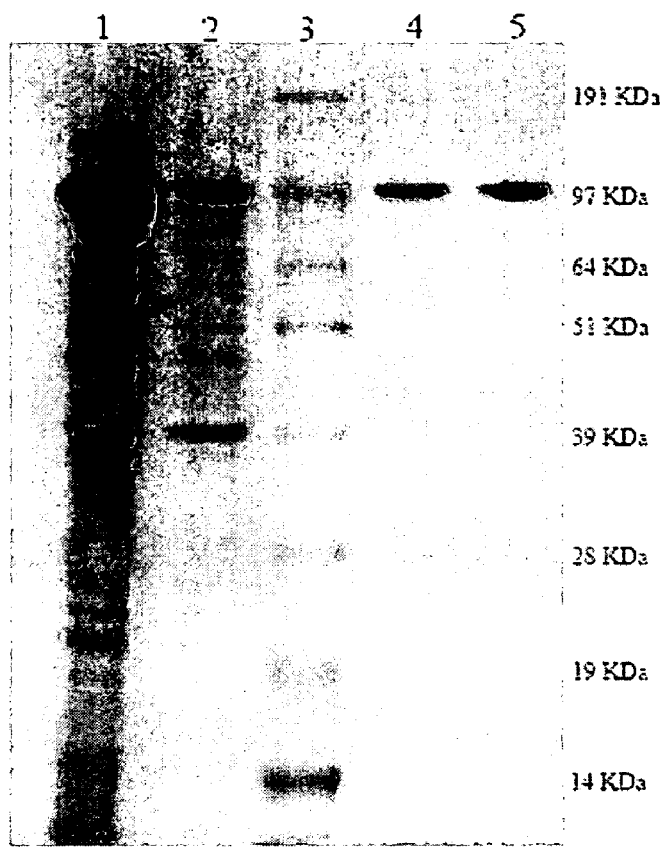
FIG. 1 provides the results from the SDS-PAGE analysis of the purification of recombinant chondroitinase ABC I. The figure shows a summary of protein expression and purification following expression in BL21(DE3) as 6x N-terminal fusion proteins. Lanes: 1, cell pellet; 2, crude lysate; 3, Invitrogen SeeBlue Plus2 Pre-Stained Standard; 4, inactive recombinant chondroitinase ABC I; 5, active recombinant chondroitinase ABC I (altered via site-directed mutagenesis).

To establish the functionality of the "fixed" cABC I clone, the protein in *E. coli* was recombinantly expressed. Expression of the original full-length clone generated an enzyme almost wholly present in the insoluble fraction. The yield of soluble recombinant enzyme was greatly improved by the engineered removal of the hydrophobic N-terminal signal sequence. This result is consistent with other GAG-degrading enzymes studied [8]. This sequence tag is most likely responsible for targeting to a specific location in the periplasm. Chondroitinase ABC I purification generally yielded upwards of 35 mg of protein from 500 ml of culture (Table 2). SDS-PAGE analysis (FIG. 1) revealed a highly pure band at ~110 kDa, in close agreement with previously reported masses of cABC I [9, 13] and its theoretical mass 112,614 Da based solely on amino acid composition.

TABLE 2

Purification of Recombinant Chondroitinase ABC I

| Fraction | Protein yield (mg) | Specific activity (1 mg/ml C6S) (Units/mg) | x-fold Purification[a] |
|---|---|---|---|
| Crude lysate | 195 | 92.1 | |
| Elution from $Ni^{+2}$ column | 35 | 197.9 | 2.1 |
| Thrombin cleavage[b] | 35 | 230.6 | 2.5 |

[a]The x-fold purification was determined relative to the specific activity measured for crude lysate.
[b]Cleavage of the 6x His tag from the recombinant protein was confirmed by Western blot analysis using an anti-His tag antibody (Amersham Biosciences, Piscataway, NJ). No detectable difference in activity against GalAG substrates was observed between the recombinant cABC I and its His tag-cleaved counterpart.

A check for the absorbance at 232 nm, suggestive of the double bond formed in the degradation reaction, was performed spectrophotometrically with 5.0 µg of each recombinant enzyme (the original and the clone that underwent mutagenesis repair) and 1 mg/ml C6S or DS. Expression and purification of the "fixed" truncated clone restored robust processing activity against a variety of GAG substrates. The original enzyme showed a low level of activity against both of the GalAG substrates, whereas the "fixed" version acted on both C6S and DS at healthy rates.

Biochemical Conditions for Optimal in Vitro Activity

Figure 2:
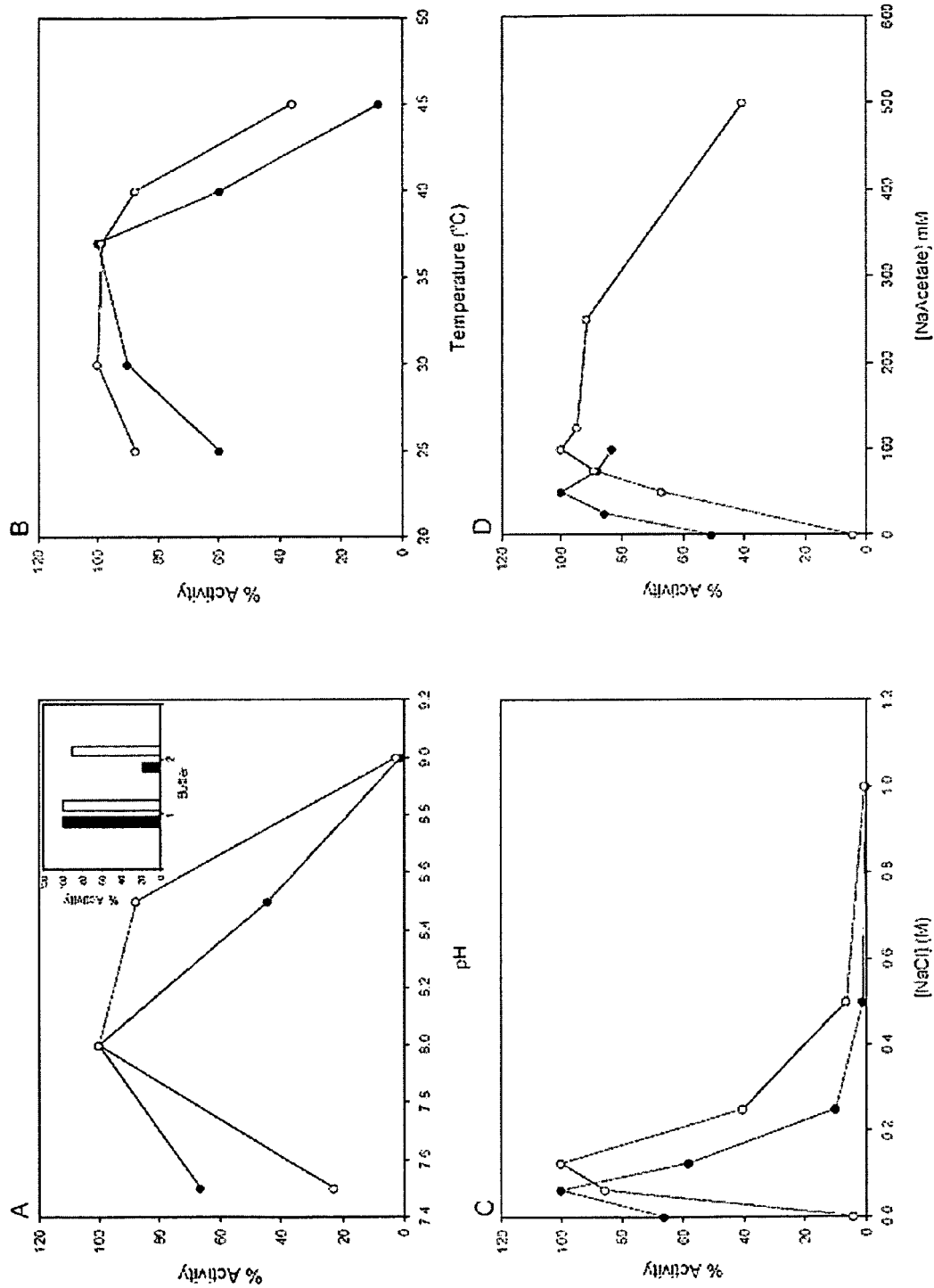
FIG. 2 illustrates the effect of varying chondroitinase ABC I biochemical reaction conditions. (A) pH profile; Inset (A) effect of buffer system on enzyme activity: (1) 50 mM Tris buffer pH 8.0; (2) 50 mM sodium phosphate buffer pH 8.0; white bars indicate dermatan sulfate; black bars indicate chondroitin-6-sulfate; (B) effect of reaction temperature; (C) NaCl titration; (D) sodium acetate titration. Open white circles indicate dermatan sulfate; filled black circles indicate chondroitin-6-sulfate.

Having established the broad substrate specificity of the recombinant cABC I, the reaction conditions were then optimized so as to achieve maximal enzyme activity. These parameters included temperature, pH, ionic strength, and dependence on sodium acetate. A Tris buffer system was chosen, as it resulted in a greater relative activity than phosphate buffer. The enzyme displayed maximal activity at pH 8.0 and was essentially inactive for both C6S and DS at pH 9.0 (FIG. 2).

The recombinant enzyme's activity against C6S and DS was also examined with regard to ionic strength. Recombinant cABC I was optimally active at 62.5 mM NaCl for C6S and 125 mM for DS. For C6S, 50% inhibition occurred at slightly more than 125 mM NaCl, with activity virtually ablated at ~400 mM NaCl. For DS, 50% inhibition occurred at under 250 mM NaCl, and activity was essentially negligible over 500 mM NaCl.

In terms of temperature optima, with C6S as the substrate, the recombinant enzyme demonstrated maximal activity at 37° C. At slightly over 40° C., enzyme activity was 50% inhibited, and activity fell dramatically at 45° C. For DS, a greater level of enzyme activity was evident over the range from 25° C. to 40° C., with an optima between 30° C. and 37° C. At 45° C., processing of DS by the recombinant cABC I was inhibited by over 60%. For both GalAG substrates, 37° C. was chosen as the optimal temperature for biochemical experiments.

It has previously been reported that acetate promotes cABC I activity [9]. Our investigation found that 50 mM sodium acetate provided optimal activity with C6S as the substrate, and 100 mM sodium acetate with DS as the substrate. An absence of sodium acetate in the reaction buffer inhibited enzyme activity against C6S by ~50% and resulted in an almost complete decline in activity against DS.

Chondroitinase ABC I Activity Analysis

The specific activity of recombinant cABC I acting on various substrates (Table 3) was determined by monitoring the increase in absorbance at 232 nm for 5 minutes. The initial rate of increase in $A_{232}$ was determined for each substrate. The enzyme activity in units (1 U=1 µmole product formed/min.) was calculated from the initial rate using $\epsilon=3800$ M$^{-1}$ for reaction products at pH 8.0. Recombinant chondroitinase ABC I shows maximum activity on C4S. Specific activity values for C6S and DS are lower and suggest a slight preference for C6S as compared to DS. Other chondroitin substrates are processed at comparable, albeit much lower rates (Table 3). The enzyme shows very low activity against hyaluronan and was inactive against heparin and heparan sulfate substrates. These results are consistent with previously reported data for the chondroitinase ABC I enzyme purified from *P. vulgaris* and available commercially as "protease-free chondroitinase ABC" from Seikagaku [9].

TABLE 3

Specific Activity of Recombinant Chondroitinase ABC I on Glycosaminoglycan Substrates

| Substrate | Specific activity (Units/mg protein) |
| --- | --- |
| Chondroitin-4-sulfate | 290.8 |
| Chondroitin-6-sulfate | 174.6 |
| Dermatan sulfate | 122.3 |
| Chondroitin | 69.8 |
| Chondroitin sulfate D | 54.2 |
| Chondroitin sulfate E | 34.8 |
| Hyaluronan | 14.8 |
| Heparin/Heparan sulfate | n.d. |

Figure 3:
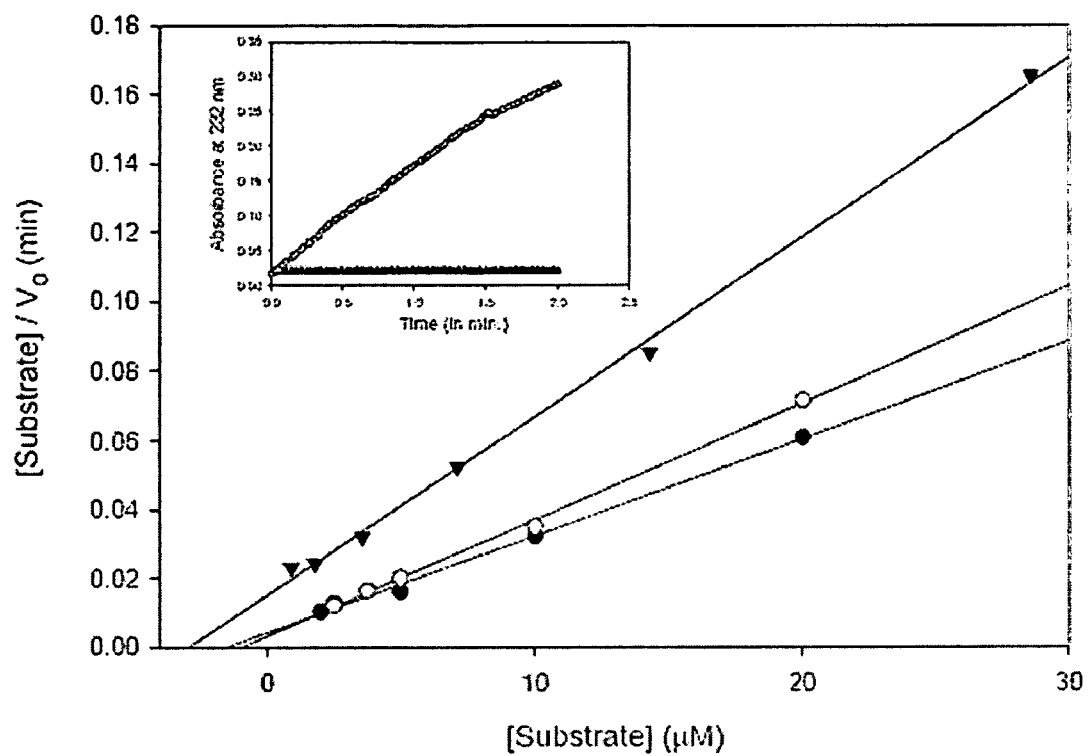
FIG. 3 provides the results of the kinetic analysis of chondroitinase ABC I on GalAG substrates. The figure depicts the Hanes representations of recombinant chondroitinase ABC I on chondroitin-4-sulfate (●), chondroitin-6-sulfate (○), and dermatan sulfate (▼).

Kinetic parameters were determined for recombinant cABC I against C6S, DS and C4S substrates and are summarized in Table 4. The kinetic analysis corroborates the specific activity results, wherein cABC I seems to prefer C4S and C6S over DS (FIG. 3).

TABLE 4

Kinetic Analysis of Chondroitinase ABC I with Various Substrates[a]

| Substrate | $K_m$ µM | $K_{cat}$ min$^{-1}$ | $K_{cat}/K_m$ µM$^{-1}$ min$^{-1}$ |
| --- | --- | --- | --- |
| Chondroitin-6-Sulfate | 1.2 ± 0.6 | 37362 ± 6538 | 32162 |
| Dermatan Sulfate | 2.5 ± 0.5 | 27102 ± 2527 | 10727 |
| Chondroitin-4-Sulfate | 1.5 ± 0.1 | 52263 ± 1344 | 35920 |

[a]Values are the mean of at least three experiments ± standard deviation.

The specific activity of the recombinant active chondroitinase ABC I was also compared with the commercially available purified "protease-free" cABC I from Seikagaku. Rate of product formation ($\Delta A_{232}$/min) was measured for 2-4 min. at 37° C. using a 1 mg/mL C6S solution in 50 mM Tris buffer (pH 8.0) containing 50 mM sodium acetate. The Bradford assay was used to calculate the amount of protein present in each sample. Based on the results our recombinant enzyme gave us a specific activity value of 164.2 mU/µg, whereas the Seikagaku enzyme had a specific activity of 20.2 mU/µg. The difference in specific activity could be the result of enzyme stability or storage conditions.

Figure 4:
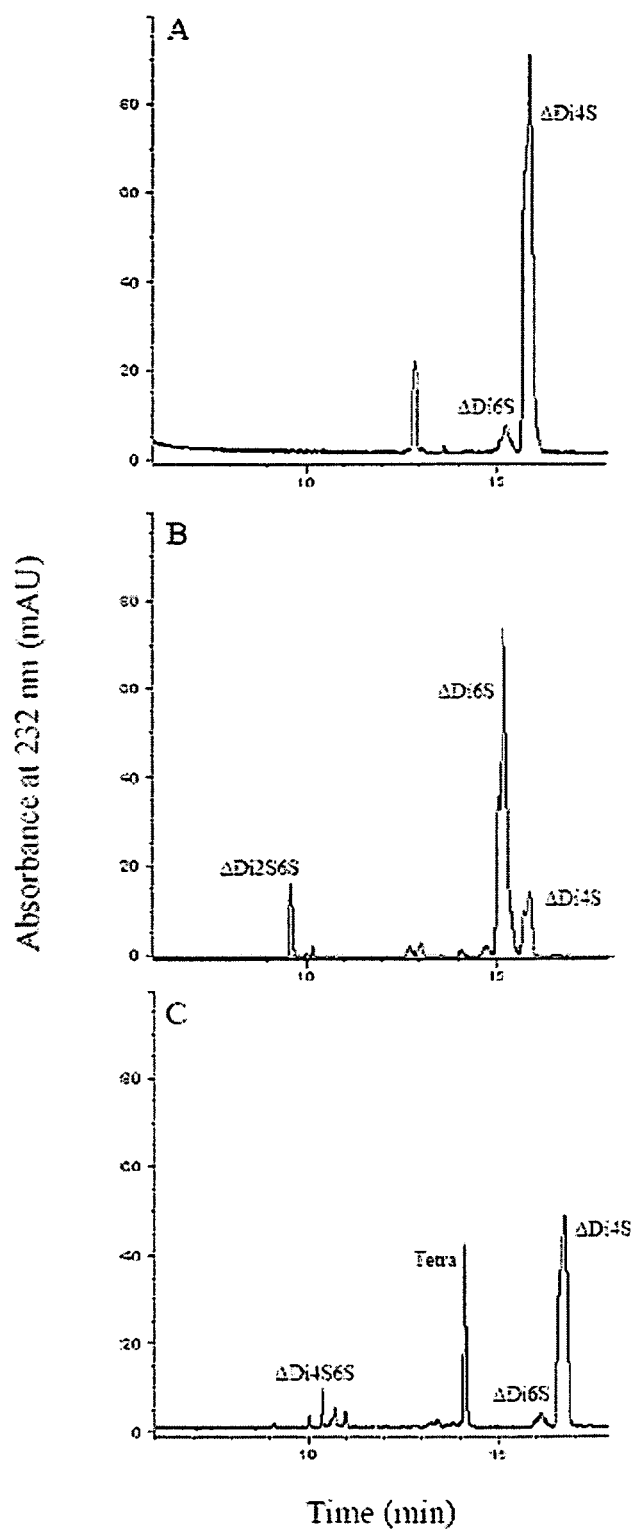
FIG. 4 depicts the results of the capillary electrophoretic analysis of recombinant active chondroitinase ABC I. The figure provides the product profiles for chondroitinase ABC I acting on (A) chondroitin-4-sulfate; (B) chondroitin-6-sulfate; and (C) dermatan sulfate (ΔDi4S=ΔUA-GalNAc4S, ΔDi6S=ΔUA-GalNAc6S, ΔDi2S6S=ΔUA2S-GalNAc6S, ΔDi4S6S=ΔUA-GalNAc4S6S). Impurities in commercial substrate preparations result in the ΔDi6S peak in electrophoretogram (A) and the ΔDi4S peak in electrophoretogram (B).

The activity of cABC I on these three substrates was also analyzed by CE. This study represented an end-point assay for activity and allowed for a characterization of the final products of cABC I digestion on all of the substrates after an 18 hour incubation at 37° C. For C4S and C6S, the product profile shows predominantly disaccharide products with minor tetrasaccharide products also detected (FIG. 4). In both of these cases the respective monosulfated disaccharide (i.e., ΔUA-GalNAc4S or ΔUA-GalNAc6S) represents the major product. In the case of DS a mixture of disaccharides and tetrasaccharides is observed as the final product of digestion. However, one of the tetrasaccharide peaks is much larger than those observed for the C4S and C6S substrates. This suggests that there may be some resistance by tetrasaccharide fragments within DS to cleavage by cABC I. The structure of the resistant tetrasaccharide was determined to be ΔUA-GalNAc4S-IdoA-GalNAc4S based on co-elution (on CE) with a previously isolated pure dermatan tetrasaccharide having the same structure. In order to confirm that this tetrasaccharide is indeed resistant to cABC I action, the pure tetrasaccharide was incubated with enzyme at 37° C., and the resulting products were analyzed by CE. The CE trace showed that there is no breakdown of the tetrasaccharide, thereby confirming that cABC I cannot degrade this tetrasaccharide fraction in DS. The diminished ability of the recombinant cABC I to cleave DS tetrasaccharides is consistent with previous reports on cABC I action pattern [9].

Mutagenesis Studies

A comparison between the crystal structures of *F. heparinum* cAC and *P. vulgaris* cABC I revealed a similar linear arrangement of domains that are superficially similar in terms of overall structure. On a closer inspection of the catalytic domain of cAC with the middle domain of cABC I, a paucity of sequence identity can be observed. This is consistent with the exception of the several amino acid residues that have previously been implicated as active site players in cAC [20] and that seem to have counterparts in cABC I. Using this framework of potential conserved catalytic active site residues, site-directed mutagenesis studies were undertaken to probe the importance of several residues in enzyme activity. His501, Tyr508, Glu653, and Arg560 were all mutated to alanine and characterized in activity experiments. These residues were previously suggested by Huang et al [11] and could constitute the active site, whereby the proton acceptance and donation mechanism could take place [21]. The general reaction requires a residue with positive character to stabilize the uronic acid carboxylate group, a general base with which to abstract a proton from the uronic acid C5 and a residue capable of proton donation to the glycosidic oxygen in the elimination phase of the reaction. Since a general base, like histidine, is believed to be a key component for this catalysis, histidine residues (His561 and His712) were also mutated. These residues are not conserved between the two enzymes but are in close proximity to the proposed active site.

Figure 5:
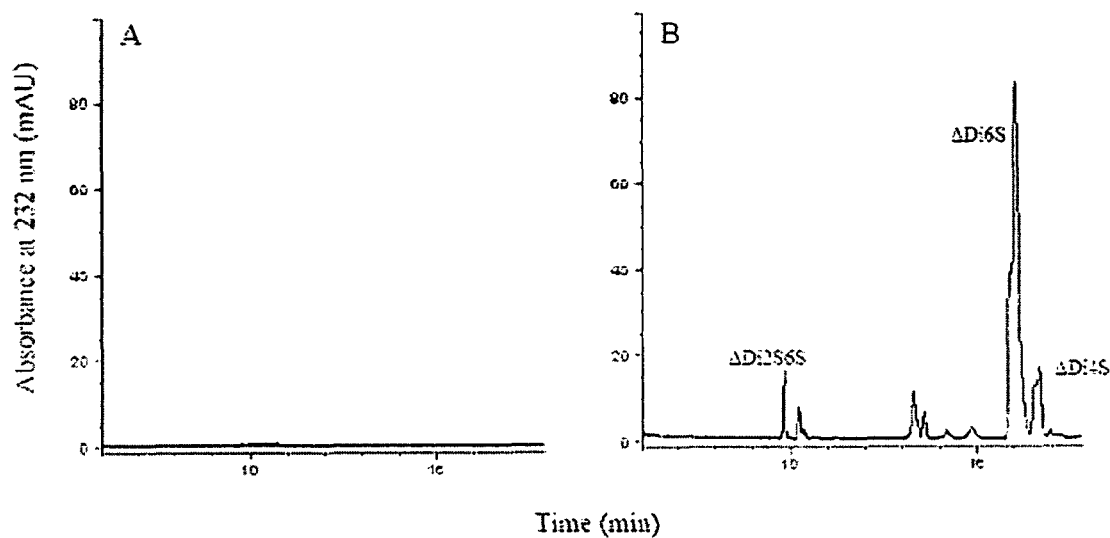
FIG. 5 provides representative capillary electrophoresis profiles of chondroitinase ABC I mutants. The products of chondroitin-6-sulfate degradation following digestion by (A) His501Ala and (B) His561Ala are shown. Tables 4 and 5 provide further information regarding the substrate specificity of recombinant chondroitinase ABC I and its mutants.

Examination of the mutant enzymes in an end-point assay by CE demonstrated a number of residues which seem to be important to catalysis. His501Ala produced no products on overnight digestion with C6S, DS, or C4S as the substrate (FIG. 5). This is in sharp contrast with His561Ala and His712Ala, which both produced a product profile comparable to recombinant active cABC I against all three of these GalAGs after an overnight digestion. Tyr508Ala, Glu653Ala, and Arg560Ala all were unable to yield products in an exhaustive digestion with any of these substrates. These observations provide direct evidence that His501, Tyr508, Glu653, and Arg560 are important for the activity of recombinant cABC I. The relative positions between these residues within the active site cleft of cABC I lends further credence to the notion of this amino acid grouping as the enzyme active site.

Figure 6:
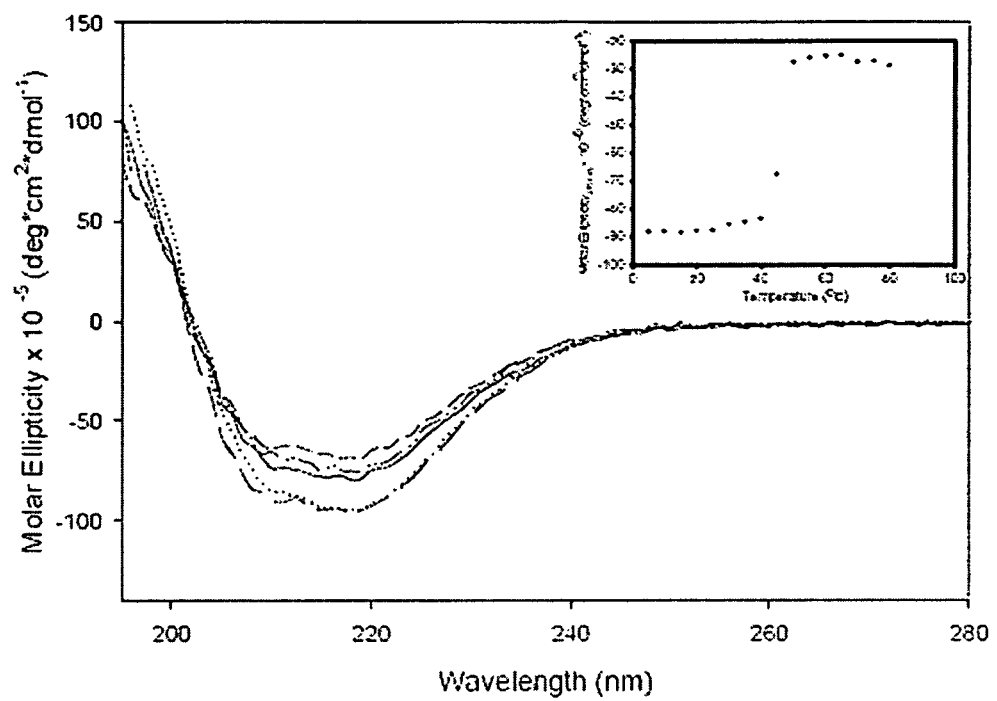
FIG. 6 provides the circular dichroism spectra of chondroitinase ABC I and the inactive mutants. The recombinant chondroitinase ABC I (-) and the mutants His501Ala (⋯), Tyr508Ala (- - -), Glu653Ala ( ), and Arg560Ala (- -) were concentrated and buffer-exchanged into 50 mM sodium phosphate buffer, pH 8.0. Proteins were analyzed in a quartz cell with a 1-mm path length. All spectra were collected using a protein concentration of 0.2 mg/ml in sodium phosphate pH 7.0. For melting experiments (inset), spectra were collected in 5° C. intervals from 5° C. to 80° C. The slight deviations in spectra intensity can be attributed to errors inherent in protein quantification.

Circular dichroism spectroscopy was used to analyze the overall secondary structure of the proteins. The resulting spectra displayed a high α-helix and β-sheet content (FIG. 6). These results are in agreement with the crystal structure of cABC I [11]. CD analysis was also used to confirm that the loss of activity displayed by the mutants (His501Ala, Tyr508Ala, Glu653Ala, and Arg560Ala) was not due to an alteration of the overall secondary structure of the protein. As shown in FIG. 5, no significant differences on the CD spectra between the mutants and the recombinant cABC I were observed. To further address the effect of mutations on protein stability, heat denaturation studies were used to compare the recombinant enzyme to its mutants. All proteins displayed melting transitions of 45±5° C. (FIG. 6, inset). Although these results do not exclude the possibility of minor structural perturbations in the local environment, they do suggest that the overall structure and stability of the protein are not compromised when these particular residues are mutated to alanine.

TABLE 5

Activity Analysis of Chondroitinase ABC I Mutants[a]

| cABC I Mutant | C6S Kinetics | | DS Kinetics | | Activity on C.E.[b] | | |
|---|---|---|---|---|---|---|---|
| | $K_m$ | $k_{cat}$ | $K_m$ | $k_{cat}$ | C6S | C4S | DS |
| H501A | n.d. | n.d. | n.d. | n.d. | − | − | − |
| H561A | 15.2 | 39103 | 6.9 | 3969 | + | + | + |
| H712A | 8.6 | 1140 | 5.1 | 613 | + | + | + |
| Y508A | n.d. | n.d. | n.d. | n.d. | − | − | − |
| R537A | n.d. | n.d. | n.d. | n.d. | − | − | −[c] |
| R477A | 19.9 | 419 | 35.7 | 162 | + | + | + |
| E653A | n.d. | n.d. | n.d. | n.d. | − | − | − |

[a]Kinetic parameters are reported in µM ($K_m$) and min$^{-1}$ ($k_{cat}$).
n.d., activity was too low to be detected.
[b](+) refers to an exhaustive digestion of the substrate; (−) indicates that no products were detected.
[c]The R537A mutant did display some residual activity on DS.

TABLE 6

Kinetic Analysis of cABC I and Mutants with C6S as Substrate

| Enzyme | $K_m$ µM | $K_{cat}$ min$^{-1}$ | $K_{cat}/K_m$ µM$^{-1}$ min$^{-1}$ |
|---|---|---|---|
| Chondroitinase ABC I | 1.2 | 37362 | 32162 |
| His501 Ala or Lys or Arg | na | na | na |
| Tyr508Ala | na | na | na |
| Tyr508Phe | 36.4 | 31.2 | 0.9 |
| Arg560Ala | na | na | na |
| Glu653Ala or Asp | na | na | na |
| Glu653Gln | 6.1 | 1607.6 | 262.1 |
| Arg500Ala | 19.9 | 418.6 | 21.0 |

TABLE 7

Kinetic Analysis of cABC I and Mutants with DS as Substrate

| Enzyme | $K_m$ µM | $K_{cat}$ min$^{-1}$ | $K_{cat}/K_m$ µM$^{-1}$ min$^{-1}$ |
|---|---|---|---|
| Chondroitinase ABC I | 2.5 | 27102 | 10727 |
| His501Ala or Lys or Arg | na | na | na |
| Tyr508Ala | na | na | na |
| Tyr508Phe | 48.9 | 104.8 | 2.11 |
| Arg560Ala | na | na | na |
| Glu653Ala or Asp | na | na | na |
| Glu653Gln | 4.16 | 5174.8 | 1245 |
| Arg500Ala | 35.68 | 162.0 | 4.54 |

Discussion

The sub-cloning of the cABC I gene from *P. vulgaris* and its recombinant expression in *E. coli* are described herein. This recombinant cABC I was also examined biochemically, providing the first conclusive evidence of the residues that constitute the enzyme active site. The establishment of a well-characterized enzyme with defined GalAG substrate specificity provides insight into structure-function relationships in biology.

Purification of cABC I directly from cultures of *P. vulgaris* resulted in preparations with low yields and considerable protease contamination [22, 23]. These conditions spurred investigators toward recombinant production approaches. Early attempts to recombinantly express cABC I in *E. coli* were laden with difficulty. Expression of a soluble protein was hampered by both the size of the gene and the signal sequence. Random proteolysis also proved to be a nuisance to achieving the recombinant protein, and this complication has been observed previously [13]. The one-step purification process described allowed for the preparation of an abundance of soluble protein. Sequence anomalies in the original clone suggest that there may have been underlying structural changes responsible for this eradication of enzyme activity.

The sequential repair via site-directed mutagenesis of the original truncated clone was accompanied by a restoration of enzyme activity. Indeed, the "repaired" recombinant enzyme was able to process C4S, DS, and C6S at robust rates. It was also able to degrade a variety of other GalAG substrates and hyaluronan at lesser rates. It is clear that the recombinant active cABC I described possessed a specific activity that far exceeded that of the commercially-available enzyme. Therefore it is evident that the cloning, expression, and purification system provided does not at all compromise the activity of the cloned enzyme. It is possible that the disparity in specific activities between the recombinant enzyme and the commercially-available cABC I is the result of different purification and storage practices rather than intrinsic enzymatic properties. It is also feasible that an overestimation of active protein content for the commercial enzyme led to a dramatically diminished observed rate, as some portion of quantified protein may have been distorted in the isolation process.

The optimal conditions for activity of recombinant cABC I are similar to those obtained for the purified enzyme. However, it was also observed that different buffer systems affect the processing activity on different substrates. For enzyme activity on C6S in 50 mM sodium phosphate, the optimal pH was determined to be pH 7.0; however, in 50 mM Tris buffer optimal activity was observed at pH 8.0. This discrepancy was not observed with DS as substrate, where the activity maximum was at pH 8.0 regardless of the buffer system. In both cases, however, the enzyme showed more activity in Tris buffer than sodium phosphate. It was also observed that there was a slight inconsistency in the concentration of NaCl and sodium acetate required for maximum activity on C6S as compared to DS. For DS, a higher concentration (approximately double) of both NaCl and sodium acetate in the buffer showed the highest activity in terms of product formation. Another interesting observation is the importance of the presence of salt (i.e., either NaCl or sodium acetate) in the buffer system for activity of recombinant cABC I on DS. From FIG. 2 (panels C and D) it can be seen that in the absence of any salt in the buffer the enzyme activity on DS is about 5% of the observed maximum activity. However, with C6S as substrate, even when there is no salt in the buffer, 50-60% of the maximum activity was observed.

It could be that the salt requirement for DS is important in abolishing non-specific interactions of this substrate with the enzyme. Dermatan sulfate has considerable intrinsic flexibility due to the presence of iduronic acid in its structure. Therefore, it can potentially display a wider range of interactions than C6S and may bind to positively charged patches on the surface of the enzyme, rather than in the active site. In the presence of salt, these non-specific interactions would be markedly reduced.

The results with CE indicate that cABC I was unable to cleave a tetrasaccharide fragment within DS and this fragment was identified to be ΔUA-GalNAc4S-IdoA-GalNAc4S. This is in contrast to the product profile obtained on treating DS with cB, where the major products are predominantly disaccharides [19]. cABC I and cB have totally different structures and, therefore, may bind to and process DS very differently.

The crystal structure of cABC I [11] revealed a three domain protein. The middle domain contains the catalytic site in a wide-open cleft. Despite very limited sequence homology with the catalytic domain of F. heparinum cAC, this middle domain of cABC I did contain a conserved grouping of residues that were implicated in catalysis in cAC [20]. These cABC I residues were His501, Tyr508, Arg560, and Glu653. Manipulation of these residues via mutagenesis to alanine resulted in knockout proteins—enzymes with a complete inability to degrade GAG substrates. Thus this tetrad of residues is important for enzyme activity. With regard to the β-elimination mechanism previously suggested for GAG lyases, it seems that this group of residues is potentially capable of performing the stabilization and proton shuffling responsibilities required for GAG degradation. This study provides the first experimental evidence that this grouping of amino acids comprises the cABC I active site.

It was demonstrated that His501 was, in fact, the histidine important in catalysis. Two other histidines were examined, His561 and His712. Alanine mutants of these residues demonstrated that these histidines were not critical for GAG degradation. In fact, on an exhaustive digestion with GalAG substrate, these mutants both provided a full product profile.

Previously, it was suggested that Arg500 was essential for cABC I's ability to process both CS and DS [11]. Arg500's sidechain was predicted to be positioned toward the uronate carboxylate group of either substrate, serving some role in charge neutralization. However, our product profile analysis and specific activity determinations with the mutant Arg500Ala suggest that this residue is not actually critical for catalysis. In fact, with C6S, C4S, and DS, an exhaustive digestion with Arg500Ala resulted in a product profile virtually indistinguishable from those generated with our recombinant cABC I.

Chondroitinase ABC I's broad substrate specificity complicates fine understanding of its GAG degradation mechanism. The studies provided herein outline the cloning and expression of cABC I, provide a biochemical characterization of this enzyme, and offer the first conclusive proof of the active site. This will advance GAG sequencing biotechnology. The sequencing of GAGs remains a challenging enterprise. Isolating pure GAGs in sufficient quantity for analysis is technically difficult for a variety of reasons, including GAG structural heterogeneity and high negative charge. Enzymatic tools, when used in conjunction with analytical approaches such as coupled mass spectrometry/capillary electrophoresis, have allowed for the rapid and precise elucidation of biologically relevant GAGs using a bare minimum of material [5, 18]. The thorough characterization of new tools, especially GAG-degrading enzymes, will extend the scope and rigor of GAG sequencing.

REFERENCES FOR EXAMPLE 1

1 Bemfield, M., Gotte, M., Park, P. W., Reizes, O., Fitzgerald, M. L., Lincecum, J. and Zako, M. (1999) Functions of cell surface heparan sulfate proteoglycans. Annu Rev Biochem 68, 729-777
2 Sugahara, K., Mikami, T., Uyama, T., Mizuguchi, S., Nomura, K. and Kitagawa, H. (2003) Recent advances in the structural biology of chondroitin sulfate and dermatan sulfate. Curr Opin Struct Biol 13, 612-620
3 Bao, X., Nishimura, S., Mikami, T., Yamada, S., Itoh, N. and Sugahara, K. (2004) Chondroitin sulfate/dermatan sulfate hybrid chains from embryonic pig brain, which contain a higher proportion of L-iduronic acid than those from adult pig brain, exhibit neuritogenic and growth factor binding activities. J Biol Chem 279, 9765-9776
4 Ernst, S., Langer, R., Cooney, C. L. and Sasisekharan, R. (1995) Enzymatic degradation of glycosaminoglycans. Crit Rev Biochem Mol Biol 30, 387-444
5 Venkataraman, G., Shriver, Z., Raman, R. and Sasisekharan, R. (1999) Sequencing complex polysaccharides. Science 286, 537-542
6 Sasisekharan, R., Bulmer, M., Moremen, K. W., Cooney, C. L. and Langer, R. (1993) Cloning and expression of heparinase I gene from Flavobacterium heparinum. Proc Natl Acad Sci U S A 90, 3660-3664
7 Godavarti, R., Davis, M., Venkataraman, G., Cooney, C., Langer, R. and Sasisekharan, R. (1996) Heparinase III from Flavobacterium heparinum: cloning and recombinant expression in Escherichia coli. Biochem Biophys Res Commun 225, 751-758
8 Pojasek, K., Shriver, Z., Kiley, P., Venkataraman, G. and Sasisekharan, R. (2001) Recombinant expression, purification, and kinetic characterization of chondroitinase AC and chondroitinase B from Flavobacterium heparinum. Biochem Biophys Res Commun 286, 343-351
9 Hamai, A., Hashimoto, N., Mochizuki, H., Kato, F., Makiguchi, Y., Horie, K. and Suzuki, S. (1997) Two distinct chondroitin sulfate ABC lyases. An endoeliminase yielding tetrasaccharides and an exoeliminase preferentially acting on oligosaccharides. J Biol Chem 272, 9123-9130

10 Huang, W., Matte, A., Li, Y., Kim, Y. S., Linhardt, R. J., Su, H. and Cygler, M. (1999) Crystal structure of chondroitinase B from *Flavobacterium heparinum* and its complex with a disaccharide product at 1.7 A resolution. J Mol Biol 294, 1257-1269

11 Huang, W., Lunin, V. V., Li, Y., Suzuki, S., Sugiura, N., Miyazono, H. and Cygler, M. (2003) Crystal structure of *Proteus vulgaris* chondroitin sulfate ABC lyase I at 1.9A resolution. J Mol Biol 328, 623-634

12 Fethiere, J., Eggimann, B. and Cygler, M. (1999) Crystal structure of chondroitin AC lyase, a representative of a family of glycosaminoglycan-degrading enzymes. J Mol Biol 288, 635-647

13 Sato, N., Shimada, M., Nakajima, H., Oda, H. and Kimura, S. (1994) Cloning and expression in *Escherichia coli* of the gene encoding the *Proteus vulgaris* chondroitin ABC lyase. Appl Microbiol Biotechnol 41, 39-46

14 Ryan, M. J., Khandke, K. M., Tilley, B. C. and Lotvin, J. A. (1994), (international application published under the patent cooperation treaty) WO 94/25567

15 Bradbury, E. J., Moon, L. D., Popat, R. J., King, V. R., Bennett, G. S., Patel, P. N., Fawcett, J. W. and McMahon, S. B. (2002) Chondroitinase ABC promotes functional recovery after spinal cord injury. Nature 416, 636-640

16 Morgenstern, D. A., Asher, R. A. and Fawcett, J. W. (2002) Chondroitin sulphate proteoglycans in the CNS injury response. Prog Brain Res 137, 313-332

17 Myette, J. R., Shriver, Z., Kiziltepe, T., McLean, M. W., Venkataraman, G. and Sasisekharan, R. (2002) Molecular cloning of the heparin/heparan sulfate delta 4,5 unsaturated glycuronidase from *Flavobacterium heparinum*, its recombinant expression in *Escherichia coli*, and biochemical determination of its unique substrate specificity. Biochemistry 41, 7424-7434

18 Rhomberg, A. J., Ernst, S., Sasisekharan, R. and Biemann, K. (1998) Mass spectrometric and capillary electrophoretic investigation of the enzymatic degradation of heparin-like glycosaminoglycans. Proc Natl Acad Sci U S A 95, 4176-4181

19 Pojasek, K., Raman, R., Kiley, P., Venkataraman, G. and Sasisekharan, R. (2002) Biochemical characterization of the chondroitinase B active site. J Biol Chem 277, 31179-31186

20 Huang, W., Boju, L., Tkalec, L., Su, H., Yang, H. O., Gunay, N. S., Linhardt, R. J., Kim, Y. S., Matte, A. and Cygler, M. (2001) Active site of chondroitin AC lyase revealed by the structure of enzyme-oligosaccharide complexes and mutagenesis. Biochemistry 40, 2359-2372

21 Jedrzejas, M. J. (2000) Structural and functional comparison of polysaccharide-degrading enzymes. Crit Rev Biochem Mol Biol 35, 221-251

22 Oike, Y., Kimata, K., Shinomura, T. and Suzuki, S. (1980) Proteinase activity in chondroitin lyase (chondroitinase) and endo-beta-D-galactosidase (keratanase) preparations and a method to abolish their proteolytic effect on proteoglycan. Biochem J 191, 203-207

23 Harrisson, F., van Hoof, J. and Vanroelen, C. (1986) On the presence of proteolytic activity in glycosaminoglycan-degrading enzyme preparations. J Histochem Cytochem 34, 1231-1235

Example 2

Materials and Methods

Materials

Porcine intestinal mucosa DS (average MW 35,000 g/mol) and shark cartilage C6S (average MW 50,000 g/mol) were purchased from Sigma. C4S (super special grade, average MW 50,000 g/mol) was purchased from Seikagaku/Associates of Cape Cod (Falmouth, Mass.). Oligonucleotides were purchased from Invitrogen. The QuikChange Site-Directed Mutagenesis Kit was purchased from Stratagene. All other materials are from common sources or are as noted.

Sub-Cloning and Site-Directed Mutagenesis of cABC I

Genomic DNA was isolated from cultures of *Proteus vulgaris* (ATCC #6896) using a Qiagen DNeasy purification kit. Sub-cloning procedures were as previously described [29] and above. The QuikChange Site-Directed Mutagenesis Kit was used to produce mutants of cABC I, as described above. Primer sequences for all studies are presented in Table 8. The plasmids were prepared using a miniprep kit (Qiagen). Each clone was sequenced to confirm the presence of the desired mutation. Plasmid DNA was used to transform BL21 (DE3) E. coli.

TABLE 8

Summary of Primer Sequences for Site-Directed Mutagenesis

| Mutant | Primer Pair Sequences$^a$ | |
|---|---|---|
| Thr154Ala | 5'-ACTGGCTGGCGTGCTGTGGGAGTCTCT-3' | (SEQ ID NO: 50) |
| | 5'-AGAGACTCCCACAGCACGCCAGCCAGT-3' | (SEQ ID NO: 51) |
| Val309Ile | 5'-GGAACGCAAGGCAGACATCTGATCACTGATAAACAAATC-3' | (SEQ ID NO: 52) |
| | 5'-GATTTGTTTATCAGTGATCAGATGTCTGCCTTGCGTTCC-3' | (SEQ ID NO: 53) |
| Pro322Leu | 5'-CAACCAGAGAATCTTAACTCTCAAGATAAACAACTATTTG-3' | (SEQ ID NO: 54) |
| | 5'-CAAATAGTTGTTTATCTTGAGAGTTAAGATTCTCTGGTTG-3' | (SEQ ID NO: 55) |
| Pro694Gln | 5'-GGTTGGGATTGGAATAGAATGCAAGGGGCAACCACT-3' | (SEQ ID NO: 56) |
| | 5'-AGTGGTTGCCCCTTGCATTCTATTCCAATCCCAACC-3' | (SEQ ID NO: 57) |
| His501Ala | 5'-TGATGGTACAGCATGGCGAGCTGAAGGCAACTATCCGGGCTA-3' | (SEQ ID NO: 58) |
| | 5'-TAGCCCGGATAGTTGCCTTCAGCTCGCCATGCTGTACCATCA-3' | (SEQ ID NO: 59) |
| Tyr508Ala | 5'-GGCAACTATCCGGGCGCCTCTTTCCCAGCC-3' | (SEQ ID NO: 60) |
| | 5'-GGCTGGGAAAGAGGCGCCCGGATAGTTGCC-3' | (SEQ ID NO: 61) |
| Arg560Ala | 5'-CCGCTTGCAGGAGCACACCCTTTTAACTCACCTTCG-3' | (SEQ ID NO: 62) |
| | 5'-CGAAGGTGAGTTAAAAGGGTGTGCTCCTGCAAGCGG-3' | (SEQ ID NO: 63) |

TABLE 8-continued

Summary of Primer Sequences for Site-Directed Mutagenesis

| Mutant | Primer Pair Sequences[a] | |
|---|---|---|
| Glu653Ala | 5'-CACCAATGTTTGGTCATCTGCAATTTATAACAAAGATAACCGT-3' | (SEQ ID NO: 64) |
|  | 5'-ACGGTTATCTTTGTTATAAATTGCAGATGACCAAACATTGGTG-3' | (SEQ ID NO: 65) |
| Arg500Ala | 5'-CCTGATGGTACAGCATGGGCACATGAAGGCAACTATCCGGGC-3' | (SEQ ID NO: 66) |
|  | 5'-GCCCGGATAGTTGCCTTCATGTGCCCATGCTGTACCATCAGG-3' | (SEQ ID NO: 67) |
| His501Lys | 5'-GGTACAGCATGGCGAAAGGAAGGCAACTATCCGGGC-3' | (SEQ ID NO: 68) |
|  | 5'-GCCCGGATAGTTGCCTTCCTTTCGCCATGCTGTACC-3' | (SEQ ID NO: 69) |
| His501Arg | 5'-ACAGCATGGCGACGTGAAGGCAACTATCCGGGC-3' | (SEQ ID NO: 70) |
|  | 5'-GCCCGGATAGTTGCCTTCACGTCGCCATGCTGT-3' | (SEQ ID NO: 71) |
| Tyr508Phe | 5'-AACTATCCGGCTTCTCTTTCCCAGCC-3' | (SEQ ID NO: 72) |
|  | 5'-GGCTGGGAAAGAGAAGCCCGGATAGTT-3' | (SEQ ID NO: 73) |
| Glu653Asp | 5'-CAATGTTTGGTCATCTGATATTTATAACAAAGATAACCGTTATGG-3' | (SEQ ID NO: 74) |
|  | 5'-CCATAACGGTTATCTTTGTTATAAATATCAGATGACCAAACATTG-3' | (SEQ ID NO: 75) |
| Glu653Gln | 5'-CAATGTTTGGTCATCTCAAATTTATAACAAAGATAACCGTTATGG-3' | (SEQ ID NO: 76) |
|  | 5'-CCATAACGGTTATCTTTGTTATAAATTTGAGATGACCAAACATTG-3' | (SEQ ID NO: 77) |

[a]Mutation codons are indicated in bold; bases modified in order to create the desired point mutations are underscored.

Recombinant Expression and Protein Purification of cABC I and Mutants

Recombinant cABC I and the site-directed mutants were expressed and purified as previously described [29] and above. The purity of the enzymes was assessed by SDS-polyacrylamide gel electrophoresis using a pre-cast Invitrogen NuPAGE 12% Bis-Tris gel and Simply Blue SafeStain. Protein concentration was measured using the Bio-Rad Laboratories Bradford assay kit.

Capillary Electrophoresis

To study the activities and product profiles of the proteins on each substrate (C6S, DS, C4S), digests of 100 μg/ml substrate, 50 mM Tris-HCl, 50 mM sodium acetate, pH 8.0 with 1 μg of recombinant cABC I or the site-directed mutants were placed at 37° C. for 14 h. The digests were analyzed using capillary electrophoresis as previously described [29, 36].

Circular Dichroism

CD spectra were recorded at 25° C. on an Aviv 202 CD spectrophotometer using Quartz cuvettes with optical path length of 0.1 cm. Scans were collected between 300 and 195 nm with a 1.0-nm bandwidth and a scan rate of 1 nm/min. Three scans were averaged for each protein. For melting experiments, spectra were collected at 5° C. intervals from 5° C. to 75° C. Recombinantly-expressed proteins were concentrated and buffer-exchanged into 50 mM sodium phosphate, pH 7.5 using Centricon 10 filters (Millipore). All spectra were collected using a protein concentration of 0.2 mg/ml. The buffer contribution was subtracted for all spectra. The signal was normalized to molar ellipticity, θM, in degrees·cm$^2$·mol$^{-1}$.

Kinetic Analysis

Recombinant proteins were concentrated and buffer exchanged into 50 mM Tris HCl, 50 mM sodium acetate, pH 8.0. In order to evaluate the activity of chondroitinase ABC I and mutants in a semi-high throughput manner, the kinetic analysis was adapted to a 96-well plate format. The studies were performed in a quartz 96-well plate at 37° C. using a Molecular Devices Spectramax 190 (Molecular Devices). The assay was initiated by adding 1.0 μl of 0.2-6 μg/μl (0.2-6.0 μg) of enzyme to 249 μl of a solution containing different concentrations of galactosaminoglycan substrates (C4S, C6S and DS) in 50 mM Tris-HCl, 50 mM sodium acetate, pH 8.0. Each well contained different substrate concentrations ranging from 0.1 to 5 mg/ml. Product formation was monitored by measuring the absorbance at 232 nm every 2-3 seconds. Evaluation of the kinetic data was based on the initial reaction rate.

Docking of CS and DS Substrates in the Active Site of cABC I

The SARF2 program was used to determine the C-alpha (CA) atoms in cABC I and cAC structure that gave an optimal rms deviation upon superimposing the two structures. Superposition of the 452 CA atoms identified by the SARF2 program in the cAC co-crystal structures (with C4S and DS) and the cABC I crystal structure (rmsd of 2.2 Å) provided the initial location and orientation of the CS and DS substrates relative to the putative active site of cABC I. The coordinates of C4S (GlcA-GalNAc4S)$_2$ and DS (IdoA-GalNAc4S)$_2$ tetrasaccharides were available from the two cAC co-crystal structures. The initial orientation of both of these substrates had many unfavorable steric contacts which were removed by manually orienting the substrate. In the case of the DS tetrasaccharide the C5 proton was facing away from the putative active site residues (His508, Tyr508 and Arg560). Thus, this substrate was further re-oriented to ensure that the C5 proton was accessible for abstraction by the active site amino acids.

The manually adjusted orientations of the enzyme-substrate complexes were further optimized using energy minimization. The AMBER force field modified for carbohydrates was further modified to include O-sulfate and sulfamate groups. This modified AMBER force field was used to assign the potentials for both the enzyme as well as the tetrasaccharide substrates. A subset of the enzyme coordinates around the active site groove was defined to include all of the putative active site amino acids and several additional amino acids that could be involved in the catalytic activity. The enzyme-substrate complex was subject to minimization first without charges and then with charges using 500 steps of steepest descent and 500 steps of conjugate gradient methods. Most of the protein was fixed, and only the amino acids that were a part of the active site subset were allowed to move during the minimization. The final rms derivatives of the energies were below 0.1. The ring conformation of the monosaccharides was not distorted by the minimization procedure. The Viewer and Discover modules of InsightII (Release 2000.1, Accelrys, San Diego, Calif.) were used for the orientation of the substrate and the energy minimization, respectively.

Results Chondroitinase ABC I Characterization The gene for cABC I was cloned from *Proteus vulgaris* genomic DNA without its putative leader sequence. The PCR product was subcloned into pET28a and expressed in *Escherichia coli* with an N-terminal 6x histidine tag. A series of sequence discrepancies between this clone and the reported protein sequence [35, 37, 38] necessitated site-directed mutagenesis efforts to make our clone conform to the previously published protein sequence [35]. The catalytic activity of our cloned cABC I was characterized with various GalAG substrates (including C4S, C6S and DS) using a semi-high throughput procedure. This procedure enabled us to obtain multiple initial velocity measurements between one substrate-enzyme pair within one minute. $K_m$ and $V_{max}$ information could be generated from this data almost immediately. Multiple runs for each enzyme-substrate pair could also be performed in a short period of time to establish a better confidence in the data generated. The kinetic constants for the activity of cABC I on C6S and DS substrates are reported in Tables 9 and 10, respectively. For C4S, recombinant cABC I had a $K_m$ of 1.5 µM, a $k_{cat}$ of 52000 min$^{-1}$ and a catalytic efficiency of 35000 µM min$^{-1}$. The data suggests robust activity on all three substrates; however, there is a clear preference for the C4S and C6S substrates. The catalytic efficiency is about 3-fold higher for C4S and C6S compared to DS.

Site-Directed Mutagenesis Studies

The cABC I crystal structure [35] revealed 4 conserved amino acids in the putative active site of the enzyme which share high structural homology with corresponding amino acids in cAC that play a role in its catalytic activity [31]. The residues—His501, Tyr508, Arg560, and Glu653 along with Arg500, which was implicated to have a catalytic role based on its crystal structure [35], were mutated to alanine to determine their importance in GalAG degradation. The analyses on these mutants indicated that while Arg500Ala still retained some level of GalAG degradation activity, the other four mutants were essentially inactive. Based on the results the importance of these residues in the activity of cABC I was established.

Figure 9:
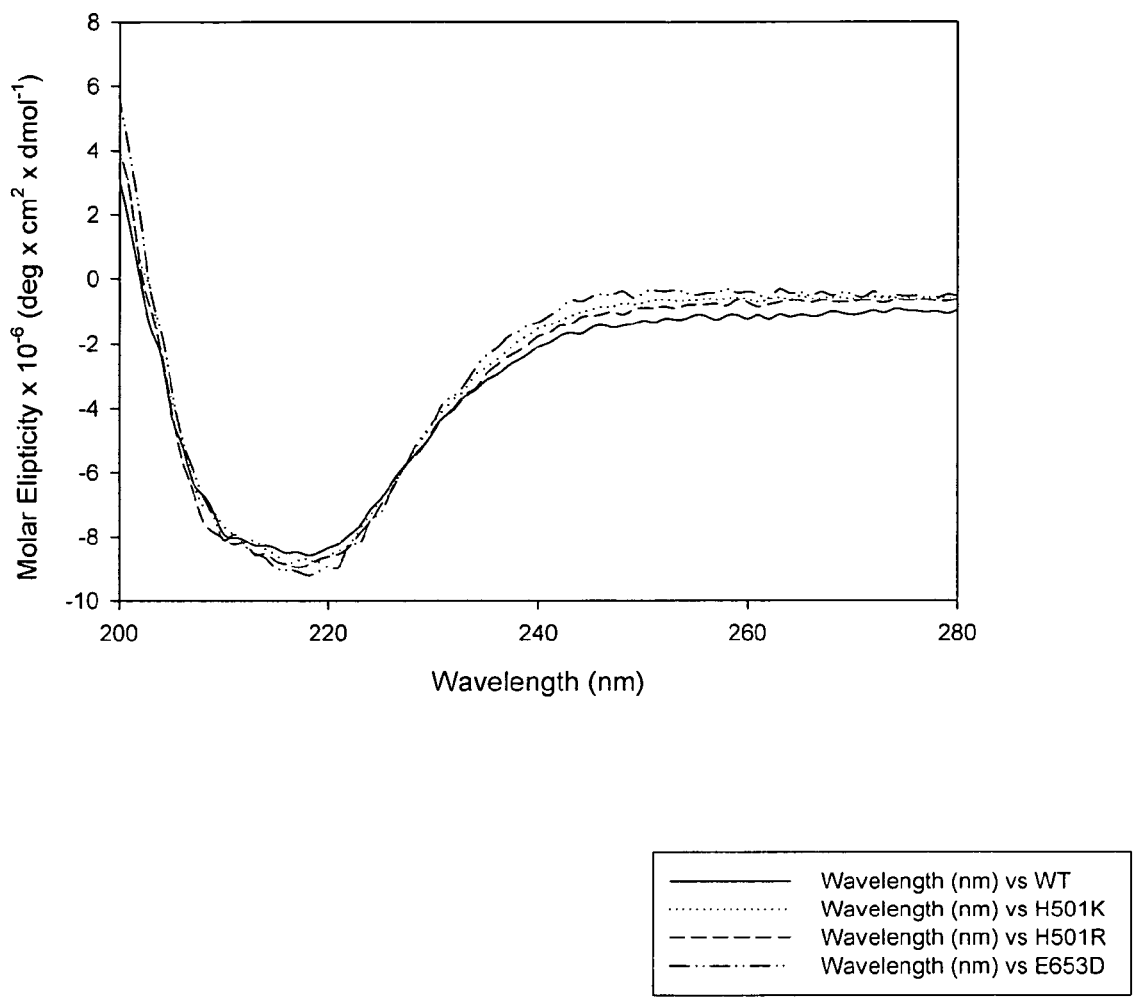
FIG. 9 provides the circular dichroism spectra of recombinant enzymes. The recombinant cABC I (----) and the mutants His501Lys (⋯), His501Arg (-- -- --) and Glu653Asp (-- . . --) were concentrated and buffer-exchanged into 50 mM sodium phosphate buffer, pH 8.0. The proteins were analyzed in a 1-mm path length quartz cell. The slight deviations in spectra intensity can be attributed to errors inherent in protein quantification.

A detailed investigation into the roles of these amino acids in the activity of cABC I was performed by generating several additional active site mutants: His501Arg, His501Lys, Tyr508Phe, Glu653Asp and Glu653Gln. A structural model of the enzyme-substrate complex was also constructed to provide a framework for interpreting the results of the mutagenesis experiments. Chondroitinase ABC I mutants were analyzed for their activity against GalAG substrates by scanning for product formation (as measured via OD$_{232}$ detection) against C6S and DS. Mutants with detectable activities were further characterized through kinetics assays. Capillary electrophoretic studies allowed for an inspection of an end-point product profile analysis following an exhaustive 14-18 hour digestion with C6S, DS, or C4S as substrate. Circular dichroism data on all mutants were also collected, and a melting curve analysis was performed to ensure that mutagenesis did not compromise the enzyme structurally (FIG. 9).

Figure 10:
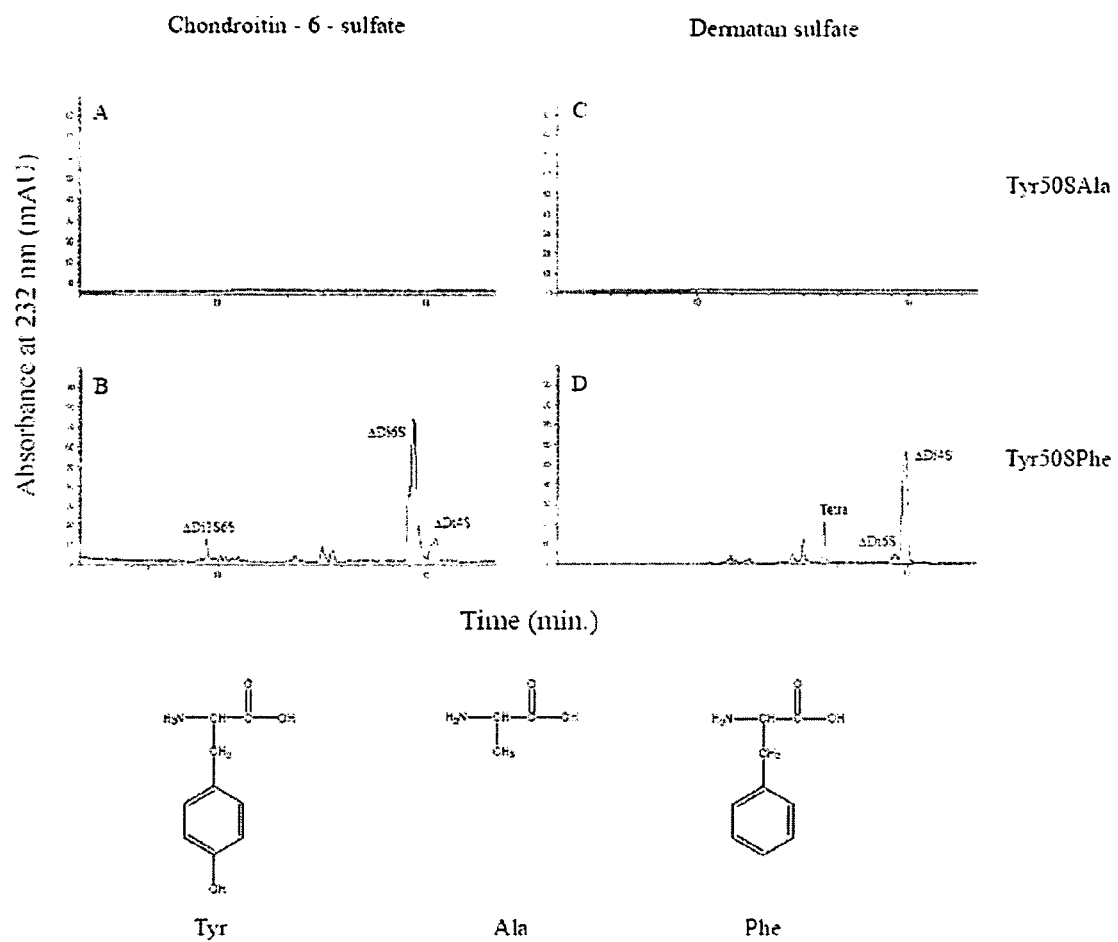
FIG. 10 shows the results from the capillary electrophoretic analysis of chondroitinase ABC I Tyr508 mutants. Product profiles for (A) Tyr508Ala acting on chondroitin-6-sulfate, (B) Tyr508Phe acting on chondroitin-6-sulfate, (C) Tyr508Ala acting on dermatan sulfate and (D) Tyr508Phe acting on dermatan sulfate are provided. Depicted are the relevant amino acids, which illustrate the nature of the chemical groups involved and the relative protrusion of each sidechain into the catalytic pocket.

All His501 mutations (His501Ala, His501Lys, and His501Arg) showed no activity against C6S and DS substrates while scanning for product formation. Additionally, the His501 mutants did not produce any products in capillary electrophoretic assays, suggesting that His501 is important for cABC I activity. Though Tyr508Ala proved inactive against C6S and DS while scanning for product formation and was unable to degrade C6S, DS, and C4S in exhaustive digestions, Tyr508Phe was able to process GalAG substrates. In an exhaustive digestion, product profile analysis revealed electropheretograms virtually indistinguishable from those produced with recombinant cABC I. Tyr508Phe processes C6S (FIG. 10) with both diminished binding ($K_m$ of 36.4 µM compared with 1.2 µM for recombinant cABC I) and markedly reduced turnover number ($k_{cat}$ of 31.2 min$^{-1}$ compared with 37362 min$^{-1}$ for recombinant cABC I). Tyr508Phe acts on DS in a similar fashion (FIG. 10) with a $K_m$ of 48.9 µM and a $k_{cat}$ of 104.8 min$^{-1}$ (compared with a $K_m$ of 2.5 µM and a $k_{cat}$ of 27102 min$^{-1}$ for recombinant cABC I). Therefore, the tyrosine to phenylalanine mutation results in an enzyme with a much higher $K_m$ and a greatly reduced $k_{cat}$ suggesting that this residue possibly plays an important role in substrate positioning and turnover. Unlike His501, the Tyr508Phe mutant does not seem to affect a critical step in GalAG degradation since it still produces products in an end-point analysis (whereas the His501 mutants were inactive). Based on these results, His501 is most likely the residue involved in proton abstraction from the C-5 position of the uronic acid, which is an important step in the GalAG degradation process.

Figure 11:
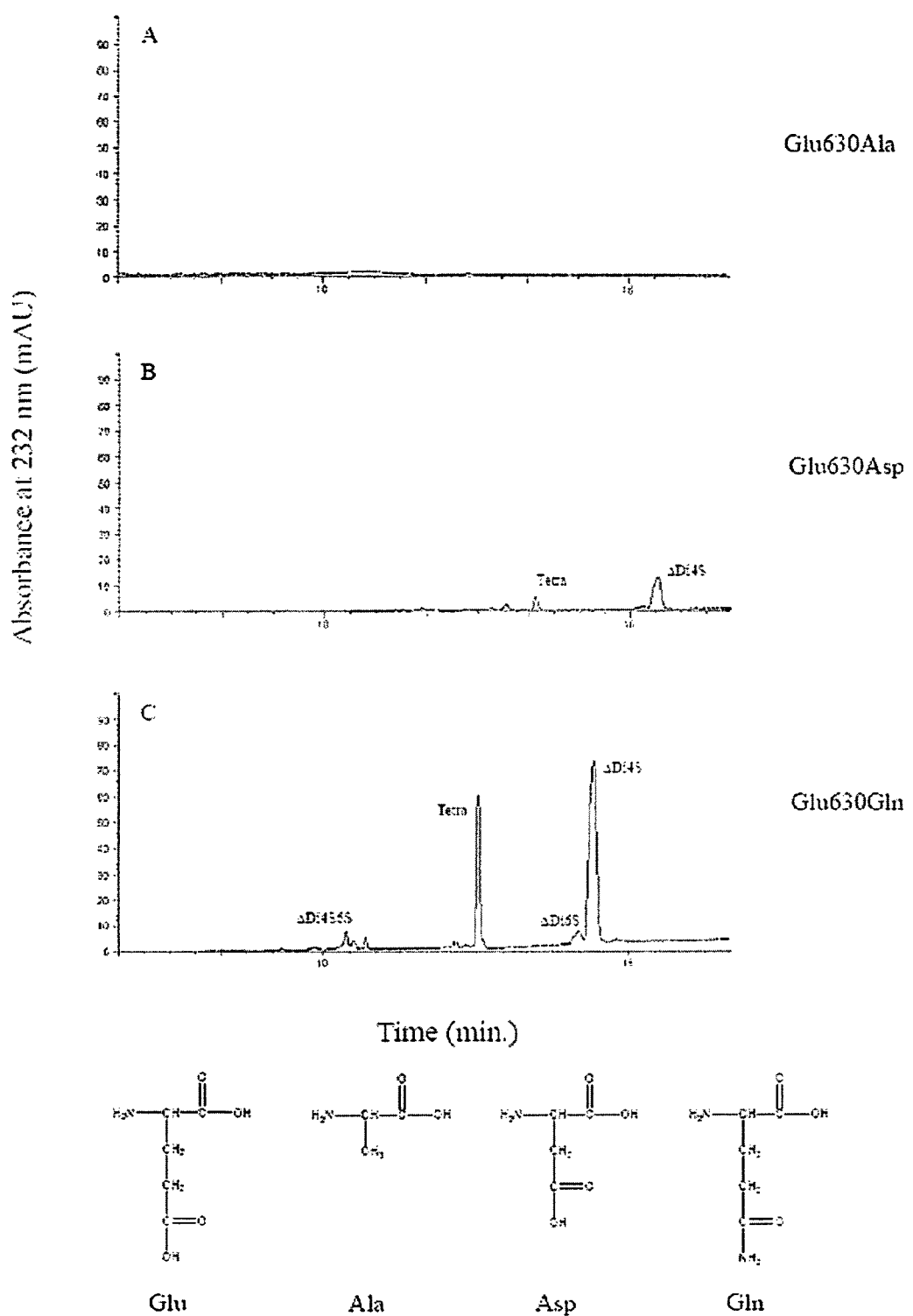
FIG. 11 provides the results from the capillary electrophoretic analysis of chondroitinase ABC I Glu653 mutants. The products of dermatan sulfate degradation following digestion by (A) Glu653Ala, (B) Glu653Asp and (C) Glu653Gln are shown. Also depicted are the relevant amino acids. For each sidechain, the relative length of protrusion into the catalytic pocket and the potential to participate in hydrogen bonding determine end-product profiles.

The other mutants were active against both C6S and DS, though with far less processing efficiency than recombinant cABC I. The Glu653 analog in cAC (Glu371) was believed to play a role in positioning adjacent histidine and arginine residues through hydrogen bonding [31]. In cABC I, Glu653 was investigated by decreasing the effective protrusion of the glutamic acid into the active site by mutating it to an aspartic acid and also by a slight perturbation of the hydrogen bonding network by mutation to a glutamine residue. Although the Glu653Asp mutant proved to be catalytically inactive against both C6S and DS in kinetics assays, on overnight digestion this mutant was able to produce products on these substrates as well as on C4S. Glu653Gln maintained some level of activity against both C6S and DS, with a slight increase in $K_m$ for both substrates and a greater than 20-fold reduction in $k_{cat}$ for C6S and a 5-fold reduction in $k_{cat}$ for DS (FIG. 11). The data suggest that while this residue does not play a major role in substrate positioning, its major role is probably in affecting the catalytic turnover of the enzyme. Against C6S, Arg500Ala remained active, but with a 17-fold increase in $K_m$ and a 1500-fold reduction in catalytic efficiency. With DS, Arg500Ala showed similar losses, with a 14-fold increase in $K_m$ and a greater than 2000-fold decrease in catalytic efficiency. To study the results of the kinetic analyses of the mutants in the context of the structure of the enzyme, theoretical models of the enzyme-substrate structural complexes were constructed.

Enzyme-Substrate Structural Complex—Putative Roles for Active Site Amino Acids

The structure of cABC I contains three domains viz. an N-terminal β-domain with a jellyroll fold, the catalytic α-helix domain [incomplete toroid $(\alpha/\alpha)_5$ fold] and a C-terminal antiparallel β sheet domain. The structural fold of cABC I, comprising the catalytic α-helix domain and the C-terminal β-sheet domain is very similar to that of cAC and bacterial hyaluronate lyases. To obtain a clearer picture of the active site and positioning of the substrate within cABC I, its structure was superimposed on the co-crystal structures of the structurally related cAC and hyaluronate lyase (HAL). The CA atoms chosen for superimposition were obtained from the SARF2 program. This superimposition aligned most of the C-terminal β-sheet domains. However, the α-helix domain did not align very well, since the cleft formed by the N-terminal and C-terminal regions of this domain was more open in cABC I as compared to the closed grooves found in cAC and HAL. Based on the contacts with the substrate and their equivalent amino acids (shown in parentheses) implicated in cAC activity, the amino acids His501 (His225), Tyr508 (Tyr234), Arg560 (Arg288) and Glu653 (Glu371) were proposed to be involved in the catalytic activity of cABC I.

Figure 12:
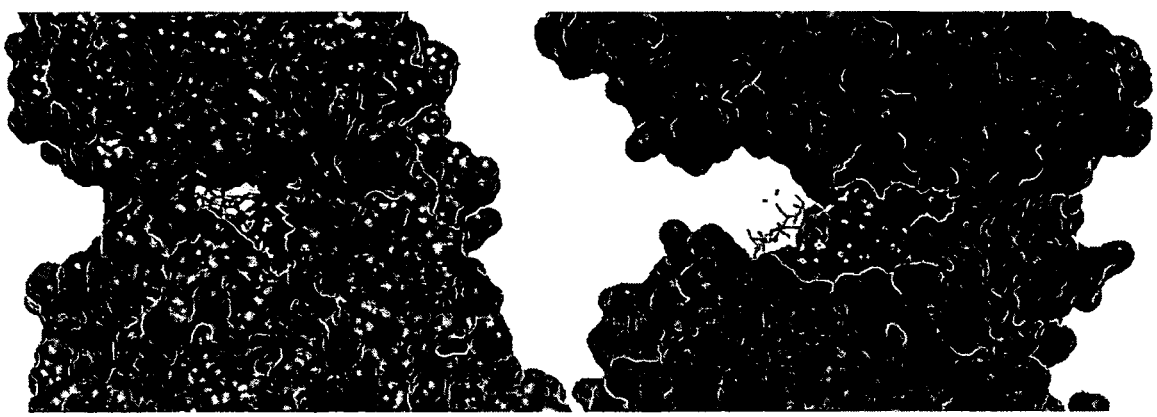
FIG. 12 provides the structural comparison of chondroitinases AC and ABC I. Grasp rendering of cAC (left) and cABC I (right) structural complexes with dermatan sulfate are shown. Note that the active site groove of cAC is more closed compared to that of cABC I. This narrower groove and the presence of Trp127 and Trp427 in cAC locks the dermatan substrate in an orientation that allows binding to the active site but does not allow cleavage. On the other hand, the wider active site of cABC I provides room for the dermatan substrate to re-orient during catalysis.

In the case of cAC, co-crystal structures with DS and chondroitin sulfates have been solved [31, 39]. Thus, the superimposition of these co-crystal structures with cABC I provided a guiding framework for modeling the enzyme-substrate structural complex. The orientation of both chondroitin and dermatan sulfate substrates in the cAC co-crystal structures are identical, despite the structural differences between these substrates. The closed nature of the active site groove and the parallel pyranose ring stacking interactions with the substrate provided by the bulky aromatic groups of Trp127 and Trp427 on the opposite faces of the groove act as constraints that fix the orientation of the substrate in the active site. In the case of cABC I, the active site groove is more open, and there are no tryptophan amino acids to provide a large steric hindrance to the positioning of the substrates in the active site. These structural differences in the active site of cAC and cABC I account for the broader substrate specificity of cABC I (FIG. 12). The interactions of the active site amino acids of cABC I with C4S and DS substrate are discussed below.

Interactions with C4S Substrate

Figure 13:
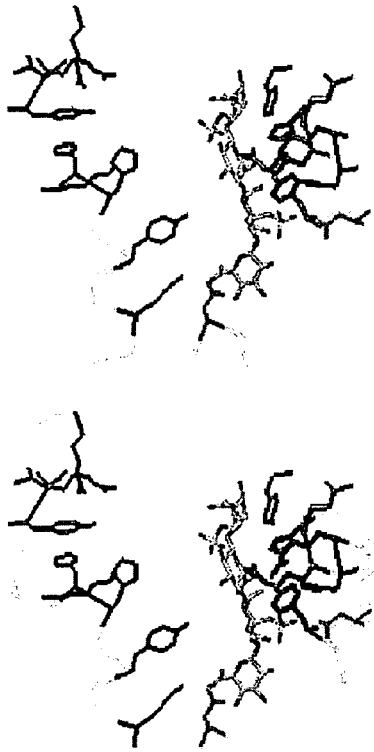
FIG. 13 depicts chondroitinase ABC I and the chondroitin-4-sulfate substrate. Shown is a stereoview of C4S substrate in the active site. The saccharide is shown as are the basic amino acids (His, Arg and Lys), acidic amino acids (Asp and Glu) and Phe. Shown is a detailed schematic of the different amino acids in the active site numbered according to the crystal structure and their proximity to the oligosaccharide.
Figure 13:
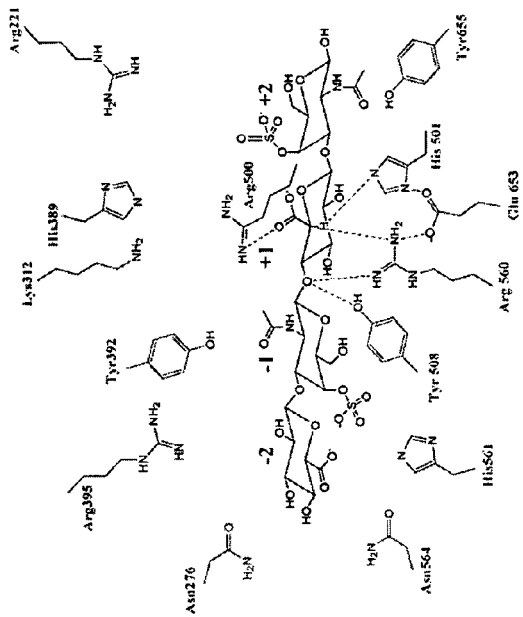

The position and orientation of C4S relative to the active site of cABC I was similar to that of the cAC co-crystal structure with the C4S substrate (FIG. 13). From the proximity of the amino acids towards the C5 proton of GlcA in the +1 subsite, His501 is positioned more favorably to abstract this proton compared to Tyr508. The close proximity between the glycosidic oxygen of the −1, +1 glycosidic bond and Tyr508 suggests that it may play a role in protonating the leaving group. Arg560 is also proximal to the glycosidic oxygen of the scissile bond and its equivalent cAC Arg288 has been implicated to play a role in protonation of the leaving group [31]. However, the Arg288Ala mutant in cAC did not completely abolish its activity [31]. Glu653 does not seem to be involved directly in the catalysis, but it is at hydrogen bonding distance with His501 and Arg560 and thus likely plays a role in positioning these residues for catalysis. The hydrogen bonding interaction of the analogous cAC Glu371 with the corresponding histidine and arginine residues has been observed in cAC and a similar role for Glu371 has been proposed. Another important step in the β-eliminative cleavage of lyases is the neutralization of the charge on the carboxyl group of the uronic acid to facilitate the abstraction of the proton. Based on our structural complex, Arg500 is positioned to interact with the carboxylate group of the uronic acid at the +1 subsite. The stabilization of the carbanion intermediate could be achieved by potential interactions of either the protonated base His501 or Arg500 or Arg560, since all of these groups are positioned to interact with the C5 carbanion on the uronic acid formed after abstraction of the α-proton.

Interactions with DS Substrate

The initial positioning of the DS substrate based on its relative orientation in the cAC active site was such that the C5 proton of the IdoA in the +1 subsite was facing away from the putative catalytic amino acids. In the cAC active site, the DS substrate is locked in this orientation due to the structural constraints imposed by the more closed active site groove and the two tryptophan amino acids. These observations are consistent with the inability of cAC to cleave DS. Rather, it has been observed that DS binds to the active site of cAC and inhibits its activity toward chondroitin substrates.

The chemical differences between IdoA in dermatan sulfate and GlcA in C4S provide further insights into differences in positioning of these substrates within the active site. While in GlcA the C5 proton and the glycosidic oxygen of the cleavable bond are in the cis orientation, in IdoA these two atoms are in the trans orientation. Since the active site amino acids involved in the proton abstraction (from C5 of uronic acid) and donation (to the glycosidic oxygen of the cleaved bond) are on the same face of the active site groove, the DS substrate would need to re-orient in order for these amino acids to cleave it. Thus, there are salient differences between the mechanism governing DS cleavage and the mechanism cABC I employs for C4S degradation.

Figure 14:
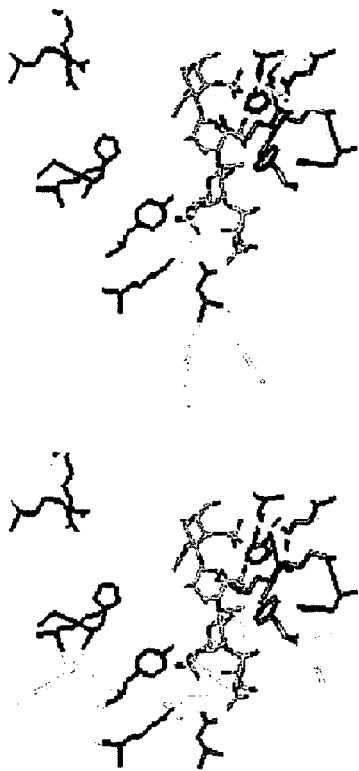
FIG. 14 depicts chondroitinase ABC I and the dermatan sulfate substrate. Shown is a stereoview of DS in the active site. Shown is a detailed schematic of the interaction between various active site amino acids and the dermatan substrate oriented optimally for proton abstraction (left) and proton donation (right). Note that the two schematics are shown for clarity. It is possible that there is a re-orientation of the substrate during catalysis.
Figure 14:
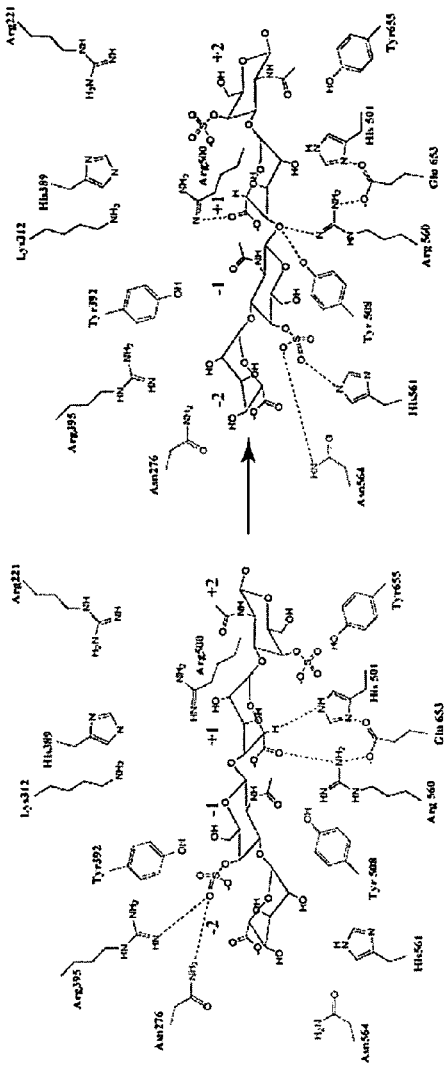
Figure 15:
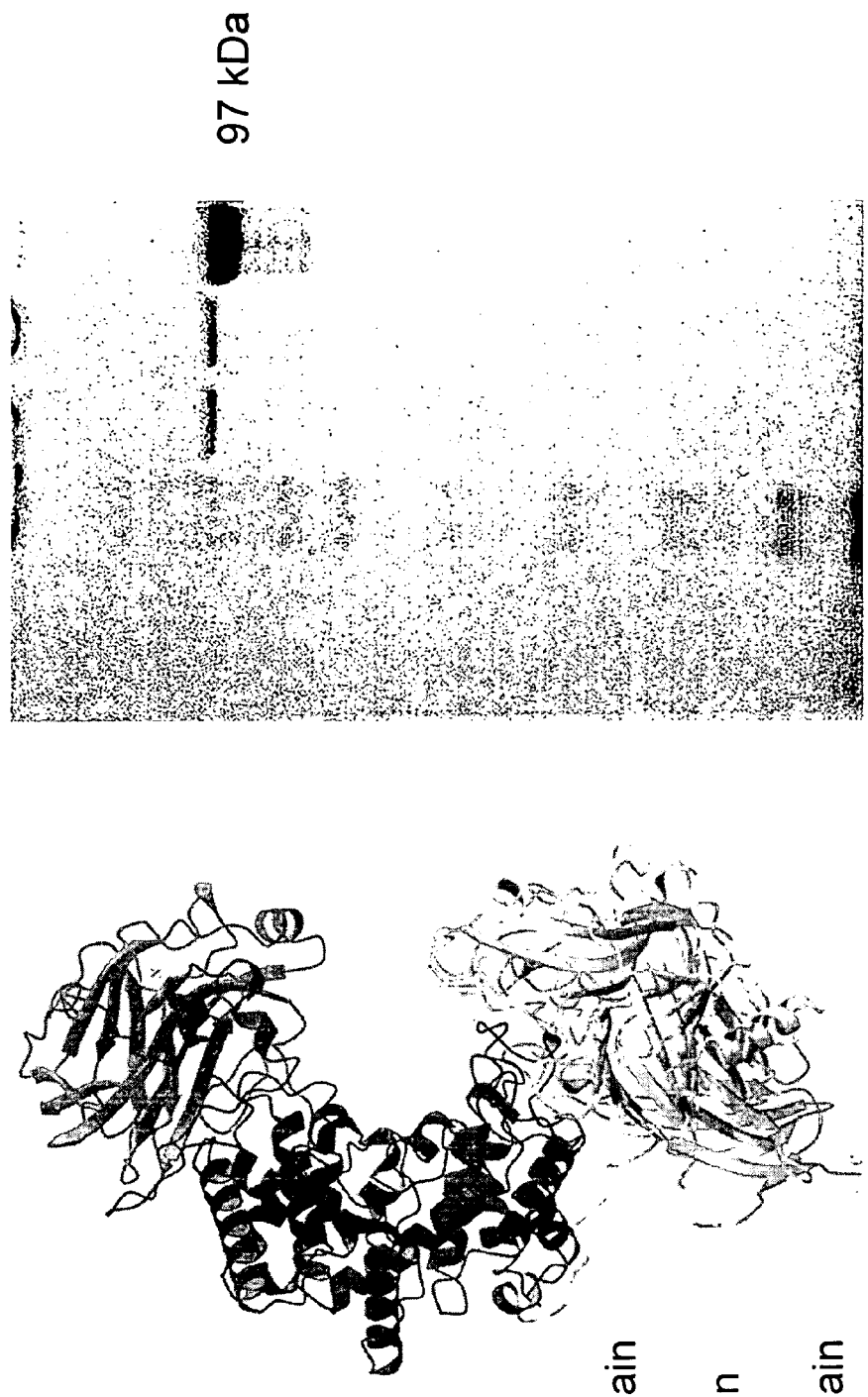
FIG. 15 provides an illustration of the structure of cABC I as well as the results from the provides the results from the purification of recombinant chondroitinase ABC I.
Figure 16:
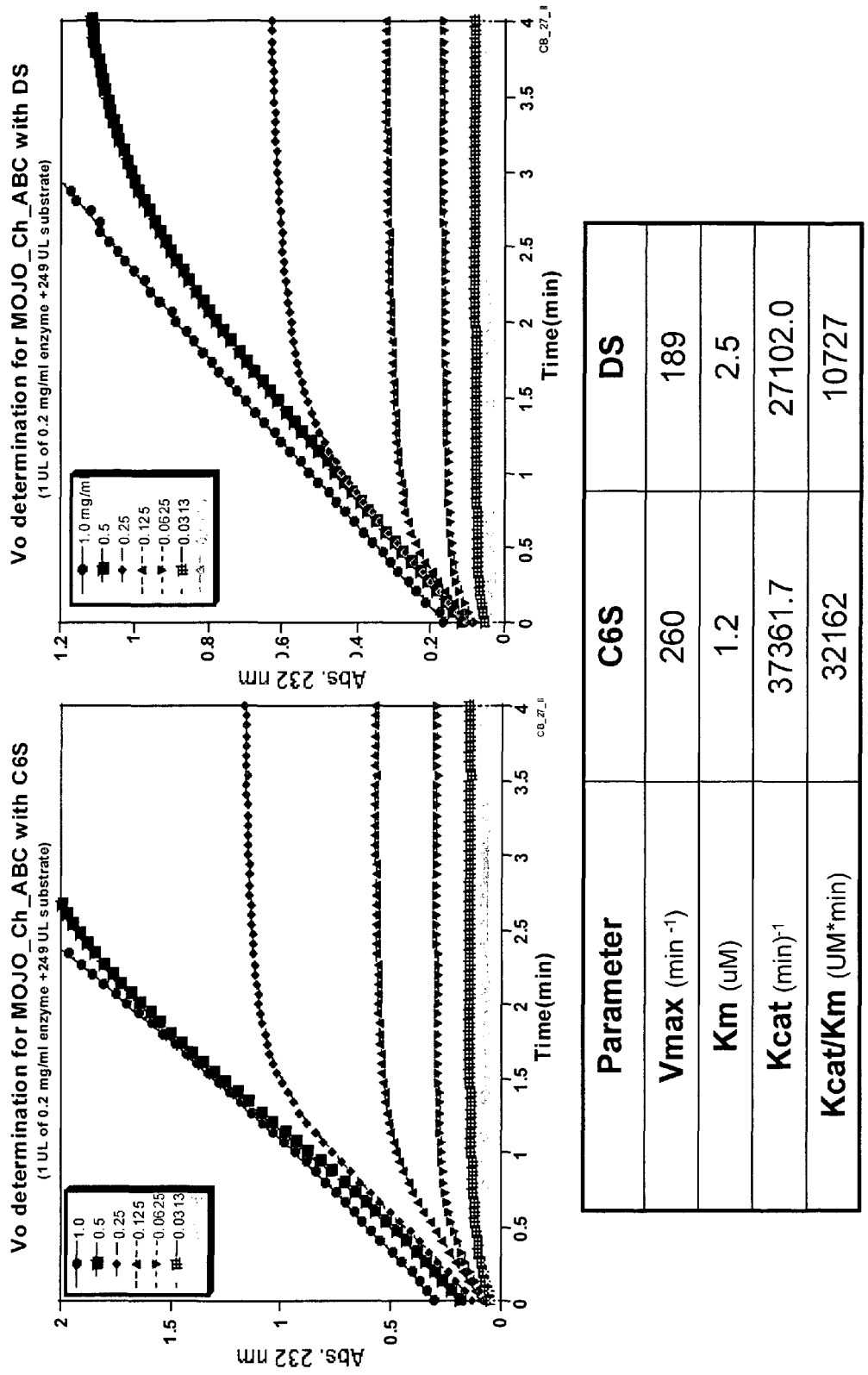
FIG. 16 provides the results from the analysis of the kinetics of recombinant cABC I on two substrates, C6S and DS.
Figure 17:
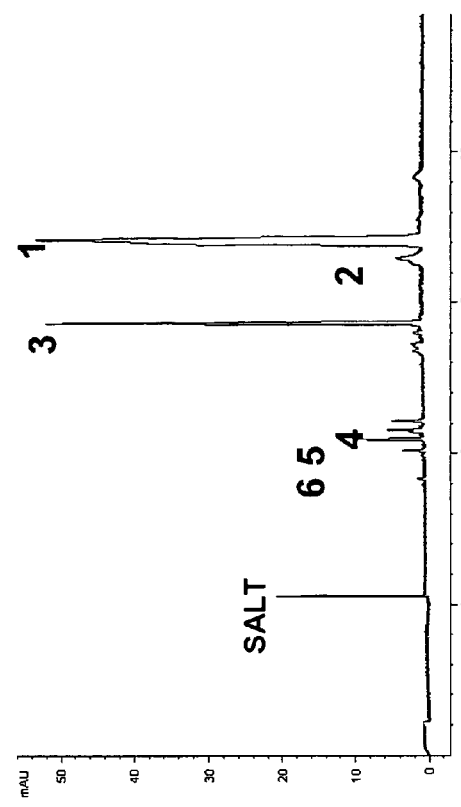
FIG. 17 provides the product profiles for the action of cABC I on two substrates, C6S and DS.
Figure 17:
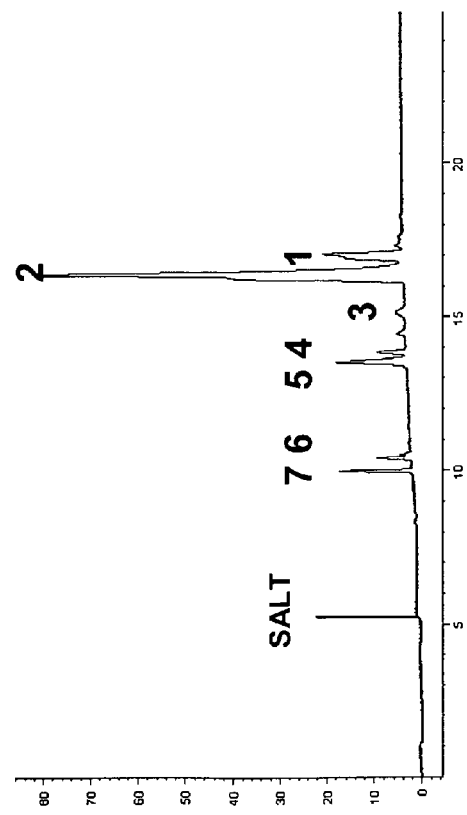
Figure 18:
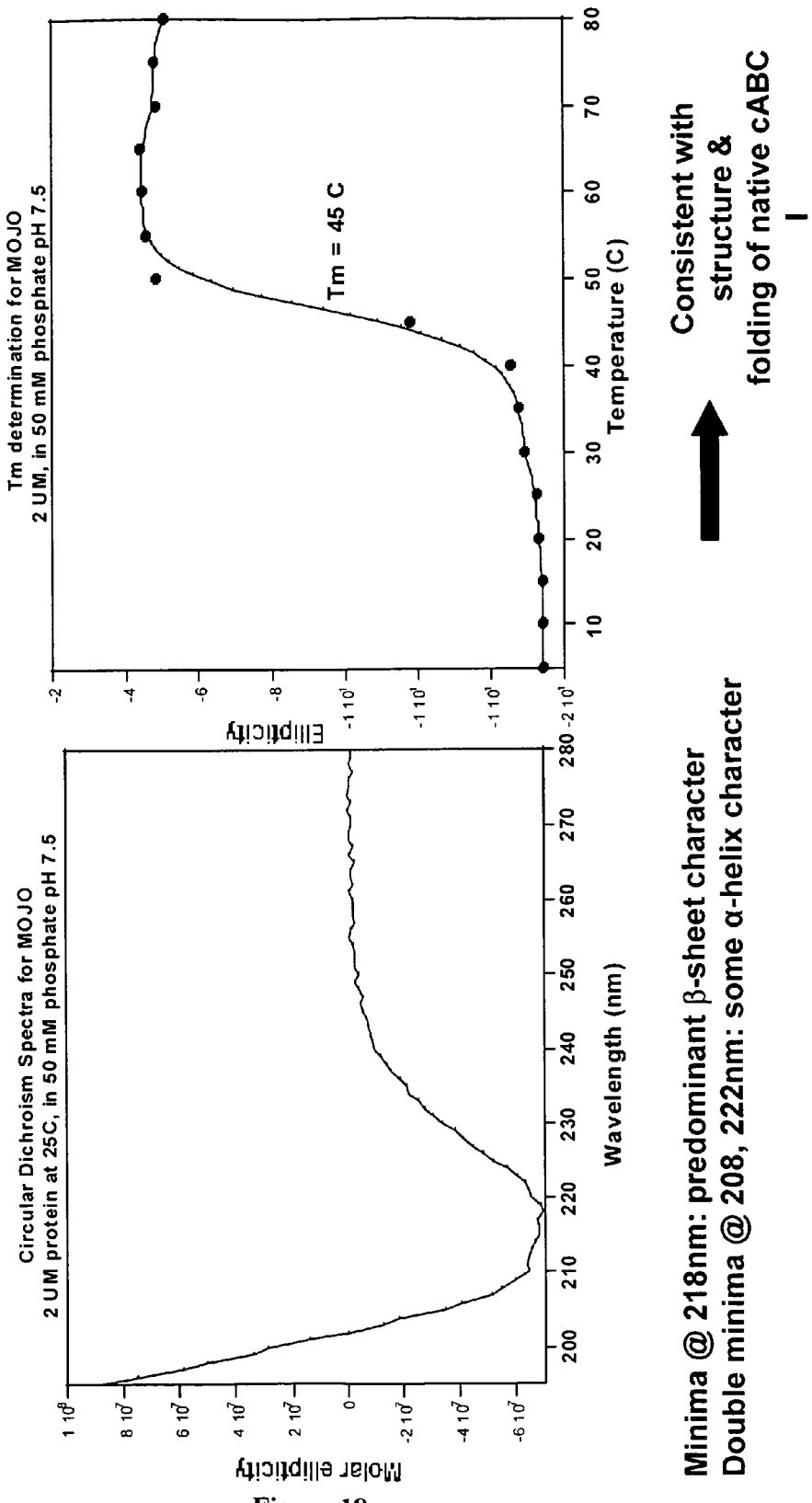
FIG. 18 provides the results of the structural characterization of recombinant cABC I. Shown are the circular dichroism spectra as well as the Tm determination.
Figure 19:
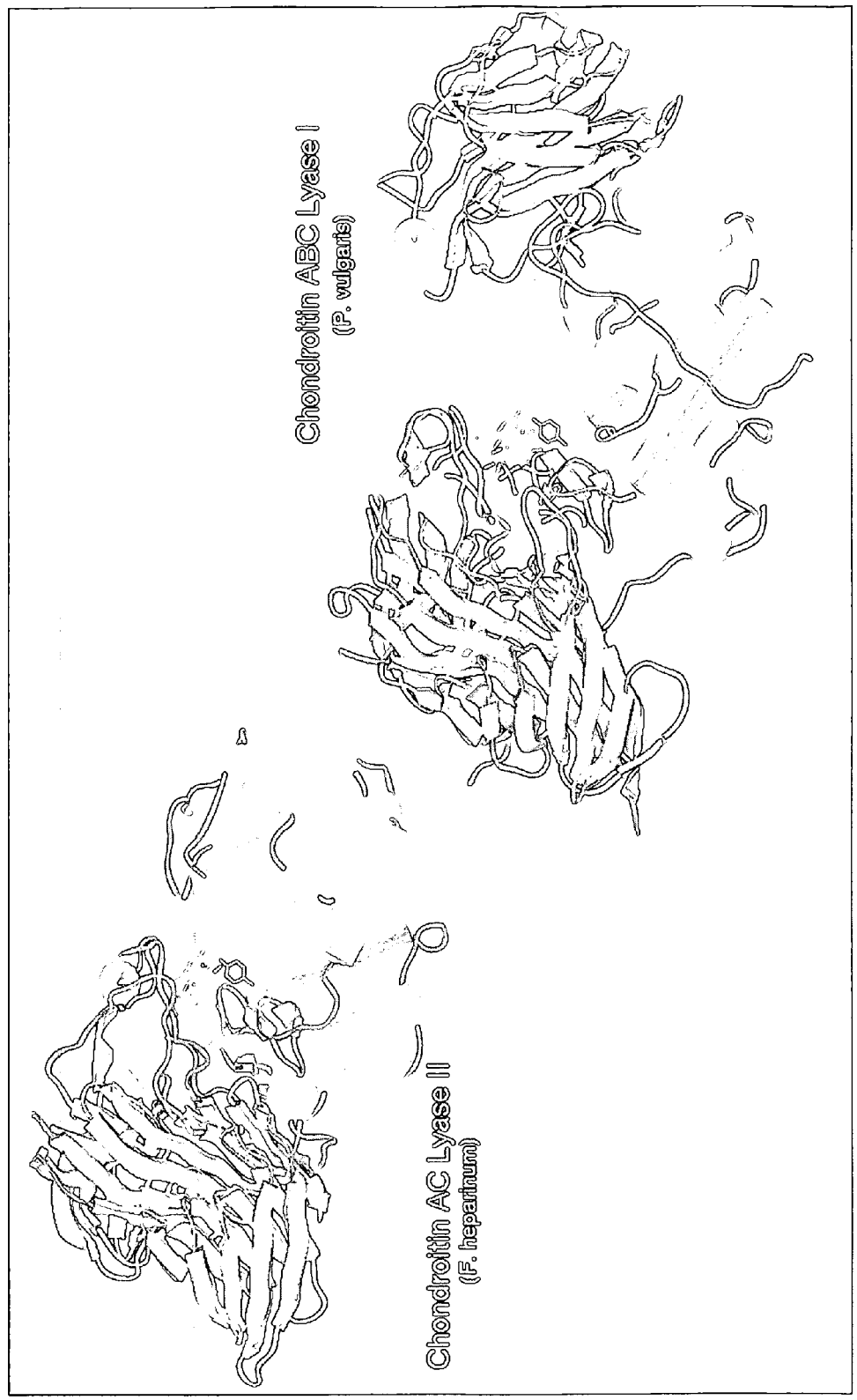
FIG. 19 shows the structures of chondroitin AC lyase II and cABC I.
Figure 20:
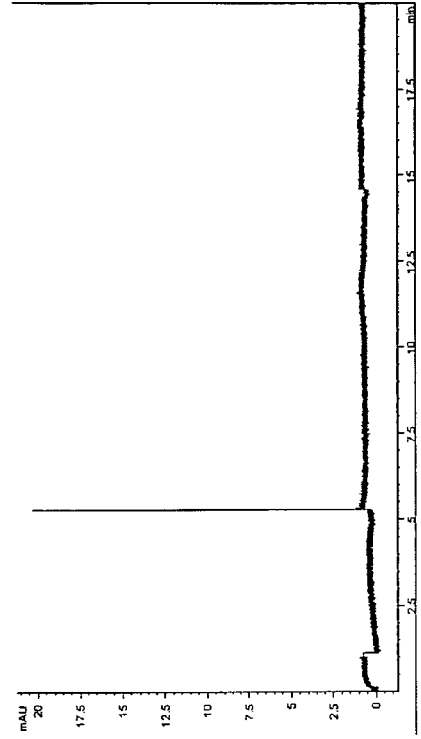
FIG. 20 shows the results from the biochemical characterization of the proposed active site. H501A, E653A, Y508A and R560A showed no activity towards C6S and DS. The product profile of H501A on DS is also shown.
Figure 21:
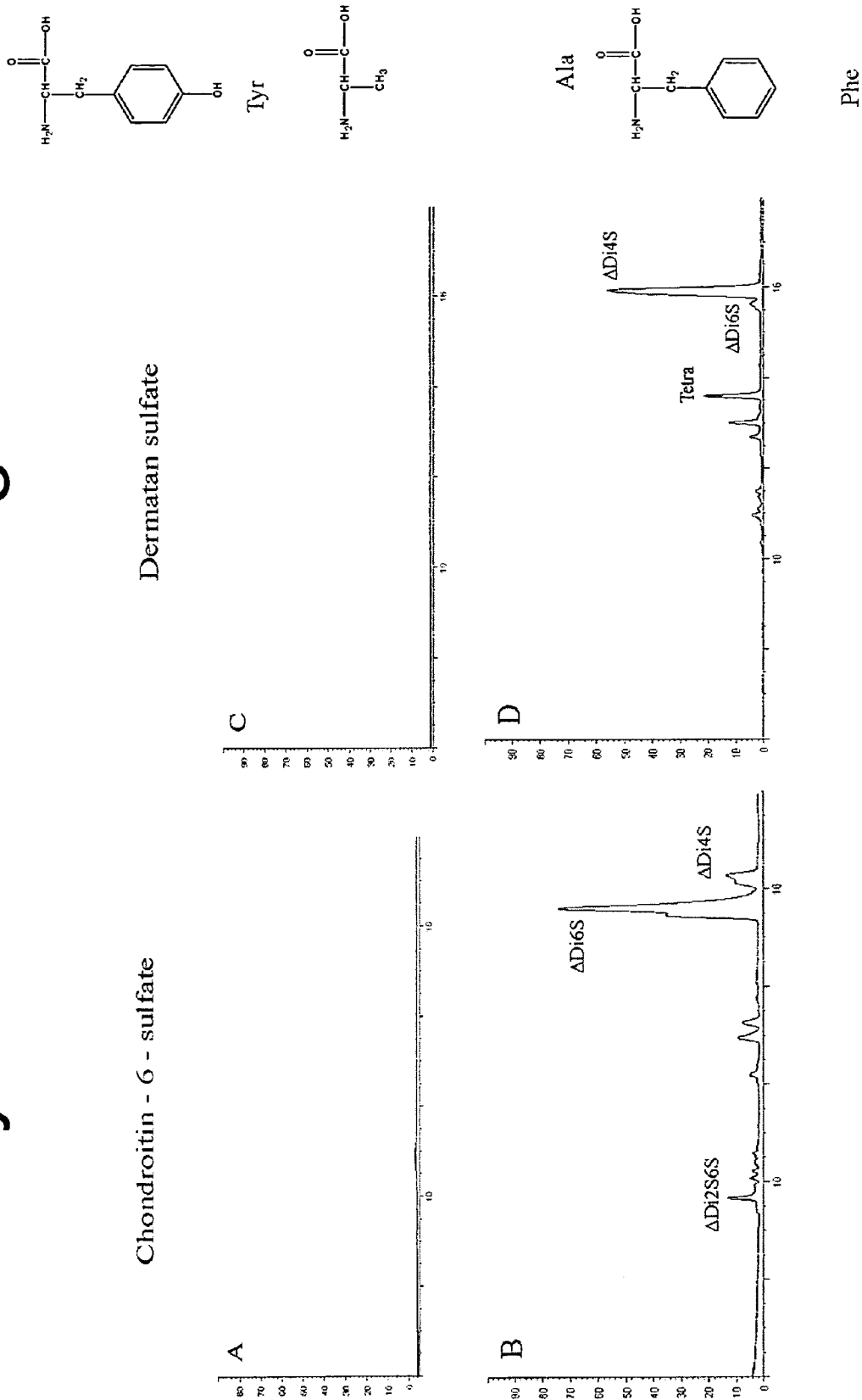
FIG. 21 shows the product profiles of tyrosine 508 mutants acting on C6S and DS.
Figure 23:
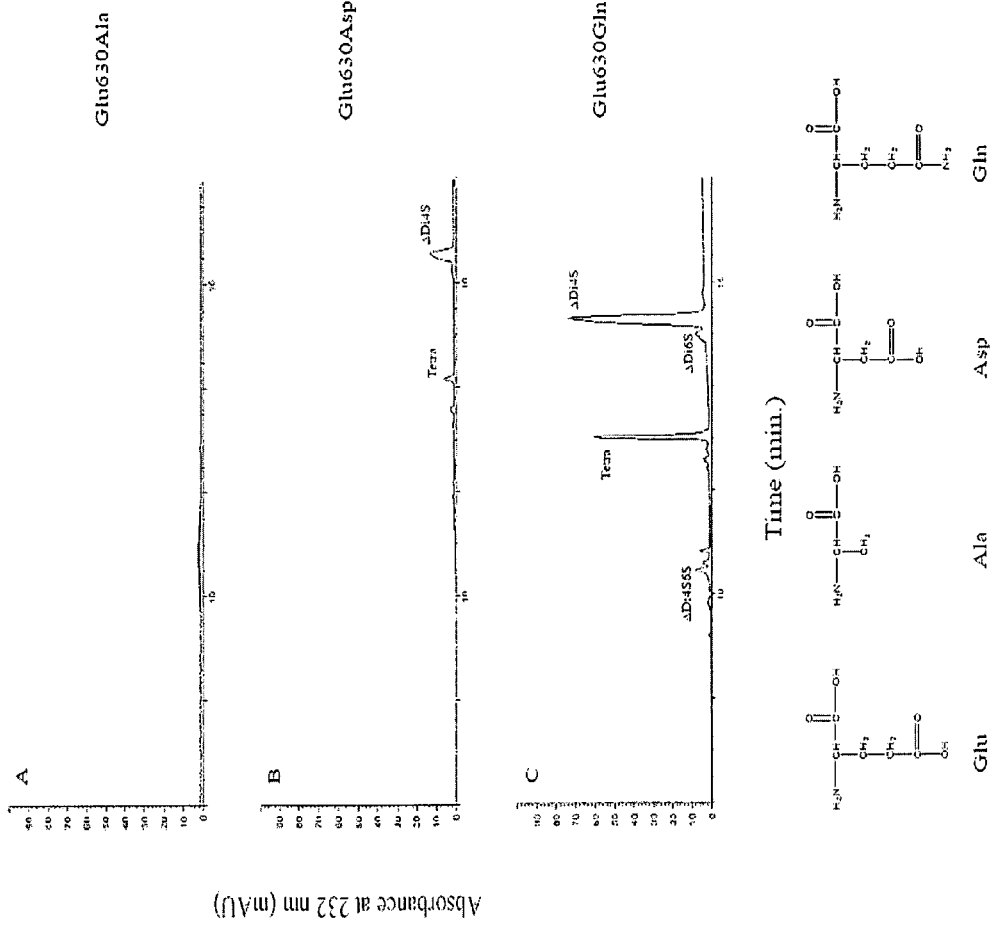
FIG. 23 provides the product profiles from the action of Glu653 mutants.

A theoretical cABC I-DS complex was constructed by docking the substrate such that the C5 proton faces the active site amino acids. Based on the model, His501 is the best candidate to serve as the general base that abstracts the C5 proton from the IdoA in the +1 subsite (FIG. 14). The positioning of the C5 proton such that it would be abstracted by His501 results in the carboxylate group of the IdoA being proximal to Arg560. Thus, Arg560 could play a role in neutralizing the charge on this group to make the C5 proton more labile (FIG. 14). It is possible that the dermatan substrate reorients itself after proton abstraction for the lone pairs of the glycosidic oxygen to face the active site Tyr508 or Arg560. The fact that Arg560 and Arg500 are on opposing sides of the substrate provide further flexibility for interaction with substrate during the proton abstraction and donation processes (FIG. 14).

Implications for the Mode of Action of cABC I

The results from the site-directed mutagenesis of the active site amino acids are consistent with observations from the theoretical enzyme-substrate structural complex. Coupled analysis of both the kinetics experiments and the investigations of product profiles by capillary electrophoresis strongly support the notion that His501 is important for the activity of cABC I on C6S, DS, and C4S. Indeed, no products were observed in any reaction involving any of these substrates with any of the His501 mutants. From this, it appears that His501 plays a central role in catalysis—the abstraction of the C5 proton from the uronic acid moiety. The proximity of Tyr508 to the C5 proton and the glycosidic oxygen in the cABC I-chondroitin structural complex suggested its potential role in protonating the leaving group. However, the Tyr508Phe mutant did produce products against both C6S and DS in the overnight digestion. This mutant retains the hydrophobic group of tyrosine but abolishes the proton donating hydroxyl group. Thus the role of Tyr508 in proton donation is less conclusive, and it can potentially be compensated for by water molecules in the active site, albeit at reduced catalytic efficiency consistent with the kinetics data. The aromatic ring of Tyr508 likely plays a role in the positioning of substrate.

Since the Glu653Ala mutant proved to be inactive against C6S, DS, and C4S, this residue is important for activity. The crystal structure of cABC I and the enzyme-substrate model reveal that Glu653 forms an hydrogen bonding network with Arg560 and His501, thus positioning these amino acids for catalysis. This role is confirmed by the product formation (in the overnight digestion) of the Glu653Asp and Glu653Gln mutants. Indeed, the relatively unchanged $K_m$ between cABC I and Glu653Gln for both C6S (Table 9) and DS (Table 10) suggests that this residue is not important for directly binding substrate. Further, the diminished protrusion of the aspartic acid hydrogen bonding sidechain as compared with the glutamic acid and glutamine sidechains is consistent with the relative order of activities (FIG. 11). Chondroitinase ADC I, with its glutamic acid at position 653, has the most effective hydrogen bonding network with which to position its catalytic neighbors, Arg560 and His501; Glu653Ala contains no hydrogen bonding capability at all. Glu653Gln has a more effective hydrogen bonding network than does Glu653Asp, which has shorter sidechain length and thus is not in close enough proximity to act effectively.

TABLE 9

Kinetic Analysis of cABC I and Mutants with C6S as Substrate[a]

| Enzyme | $K_m$ μM | $K_{cat}$ min$^{-1}$ | $K_{cat}/K_m$ μM$^{-1}$min$^{-1}$ |
|---|---|---|---|
| Chondroitinase ABC I | 1.2 ± 0.6 | 37000 ± 6500 | 31000 |
| His501Ala or Lys or Arg | na[b] | na | na |
| Tyr508Ala | na | na | na |
| Tyr508Phe | 36.4 | 31.2 | 0.9 |
| Arg560Ala | na | na | na |
| Glu653Ala or Asp | na | na | na |
| Glu653Gln | 6.1 | 1607.6 | 262.1 |
| Arg500Ala | 19.9 | 418.6 | 21.0 |

[a]Values are the mean of at least three experiments ± standard deviation.
[b]na, not available.

TABLE 10

Kinetic Analysis of cABC I and Mutants with DS as Substrate[a]

| Enzyme | $K_m$ μM | $K_{cat}$ min$^{-1}$ | $K_{cat}/K_m$ μM$^{-1}$min$^{-1}$ |
|---|---|---|---|
| Chondroitinase ABC I | 2.5 ± 0.5 | 27000 ± 2500 | 11000 |
| His501Ala or Lys or Arg | na[b] | na | na |
| Tyr508Ala | na | na | na |
| Tyr508Phe | 48.9 | 104.8 | 2.11 |
| Arg560Ala | na | na | na |
| Glu653Ala or Asp | na | na | na |
| Glu653Gln | 4.16 | 5174.8 | 1245 |
| Arg500Ala | 35.68 | 162.0 | 4.54 |

[a]Values are the mean of at least three experiments ± standard deviation.
[b]na, not available.

Arg560Ala produces no products of C6S or C4S and negligible products of DS by CE analysis. The proximity of Arg560 to the C5 atom and the glycosidic oxygen suggests that it plays a role in proton donation and/or stabilization of the carbanion intermediate following proton abstraction. It is likely to play the latter role since proton donation can be compensated via neighboring water molecules, and further, the Tyr508 is better positioned to protonate the leaving group based on the model. Arg560 could play an additional role in neutralizing the carboxylate of the IdoA in DS based on its proximity to this group in the modeled cABC I-dermatan structural complex. The structural model of the cABC I-chondrotin complex and the earlier crystal structure studies [31, 35] suggest that Arg500 is likely to neutralize the charge on the carboxylate group of GlcA in CS. However, the Arg500Ala mutant does not conclusively support this role since this mutant retains its activity towards chondroitin and dermatan substrates.

In addition to the catalytic amino acids already described, the cABC I active site contains several other basic residues. While some of these have structural analogs in the cAC and HAL co-crystal structures, there are many others which are unique to cABC I. The highly basic nature of the active site could be involved in accommodating a wide variety of substrates including C4S, C6S, DS and HA which have different charge distributions due to their differences in sulfation pattern. His561 and Asn564 are positioned to interact with the 4-O sulfate group of the GalNAc4S at the −1 subsite (present in both C4S and DS). Furthermore, several additional basic amino acids, including His388, Arg395, Arg105, Lys312, are located on the upper side of the active site cleft towards the N-terminal β-sheet domain (FIG. 12). These basic amino acids could play a role in governing the specificity of cABC I towards different substrates.

Discussion

There is accumulating evidence that implicate GalAGs in numerous biological processes ranging from cell growth and development to anticoagulation and microbial pathogenesis. Biochemical characterization of chondroitinases [GalAG depolymerizing enzymes] in terms of their catalytic mechanism and substrate specificities is important for the development of enzymatic tools for decoding structure-function relationships of GalAGs. The biochemical characterization of heparinases has been quite successful in developing these enzymes into valuable tools for the sequencing of HSGAGs [27] and in directly probing the biological roles of HSGAGs, such as in cancer [40]. Of the various chondroitinases, cABC is the enzyme with the broadest substrate specificity in terms of cleaving chondroitin and dermatan sulfates. Engineering cABC enzymes via site-directed mutagenesis provides a repertoire of mutants with fine-tuned substrate specificities. These mutants not only facilitate the structural characterization of GalAGs, but they can also be directly utilized in physiological scenarios such as nerve regeneration after spinal cord injury, thus expanding the scope of treatment strategies. While the broad substrate specificity of cABC offers the ability to engineer novel mutants of this enzyme with defined specificities, it has made it challenging to characterize the structure-function relationship of the enzyme.

GalAG lyases are believed to cleave substrate through a stepwise β-elimination mechanism [41]. The fundamental steps involved in this mechanism are proton acceptance and donation [42]. First, the substrate binds to the catalytic cleft of the enzyme and the carboxyl group on the C-5 carbon of the uronic acid moiety is neutralized. The next three features of the reaction are central: (1) the abstraction of the C-5 proton on the uronic acid moiety, causing the formation of a double bond between C-4 and C-5, (2) the stabilization of the carbanion intermediate, and (3) the protonation of the anomeric oxygen, breaking the glycosidic bond. Finally, the cleaved disaccharide is released from the active site and the catalytic residues balance protons via exchange with water.

The wealth of crystal structures of chondroitinase AC and B with different substrates and reaction products have provided structural insights into the roles of active site amino acids in governing the substrate specificity and catalytic mechanism [30, 31]. In the studies presented herein cABC I from *P. vulgaris* was cloned and recombinantly expressed, and a kinetic analysis of each of these residues mutated to alanine was conducted.

The studies presented provide the identification and defining of the roles of the active site amino acids in substrate recognition, positioning, and processing functions of the enzyme. By coupling kinetic analysis of site-directed mutants of the active site amino acids with the construction of theoretical enzyme-substrate structural complexes to interpret the effects of the mutants, the detailed roles of the 4 active site amino acids have been outlined. His501 is an important residue, as its mutants (Ala, Lys, Arg) proved null against all GalAG substrates. This residue is likely involved in proton abstraction from the uronic acid moiety of the GalAG. Though the studies with Tyr508Ala proved consistent with its acting as a general base, the Tyr508Phe mutant diminished the likelihood of this function. Tyr508Phe generated products on overnight digestion with all GalAG substrates, making it unlikely that this residue modulates such a central role in catalysis. The results suggest that Tyr508 plays a role in the positioning of substrate via hydrogen bonding with the glycosidic bond of the GalAG. Similarly, the role of Glu653 with other catalytic residues via hydrogen bonding is confirmed by the mutagenesis studies presented herein. Arg560 seems to play a part in cABC I's activity, perhaps in stabilizing the enolate intermediate through its positive charge. It also may act as the general acid in the reaction.

Mutagenesis of Arg500 was also performed, since it was previously suggested that Arg500 would be able to interact with the carboxylate group of either epimer of uronic acid, thus enabling cABC I's most remarkable ability to process both CS and DS [35]. Through its sidechain flexibility, Arg500's guanidinium group was thought to aid in charge neutralization of either uronic acid configuration. However, the results indicate that Arg500 is not crucial for the processing of GalAG substrates, since the Arg500Ala mutant did generate products in both product profile studies and kinetics assays. It may be that a number of residues are important in this charge neutralization process.

Based on the enzyme-substrate structural complexes insights into the differences in processing of chondroitin and dermatan sulfate by cABC I were obtained. The structural models suggest that the catalytic residues in cABC I are positioned to cleave chondroitin substrates more favorably than dermatan substrates. This is consistent with the kinetics of the wild-type enzyme which shows better catalytic efficiency towards chondroitin versus dermatan substrates. The enzyme-substrate structural models also revealed several other amino acids in the active site that likely play a role in substrate positioning and specificity.

REFERENCES FOR EXAMPLE 2

1 Ernst, S., Langer, R., Cooney, C. L. and Sasisekharan, R. (1995) Enzymatic degradation of glycosaminoglycans. Crit Rev Biochem Mol Biol 30, 387-444
2 Nadanaka, S. and Sugahara, K. (1997) The unusual tetrasaccharide sequence GlcA beta 1-3GalNAc(4-sulfate)beta 1-4GlcA(2-sulfate)beta 1-3GalNAc(6-sulfate) found in the hexasaccharides prepared by testicular hyaluronidase digestion of shark cartilage chondroitin sulfate D. Glycobiology 7, 253-263
3 Sugahara, K., Tanaka, Y., Yamada, S., Seno, N., Kitagawa, H., Haslam, S. M., Morris, H. R. and Dell, A. (1996) Novel sulfated oligosaccharides containing 3-O-sulfated glucuronic acid from king crab cartilage chondroitin sulfate K. Unexpected degradation by chondroitinase ABC. J Biol Chem 271, 26745-26754
4 Trowbridge, J. M. and Gallo, R. L. (2002) Dermatan sulfate: new functions from an old glycosaminoglycan. Glycobiology 12, 117R-125R
5 Sugahara, K., Mikami, T., Uyama, T., Mizuguchi, S., Nomura, K. and Kitagawa, H. (2003) Recent advances in the structural biology of chondroitin sulfate and dermatan sulfate. Curr Opin Struct Biol 13, 612-620
6 Liaw, P. C., Austin, R. C., Fredenburgh, J. C., Stafford, A. R. and Weitz, J. I. (1999) Comparison of heparin- and dermatan sulfate-mediated catalysis of thrombin inactivation by heparin cofactor II. J Biol Chem 274, 27597-27604
7 Fernandez, J. A., Petaja, J. and Griffin, J. H. (1999) Dermatan sulfate and LMW heparin enhance the anticoagulant action of activated protein C. Thromb Haemost 82, 1462-1468
8 Iozzo, R. V. (1997) The family of the small leucine-rich proteoglycans: key regulators of matrix assembly and cellular growth. Crit Rev Biochem Mol Biol 32, 141-174
9 Tumova, S., Woods, A. and Couchman, J. R. (2000) Heparan sulfate chains from glypican and syndecans bind the Hep II domain of fibronectin similarly despite minor structural differences. J Biol Chem 275, 9410-9417
10 Schmidt, G., Robenek, H., Harrach, B., Glossl, J., Nolte, V., Hormann, H., Richter, H. and Kresse, H. (1987) Interaction of small dermatan sulfate proteoglycan from fibroblasts with fibronectin. J Cell Biol 104, 1683-1691
11 Walker, A. and Gallagher, J. T. (1996) Structural domains of heparan sulphate for specific recognition of the C-terminal heparin-binding domain of human plasma fibronectin (HEPII). Biochem J 317 (Pt 3), 871-877
12 Elefteriou, F., Exposito, J. Y., Garrone, R. and Lethias, C. (2001) Binding of tenascin-X to decorin. FEBS Lett 495, 44-47
13 Yamaguchi, Y., Mann, D. M. and Ruoslahti, E. (1990) Negative regulation of transforming growth factor-beta by the proteoglycan decorin. Nature 346, 281-284
14 Hildebrand, A., Romaris, M., Rasmussen, L. M., Heinegard, D., Twardzik, D. R., Border, W. A. and Ruoslahti, E. (1994) Interaction of the small interstitial proteoglycans biglycan, decorin and fibromodulin with transforming growth factor beta. Biochem J 302 (Pt 2), 527-534
15 Lyon, M., Deakin, J. A., Mizuno, K., Nakamura, T. and Gallagher, J. T. (1994) Interaction of hepatocyte growth factor with heparan sulfate. Elucidation of the major heparan sulfate structural determinants. J Biol Chem 269, 11216-11223
16 Lyon, M., Deakin, J. A., Rahmoune, H., Fernig, D. G., Nakamura, T. and Gallagher, J. T. (1998) Hepatocyte growth factor/scatter factor binds with high affinity to dermatan sulfate. J Biol Chem 273, 271-278
17 Mascellani, G., Liverani, L., Bianchini, P., Parma, B., Torri, G., Bisio, A., Guerrini, M. and Casu, B. (1993) Structure and contribution to the heparin cofactor II-mediated inhibition of thrombin of naturally oversulphated sequences of dermatan sulphate. Biochem J 296 (Pt 3), 639-648
18 Maimone, M. M. and Tollefsen, D. M. (1991) Structure of a dermatan sulfate hexasaccharide that binds to heparin cofactor II with high affinity. J Biol Chem 266, 14830
19 Denholm, E. M., Lin, Y. Q. and Silver, P. J. (2001) Anti-tumor activities of chondroitinase AC and chondroitinase B: inhibition of angiogenesis, proliferation and invasion. Eur J Pharmacol 416, 213-221
20 Iozzo, R. V. and Cohen, I. (1993) Altered proteoglycan gene expression and the tumor stroma. Experientia 49, 447-455
21 Makatsori, E., Lamari, F. N., Theocharis, A. D., Anagnostides, S., Hjerpe, A., Tsegenidis, T. and Karamanos, N. K. (2003) Large matrix proteoglycans, versican and perlecan, are expressed and secreted by human leukemic monocytes. Anticancer Res 23, 3303-3309
22 Papadas, T. A., Stylianou, M., Mastronikolis, N. S., Papageorgakopoulou, N., Skandalis, S., Goumas, P., Theocharis, D. A. and Vynios, D. H. (2002) Alterations in the content and composition of glycosaminoglycans in human laryngeal carcinoma. Acta Otolaryngol 122, 330-337
23 Vicente, C. P., Zancan, P., Peixoto, L. L., Alves-Sa, R., Araujo, F. S., Mourao, P. A. and Pavao, M. S. (2001)

Unbalanced effects of dermatan sulfates with different sulfation patterns on coagulation, thrombosis and bleeding. Thromb Haemost 86, 1215-1220

24 Gandra, M., Cavalcante, M. and Pavao, M. (2000) Anticoagulant sulfated glycosaminoglycans in the tissues of the primitive chordate Styela plicata (Tunicata). Glycobiology 10, 1333-1340

25 Rhomberg, A. J., Ernst, S., Sasisekharan, R. and Biemann, K. (1998) Mass spectrometric and capillary electrophoretic investigation of the enzymatic degradation of heparin-like glycosaminoglycans. Proc Natl Acad Sci U S A 95, 4176-4181

26 Guerrini, M., Raman, R., Venkataraman, G., Torri, G., Sasisekharan, R. and Casu, B. (2002) A novel computational approach to integrate NMR spectroscopy and capillary electrophoresis for structure assignment of heparin and heparan sulfate oligosaccharides. Glycobiology 12, 713-719

27 Venkataraman, G., Shriver, Z., Raman, R. and Sasisekharan, R. (1999) Sequencing complex polysaccharides. Science 286, 537-542

28 Ernst, S., Rhomberg, A. J., Biemann, K. and Sasisekharan, R. (1998) Direct evidence for a predominantly exolytic processive mechanism for depolymerization of heparin-like glycosaminoglycans by heparinase I. Proc Natl Acad Sci U S A 95, 4182-4187

29 Pojasek, K., Shriver, Z., Kiley, P., Venkataraman, G. and Sasisekharan, R. (2001) Recombinant expression, purification, and kinetic characterization of chondroitinase AC and chondroitinase B from *Flavobacterium heparinum*. Biochem Biophys Res Commun 286, 343-351

30 Huang, W., Matte, A., Li, Y., Kim, Y. S., Linhardt, R. J., Su, H. and Cygler, M. (1999) Crystal structure of chondroitinase B from *Flavobacterium heparinum* and its complex with a disaccharide product at 1.7 A resolution. J Mol Biol 294, 1257-1269

31 Huang, W., Boju, L., Tkalec, L., Su, H., Yang, H. O., Gunay, N. S., Linhardt, R. J., Kim, Y. S., Matte, A. and Cygler, M. (2001) Active site of chondroitin AC lyase revealed by the structure of enzyme-oligosaccharide complexes and mutagenesis. Biochemistry 40, 2359-2372

32 Michel, G., Pojasek, K., Li, Y., Sulea, T., Linhardt, R. J., Raman, R., Prabhakar, V., Sasisekharan, R. and Cygler, M. (2004) The structure of chondroitin B lyase complexed with glycosaminoglycan oligosaccharides unravels a calcium-dependent catalytic machinery. J Biol Chem 279, 32882-32896

34 Bradbury, E. J., Moon, L. D., Popat, R. J., King, V. R., Bennett, G. S., Patel, P. N., Fawcett, J. W. and McMahon, S. B. (2002) Chondroitinase ABC promotes functional recovery after spinal cord injury. Nature 416, 636-640

35 Huang, W., Lunin, V. V., Li, Y., Suzuki, S., Sugiura, N., Miyazono, H. and Cygler, M. (2003) Crystal structure of *Proteus vulgaris* chondroitin sulfate ABC lyase I at 1.9A resolution. J Mol Biol 328, 623-634

36 Pojasek, K., Raman, R., Kiley, P., Venkataraman, G. and Sasisekharan, R. (2002) Biochemical characterization of the chondroitinase B active site. J Biol Chem 277, 31179-31186

37 Hamai, A., Hashimoto, N., Mochizuki, H., Kato, F., Makiguchi, Y., Horie, K. and Suzuki, S. (1997) Two distinct chondroitin sulfate ABC lyases. An endoeliminase yielding tetrasaccharides and an exoeliminase preferentially acting on oligosaccharides. J Biol Chem 272, 9123-9130

38 Sato, N., Shimada, M., Nakajima, H., Oda, H. and Kimura, S. (1994) Cloning and expression in *Escherichia coli* of the gene encoding the *Proteus vulgaris* chondroitin ABC lyase. Appl Microbiol Biotechnol 41, 39-46

39 Lunin, V. V., Li, Y., Linhardt, R. J., Miyazono, H., Kyogashima, M., Kaneko, T., Bell, A. W. and Cygler, M. (2004) High-resolution crystal structure of Arthrobacter aurescens chondroitin AC lyase: an enzyme-substrate complex defines the catalytic mechanism. J Mol Biol 337, 367-386

40 Liu, D., Shriver, Z., Venkataraman, G., El Shabrawi, Y. and Sasisekharan, R. (2002) Tumor cell surface heparan sulfate as cryptic promoters or inhibitors of tumor growth and metastasis. Proc Natl Acad Sci U S A 99, 568-573

41 Gerlt, J. A. and Gassman, P. G. (1993) Understanding the rates of certain enzyme-catalyzed reactions: proton abstraction from carbon acids, acyl-transfer reactions, and displacement reactions of phosphodiesters. Biochemistry 32, 11943-11952

42 Jedrzejas, M. J. (2000) Structural and functional comparison of polysaccharide-degrading enzymes. Crit Rev Biochem Mol Biol 35, 221-251

Example 3

Materials and Methods

Determination of Effect of Divalents on Recombinant cABC I Activity

For these studies, C6S and DS were dissolved at a 1 mg/mL concentration in 50 mM Tris pH 8.0 (no salt) containing a fixed concentration (10 mM) of different divalent ion salts ($Ca^{2+}$, $Mg^{2+}$, $Mn^{2+}$, $Zn^{2+}$). Recombinant cABC I (0.2 µg) was added to each of these solutions, and the activity of the enzyme was assessed based on the change in absorbance at 232 nm ($A_{232}$/minute). These experiments were carried out on a SpectraMax 190 (Molecular Devices) using a 96 well quartz plate. The temperature was set at 37° C. for these experiments, and enzyme activity was calculated based on the initial rate of product formation.

Results

Table 11 provides an activity summary of wildtype cABC1 and cABC1 mutants.

TABLE 11

Activity Summary of cABC I Wildtype and Mutants

| Enzyme | C6S | Capillary Electrophoresis DS | C4S |
| --- | --- | --- | --- |
| WILDTYPE | + | + | + |
| H501A | − | − | − |
| Y508A | − | − | − |
| R560A | − | mod | − |
| E653A | − | − | − |
| R500A | + | partial | + |
| H388A | + | − | + |
| H389A | + | − | + |
| H501K | − | − | − |
| H501R | − | − | − |
| Y508F | + | + | + |
| R560K | − | + | − |
| E653D | + | low | + |
| E653Q | + | + | + |
| H388K | + | − | + |
| H389K | + | + | + |
| H388R | + | − | + |
| H389R | + | − | + |

Figure 26:
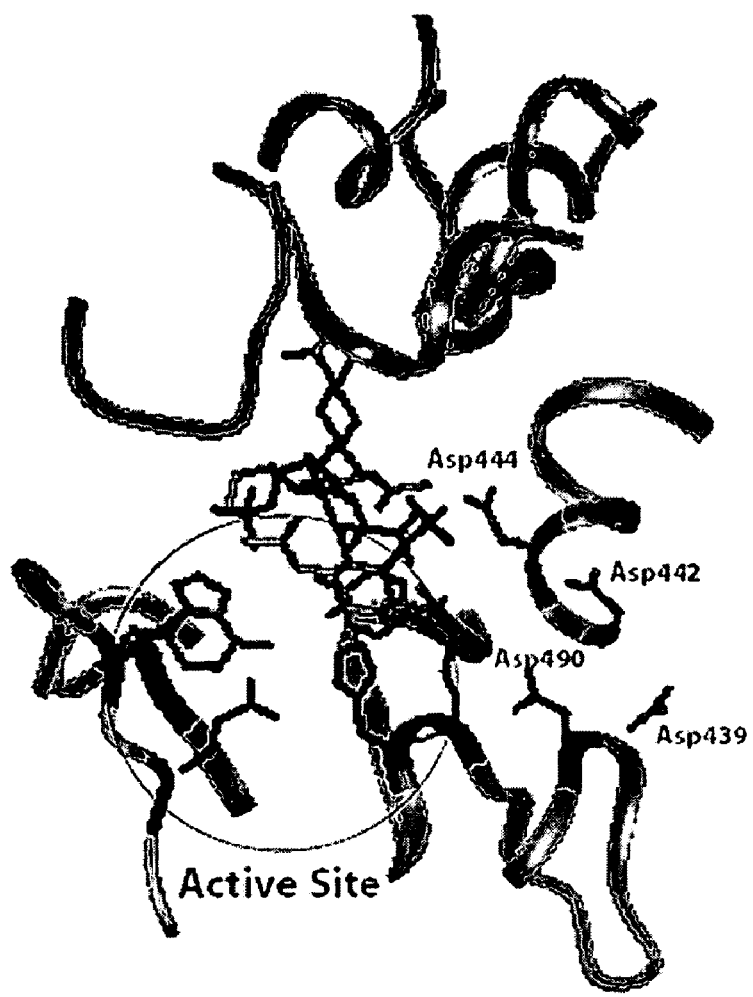
FIG. 26 provides a schematic depicting the calcium coordination motif.

FIG. 26 provides a schematic depicting the calcium coordination motif. The effect of different divalents on the activity of cABC I on chondroitin-6-sulfate and dermatan sulfate was assessed. With C6S as the substrate there was no apparent change in enzyme activity upon addition of calcium, magnesium or manganese. The addition of zinc appeared to have an inhibitory effect as reported previously. Interestingly, the activity of cABC I on dermatan sulfate increased drastically in the presence of added calcium and magnesium, when compared to the control (1 mg/mL DS in 50 mM Tris pH 8.0). The presence of zinc was again found to be inhibitory.

In order to further understand the role of calcium in the selective enhancement of cABC I activity towards DS, the calcium concentration at which maximal activity was observed was evaluated. For these calcium titration experiments the same experimental set-up was used and the concentration of added $CaCl_2$ was varied from 0-20 mM. The data clearly indicated that maximum activity was obtained at 10 mM $CaCl_2$.

Figure 27:
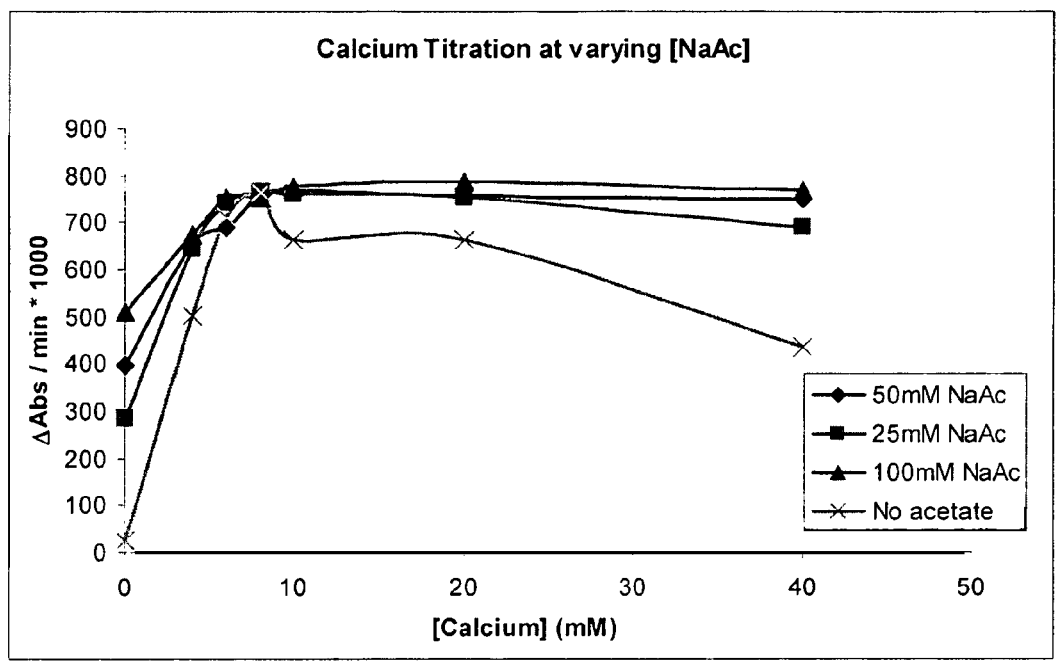
FIG. 27 provides the results of the calcium titration experiment.

It is important to note that the initial experiments with added calcium were done in the absence of any additional salt in the buffer; therefore, it was ascertained that the enhancement observed for DS processing is not just due to a salt effect. To address this a comparison of the activity of the enzyme on DS in presence of an optimal amount of sodium acetate and varying the calcium concentration was performed. Dermatan sulfate at a 1 mg/mL concentration was dissolved in 50 mM Tris pH 8.0 buffer containing 25 mM, 50 mM or 100 mM sodium acetate. Using each of these as starting solutions the calcium titration experiment was repeated by adding various amounts of $CaCl_2$ (0-20 mM). FIG. 27 shows that the rate enhancement observed upon the addition of 10 mM $CaCl_2$ still exceeds that observed when using the optimum salt concentration (100 mM sodium acetate). The results also indicate that the maximum enhancement observed is constant at 10 mM calcium irrespective of the sodium acetate content in the starting buffer. This is probably an indication that the effect of calcium is independent from a salt effect.

Based on these observations a kinetic analysis of cABC I processing on DS in the presence and absence of 10 mM $CaCl_2$ was also performed. The kinetic parameters of cABC I with and without calcium were as follows:

with 10 mM calcium chloride
$K_m$=3.53 mM
$k_{cat}$=33183.91 $min^{-1}$
without calcium
$K_m$=1.42 mM
$k_{cat}$=17237.07 $min^{-1}$ Four aspartic acid residues were probed as players in a potential calcium coordination motif. D439 (likely played the part of a "control" for the studies). D442, D444, and D490 were individually mutated to alanine. The results of an activity study are provided below in Table 12.

TABLE 12

MOJO Calcium Coordination Mutants: Activity Assessments (units are raw readouts)

|  | MOJO (0.2 μg) | D439A (5.0 μg) | D442A (5.0 μg) | D444A (5.0 μg) | D490A (5.0 μg) |
|---|---|---|---|---|---|
| 1 mg/ml DS 50 mM NaAC | 458 | 4126 | 115.5 | −2.07 | 23 |
| 1 mg/ml DS 50 mM NaAC 10 mM Calcium | 768 | 3661 | 86.5 | 0.79 | 19 |
| 1 mg/ml DS 50 mM NaAC 10 mM Calcium 10 mM EDTA | 365 | 3162 | 127 | −5.7 | 59 |

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference.

We claim:

1. A method of degrading a glycosaminoglycan or galactosaminoglycan, comprising: contacting the glycosaminoglycan or galactosaminoglycan with a modified chondroitinase ABC I in an amount effective to degrade the glycosaminoglycan or galactosaminoglycan, wherein the modified chondroitinase ABC I comprises the amino acid sequence of the native chondroitinase ABC I encoded by the nucleic acid sequence of SEQ ID NO: 1, wherein at least one substrate specific residue has been substituted with a different amino acid than in the native chondroitinase ABC I, and wherein the nucleic acid that encodes the modified chondroitinase ABC I is at least 90% homologous to the nucleic acid of SEQ ID NO: 1, and wherein the amino acid sequence of the modified chondroitinase ABC I is not the amino acid sequence of any of SEQ ID NOs: 3-24, wherein the at least one substrate specific residue is the residue at position 105, 221, 312, 388, 389, 392, 395, 500, 501, 508, 560 or 653 which corresponds to the residue at position 82, 198, 289, 365, 366, 369, 372, 477, 478, 485, 537 or 630 of the native chondroitinase ABC I of SEQ ID NO: 2.

2. The method of claim 1, wherein the residue at position 221 has been substituted with alanine, lysine, methionine or glutamine.

3. The method of claim 1, wherein the residue at position 312 has been substituted with alanine.

4. The method of claim 1, wherein the residue at position 388 has been substituted with alanine, lysine or arginine.

5. The method of claim 1, wherein the residue at position 389 has been substituted with alanine, lysine or arginine.

6. The method of claim 1, wherein the residue at position 392 has been substituted with alanine or phenylalanine.

7. The method of claim 1, wherein the residue at position 500 has been substituted with alanine, cysteine or glutamine.

8. The method of claim 1, wherein the residue at position 501 has been substituted with alanine, lysine or arginine.

9. The method of claim 1, wherein the residue at position 508 has been substituted with phenylalanine.

10. The method of claim 1, wherein the residue at position 560 has been substituted with alanine or lysine.

11. The method of claim 1, wherein the residue at position 653 has been substituted with alanine, aspartic acid or glutamine.

12. The method of claim 1, wherein a glycosaminoglycan is contacted.

13. The method of claim 1, wherein a galactosaminoglycan is contacted.

14. The method of claim 1, wherein the substituted amino acid is a conservative amino acid substitution.

15. The method of claim 1, wherein the modified chondroitinase ABC I is a substantially purified recombinant form.

16. The method of claim 1, wherein the modified chondroitinase ABC I has a $k_{cat}$ or $K_M$ value for a substrate that is at least 10% different than a native chondroitinase ABC I $k_{cat}$ or $K_M$ value.

17. The method of claim 16, wherein the modified chondroitinase ABC I $k_{cat}$ or $K_M$ value is at least 20% different than a native chondroitinase ABC I $k_{cat}$ or $K_M$ value.

18. The method of claim 17, wherein the modified chondroitinase ABC I $k_{cat}$ or $K_M$ value is at least 50% different than a native chondroitinase ABC I $k_{cat}$ or $K_M$ value.

19. The method of claim 16, wherein the substrate is a glycosaminoglycan.

20. The method of claim 16, wherein the substrate is a galactosaminoglycan.

21. The method of claim 1, wherein the nucleic acid that encodes the modified chondroitinase ABC I is at least 95% homologous to the nucleic acid of the native chondroitinase ABC I.

22. The method of claim 21, wherein the nucleic acid that encodes the modified chondroitinase ABC I is at least 97% homologous to the nucleic acid of the native chondroitinase ABC I.

23. The method of claim 22, wherein the nucleic acid that encodes the modified chondroitinase ABC I is at least 99% homologous to the nucleic acid of the native chondroitinase ABC I.

24. The method of claim 1, wherein the modified chondroitinase ABC I selectively degrades chondroitin sulfate or dermatan sulfate.

25. The method of claim 24, wherein the residue at position 388 has been substituted with alanine, lysine or arginine.

26. The method of claim 24, wherein the residue at position 389 has been substituted with alanine, lysine or arginine.

27. The method of claim 24, wherein the residue at position 500 has been substituted with alanine.

28. The method of claim 24, wherein the residue at position 653 has been substituted with alanine, lysine or arginine.

29. The method of claim 1, wherein the modified chondroitinase ABC I selectively degrades dermatan sulfate.

30. The method of claim 29, wherein the residue at position 560 has been substituted with alanine or lysine.

31. The method of claim 1, wherein the modified chondroitinase ABC I selectively degrades chondroitin 6-sulfate or chondroitin 4-sulfate.

32. The method of claim 31, wherein the residue at position 500 has been substituted with cysteine or lysine.

33. The method of claim 1, wherein the modified chondroitinase ABC I selectively degrades chondroitin 4-sulfate.

34. The method of claim 33, wherein the residue at position 221 has been substituted with alanine.

35. The method of claim 33, wherein the residue at position 500 has been substituted with glutamine.

* * * * *

UNITED STATES PATENT AND TRADEMARK OFFICE
CERTIFICATE OF CORRECTION

| | |
|---|---|
| PATENT NO. | : 8,338,119 B2 |
| APPLICATION NO. | : 11/638318 |
| DATED | : December 25, 2012 |
| INVENTOR(S) | : Vikas Prabhakar et al. |

It is certified that error appears in the above-identified patent and that said Letters Patent is hereby corrected as shown below:

At Column 1, Line 17, "GOVERNMENT SUPPORT" should read:

"This invention was made with government support under Grant No. R01 GM057073 awarded by the National Institutes of Health. The government has certain rights in the invention."

Signed and Sealed this
Twelfth Day of March, 2013

Teresa Stanek Rea
*Acting Director of the United States Patent and Trademark Office*

SEQUENCE LISTING

```
<160> NUMBER OF SEQ ID NOS: 77

<210> SEQ ID NO 1
<211> LENGTH: 2997
<212> TYPE: DNA
<213> ORGANISM: Proteus vulgaris

<400> SEQUENCE: 1
atggccacca gcaatcctgc atttgatcct aaaaatctga tgcagtcaga aatttaccat      60
tttgcacaaa ataacccatt agcagacttc tcatcagata aaaactcaat actaacgtta     120
tctgataaac gtagcattat gggaaaccaa tctcttttat ggaaatggaa aggtggtagt     180
agctttactt tacataaaaa actgattgtc cccaccgata aagaagcatc taaagcatgg     240
ggacgctcat ctaccccgt tttctcattt tggctttaca atgaaaaacc gattgatggt      300
tatcttacta tcgatttcgg agaaaaactc atttcaacca gtgaggctca ggcaggcttt     360
aaagtaaaat tagatttcac tggctggcgt actgtgggag tctctttaaa taacgatctt     420
gaaaatcgag agatgaccct aaatgcaacc aatacctcct ctgatggtac tcaagacagc     480
```

```
attgggcgtt ctttaggtgc taaagtcgat agtattcgtt ttaaagcgcc ttctaatgtg    540
agtcagggtg aaatctatat cgaccgtatt atgttttctg tcgatgatgc tcgctaccaa    600
tggtctgatt atcaagtaaa aactcgctta tcagaacctg aaattcaatt tcacaacgta    660
aagccacaac tacctgtaac acctgaaaat ttagcggcca ttgatcttat ccgccaacgt    720
ctaattaatg aatttgtcgg aggtgaaaaa gagacaaacc tcgcattaga agagaatatc    780
agcaaattaa aaagtgattt cgatgctctt aatattcaca ctttagcaaa tggtggaacg    840
caaggcagac atctggtcac tgataaacaa atcattattt atcaaccaga gaatcctaac    900
tctcaagata aacaactatt tgataattat gttattttag gtaattacac gacattaatg    960
tttaatatta gccgtgctta tgtgctggaa aaagatccca cacaaaaggc gcaactaaag   1020
cagatgtact tattaatgac aaagcattta ttagatcaag gctttgttaa agggagtgct   1080
ttagtgacaa cccatcactg gggatacagt tctcgttggt ggtatatttc cacgttatta   1140
atgtctgatg cactaaaaga agcgaaccta caaactcaag tttatgattc attactgtgg   1200
tattcacgtg agtttaaaag tagttttgat atgaaagtaa gtgctgatag ctctgatcta   1260
gattatttca atacccttatc tcgccaacat ttagccttat tactactaga gcctgatgat   1320
caaaagcgta tcaacttagt taatactttc agccattata tcactggcgc attaacgcaa   1380
gtgccaccgg gtggtaaaga tggtttacgc cctgatggta cagcatggcg acatgaaggc   1440
aactatccgg gctactcttt cccagccttt aaaaatgcct ctcagcttat ttatttatta   1500
cgcgatacac cattttcagt gggtgaaagt ggttggaata acctgaaaaa agcgatggtt   1560
tcagcgtgga tctacagtaa tccagaagtt ggattaccgc ttgcaggaag acacccttt   1620 aactcacctt cgttaaaatc agtcgctcaa ggctattact ggcttgccat gtctgcaaaa   1680
tcatcgcctg ataaaacact tgcatctatt tatcttgcga ttagtgataa aacacaaaat   1740
gaatcaactg ctattttttgg agaaactatt acaccagcgt ctttacctca aggtttctat   1800
gcctttaatg gcggtgcttt tggtattcat cgttggcaag ataaaatggt gacactgaaa   1860
gcttataaca ccaatgtttg gtcatctgaa atttataaca aagataaccg ttatggccgt   1920
taccaaagtc atggtgtcgc tcaaatagtg agtaatggct cgcagctttc acagggctat   1980
cagcaagaag gttgggattg aatagaatg ccaggggcaa ccactattca ccttcctctt   2040
aaagacttag acagtcctaa acctcatacc ttaatgcaac gtggagagcg tggatttagc   2100
ggaacatcat cccttgaagg tcaatatggc atgatggcat tcgatcttat ttatcccgcc   2160
aatcttgagc gttttgatcc taatttcact gcgaaaaaga gtgtattagc cgctgataat   2220
cacttaattt ttattggtag caatataaat agtagtgata aaaataaaaa tgttgaaacg   2280
accttattcc aacatgccat tactccaaca ttaaatacccc tttggattaa tggacaaaag   2340
atagaaaaca tgccttatca aacaacactt caacaaggtg attggttaat tgatagcaat   2400
ggcaatggtt acttaattac tcaagcagaa aaagtaaatg taagtcgcca acatcaggtt   2460
tcagcggaaa ataaaaatcg ccaaccgaca gaaggaaact ttagctcggc atggatcgat   2520
cacagcactc gccccaaaga tgccagttat gagtatatgg tcttttaga tgcgacacct   2580 gaaaaaatgg gagagatggc acaaaaattc cgtgaaaata atgggttata tcaggttctt   2640
cgtaaggata aagacgttca tattattctc gataaactca gcaatgtaac gggatatgcc   2700
ttttatcagc cagcatcaat tgaagacaaa tggatcaaaa aggttaataa acctgcaatt   2760
gtgatgactc atcgacaaaa agacactctt attgtcagtg cagttacacc tgatttaaat   2820
atgactcgcc aaaaagcagc aactcctgtc accatcaatg tcacgattaa tggcaaatgg   2880
```

```
caatctgctg ataaaaatag tgaagtgaaa tatcaggttt ctggtgataa cactgaactg    2940
acgtttacga gttactttgg tattccacaa gaaatcaaac tctcgccact cccttga       2997

<210> SEQ ID NO 2
<211> LENGTH: 998
<212> TYPE: PRT
<213> ORGANISM: Proteus vulgaris

<400> SEQUENCE: 2

Met Ala Thr Ser Asn Pro Ala Phe Asp Pro Lys Asn Leu Met Gln Ser
1               5                   10                  15

Glu Ile Tyr His Phe Ala Gln Asn Asn Pro Leu Ala Asp Phe Ser Ser
            20                  25                  30

Asp Lys Asn Ser Ile Leu Thr Leu Ser Asp Lys Arg Ser Ile Met Gly
        35                  40                  45

Asn Gln Ser Leu Leu Trp Lys Trp Lys Gly Gly Ser Ser Phe Thr Leu
    50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Leu Thr Ile Asp Phe Gly Glu Lys Leu Ile Ser
            100                 105                 110

Thr Ser Glu Ala Gln Ala Gly Phe Lys Val Lys Leu Asp Phe Thr Gly
        115                 120                 125

Trp Arg Thr Val Gly Val Ser Leu Asn Asn Asp Leu Glu Asn Arg Glu
    130                 135                 140

Met Thr Leu Asn Ala Thr Asn Thr Ser Ser Asp Gly Thr Gln Asp Ser
145                 150                 155                 160

Ile Gly Arg Ser Leu Gly Ala Lys Val Asp Ser Ile Arg Phe Lys Ala
                165                 170                 175

Pro Ser Asn Val Ser Gln Gly Glu Ile Tyr Ile Asp Arg Ile Met Phe
            180                 185                 190

Ser Val Asp Asp Ala Arg Tyr Gln Trp Ser Asp Tyr Gln Val Lys Thr
        195                 200                 205

Arg Leu Ser Glu Pro Glu Ile Gln Phe His Asn Val Lys Pro Gln Leu
    210                 215                 220

Pro Val Thr Pro Glu Asn Leu Ala Ala Ile Asp Leu Ile Arg Gln Arg
225                 230                 235                 240

Leu Ile Asn Glu Phe Val Gly Gly Glu Lys Glu Thr Asn Leu Ala Leu
                245                 250                 255

Glu Glu Asn Ile Ser Lys Leu Lys Ser Asp Phe Asp Ala Leu Asn Ile
            260                 265                 270

His Thr Leu Ala Asn Gly Gly Thr Gln Gly Arg His Leu Val Thr Asp
        275                 280                 285

Lys Gln Ile Ile Ile Tyr Gln Pro Glu Asn Pro Asn Ser Gln Asp Lys
    290                 295                 300

Gln Leu Phe Asp Asn Tyr Val Ile Leu Gly Asn Tyr Thr Thr Leu Met
305                 310                 315                 320

Phe Asn Ile Ser Arg Ala Tyr Val Leu Glu Lys Asp Pro Thr Gln Lys
                325                 330                 335

Ala Gln Leu Lys Gln Met Tyr Leu Leu Met Thr Lys His Leu Leu Asp
            340                 345                 350

Gln Gly Phe Val Lys Gly Ser Ala Leu Val Thr Thr His His Trp Gly
        355                 360                 365
```

```
Tyr Ser Ser Arg Trp Trp Tyr Ile Ser Thr Leu Leu Met Ser Asp Ala
    370                 375                 380
Leu Lys Glu Ala Asn Leu Gln Thr Gln Val Tyr Asp Ser Leu Leu Trp
385                 390                 395                 400
Tyr Ser Arg Glu Phe Lys Ser Ser Phe Asp Met Lys Val Ser Ala Asp
                405                 410                 415
Ser Ser Asp Leu Asp Tyr Phe Asn Thr Leu Ser Arg Gln His Leu Ala
        420                 425                 430
Leu Leu Leu Leu Glu Pro Asp Asp Gln Lys Arg Ile Asn Leu Val Asn
            435                 440                 445
Thr Phe Ser His Tyr Ile Thr Gly Ala Leu Thr Gln Val Pro Pro Gly
    450                 455                 460
Gly Lys Asp Gly Leu Arg Pro Asp Gly Thr Ala Trp Arg His Glu Gly
465                 470                 475                 480
Asn Tyr Pro Gly Tyr Ser Phe Pro Ala Phe Lys Asn Ala Ser Gln Leu
                485                 490                 495
Ile Tyr Leu Leu Arg Asp Thr Pro Phe Ser Val Gly Glu Ser Gly Trp
        500                 505                 510
Asn Asn Leu Lys Lys Ala Met Val Ser Ala Trp Ile Tyr Ser Asn Pro
            515                 520                 525
Glu Val Gly Leu Pro Leu Ala Gly Arg His Pro Phe Asn Ser Pro Ser
530                 535                 540
Leu Lys Ser Val Ala Gln Gly Tyr Tyr Trp Leu Ala Met Ser Ala Lys
545                 550                 555                 560
Ser Ser Pro Asp Lys Thr Leu Ala Ser Ile Tyr Leu Ala Ile Ser Asp
                565                 570                 575
Lys Thr Gln Asn Glu Ser Thr Ala Ile Phe Gly Glu Thr Ile Thr Pro
        580                 585                 590
Ala Ser Leu Pro Gln Gly Phe Tyr Ala Phe Asn Gly Gly Ala Phe Gly
            595                 600                 605
Ile His Arg Trp Gln Asp Lys Met Val Thr Leu Lys Ala Tyr Asn Thr
    610                 615                 620
Asn Val Trp Ser Ser Glu Ile Tyr Asn Lys Asp Asn Arg Tyr Gly Arg
625                 630                 635                 640
Tyr Gln Ser His Gly Val Ala Gln Ile Val Ser Asn Gly Ser Gln Leu
                645                 650                 655
Ser Gln Gly Tyr Gln Gln Glu Gly Trp Asp Trp Asn Arg Met Pro Gly
        660                 665                 670
Ala Thr Thr Ile His Leu Pro Leu Lys Asp Leu Asp Ser Pro Lys Pro
            675                 680                 685
His Thr Leu Met Gln Arg Gly Glu Arg Gly Phe Ser Gly Thr Ser Ser
    690                 695                 700
Leu Glu Gly Gln Tyr Gly Met Met Ala Phe Asp Leu Ile Tyr Pro Ala
705                 710                 715                 720
Asn Leu Glu Arg Phe Asp Pro Asn Phe Thr Ala Lys Lys Ser Val Leu
                725                 730                 735
Ala Ala Asp Asn His Leu Ile Phe Ile Gly Ser Asn Ile Asn Ser Ser
        740                 745                 750
Asp Lys Asn Lys Asn Val Glu Thr Thr Leu Phe Gln His Ala Ile Thr
            755                 760                 765
Pro Thr Leu Asn Thr Leu Trp Ile Asn Gly Gln Lys Ile Glu Asn Met
    770                 775                 780
Pro Tyr Gln Thr Thr Leu Gln Gln Gly Asp Trp Leu Ile Asp Ser Asn
```

```
                785                 790                 795                 800
Gly Asn Gly Tyr Leu Ile Thr Gln Ala Glu Lys Val Asn Val Ser Arg
            805                 810                 815
Gln His Gln Val Ser Ala Glu Asn Lys Asn Arg Gln Pro Thr Glu Gly
            820                 825                 830
Asn Phe Ser Ser Ala Trp Ile Asp His Ser Thr Arg Pro Lys Asp Ala
            835                 840                 845
Ser Tyr Glu Tyr Met Val Phe Leu Asp Ala Thr Pro Glu Lys Met Gly
        850                 855                 860
Glu Met Ala Gln Lys Phe Arg Glu Asn Asn Gly Leu Tyr Gln Val Leu
865                 870                 875                 880
Arg Lys Asp Lys Asp Val His Ile Ile Leu Asp Lys Leu Ser Asn Val
                885                 890                 895
Thr Gly Tyr Ala Phe Tyr Gln Pro Ala Ser Ile Glu Asp Lys Trp Ile
            900                 905                 910
Lys Lys Val Asn Lys Pro Ala Ile Val Met Thr His Arg Gln Lys Asp
            915                 920                 925
Thr Leu Ile Val Ser Ala Val Thr Pro Asp Leu Asn Met Thr Arg Gln
        930                 935                 940
Lys Ala Ala Thr Pro Val Thr Ile Asn Val Thr Ile Asn Gly Lys Trp
945                 950                 955                 960
Gln Ser Ala Asp Lys Asn Ser Glu Val Lys Tyr Gln Val Ser Gly Asp
                965                 970                 975
Asn Thr Glu Leu Thr Phe Thr Ser Tyr Phe Gly Ile Pro Gln Glu Ile
            980                 985                 990
Lys Leu Ser Pro Leu Pro
            995

<210> SEQ ID NO 3
<211> LENGTH: 1021
<212> TYPE: PRT
<213> ORGANISM: Proteus vulgaris

<400> SEQUENCE: 3

Met Pro Ile Phe Arg Phe Thr Ala Leu Ala Met Thr Leu Gly Leu Leu
1               5                   10                  15
Ser Ala Pro Tyr Asn Ala Met Ala Thr Ser Asn Pro Ala Phe Asp
            20                  25                  30
Pro Lys Asn Leu Met Gln Ser Glu Ile Tyr His Phe Ala Gln Asn Asn
        35                  40                  45
Pro Leu Ala Asp Phe Ser Ser Asp Lys Asn Ser Ile Leu Thr Leu Ser
    50                  55                  60
Asp Lys Arg Ser Ile Met Gly Asn Gln Ser Leu Leu Trp Lys Trp Lys
65                  70                  75                  80
Gly Gly Ser Ser Phe Thr Leu His Lys Lys Leu Ile Val Pro Thr Asp
                85                  90                  95
Lys Glu Ala Ser Lys Ala Trp Gly Arg Ser Ser Thr Pro Val Phe Ser
            100                 105                 110
Phe Trp Leu Tyr Asn Glu Lys Pro Ile Asp Gly Tyr Leu Thr Ile Asp
            115                 120                 125
Phe Gly Glu Lys Leu Ile Ser Thr Ser Glu Ala Gln Ala Gly Phe Lys
        130                 135                 140
Val Lys Leu Asp Phe Thr Gly Trp Arg Ala Val Gly Val Ser Leu Asn
145                 150                 155                 160
Asn Asp Leu Glu Asn Arg Glu Met Thr Leu Asn Ala Thr Asn Thr Ser
```

```
                    165                 170                 175
Ser Asp Gly Thr Gln Asp Ser Ile Gly Arg Ser Leu Gly Ala Lys Val
                180                 185                 190

Asp Ser Ile Arg Phe Lys Ala Pro Ser Asn Val Ser Gln Gly Glu Ile
            195                 200                 205

Tyr Ile Asp Arg Ile Met Phe Ser Val Asp Asp Ala Arg Tyr Gln Trp
        210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Ala Asp Ser Ser Asp Leu Asp Tyr Phe Asn Thr
        435                 440                 445

Leu Ser Arg Gln His Leu Ala Leu Leu Leu Leu Glu Pro Asp Asp Gln
    450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ser Gln Leu Ile Tyr Leu Leu Arg Asp Thr Pro Phe
        515                 520                 525

Ser Val Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
            580                 585                 590
```

```
Ile Tyr Leu Ala Ile Ser Asp Lys Thr Gln Asn Glu Ser Thr Ala Ile
        595                 600                 605

Phe Gly Glu Thr Ile Thr Pro Ala Ser Leu Pro Gln Gly Phe Tyr Ala
        610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
                660                 665                 670

Val Ser Asn Gly Ser Gln Leu Ser Gln Gly Tyr Gln Gln Glu Gly Trp
                675                 680                 685

Asp Trp Asn Arg Met Gln Gly Ala Thr Thr Ile His Leu Pro Leu Lys
        690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asp Leu Ile Tyr Pro Ala Asn Leu Glu Arg Phe Asp Pro Asn Phe
        740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
                820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
                900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
                980                 985                 990

Lys Tyr Gln Val Ser Gly Asp Asn Thr Glu Leu Thr Phe Thr Ser Tyr
        995                 1000                1005

Phe Gly  Ile Pro Gln Glu Ile  Lys Leu Ser Pro Leu Pro
     1010                1015                1020
```

<210> SEQ ID NO 4
<211> LENGTH: 1021
<212> TYPE: PRT
<213> ORGANISM: Proteus vulgaris

<400> SEQUENCE: 4

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Pro Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365

Val Thr Lys His Leu Leu Asp Gln Gly Phe Val Lys Gly Ser Ala Leu
    370                 375                 380

```
Val Thr Thr His His Trp Gly Tyr Ser Ser Arg Trp Tyr Ile Ser
385                 390                 395                 400

Thr Leu Leu Met Ser Asp Ala Leu Lys Glu Ala Asn Leu Gln Thr Gln
            405                 410                 415

Val Tyr Asp Ser Leu Leu Trp Tyr Ser Arg Glu Phe Lys Ser Ser Phe
        420                 425                 430

Asp Met Lys Val Ser Ala Asp Ser Ser Asp Leu Asp Tyr Phe Asn Thr
        435                 440                 445

Leu Ser Arg Gln His Leu Ala Leu Leu Leu Glu Pro Asp Asp Gln
    450                 455                 460

Lys Arg Ile Asn Leu Val Asn Thr Phe Ser His Tyr Ile Thr Gly Ala
465                 470                 475                 480

Leu Thr Gln Val Pro Pro Gly Lys Asp Gly Leu Arg Leu Met Val
                485                 490                 495

Gln His Gly Asp Met Lys Ala Thr Ile Arg Val Thr Leu Ser Gln Pro
                500                 505                 510

Leu Lys Met Pro Leu Ser Leu Phe Ile Tyr Tyr Ala Ile His His Phe
    515                 520                 525

Gln Leu Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
                580                 585                 590

Ile Tyr Leu Ala Ile Ser Asp Lys Thr Gln Asn Glu Ser Thr Ala Ile
            595                 600                 605

Phe Gly Glu Thr Ile Thr Pro Ala Ser Leu Pro Gln Gly Phe Tyr Ala
        610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Gly Gln Ile
                660                 665                 670

Val Ser Asn Gly Ser Gln Leu Ser Gln Gly Tyr Gln Gln Glu Gly Trp
            675                 680                 685

Asp Trp Asn Arg Met Gln Gly Ala Thr Thr Ile His Leu Pro Leu Lys
        690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asp Leu Ile Tyr Pro Ala Asn Leu Glu Arg Phe Asp Pro Asn Phe
        740                 745                 750

Thr Ala Lys Lys Ser Val Leu Ala Ala Asp Asn His Leu Ile Phe Ile
    755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
```

```
                805                 810                 815
Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
            835                 840                 845

Asn Arg Gln Pro Thr Glu Gly Asn Phe Ser Ser Ala Trp Ile Asp His
            850                 855                 860

Arg Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
            915                 920                 925

Ser Ile Glu Asp Lys Trp Ile Lys Lys Val Asn Lys Pro Ala Ile Val
            930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn Thr Glu Leu Thr Phe Thr Ser Tyr
            995                 1000                1005

Phe Gly Ile Pro Gln Glu Ile Lys Leu Ser Pro Leu Pro
    1010                1015                1020

<210> SEQ ID NO 5
<211> LENGTH: 1021
<212> TYPE: PRT
<213> ORGANISM: Proteus vulgaris

<400> SEQUENCE: 5

Met Pro Ile Phe Arg Phe Thr Ala Leu Ala Met Thr Leu Gly Leu Leu
1               5                   10                  15

Ser Ala Pro Tyr Asn Ala Met Ala Thr Ser Asn Pro Ala Phe Asp
            20                  25                  30

Pro Lys Asn Leu Met Gln Ser Glu Ile Tyr His Phe Ala Gln Asn Asn
            35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
            115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
```

-continued

```
                165                 170                 175
Ser Asp Gly Thr Gln Asp Ser Ile Gly Arg Ser Leu Gly Ala Lys Val
                180                 185                 190

Asp Ser Ile Arg Phe Lys Ala Pro Ser Asn Val Ser Gln Gly Glu Ile
                195                 200                 205

Tyr Ile Asp Arg Ile Met Phe Ser Val Asp Asp Ala Arg Tyr Gln Trp
                210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
                260                 265                 270

Lys Glu Thr Asn Leu Ala Leu Glu Glu Asn Ile Ser Lys Leu Lys Ser
                275                 280                 285

Asp Phe Asp Ala Leu Asn Ile His Thr Leu Ala Asn Gly Gly Thr Gln
                290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
                340                 345                 350

Glu Lys Asp Pro Thr Gln Lys Ala Gln Leu Lys Gln Met Tyr Leu Leu
                355                 360                 365

Met Thr Lys His Leu Leu Asp Gln Gly Phe Val Lys Gly Ser Ala Leu
                370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
                420                 425                 430

Asp Met Lys Val Ser Ala Asp Ser Ser Asp Leu Asp Tyr Phe Asn Thr
                435                 440                 445

Leu Ser Arg Gln His Leu Ala Leu Leu Leu Leu Glu Pro Asp Asp Gln
                450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
                500                 505                 510

Phe Lys Asn Ala Ser Gln Leu Ile Tyr Leu Leu Arg Asp Thr Pro Phe
                515                 520                 525

Ser Val Gly Glu Ser Gly Trp Asn Asn Leu Lys Lys Ala Met Val Ser
                530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
                580                 585                 590
```

```
Ile Tyr Leu Ala Ile Ser Asp Lys Thr Gln Asn Glu Ser Thr Ala Ile
        595                 600                 605

Phe Gly Glu Thr Ile Thr Pro Ala Ser Leu Pro Gln Gly Phe Tyr Ala
        610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
            660                 665                 670

Val Ser Asn Gly Ser Gln Leu Ser Gln Gly Tyr Gln Gln Glu Gly Trp
        675                 680                 685

Asp Trp Asn Arg Met Glu Gly Ala Thr Thr Ile His Leu Pro Leu Lys
        690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
        770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
        850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
        930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990

Lys Tyr Gln Val Ser Gly Asp Asn Thr Glu Leu Thr Phe Thr Ser Tyr
        995                 1000                1005

Phe Gly  Ile Pro Gln Glu Ile  Lys Leu Ser Pro Leu  Pro
        1010                1015                1020
```

<210> SEQ ID NO 6
<211> LENGTH: 1021
<212> TYPE: PRT
<213> ORGANISM: Proteus vulgaris

<400> SEQUENCE: 6

```
Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
                20                  25                  30

Pro Lys Asn Leu Met Gln Ser Glu Ile Tyr His Phe Ala Gln Asn Asn
            35                  40                  45

Pro Leu Ala Asp Phe Ser Ser Asp Lys Asn Ser Ile Leu Thr Leu Ser
        50                  55                  60

Asp Lys Arg Ser Ile Met Gly Asn Gln Ser Leu Leu Trp Lys Trp Lys
65                  70                  75                  80

Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380
```

```
Val Thr Thr His His Trp Gly Tyr Ser Ser Arg Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Ala Asp Ser Ser Asp Leu Asp Tyr Phe Asn Thr
        435                 440                 445

Leu Ser Arg Gln His Leu Ala Leu Leu Leu Glu Pro Asp Asp Gln
    450                 455                 460

Lys Arg Ile Asn Leu Val Asn Thr Phe Ser His Tyr Ile Thr Gly Ala
465                 470                 475                 480

Leu Thr Gln Val Pro Pro Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ser Gln Leu Ile Tyr Leu Leu Arg Asp Thr Pro Phe
        515                 520                 525

Ser Val Gly Glu Ser Gly Trp Asn Asn Leu Lys Lys Ala Met Val Ser
530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
        595                 600                 605

Phe Gly Glu Thr Ile Thr Pro Ala Ser Leu Pro Gln Gly Phe Tyr Ala
610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
            660                 665                 670

Val Ser Asn Gly Ser Gln Leu Ser Gln Gly Tyr Gln Gln Glu Gly Trp
        675                 680                 685

Asp Trp Asn Arg Met Glu Gly Ala Thr Thr Ile His Leu Pro Leu Lys
690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
```

-continued

```
                805                 810                 815
Asp Trp Leu Ile Asp Ser Asn Gly Asn Gly Tyr Leu Ile Thr Gln Ala
            820                 825                 830
Glu Lys Val Asn Val Ser Arg Gln His Gln Val Ser Ala Glu Asn Lys
            835                 840                 845
Asn Arg Gln Pro Thr Glu Gly Asn Phe Ser Ser Ala Trp Ile Asp His
        850                 855                 860
Ser Thr Arg Pro Lys Asp Ala Ser Tyr Glu Tyr Met Val Phe Leu Asp
865                 870                 875                 880
Ala Thr Pro Glu Lys Met Gly Glu Met Ala Gln Lys Phe Arg Glu Asn
            885                 890                 895
Asn Gly Leu Tyr Gln Val Leu Arg Lys Asp Lys Asp Val His Ile Ile
            900                 905                 910
Leu Asp Lys Leu Ser Asn Val Thr Gly Tyr Ala Phe Tyr Gln Pro Ala
            915                 920                 925
Ser Ile Glu Asp Lys Trp Ile Lys Lys Val Asn Lys Pro Ala Ile Val
            930                 935                 940
Met Thr His Arg Gln Lys Asp Thr Leu Ile Val Ser Ala Val Thr Pro
945                 950                 955                 960
Asp Leu Asn Met Thr Arg Gln Lys Ala Ala Thr Pro Val Thr Ile Asn
                965                 970                 975
Val Thr Ile Asn Gly Lys Trp Gln Ser Ala Asp Lys Asn Ser Glu Val
            980                 985                 990
Lys Tyr Gln Val Ser Gly Asp Asn  Thr Glu Leu Thr Phe  Thr Ser Tyr
            995                 1000                1005
Phe Gly  Ile Pro Gln Glu Ile  Lys Leu Ser Pro Leu  Pro
    1010                1015                1020

<210> SEQ ID NO 7
<211> LENGTH: 1021
<212> TYPE: PRT
<213> ORGANISM: Proteus vulgaris

<400> SEQUENCE: 7

Met Pro Ile Phe Arg Phe Thr Ala Leu Ala Met Thr Leu Gly Leu Leu
1               5                   10                  15
Ser Ala Pro Tyr Asn Ala Met Ala Thr Ser Asn Pro Ala Phe Asp
            20                  25                  30
Pro Lys Asn Leu Met Gln Ser Glu Ile Tyr His Phe Ala Gln Asn Asn
        35                  40                  45
Pro Leu Ala Asp Phe Ser Ser Asp Lys Asn Ser Ile Leu Thr Leu Ser
    50                  55                  60
Asp Lys Arg Ser Ile Met Gly Asn Gln Ser Leu Leu Trp Lys Trp Lys
65                  70                  75                  80
Gly Gly Ser Ser Phe Thr Leu His Lys Lys Leu Ile Val Pro Thr Asp
            85                  90                  95
Lys Glu Ala Ser Lys Ala Trp Gly Arg Ser Ser Thr Pro Val Phe Ser
            100                 105                 110
Phe Trp Leu Tyr Asn Glu Lys Pro Ile Asp Gly Tyr Leu Thr Ile Asp
        115                 120                 125
Phe Gly Glu Lys Leu Ile Ser Thr Ser Glu Ala Gln Ala Gly Phe Lys
    130                 135                 140
Val Lys Leu Asp Phe Thr Gly Trp Arg Ala Val Gly Val Ser Leu Asn
145                 150                 155                 160
Asn Asp Leu Glu Asn Arg Glu Met Thr Leu Asn Ala Thr Asn Thr Ser
```

```
                    165                 170                 175
Ser Asp Gly Thr Gln Asp Ser Ile Gly Arg Ser Leu Gly Ala Lys Val
                180                 185                 190

Asp Ser Ile Arg Phe Lys Ala Pro Ser Asn Val Ser Gln Gly Glu Ile
                195                 200                 205

Tyr Ile Asp Arg Ile Met Phe Ser Val Asp Asp Ala Arg Tyr Gln Trp
                210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
                260                 265                 270

Lys Glu Thr Asn Leu Ala Leu Glu Glu Asn Ile Ser Lys Leu Lys Ser
                275                 280                 285

Asp Phe Asp Ala Leu Asn Ile His Thr Leu Ala Asn Gly Gly Thr Gln
                290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
                340                 345                 350

Glu Lys Asp Pro Thr Gln Lys Ala Gln Leu Lys Gln Met Tyr Leu Leu
                355                 360                 365

Met Thr Lys His Leu Leu Asp Gln Gly Phe Val Lys Gly Ser Ala Leu
                370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
                420                 425                 430

Asp Met Lys Val Ser Ala Asp Ser Ser Asp Leu Asp Tyr Phe Asn Thr
                435                 440                 445

Leu Ser Arg Gln His Leu Ala Leu Leu Leu Leu Glu Pro Asp Asp Gln
                450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
                500                 505                 510

Phe Lys Asn Ala Ser Gln Leu Ile Tyr Leu Leu Arg Asp Thr Pro Phe
                515                 520                 525

Ser Val Gly Glu Ser Gly Trp Asn Asn Leu Lys Lys Ala Met Val Ser
                530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
                580                 585                 590
```

```
Ile Tyr Leu Ala Ile Ser Asp Lys Thr Gln Asn Glu Ser Thr Ala Ile
            595                 600                 605

Phe Gly Glu Thr Ile Thr Pro Ala Ser Leu Pro Gln Gly Phe Tyr Ala
610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
                660                 665                 670

Val Ser Asn Gly Ser Gln Leu Ser Gln Gly Tyr Gln Gln Glu Gly Trp
                675                 680                 685

Asp Trp Asn Arg Met Gln Gly Ala Thr Thr Ile His Leu Pro Leu Lys
690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asp Leu Ile Tyr Pro Ala Asn Leu Glu Arg Phe Asp Pro Asn Phe
                740                 745                 750

Thr Ala Lys Lys Ser Val Leu Ala Ala Asp Asn His Leu Ile Phe Ile
                755                 760                 765

Gly Ser Asn Ile Asn Ser Ser Asp Lys Asn Lys Asn Val Glu Thr Thr
770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
                820                 825                 830

Glu Lys Val Asn Val Ser Arg Gln His Gln Val Ser Ala Glu Asn Lys
                835                 840                 845

Asn Arg Gln Pro Thr Glu Gly Asn Phe Ser Ser Ala Trp Ile Asp His
850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
                900                 905                 910

Leu Asp Lys Leu Ser Asn Val Thr Gly Tyr Ala Phe Tyr Gln Pro Ala
                915                 920                 925

Ser Ile Glu Asp Lys Trp Ile Lys Lys Val Asn Lys Pro Ala Ile Val
930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
                980                 985                 990

Lys Tyr Gln Val Ser Gly Asp Asn  Thr Glu Leu Thr Phe  Thr Ser Tyr
                995                1000                1005

Phe Gly  Ile Pro Gln Glu Ile  Lys Leu Ser Pro Leu  Pro
            1010                1015                1020
```

<210> SEQ ID NO 8
<211> LENGTH: 998
<212> TYPE: PRT
<213> ORGANISM: Proteus vulgaris

<400> SEQUENCE: 8

Met Ala Thr Ser Asn Pro Ala Phe Asp Pro Lys Asn Leu Met Gln Ser
1               5                   10                  15

Glu Ile Tyr His Phe Ala Gln Asn Asn Pro Leu Ala Asp Phe Ser Ser
            20                  25                  30

Asp Lys Asn Ser Ile Leu Thr Leu Ser Asp Lys Arg Ser Ile Met Gly
        35                  40                  45

Asn Gln Ser Leu Leu Trp Lys Trp Lys Gly Gly Ser Ser Phe Thr Leu
    50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Leu Thr Ile Asp Phe Gly Glu Lys Leu Ile Ser
            100                 105                 110

Thr Ser Glu Ala Gln Ala Gly Phe Lys Val Lys Leu Asp Phe Thr Gly
        115                 120                 125

Trp Arg Ala Val Gly Val Ser Leu Asn Asn Asp Leu Glu Asn Arg Glu
    130                 135                 140

Met Thr Leu Asn Ala Thr Asn Thr Ser Ser Asp Gly Thr Gln Asp Ser
145                 150                 155                 160

Ile Gly Arg Ser Leu Gly Ala Lys Val Asp Ser Ile Arg Phe Lys Ala
                165                 170                 175

Pro Ser Asn Val Ser Gln Gly Glu Ile Tyr Ile Asp Arg Ile Met Phe
            180                 185                 190

Ser Val Asp Asp Ala Arg Tyr Gln Trp Ser Asp Tyr Gln Val Lys Thr
        195                 200                 205

Arg Leu Ser Glu Pro Glu Ile Gln Phe His Asn Val Lys Pro Gln Leu
    210                 215                 220

Pro Val Thr Pro Glu Asn Leu Ala Ala Ile Asp Leu Ile Arg Gln Arg
225                 230                 235                 240

Leu Ile Asn Glu Phe Val Gly Gly Lys Glu Thr Asn Leu Ala Leu
                245                 250                 255

Glu Glu Asn Ile Ser Lys Leu Lys Ser Asp Phe Asp Ala Leu Asn Ile
            260                 265                 270

His Thr Leu Ala Asn Gly Gly Thr Gln Gly Arg His Leu Ile Thr Asp
        275                 280                 285

Lys Gln Ile Ile Ile Tyr Gln Pro Glu Asn Leu Asn Ser Gln Asp Lys
    290                 295                 300

Gln Leu Phe Asp Asn Tyr Val Ile Leu Gly Asn Tyr Thr Thr Leu Met
305                 310                 315                 320

Phe Asn Ile Ser Arg Ala Tyr Val Leu Glu Lys Asp Pro Thr Gln Lys
                325                 330                 335

Ala Gln Leu Lys Gln Met Tyr Leu Leu Met Thr Lys His Leu Leu Asp
            340                 345                 350

Gln Gly Phe Val Lys Gly Ser Ala Leu Val Thr Thr His His Trp Gly
        355                 360                 365

Tyr Ser Ser Arg Trp Trp Tyr Ile Ser Thr Leu Leu Met Ser Asp Ala
    370                 375                 380

```
Leu Lys Glu Ala Asn Leu Gln Thr Gln Val Tyr Asp Ser Leu Leu Trp
385                 390                 395                 400

Tyr Ser Arg Glu Phe Lys Ser Ser Phe Asp Met Lys Val Ser Ala Asp
            405                 410                 415

Ser Ser Asp Leu Asp Tyr Phe Asn Thr Leu Ser Arg Gln His Leu Ala
        420                 425                 430

Leu Leu Leu Leu Glu Pro Asp Asp Gln Lys Arg Ile Asn Leu Val Asn
            435                 440                 445

Thr Phe Ser His Tyr Ile Thr Gly Ala Leu Thr Gln Val Pro Pro Gly
        450                 455                 460

Gly Lys Asp Gly Leu Arg Pro Asp Gly Thr Ala Trp Arg His Glu Gly
465                 470                 475                 480

Asn Tyr Pro Gly Tyr Ser Phe Pro Ala Phe Lys Asn Ala Ser Gln Leu
                485                 490                 495

Ile Tyr Leu Leu Arg Asp Thr Pro Phe Ser Val Gly Glu Ser Gly Trp
            500                 505                 510

Asn Asn Leu Lys Lys Ala Met Val Ser Ala Trp Ile Tyr Ser Asn Pro
        515                 520                 525

Glu Val Gly Leu Pro Leu Ala Gly Arg His Pro Phe Asn Ser Pro Ser
            530                 535                 540

Leu Lys Ser Val Ala Gln Gly Tyr Tyr Trp Leu Ala Met Ser Ala Lys
545                 550                 555                 560

Ser Ser Pro Asp Lys Thr Leu Ala Ser Ile Tyr Leu Ala Ile Ser Asp
                565                 570                 575

Lys Thr Gln Asn Glu Ser Thr Ala Ile Phe Gly Glu Thr Ile Thr Pro
            580                 585                 590

Ala Ser Leu Pro Gln Gly Phe Tyr Ala Phe Asn Gly Gly Ala Phe Gly
        595                 600                 605

Ile His Arg Trp Gln Asp Lys Met Val Thr Leu Lys Ala Tyr Asn Thr
            610                 615                 620

Asn Val Trp Ser Ser Glu Ile Tyr Asn Lys Asp Asn Arg Tyr Gly Arg
625                 630                 635                 640

Tyr Gln Ser His Gly Val Ala Gln Ile Val Ser Asn Gly Ser Gln Leu
                645                 650                 655

Ser Gln Gly Tyr Gln Gln Glu Gly Trp Asp Trp Asn Arg Met Gln Gly
            660                 665                 670

Ala Thr Thr Ile His Leu Pro Leu Lys Asp Leu Asp Ser Pro Lys Pro
        675                 680                 685

His Thr Leu Met Gln Arg Gly Glu Arg Gly Phe Ser Gly Thr Ser Ser
        690                 695                 700

Leu Glu Gly Gln Tyr Gly Met Met Ala Phe Asp Leu Ile Tyr Pro Ala
705                 710                 715                 720

Asn Leu Glu Arg Phe Asp Pro Asn Phe Thr Ala Lys Lys Ser Val Leu
                725                 730                 735

Ala Ala Asp Asn His Leu Ile Phe Ile Gly Ser Asn Ile Asn Ser Ser
            740                 745                 750

Asp Lys Asn Lys Asn Val Glu Thr Thr Leu Phe Gln His Ala Ile Thr
        755                 760                 765

Pro Thr Leu Asn Thr Leu Trp Ile Asn Gly Gln Lys Ile Glu Asn Met
        770                 775                 780

Pro Tyr Gln Thr Thr Leu Gln Gln Gly Asp Trp Leu Ile Asp Ser Asn
785                 790                 795                 800

Gly Asn Gly Tyr Leu Ile Thr Gln Ala Glu Lys Val Asn Val Ser Arg
```

805                 810                 815
Gln His Gln Val Ser Ala Glu Asn Lys Asn Arg Gln Pro Thr Glu Gly
                820                 825                 830

Asn Phe Ser Ser Ala Trp Ile Asp His Ser Thr Arg Pro Lys Asp Ala
            835                 840                 845

Ser Tyr Glu Tyr Met Val Phe Leu Asp Ala Thr Pro Glu Lys Met Gly
        850                 855                 860

Glu Met Ala Gln Lys Phe Arg Glu Asn Asn Gly Leu Tyr Gln Val Leu
865                 870                 875                 880

Arg Lys Asp Lys Asp Val His Ile Ile Leu Asp Lys Leu Ser Asn Val
                885                 890                 895

Thr Gly Tyr Ala Phe Tyr Gln Pro Ala Ser Ile Glu Asp Lys Trp Ile
            900                 905                 910

Lys Lys Val Asn Lys Pro Ala Ile Val Met Thr His Arg Gln Lys Asp
        915                 920                 925

Thr Leu Ile Val Ser Ala Val Thr Pro Asp Leu Asn Met Thr Arg Gln
    930                 935                 940

Lys Ala Ala Thr Pro Val Thr Ile Asn Val Thr Ile Asn Gly Lys Trp
945                 950                 955                 960

Gln Ser Ala Asp Lys Asn Ser Glu Val Lys Tyr Gln Val Ser Gly Asp
                965                 970                 975

Asn Thr Glu Leu Thr Phe Thr Ser Tyr Phe Gly Ile Pro Gln Glu Ile
            980                 985                 990

Lys Leu Ser Pro Leu Pro
        995

<210> SEQ ID NO 9
<211> LENGTH: 998
<212> TYPE: PRT
<213> ORGANISM: Proteus vulgaris

<400> SEQUENCE: 9

Ala Thr Ser Asn Pro Ala Phe Asp Pro Lys Asn Leu Ile Asn Gly Ser
1               5                   10                  15

Glu Ile Tyr His Phe Ala Gln Asn Asn Pro Leu Ala Asp Phe Ser Ser
                20                  25                  30

Asp Lys Asn Ser Ile Leu Thr Leu Ser Asp Lys Arg Ser Ile Met Gly
            35                  40                  45

Asn Gln Ser Leu Leu Trp Lys Trp Lys Gly Gly Ser Ser Phe Thr Leu
        50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Leu Thr Ile Asp Phe Gly Glu Lys Leu Ile Ser
            100                 105                 110

Thr Ser Glu Ala Gln Ala Gly Phe Lys Val Lys Leu Asp Phe Thr Gly
        115                 120                 125

Trp Arg Thr Val Gly Val Ser Leu Asn Asn Asp Leu Glu Asn Arg Glu
    130                 135                 140

Met Thr Leu Asn Ala Thr Asn Thr Ser Ser Asp Gly Thr Gly Asp Ser
145                 150                 155                 160

Ile Gly Arg Ser Leu Gly Ala Lys Val Asp Ser Ile Arg Phe Lys Ala
                165                 170                 175

Pro Ser Asn Val Ser Gln Gly Glu Ile Tyr Ile Asp Arg Ile Met Phe

-continued

```
                180                 185                 190
Ser Val Asp Asp Ala Arg Tyr Gln Trp Ser Asp Tyr Gln Val Lys Thr
                    195                 200                 205

Arg Leu Ser Glu Pro Glu Ile Gly Phe His Asn Val Lys Pro Gln Leu
    210                 215                 220

Pro Val Thr Pro Glu Asn Leu Ala Ala Ile Asp Leu Ile Arg Gln Arg
225                 230                 235                 240

Leu Ile Asn Glu Phe Val Gly Gly Lys Glu Thr Asn Leu Ala Leu
                245                 250                 255

Glu Glu Asn Ile Ser Lys Leu Lys Ser Asp Phe Asp Ala Leu Asn Thr
                260                 265                 270

His Thr Leu Ala Asn Gly Gly Thr Gln Gly Arg His Leu Ile Thr Asp
            275                 280                 285

Lys Gln Ile Ile Ile Tyr Gln Pro Glu Asn Leu Asn Ser Gly Asp Lys
            290                 295                 300

Gln Leu Phe Asp Asn Tyr Val Ile Leu Gly Asn Tyr Thr Thr Leu Met
305                 310                 315                 320

Phe Asn Ile Ser Arg Ala Tyr Val Leu Glu Lys Asp Pro Thr Gln Lys
                    325                 330                 335

Ala Gln Leu Lys Gln Met Tyr Leu Leu Met Thr Lys His Leu Leu Asp
            340                 345                 350

Gln Gly Phe Val Lys Gly Ser Ala Leu Val Thr Thr His His Trp Gly
                355                 360                 365

Tyr Ser Ser Arg Trp Trp Tyr Ile Ser Thr Leu Leu Met Ser Asp Ala
            370                 375                 380

Leu Lys Glu Ala Asn Leu Gln Thr Gln Val Tyr Asp Ser Leu Leu Trp
385                 390                 395                 400

Tyr Ser Arg Glu Phe Lys Ser Ser Phe Asp Met Lys Val Ser Ala Asp
                    405                 410                 415

Ser Ser Asp Leu Asp Tyr Phe Asn Thr Leu Ser Arg Gln His Leu Ala
            420                 425                 430

Leu Leu Leu Leu Glu Pro Asp Asp Gly Lys Arg Ile Asn Leu Tyr Asn
        435                 440                 445

Thr Phe Ser His Tyr Ile Thr Gly Ala Leu Thr Gly Val Pro Pro Gly
        450                 455                 460

Gly Lys Asp Gly Leu Arg Pro Asp Gly Thr Ala Trp Arg His Glu Gly
465                 470                 475                 480

Asn Tyr Pro Gly Tyr Ser Phe Pro Ala Phe Lys Asn Ala Ser Gly Leu
                485                 490                 495

Ile Tyr Leu Leu Arg Asp Thr Pro Phe Ser Val Gly Glu Ser Gly Trp
                500                 505                 510

Asn Asn Leu Lys Lys Ala Met Val Ser Ala Trp Ile Tyr Ser Asn Pro
            515                 520                 525

Glu Val Gly Leu Pro Leu Ala Gly Arg His Pro Phe Asn Ser Pro Ser
            530                 535                 540

Leu Lys Ser Val Ala Gln Gly Tyr Tyr Trp Leu Ala Met Ser Ala Lys
545                 550                 555                 560

Ser Ser Pro Asp Lys Thr Leu Ala Ser Ile Tyr Leu Ala Ile Ser Asp
                565                 570                 575

Lys Thr Gln Asn Glu Ser Thr Ala Ile Phe Gly Glu Thr Ile Thr Pro
            580                 585                 590

Ala Ser Leu Pro Gln Gly Phe Tyr Ala Phe Asn Gly Gly Ala Phe Gly
            595                 600                 605
```

```
Ile His Arg Trp Gln Asp Lys Met Val Thr Leu Lys Ala Tyr Asn Thr
610                 615                 620

Asn Val Trp Ser Ser Glu Ile Tyr Asn Lys Asp Asn Arg Tyr Gly Arg
625                 630                 635                 640

Tyr Gln Ser His Gly Val Ala Gln Ile Val Ser Asn Gly Ser Gln Leu
            645                 650                 655

Ser Gln Gly Tyr Gln Gln Glu Gly Trp Asp Trp Asn Arg Met Glu Gly
            660                 665                 670

Ala Thr Thr Ile His Leu Pro Leu Lys Asp Leu Asp Ser Pro Lys Pro
            675                 680                 685

His Thr Leu Met Gly Arg Gly Glu Arg Gly Phe Ser Gly Thr Ser Ser
690                 695                 700

Leu Glu Gly Gly Tyr Gly Met Met Ala Phe Asn Leu Ile Tyr Pro Ala
705                 710                 715                 720

Asn Leu Glu Arg Phe Asp Pro Asn Phe Thr Ala Lys Lys Ser Val Leu
                725                 730                 735

Ala Ala Asp Asn His Leu Ile Phe Ile Gly Ser Asn Ile Asn Ser Ser
                740                 745                 750

Asp Lys Asn Lys Asn Val Glu Thr Thr Leu Phe Gln His Ala Ile Thr
            755                 760                 765

Pro Thr Leu Asn Thr Leu Trp Ile Asn Gly Gln Lys Ile Glu Asn Met
770                 775                 780

Pro Tyr Gln Thr Thr Leu Gln Gln Gly Asp Trp Leu Ile Asp Ser Asn
785                 790                 795                 800

Gly Asn Gly Tyr Leu Ile Thr Gln Ala Glu Lys Val Asn Val Ser Arg
                805                 810                 815

Gln His Gln Val Ser Ala Glu Asn Lys Asn Arg Gln Pro Thr Glu Gly
                820                 825                 830

Asn Phe Ser Ser Ala Trp Ile Asp His Ser Thr Arg Pro Lys Asp Ala
                835                 840                 845

Ser Tyr Glu Tyr Met Val Phe Leu Asp Ala Thr Pro Glu Lys Met Gly
            850                 855                 860

Glu Met Ala Gln Lys Phe Arg Glu Asn Asn Gly Leu Tyr Gln Val Leu
865                 870                 875                 880

Arg Lys Asp Lys Asp Val His Ile Ile Leu Asp Lys Leu Ser Asn Val
                885                 890                 895

Thr Gly Tyr Ala Phe Tyr Gln Pro Ala Ser Ile Glu Asp Lys Trp Ile
            900                 905                 910

Lys Lys Val Asn Lys Pro Ala Ile Val Met Thr His Arg Gln Lys Asp
            915                 920                 925

Thr Leu Ile Val Ser Ala Val Thr Pro Asp Leu Asn Met Thr Arg Gly
930                 935                 940

Lys Ala Ala Thr Pro Val Thr Ile Asn Val Thr Ile Asn Gly Lys Trp
945                 950                 955                 960

Gln Ser Ala Asp Lys Asn Ser Glu Val Lys Tyr Gln Val Ser Gly Asp
                965                 970                 975

Asn Thr Glu Leu Thr Phe Thr Ser Tyr Phe Gly Ile Pro Gly Glu Ile
            980                 985                 990

Lys Leu Ser Pro Leu Pro
            995

<210> SEQ ID NO 10
<211> LENGTH: 978
<212> TYPE: PRT
<213> ORGANISM: Proteus vulgaris
```

<400> SEQUENCE: 10

```
Ala Gln Asn Asn Pro Leu Ala Asp Phe Ser Asp Lys Asn Ser Ile
1               5                   10                  15

Leu Thr Leu Ser Asp Lys Arg Ser Ile Met Gly Asn Gln Ser Leu Leu
            20                  25                  30

Trp Lys Trp Lys Gly Gly Ser Ser Phe Thr Leu His Lys Lys Leu Ile
            35                  40                  45

Val Pro Thr Asp Lys Glu Ala Ser Lys Ala Trp Gly Arg Ser Ser Thr
50                  55                  60

Pro Val Phe Ser Phe Trp Leu Tyr Asn Glu Lys Pro Ile Asp Gly Tyr
65                  70                  75                  80

Leu Thr Ile Asp Phe Gly Glu Lys Leu Ile Ser Thr Ser Glu Ala Gln
                85                  90                  95

Ala Gly Phe Lys Val Lys Leu Asp Phe Thr Gly Trp Arg Thr Val Gly
            100                 105                 110

Val Ser Leu Asn Asn Asp Leu Glu Asn Arg Glu Met Thr Leu Asn Ala
            115                 120                 125

Thr Asn Thr Ser Ser Asp Gly Thr Gly Asp Ser Ile Gly Arg Ser Leu
130                 135                 140

Gly Ala Lys Val Asp Ser Ile Arg Phe Lys Ala Pro Ser Asn Val Ser
145                 150                 155                 160

Gln Gly Glu Ile Tyr Ile Asp Arg Ile Met Phe Ser Val Asp Asp Ala
                165                 170                 175

Arg Tyr Gln Trp Ser Asp Tyr Gln Val Lys Thr Arg Leu Ser Glu Pro
            180                 185                 190

Glu Ile Gly Phe His Asn Val Lys Pro Gln Leu Pro Val Thr Pro Glu
            195                 200                 205

Asn Leu Ala Ala Ile Asp Leu Ile Arg Gln Arg Leu Ile Asn Glu Phe
210                 215                 220

Val Gly Gly Glu Lys Glu Thr Asn Leu Ala Leu Glu Glu Asn Ile Ser
225                 230                 235                 240

Lys Leu Lys Ser Asp Phe Asp Ala Leu Asn Thr His Thr Leu Ala Asn
                245                 250                 255

Gly Gly Thr Gln Gly Arg His Leu Ile Thr Asp Lys Gln Ile Ile Ile
            260                 265                 270

Tyr Gln Pro Glu Asn Leu Asn Ser Gly Asp Lys Gln Leu Phe Asp Asn
            275                 280                 285

Tyr Val Ile Leu Gly Asn Tyr Thr Thr Leu Met Phe Asn Ile Ser Arg
290                 295                 300

Ala Tyr Val Leu Glu Lys Asp Pro Thr Gln Lys Ala Gln Leu Lys Gln
305                 310                 315                 320

Met Tyr Leu Leu Met Thr Lys His Leu Leu Asp Gln Gly Phe Val Lys
                325                 330                 335

Gly Ser Ala Leu Val Thr Thr His His Trp Gly Tyr Ser Ser Arg Trp
            340                 345                 350

Trp Tyr Ile Ser Thr Leu Leu Met Ser Asp Ala Leu Lys Glu Ala Asn
            355                 360                 365

Leu Gln Thr Gln Val Tyr Asp Ser Leu Leu Trp Tyr Ser Arg Glu Phe
370                 375                 380

Lys Ser Ser Phe Asp Met Lys Val Ser Ala Asp Ser Ser Asp Leu Asp
385                 390                 395                 400

Tyr Phe His Thr Leu Ser Arg Gln His Leu Ala Leu Leu Leu Leu Glu
                405                 410                 415
```

```
Pro Asp Asp Gly Lys Arg Ile Asn Leu Tyr Asn Thr Phe Ser His Tyr
            420                 425                 430

Ile Thr Gly Ala Leu Thr Gly Val Pro Pro Gly Gly Lys Asp Gly Leu
            435                 440                 445

Arg Pro Asp Gly Thr Ala Trp Arg His Glu Gly Asn Tyr Pro Gly Tyr
450                 455                 460

Ser Phe Pro Ala Phe Lys Asn Ala Ser Gln Leu Ile Tyr Leu Leu Arg
465                 470                 475                 480

Asp Thr Pro Phe Ser Val Gly Glu Ser Gly Val Val Asn Asn Lys Lys
                485                 490                 495

Ala Met Val Ser Ala Trp Ile Tyr Ser Asn Pro Glu Val Gly Leu Pro
            500                 505                 510

Leu Ala Gly Arg His Pro Phe Asn Ser Pro Ser Leu Lys Ser Val Ala
            515                 520                 525

Gln Gly Tyr Tyr Trp Leu Ala Met Ser Ala Lys Ser Ser Pro Asp Lys
            530                 535                 540

Thr Leu Ala Ser Ile Tyr Leu Ala Ile Ser Asp Lys Thr Gln Asn Glu
545                 550                 555                 560

Ser Thr Ala Ile Phe Gly Glu Thr Ile Thr Pro Ala Ser Leu Pro Gln
                565                 570                 575

Gly Phe Tyr Ala Phe Asn Gly Gly Ala Phe Gly Ile His Arg Trp Gln
            580                 585                 590

Asp Lys Met Val Thr Leu Lys Ala Tyr Asn Thr Asn Val Trp Ser Ser
            595                 600                 605

Glu Ile Tyr Asn Lys Asp Asn Arg Tyr Gly Arg Tyr Gln Ser His Gly
            610                 615                 620

Val Ala Gln Ile Val Ser Asn Gly Ser Gln Leu Ser Gly Tyr Gln
625                 630                 635                 640

Gln Glu Gly Trp Asp Trp Asn Arg Met Glu Gly Ala Thr Thr Ile His
                645                 650                 655

Leu Pro Leu Lys Asp Leu Asp Ser Pro Lys Pro His Thr Leu Met Gly
            660                 665                 670

Arg Gly Glu Arg Gly Phe Ser Gly Thr Ser Ser Leu Glu Gly Gly Tyr
            675                 680                 685

Gly Met Met Ala Phe Ile Ile Leu Ile Tyr Pro Ala Asn Leu Glu Arg
            690                 695                 700

Phe Asp Pro Asn Phe Thr Ala Lys Lys Ser Val Leu Ala Ala Asp Asn
705                 710                 715                 720

His Leu Ile Phe Ile Gly Ser Asn Ile Asn Ser Ser Asp Lys Asn Lys
                725                 730                 735

Asn Val Glu Thr Thr Leu Phe Gln His Ala Ile Thr Pro Thr Leu Asn
            740                 745                 750

Thr Leu Trp Ile Asn Gly Gly Lys Ile Glu Asn Met Pro Tyr Gln Thr
            755                 760                 765

Thr Leu Gln Gln Gly Asp Trp Leu Ile Asp Ser Asn Gly Asn Gly Tyr
            770                 775                 780

Leu Ile Thr Gln Ala Glu Lys Val Asn Val Ser Arg Gln His Gln Val
785                 790                 795                 800

Ser Ala Glu Asn Lys Asn Arg Gln Pro Thr Glu Gly Asn Phe Ser Ser
                805                 810                 815

Ala Trp Ile Asp His Ser Thr Arg Pro Lys Asp Ala Ser Tyr Glu Tyr
            820                 825                 830

Met Val Phe Leu Asp Ala Thr Pro Glu Lys Met Gly Glu Met Ala Gln
```

```
                   835                 840                 845
Lys Phe Arg Glu Asn Asn Gly Leu Tyr Gln Val Leu Arg Lys Asp Lys
850                 855                 860

Asp Val His Ile Ile Leu Asp Lys Leu Ser Asn Val Thr Gly Tyr Ala
865                 870                 875                 880

Phe Tyr Gln Pro Ala Ser Ile Glu Asp Lys Trp Ile Lys Val Asn
                    885                 890                 895

Lys Pro Ala Ile Val Met Thr His Arg Gln Lys Asp Thr Leu Ile Val
                900                 905                 910

Ser Ala Val Thr Pro Asp Leu Asn Met Thr Arg Gly Lys Ala Ala Thr
                915                 920                 925

Pro Val Thr Ile Asn Val Thr Ile Asn Gly Lys Trp Gln Ser Ala Asp
                930                 935                 940

Lys Asn Ser Glu Val Lys Tyr Gln Val Ser Gly Asp Asn Thr Glu Leu
945                 950                 955                 960

Thr Phe Thr Ser Tyr Phe Gly Ile Pro Gly Glu Ile Lys Leu Ser Pro
                    965                 970                 975

Leu Pro

<210> SEQ ID NO 11
<211> LENGTH: 936
<212> TYPE: PRT
<213> ORGANISM: Proteus vulgaris

<400> SEQUENCE: 11

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
                20                  25                  30

Asn Glu Lys Pro Ile Asp Gly Tyr Leu Thr Ile Asp Phe Gly Glu Lys
                35                  40                  45

Leu Ile Ser Thr Ser Glu Ala Gln Ala Gly Phe Lys Val Lys Leu Asp
        50                  55                  60

Phe Thr Gly Trp Arg Thr Val Gly Val Ser Leu Asn Asn Asp Leu Glu
65                  70                  75                  80

Asn Arg Glu Met Thr Leu Asn Ala Thr Asn Thr Ser Ser Asp Gly Thr
                85                  90                  95

Gly Asp Ser Ile Gly Arg Ser Leu Gly Ala Lys Val Asp Ser Ile Arg
                100                 105                 110

Phe Lys Ala Pro Ser Asn Val Ser Gln Gly Glu Ile Tyr Ile Asp Arg
            115                 120                 125

Ile Met Phe Ser Val Asp Asp Ala Arg Tyr Gln Trp Ser Asp Tyr Gln
130                 135                 140

Val Lys Thr Arg Leu Ser Glu Pro Glu Ile Gly Phe His Asn Val Lys
145                 150                 155                 160

Pro Gln Leu Pro Val Thr Pro Glu Asn Leu Ala Ala Ile Asp Leu Ile
                165                 170                 175

Arg Gln Arg Leu Ile Asn Glu Phe Val Gly Gly Glu Lys Glu Thr Asn
                180                 185                 190

Leu Ala Leu Glu Glu Asn Ile Ser Lys Leu Lys Ser Asp Phe Asp Ala
            195                 200                 205

Leu Asn Thr His Thr Leu Ala Asn Gly Gly Thr Gln Gly Arg His Leu
        210                 215                 220

Ile Thr Asp Lys Gln Ile Ile Tyr Gln Pro Glu Asn Leu Asn Ser
225                 230                 235                 240
```

```
Gly Asp Lys Gly Leu Phe Asp Asn Tyr Val Ile Leu Gly Asn Tyr Thr
                245                 250                 255

Thr Leu Met Phe Asn Ile Ser Arg Ala Tyr Val Leu Glu Lys Asp Pro
            260                 265                 270

Thr Gln Lys Ala Gln Leu Lys Gln Met Tyr Leu Leu Met Thr Lys His
        275                 280                 285

Leu Leu Asp Gln Gly Phe Val Lys Gly Ser Ala Leu Val Thr Thr His
    290                 295                 300

His Trp Gly Tyr Ser Ser Arg Trp Trp Tyr Ile Ser Thr Leu Leu Met
305                 310                 315                 320

Ser Asp Ala Leu Lys Glu Ala Asn Leu Gln Thr Gln Val Tyr Asp Ser
                325                 330                 335

Leu Leu Trp Tyr Ser Arg Glu Phe Lys Ser Ser Phe Asp Met Lys Val
            340                 345                 350

Ser Ala Asp Ser Ser Asp Leu Asp Tyr Phe Asn Thr Leu Ser Arg Gln
        355                 360                 365

His Leu Ala Leu Leu Leu Glu Pro Asp Asp Gly Lys Arg Ile Asn
    370                 375                 380

Leu Tyr Asn Thr Phe Ser His Tyr Ile Thr Gly Ala Leu Thr Gly Val
385                 390                 395                 400

Pro Pro Gly Gly Lys Asp Gly Leu Arg Pro Asp Gly Thr Ala Trp Arg
                405                 410                 415

His Glu Gly Asn Tyr Pro Gly Tyr Ser Phe Pro Ala Phe Lys Asn Ala
            420                 425                 430

Ser Gly Leu Ile Tyr Leu Leu Arg Asp Thr Pro Phe Ser Val Gly Glu
        435                 440                 445

Ser Gly Trp Asn Asn Lys Lys Ala Met Val Ser Ala Trp Ile Tyr Ser
    450                 455                 460

Asn Pro Glu Val Gly Leu Pro Leu Ala Gly Arg His Pro Phe Asn Ser
465                 470                 475                 480

Pro Ser Leu Lys Ser Val Ala Gly Gly Tyr Tyr Trp Leu Ala Met Ser
                485                 490                 495

Ala Lys Ser Ser Pro Asp Lys Thr Leu Ala Ser Ile Tyr Leu Ala Ile
            500                 505                 510

Ser Asp Lys Thr Gln Asn Glu Ser Thr Ala Ile Phe Gly Glu Thr Ile
        515                 520                 525

Thr Pro Ala Ser Leu Pro Gln Gly Phe Tyr Ala Phe Asn Gly Gly Ala
    530                 535                 540

Phe Gly Ile His Arg Trp Gln Asp Lys Met Val Thr Leu Lys Ala Tyr
545                 550                 555                 560

Asn Thr Asn Val Trp Ser Ser Glu Ile Tyr Asn Lys Asp Asn Arg Tyr
                565                 570                 575

Gly Arg Tyr Gln Ser His Gly Val Ala Gln Ile Val Ser Asn Gly Ser
            580                 585                 590

Gln Leu Ser Gln Gly Tyr Gln Gln Glu Gly Trp Asp Trp Asn Arg Met
        595                 600                 605

Glu Gly Ala Thr Thr Ile His Leu Pro Leu Lys Asp Leu Asp Ser Pro
    610                 615                 620

Lys Pro His Thr Leu Met Gly Arg Gly Glu Arg Gly Phe Ser Gly Thr
625                 630                 635                 640

Ser Ser Leu Glu Gly Gln Tyr Gly Met Met Ala Phe Asn Leu Ile Tyr
                645                 650                 655

Pro Ala Asn Leu Glu Arg Phe Asp Pro Asn Phe Thr Ala Lys Lys Ser
```

```
                    660                 665                 670
Val Leu Ala Ala Asp Asn His Leu Ile Phe Ile Gly Ser Asn Ile Asn
                675                 680                 685

Ser Ser Asp Lys Asn Lys Asn Val Glu Thr Thr Leu Phe Gln His Ala
        690                 695                 700

Ile Thr Pro Thr Leu Asn Thr Leu Trp Ile Asn Gly Gln Lys Ile Glu
705                 710                 715                 720

Asn Met Pro Tyr Gln Thr Thr Leu Gln Gln Gly Asp Trp Leu Ile Asp
                725                 730                 735

Ser Asn Gly Asn Gly Tyr Leu Ile Thr Gln Ala Glu Lys Val Asn Val
            740                 745                 750

Ser Arg Gln His Gln Val Ser Ala Glu Asn Lys Asn Arg Gln Pro Thr
        755                 760                 765

Glu Gly Asn Phe Ser Ser Ala Trp Ile Asp His Ser Thr Arg Pro Lys
        770                 775                 780

Asp Ala Ser Tyr Glu Tyr Met Val Phe Leu Asp Ala Thr Pro Glu Lys
785                 790                 795                 800

Met Gly Glu Met Ala Gln Lys Phe Arg Glu Asn Asn Gly Leu Tyr Gln
                805                 810                 815

Val Leu Arg Lys Asp Lys Asp Val His Ile Ile Leu Asp Lys Leu Ser
            820                 825                 830

Asn Val Thr Gly Tyr Ala Phe Tyr Gln Pro Ala Ser Ile Glu Asp Lys
            835                 840                 845

Trp Ile Lys Lys Val Asn Lys Pro Ala Ile Val Met Thr His Arg Gln
850                 855                 860

Lys Asp Thr Leu Ile Val Ser Ala Val Thr Pro Asp Leu Asn Met Thr
865                 870                 875                 880

Arg Gly Lys Ala Ala Thr Pro Val Thr Ile Asn Val Thr Ile Asn Gly
                885                 890                 895

Lys Trp Gln Ser Ala Asp Lys Asn Ser Glu Val Lys Tyr Gln Val Ser
        900                 905                 910

Gly Asp Asn Thr Glu Leu Thr Phe Thr Ser Tyr Phe Gly Ile Pro Gly
        915                 920                 925

Glu Ile Lys Leu Ser Pro Leu Pro
930                 935

<210> SEQ ID NO 12
<211> LENGTH: 857
<212> TYPE: PRT
<213> ORGANISM: Proteus vulgaris

<400> SEQUENCE: 12

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
            20                  25                  30

Asn Glu Lys Pro Ile Asp Gly Tyr Leu Thr Ile Asp Phe Gly Glu Lys
        35                  40                  45

Leu Ile Ser Thr Ser Glu Ala Gln Ala Gly Phe Lys Val Lys Leu Asp
    50                  55                  60

Phe Thr Gly Trp Arg Thr Val Gly Val Ser Leu Asn Asn Asp Leu Glu
65                  70                  75                  80

Asn Arg Glu Met Thr Leu Asn Ala Thr Asn Thr Ser Ser Asp Gly Thr
                85                  90                  95

Gly Asp Ser Ile Gly Arg Ser Leu Gly Ala Lys Val Asp Ser Ile Arg
```

-continued

```
                100                 105                 110
Phe Lys Ala Pro Ser Asn Val Ser Gln Gly Glu Ile Tyr Ile Asp Arg
            115                 120                 125
Ile Met Phe Ser Val Asp Asp Ala Arg Tyr Gln Trp Ser Asp Tyr Gln
        130                 135                 140
Val Lys Thr Arg Leu Ser Glu Pro Glu Ile Gly Phe His Asn Val Lys
145                 150                 155                 160
Pro Gln Leu Pro Val Thr Pro Glu Asn Leu Ala Ala Ile Asp Leu Ile
                165                 170                 175
Arg Gln Arg Leu Ile Asn Glu Phe Val Gly Glu Lys Glu Thr Asn
            180                 185                 190
Leu Ala Leu Glu Glu Asn Ile Ser Lys Leu Lys Ser Asp Phe Asp Ala
        195                 200                 205
Leu Asn Thr His Thr Leu Ala Asn Gly Gly Thr Gln Gly Arg His Leu
        210                 215                 220
Ile Thr Asp Lys Gln Ile Ile Tyr Gln Pro Glu Asn Leu Asn Ser
225                 230                 235                 240
Gly Asp Lys Gly Leu Phe Asp Asn Tyr Val Ile Leu Gly Asn Tyr Thr
                245                 250                 255
Thr Leu Met Phe Asn Ile Ser Arg Ala Tyr Val Leu Glu Lys Asp Pro
            260                 265                 270
Thr Gln Lys Ala Gln Leu Lys Gln Met Tyr Leu Leu Met Thr Lys His
        275                 280                 285
Leu Leu Asp Gln Gly Phe Val Lys Gly Ser Ala Leu Val Thr Thr His
        290                 295                 300
His Trp Gly Tyr Ser Ser Arg Trp Trp Tyr Ile Ser Thr Leu Leu Met
305                 310                 315                 320
Ser Asp Ala Leu Lys Glu Ala Asn Leu Gln Thr Gln Val Tyr Asp Ser
                325                 330                 335
Leu Leu Trp Tyr Ser Arg Glu Phe Lys Ser Ser Phe Asp Met Lys Val
            340                 345                 350
Ser Ala Asp Ser Ser Asp Leu Asp Tyr Phe Asn Thr Leu Ser Arg Gln
        355                 360                 365
His Leu Ala Leu Leu Leu Glu Pro Asp Asp Gly Lys Arg Ile Asn
        370                 375                 380
Leu Tyr Asn Thr Phe Ser His Tyr Ile Thr Gly Ala Leu Thr Gly Val
385                 390                 395                 400
Pro Pro Gly Gly Lys Asp Gly Leu Arg Pro Asp Gly Thr Ala Trp Arg
                405                 410                 415
His Glu Gly Asn Tyr Pro Gly Tyr Ser Phe Pro Ala Phe Lys Asn Ala
            420                 425                 430
Ser Gly Leu Ile Tyr Leu Leu Arg Asp Thr Pro Phe Ser Val Gly Glu
        435                 440                 445
Ser Gly Trp Asn Asn Lys Lys Ala Met Val Ser Ala Trp Ile Tyr Ser
        450                 455                 460
Asn Pro Glu Val Gly Leu Pro Leu Ala Gly Arg His Pro Phe Asn Ser
465                 470                 475                 480
Pro Ser Leu Lys Ser Val Ala Gly Gly Tyr Tyr Trp Leu Ala Met Ser
                485                 490                 495
Ala Lys Ser Ser Pro Asp Lys Thr Leu Ala Ser Ile Tyr Leu Ala Ile
            500                 505                 510
Ser Asp Lys Thr Gln Asn Glu Ser Thr Ala Ile Phe Gly Glu Thr Ile
        515                 520                 525
```

```
Thr Pro Ala Ser Leu Pro Gln Gly Phe Tyr Ala Phe Ile Gly Gly Ala
    530                 535                 540

Phe Gly Ile His Arg Trp Gln Asp Lys Met Val Thr Leu Lys Ala Tyr
545                 550                 555                 560

Asn Thr Asn Val Trp Ser Ser Glu Ile Tyr Asn Lys Asp Asn Arg Tyr
                565                 570                 575

Gly Arg Tyr Gln Ser His Gly Val Ala Gln Ile Val Ser Asn Gly Ser
            580                 585                 590

Gln Leu Ser Gln Gly Tyr Gln Gln Gly Trp Asp Trp Asn Arg Met
        595                 600                 605

Glu Gly Ala Thr Thr Ile His Leu Pro Leu Lys Asp Leu Asp Ser Pro
610                 615                 620

Lys Pro His Thr Leu Met Gly Arg Gly Glu Arg Gly Phe Ser Gly Thr
625                 630                 635                 640

Ser Ser Leu Glu Gly Gln Tyr Gly Met Met Ala Phe Asn Leu Ile Tyr
                645                 650                 655

Pro Ala Asn Leu Glu Arg Phe Asp Pro Asn Phe Thr Ala Lys Lys Ser
            660                 665                 670

Val Leu Ala Ala Asp Asn His Leu Ile Phe Ile Gly Ser Asn Ile Asn
        675                 680                 685

Ser Ser Asp Lys Asn Lys Asn Val Glu Thr Thr Leu Phe Gln His Ala
    690                 695                 700

Ile Thr Pro Thr Leu Asn Thr Leu Trp Ile Asn Gly Gln Lys Ile Glu
705                 710                 715                 720

Asn Met Pro Tyr Gln Thr Thr Leu Gly Gln Gly Asp Trp Leu Ile Asp
                725                 730                 735

Ser Asn Gly Asn Gly Tyr Leu Ile Thr Gln Ala Glu Lys Val Asn Val
            740                 745                 750

Ser Arg Gln His Gln Val Ser Ala Glu Asn Lys Asn Arg Gln Pro Thr
        755                 760                 765

Glu Gly Asn Phe Ser Ser Ala Trp Ile Asp His Ser Thr Arg Pro Lys
    770                 775                 780

Asp Ala Ser Tyr Glu Tyr Met Val Phe Leu Asp Ala Thr Pro Glu Lys
785                 790                 795                 800

Met Gly Glu Met Ala Gln Lys Phe Arg Glu Asn Asn Gly Leu Tyr Gln
                805                 810                 815

Val Leu Arg Lys Asp Lys Asp Val His Ile Ile Leu Asp Lys Leu Ser
            820                 825                 830

Asn Val Thr Gly Tyr Ala Phe Tyr Gln Pro Ala Ser Ile Glu Asp Lys
        835                 840                 845

Trp Ile Lys Lys Val Asn Lys Pro Ala
    850                 855

<210> SEQ ID NO 13
<211> LENGTH: 3980
<212> TYPE: DNA
<213> ORGANISM: Proteus vulgaris

<400> SEQUENCE: 13
ggaattccat cactcaatca ttaaatttag gcacaacgat gggctatcag cgttatgaca      60
aatttaatga aggacgcatt ggtttcactg ttagccagcg tttctaagga gaaaaataat     120
gccgatattt cgttttactg cacttgcaat gacattgggg ctattatcag cgccttataa     180
cgcgatggca gccaccagca atcctgcatt tgatcctaaa aatctgatgc agtcagaaat     240
ttaccatttt gcacaaaata acccattagc agacttctca tcagataaaa actcaatact     300
```

```
aacgttatct gataaacgta gcattatggg aaaccaatct cttttatgga aatggaaagg    360
tggtagtagc tttactttac ataaaaaact gattgtcccc accgataaag aagcatctaa    420
agcatgggga cgctcatcta cccccgtttt ctcattttgg ctttacaatg aaaaaccgat    480
tgatggttat cttactatcg atttcggaga aaaactcatt tcaaccagtg aggctcaggc    540
aggctttaaa gtaaaattag atttcactgg ctggcgtgct gtgggagtct ctttaaataa    600
cgatcttgaa aatcgagaga tgaccttaaa tgcaaccaat acctcctctg atggtactca    660
agacagcatt gggcgttctt taggtgctaa agtcgatagt attcgtttta aagcgccttc    720
taatgtgagt cagggtgaaa tctatatcga ccgtattatg ttttctgtcg atgatgctcg    780
ctaccaatgg tctgattatc aagtaaaaac tcgcttatca gaacctgaaa ttcaatttca    840
caacgtaaag ccacaactac ctgtaacacc tgaaaattta gcggccattg atcttattcg    900
ccaacgtcta attaatgaat tgtcggagg tgaaaaagag acaaacctcg cattagaaga    960
gaatatcagc aaattaaaaa gtgatttcga tgctcttaat attcacactt tagcaaatgg    1020
tggaacgcaa ggcagacatc tgatcactga taaacaaatc attatttatc aaccagagaa    1080
tcttaactcc caagataaac aactatttga taattatgtt attttaggta attacacgac    1140
attaatgttt aatattagcc gtgcttatgt gctggaaaaa gatcccacac aaaaggcgca    1200
actaaagcag atgtacttat taatgacaaa gcatttatta gatcaaggct tgttaaagg    1260 gagtgcttta gtgacaaccc atcactgggg atacagttct cgttggtggt atatttccac    1320
gttattaatg tctgatgcac taaaagaagc gaacctacaa actcaagttt atgattcatt    1380
actgtggtat tcacgtgagt ttaaaagtag ttttgatatg aaagtaagtg ctgatagctc    1440
tgatctagat tatttcaata cccttatctcg ccaacattta gccttattat tactagagcc    1500
tgatgatcaa aagcgtatca acttagttaa tactttcagc cattatatca ctggcgcatt    1560
aacgcaagtg ccaccgggtg gtaaagatgg tttacgccct gatggtacag catggcgaca    1620
tgaaggcaac tatccgggct actctttccc agcctttaaa aatgcctctc agcttattta    1680
tttattacgc gatacaccat tttcagtggg tgaaagtggt tggaataacc tgaaaaaagc    1740
gatggtttca gcgtggatct acagtaatcc agaagttgga ttaccgcttg caggaagaca    1800
cccttttaac tcaccttcgt taaaatcagt cgctcaaggc tattactggc ttgccatgtc    1860
tgcaaaatca tcgcctgata aaacacttgc atctatttat cttgcgatta gtgataaaac    1920
acaaaatgaa tcaactgcta tttttggaga aactattaca ccagcgtctt tacctcaagg    1980
tttctatgcc tttaatggcg gtgcttttgg tattcatcgt tggcaagata aatggtgac    2040 actgaaagct tataacacca atgtttggtc atctgaaatt tataacaaag ataaccgtta    2100
tggccgttac caaagtcatg gtgtcgctca aatagtgagt aatggctcgc agctttcaca    2160
gggctatcag caagaaggtt gggattggaa tagaatgcaa gggggcaacca ctattcacct    2220 tcctcttaaa gacttagaca gtcctaaacc tcataccttaa tgcaacgtg gagagcgtgg    2280 atttagcgga acatcatccc ttgaaggtca atatggcatg atggcattcg atcttatta    2340 tcccgccaat cttgagcgtt ttgatcctaa tttcactgcg aaaagagtg tattagccgc    2400 tgataatcac ttaattttta ttggtagcaa tataatagt agtgataaaa ataaaatgt    2460 tgaaacgacc ttattccaac atgccattac tccaacatta aatacccttt ggattaatgg    2520
acaaaagata gaaaacatgc cttatcaaac aacacttcaa caaggtgatt ggttaattga    2580
tagcaatggc aatggttact taattactca agcagaaaaa gtaaatgtaa gtcgccaaca    2640
tcaggtttca gcggaaaata aaaatcgcca accgacagaa ggaaacttta gctcggcatg    2700
```

```
gatcgatcac agcactcgcc ccaaagatgc cagttatgag tatatggtct ttttagatgc    2760
gacacctgaa aaaatgggag agatggcaca aaaattccgt gaaaataatg ggttatatca    2820
ggttcttcgt aaggataaag acgttcatat tattctcgat aaactcagca atgtaacggg    2880
atatgccttt tatcagccag catcaattga agacaaatgg atcaaaaagg ttaataaacc    2940
tgcaattgtg atgactcatc gacaaaaaga cactcttatt gtcagtgcag ttacacctga    3000
tttaaatatg actcgccaaa aagcagcaac tcctgtcacc atcaatgtca cgattaatgg    3060
caaatggcaa tctgctgata aaatagtga agtgaaatat caggtttctg gtgataacac    3120
tgaactgacg tttacgagtt actttggtat tccacaagaa atcaaactct cgccactccc    3180
ttgatttaat caaagaacg ctcttgcgtt cctttttat ttgcaggaaa tctgattatg    3240
ctaataaaaa acccttagc ccacgcggtt acattaagcc tctgtttatc attcccgca    3300 caagcattac ccactctgtc tcatgaagct ttcggcgata tttatctttt tgaaggtgaa    3360
ttacccaata cccttaccac ttcaaataat aatcaattat cgctaagcaa acagcatgct    3420
aaagatggtg aacaatcact caaatggcaa tatcaaccac aagcaacatt aacactaaat    3480
aatattgtta attaccaaga tgataaaaat acagccacac cactcacttt tatgatgtgg    3540
atttataatg aaaaacctca atcttcccca ttaacgttag catttaaaca aaataataaa    3600
attgcactaa gttttaatgc tgaacttaat tttacggggt ggcgaggtat tgctgttcct    3660
tttcgtgata tgcaaggctc tgcgacaggt caacttgatc aattagtgat caccgctcca    3720
aaccaagccg gaacactctt ttttgatcaa atcatcatga gtgtaccgtt agacaatcgt    3780
tgggcagtac ctgactatca aacaccttac gtaaataacg cagtaaacac gatggttagt    3840
aaaaactgga gtgcattatt gatgtacgat cagatgtttc aagcccatta ccctacttta    3900
aacttcgata ctgaatttcg cgatgaccaa acagaaatgg cttcgattta tcagcgcttt    3960
gaatattatc aaggaattcc                                                 3980
```

<210> SEQ ID NO 14
<211> LENGTH: 997
<212> TYPE: PRT
<213> ORGANISM: Proteus vulgaris

<400> SEQUENCE: 14

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140
```

```
Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
            165                 170                 175

Ser Asn Val Ser Gln Gly Glu Ile Tyr Ile Asp Arg Ile Met Phe Ser
        180                 185                 190

Val Asp Asp Ala Arg Tyr Gln Trp Ser Asp Tyr Gln Val Lys Thr Arg
    195                 200                 205

Leu Ser Glu Pro Glu Ile Gln Phe His Asn Val Lys Pro Gln Leu Pro
210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575
```

```
Thr Gln Asn Glu Ser Thr Ala Ile Phe Gly Glu Thr Ile Thr Pro Ala
            580                 585                 590
Ser Leu Pro Gln Gly Phe Tyr Ala Phe Asn Gly Gly Ala Phe Gly Ile
        595                 600                 605
His Arg Trp Gln Asp Lys Met Val Thr Leu Lys Ala Tyr Asn Thr Asn
    610                 615                 620
Val Trp Ser Ser Glu Ile Tyr Asn Lys Asp Asn Arg Tyr Gly Arg Tyr
625                 630                 635                 640
Gln Ser His Gly Val Ala Gln Ile Val Ser Asn Gly Ser Gln Leu Ser
            645                 650                 655
Gln Gly Tyr Gln Gln Glu Gly Trp Asp Trp Asn Arg Met Pro Gly Ala
        660                 665                 670
Thr Thr Ile His Leu Pro Leu Lys Asp Leu Asp Ser Pro Lys Pro His
    675                 680                 685
Thr Leu Met Gln Arg Gly Glu Arg Gly Phe Ser Gly Thr Ser Ser Leu
    690                 695                 700
Glu Gly Gln Tyr Gly Met Met Ala Phe Asp Leu Ile Tyr Pro Ala Asn
705                 710                 715                 720
Leu Glu Arg Phe Asp Pro Asn Phe Thr Ala Lys Lys Ser Val Leu Ala
            725                 730                 735
Ala Asp Asn His Leu Ile Phe Ile Gly Ser Asn Ile Asn Ser Ser Asp
            740                 745                 750
Lys Asn Lys Asn Val Glu Thr Thr Leu Phe Gln His Ala Ile Thr Pro
        755                 760                 765
Thr Leu Asn Thr Leu Trp Ile Asn Gly Gln Lys Ile Glu Asn Met Pro
    770                 775                 780
Tyr Gln Thr Thr Leu Gln Gln Gly Asp Trp Leu Ile Asp Ser Asn Gly
785                 790                 795                 800
Asn Gly Tyr Leu Ile Thr Gln Ala Glu Lys Val Asn Val Ser Arg Gln
            805                 810                 815
His Gln Val Ser Ala Glu Asn Lys Asn Arg Gln Pro Thr Glu Gly Asn
            820                 825                 830
Phe Ser Ser Ala Trp Ile Asp His Ser Thr Arg Pro Lys Asp Ala Ser
        835                 840                 845
Tyr Glu Tyr Met Val Phe Leu Asp Ala Thr Pro Glu Lys Met Gly Glu
    850                 855                 860
Met Ala Gln Lys Phe Arg Glu Asn Asn Gly Leu Tyr Gln Val Leu Arg
865                 870                 875                 880
Lys Asp Lys Asp Val His Ile Ile Leu Asp Lys Leu Ser Asn Val Thr
            885                 890                 895
Gly Tyr Ala Phe Tyr Gln Pro Ala Ser Ile Glu Asp Lys Trp Ile Lys
        900                 905                 910
Lys Val Asn Lys Pro Ala Ile Val Met Thr His Arg Gln Lys Asp Thr
    915                 920                 925
Leu Ile Val Ser Ala Val Thr Pro Asp Leu Asn Met Thr Arg Gln Lys
    930                 935                 940
Ala Ala Thr Pro Val Thr Ile Asn Val Thr Ile Asn Gly Lys Trp Gln
945                 950                 955                 960
Ser Ala Asp Lys Asn Ser Glu Val Lys Tyr Gln Val Ser Gly Asp Asn
            965                 970                 975
Thr Glu Leu Thr Phe Thr Ser Tyr Phe Gly Ile Pro Gln Glu Ile Lys
        980                 985                 990
Leu Ser Pro Leu Pro
```

<210> SEQ ID NO 15
<211> LENGTH: 978
<212> TYPE: PRT
<213> ORGANISM: Proteus vulgaris

<400> SEQUENCE: 15

```
Ala Gln Asn Asn Pro Leu Ala Asp Phe Ser Ser Asp Lys Asn Ser Ile
 1               5                  10                  15

Leu Thr Leu Ser Asp Lys Arg Ser Ile Leu Asn Gly Asn Gln Ser Leu
            20                  25                  30

Leu Trp Lys Trp Lys Gly Gly Ser Ser Phe Thr Leu His Lys Lys Leu
        35                  40                  45

Ile Val Pro Thr Asp Lys Glu Ala Ser Lys Ala Trp Gly Arg Ser Ser
50                  55                  60

Thr Pro Val Phe Ser Phe Trp Leu Tyr Asn Glu Lys Pro Ile Asp Gly
65                  70                  75                  80

Tyr Leu Thr Ile Asp Phe Gly Glu Lys Leu Ile Ser Thr Ser Glu Ala
                85                  90                  95

Gln Ala Gly Phe Leu Cys Val Lys Leu Asp Phe Thr Gly Trp Arg Ala
            100                 105                 110

Val Gly Val Ser Leu Asn Asn Asp Leu Glu Asn Arg Glu Met Thr Leu
        115                 120                 125

Asn Ala Thr Asn Thr Ser Ser Asp Gly Thr Gly Asp Ser Ile Gly Arg
130                 135                 140

Ser Leu Gly Ala Lys Val Asp Ser Ile Arg Phe Lys Ala Pro Ser Asn
145                 150                 155                 160

Val Ser Gln Gly Glu Ile Tyr Ile Asp Arg Ile Met Phe Ser Val Asp
                165                 170                 175

Asp Ala Arg Tyr Gln Trp Ser Asp Tyr Gln Val Lys Thr Arg Leu Ser
            180                 185                 190

Glu Pro Glu Ile Gly Phe His Asn Val Lys Pro Gln Leu Pro Val Thr
        195                 200                 205

Pro Glu Asn Leu Ala Ala Ile Asp Leu Ile Arg Gln Arg Leu Ile Asn
210                 215                 220

Glu Phe Val Gly Gly Lys Glu Thr Asn Leu Ala Leu Glu Glu Asn
225                 230                 235                 240

Ile Ser Lys Leu Lys Ser Asp Phe Asp Ala Leu Asn Ile His Thr Leu
                245                 250                 255

Ala Asn Gly Gly Thr Gln Gly Arg His Leu Ile Thr Asp Lys Gln Ile
            260                 265                 270

Ile Ile Tyr Gln Pro Glu Asn Leu Asn Ser Gly Asp Lys Gln Leu Phe
        275                 280                 285

Asp Asn Tyr Val Ile Leu Gly Asn Tyr Thr Thr Leu Met Phe Asn Ile
290                 295                 300

Ser Arg Ala Tyr Val Leu Glu Lys Asp Pro Thr Gln Lys Ala Gln Leu
305                 310                 315                 320

Lys Gln Met Tyr Leu Leu Met Thr Lys His Leu Leu Asp Gly Gly Phe
                325                 330                 335

Val Lys Gly Ser Ala Leu Val Thr Thr His His Trp Gly Tyr Ser Ser
            340                 345                 350

Arg Trp Trp Tyr Ile Ser Thr Leu Leu Met Ser Asp Ala Leu Lys Glu
        355                 360                 365

Ala Asn Leu Gln Thr Gln Val Tyr Asp Ser Leu Leu Trp Tyr Ser Arg
```

```
              370                 375                 380
Glu Phe Lys Ser Ser Phe Asp Met Lys Val Ser Ala Asp Ser Ser Asp
385                 390                 395                 400

Leu Asp Tyr Phe Asn Thr Leu Ser Arg Gln His Leu Ala Leu Leu Leu
                405                 410                 415

Leu Glu Pro Asp Asp Gly Lys Arg Ile Asn Leu Tyr Asn Thr Phe Ser
                420                 425                 430

His Tyr Ile Thr Gly Ala Leu Thr Gly Val Pro Pro Gly Gly Lys Asp
                435                 440                 445

Gly Leu Arg Pro Asp Gly Thr Ala Trp Arg His Glu Gly Asn Tyr Pro
450                 455                 460

Gly Tyr Ser Phe Pro Ala Phe Lys Asn Ala Ser Gly Leu Ile Tyr Leu
465                 470                 475                 480

Leu Arg Asp Thr Pro Phe Ser Val Gly Glu Ser Gly Trp Asn Asn Lys
                485                 490                 495

Lys Ala Met Val Ser Ala Trp Ile Tyr Ser Asn Pro Glu Val Gly Leu
                500                 505                 510

Pro Leu Ala Gly Arg His Pro Phe Asn Ser Pro Ser Leu Lys Ser Val
                515                 520                 525

Ala Gln Gly Tyr Tyr Trp Leu Ala Met Ser Ala Lys Ser Ser Pro Asp
530                 535                 540

Lys Thr Leu Ala Ser Ile Tyr Leu Ala Ile Ser Asp Lys Thr Gln Asn
545                 550                 555                 560

Glu Ser Thr Ala Ile Phe Gly Glu Thr Ile Thr Pro Ala Ser Leu Pro
                565                 570                 575

Gln Gly Phe Tyr Ala Phe Asn Gly Gly Ala Phe Gly Ile His Arg Trp
                580                 585                 590

Gln Asp Lys Met Val Thr Leu Lys Ala Tyr Asn Thr Asn Val Trp Ser
                595                 600                 605

Ser Glu Ile Tyr Asn Lys Asp Asn Arg Tyr Gly Arg Tyr Gln Ser His
610                 615                 620

Gly Val Ala Gln Ile Val Ser Asn Gly Ser Gln Leu Ser Gln Gly Tyr
625                 630                 635                 640

Gln Gln Glu Gly Trp Asp Trp Asn Arg Met Glu Gly Ala Thr Thr Ile
                645                 650                 655

His Leu Pro Leu Lys Asp Leu Asp Ser Pro Lys Pro His Thr Leu Met
                660                 665                 670

Gly Arg Gly Glu Arg Gly Phe Ser Gly Thr Ser Ser Leu Glu Gly Gly
                675                 680                 685

Tyr Gly Met Met Ala Phe Asn Leu Ile Tyr Pro Ala Asn Leu Glu Arg
                690                 695                 700

Phe Asp Pro Asn Phe Thr Ala Lys Lys Ser Val Leu Ala Ala Asp Asn
705                 710                 715                 720

His Leu Ile Phe Ile Gly Ser Asn Ile Asn Ser Asp Lys Asn Lys
                725                 730                 735

Asn Val Glu Thr Thr Leu Phe Gln His Ala Ile Thr Pro Thr Leu Asn
                740                 745                 750

Thr Leu Trp Ile Asn Gly Gln Lys Ile Glu Asn Met Pro Tyr Gln Thr
                755                 760                 765

Thr Leu Gln Gln Gly Asp Trp Leu Ile Asp Ser Asn Gly Asn Gly Tyr
                770                 775                 780

Leu Ile Thr Gln Ala Glu Lys Val Asn Val Ser Arg Gln His Gln Val
785                 790                 795                 800
```

-continued

```
Ser Ala Glu Asn Lys Asn Arg Gln Pro Thr Glu Gly Asn Phe Ser Ser
                805                 810                 815

Ala Trp Ile Asp His Ser Thr Arg Pro Lys Asp Ala Ser Tyr Glu Tyr
        820                 825                 830

Met Val Phe Leu Asp Ala Thr Pro Glu Lys Met Gly Glu Met Ala Gln
        835                 840                 845

Lys Phe Arg Glu Asn Asn Gly Leu Tyr Gln Val Leu Arg Lys Asp Lys
    850                 855                 860

Asp Val His Ile Ile Leu Asp Lys Leu Ser Asn Val Thr Gly Tyr Ala
865                 870                 875                 880

Phe Tyr Gln Pro Ala Ser Ile Glu Asp Lys Trp Ile Lys Lys Val Asn
                885                 890                 895

Lys Pro Ala Ile Val Met Thr His Arg Gln Lys Asp Thr Leu Ile Val
            900                 905                 910

Ser Ala Val Thr Pro Asp Leu Met Asn Thr Arg Gly Lys Ala Ala Thr
        915                 920                 925

Pro Val Thr Ile Asn Val Thr Ile Asn Gly Lys Trp Gln Ser Ala Asp
    930                 935                 940

Lys Asn Ser Glu Val Lys Tyr Gln Val Ser Gly Asp Asn Thr Glu Leu
945                 950                 955                 960

Thr Phe Thr Ser Tyr Phe Gly Ile Pro Gly Glu Ile Lys Leu Ser Pro
                965                 970                 975

Leu Pro

<210> SEQ ID NO 16
<211> LENGTH: 936
<212> TYPE: PRT
<213> ORGANISM: Proteus vulgaris

<400> SEQUENCE: 16

Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
                20                  25                  30

Asn Glu Lys Pro Ile Asp Gly Tyr Leu Thr Ile Asp Phe Gly Glu Lys
            35                  40                  45

Leu Ile Ser Thr Ser Glu Ala Gln Ala Gly Phe Lys Val Lys Leu Asp
        50                  55                  60

Phe Thr Gly Trp Arg Ala Val Gly Val Ser Leu Asn Asn Asp Leu Glu
65                  70                  75                  80

Asn Arg Glu Met Thr Leu Asn Ala Thr Asn Thr Ser Ser Asp Gly Thr
                85                  90                  95

Gly Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
        115                 120                 125

Ile Met Phe Ser Val Asp Asp Ala Arg Tyr Gln Trp Ser Asp Tyr Gln
    130                 135                 140

Val Lys Thr Arg Leu Ser Glu Pro Glu Ile Gly Phe His Asn Val Lys
145                 150                 155                 160

Pro Gln Leu Pro Val Thr Pro Glu Asn Leu Ala Ala Ile Asp Leu Ile
                165                 170                 175

Arg Gln Arg Leu Ile Asn Glu Phe Val Gly Gly Glu Lys Glu Thr Asn
            180                 185                 190

Leu Ala Leu Glu Glu Asn Ile Ser Lys Leu Lys Ser Asp Phe Asp Ala
```

```
                195                 200                 205
Leu Asn Ile His Thr Leu Ala Asn Gly Gly Thr Gln Gly Arg His Leu
    210                 215                 220
Ile Thr Asp Lys Gln Ile Ile Tyr Gln Pro Glu Asn Leu Asn Ser
225                 230                 235                 240
Gly Asp Lys Gln Leu Phe Asp Asn Tyr Val Ile Leu Gly Asn Tyr Thr
                245                 250                 255
Thr Leu Met Phe Asn Ile Ser Arg Ala Tyr Val Leu Glu Lys Asp Pro
            260                 265                 270
Thr Gln Lys Ala Gln Leu Lys Gln Met Tyr Leu Leu Met Thr Lys His
            275                 280                 285
Leu Leu Asp Gly Gly Phe Val Lys Gly Ser Ala Leu Val Thr Thr His
        290                 295                 300
His Trp Gly Tyr Ser Ser Arg Trp Trp Tyr Ile Ser Thr Leu Leu Met
305                 310                 315                 320
Ser Asp Ala Leu Lys Glu Ala Asn Leu Gln Thr Gln Val Tyr Asp Ser
                325                 330                 335
Leu Leu Trp Tyr Ser Arg Glu Phe Lys Ser Ser Phe Asp Met Lys Val
            340                 345                 350
Ser Ala Asp Ser Ser Asp Leu Asp Tyr Phe Asn Thr Leu Ser Arg Gln
        355                 360                 365
His Leu Ala Leu Leu Leu Glu Pro Asp Asp Gly Lys Arg Ile Asn
    370                 375                 380
Val Asn Thr Phe Ser His Tyr Ile Thr Gly Ala Leu Thr Gly Val Pro
385                 390                 395                 400
Pro Gly Gly Lys Asp Gly Leu Arg Pro Asp Gly Thr Ala Trp Arg His
                405                 410                 415
Glu Gly Asn Tyr Pro Gly Tyr Ser Phe Pro Ala Phe Lys Asn Ala Ser
            420                 425                 430
Gly Leu Ile Tyr Leu Leu Arg Asp Thr Pro Phe Ser Val Gly Glu Ser
        435                 440                 445
Gly Trp Asn Asn Leu Lys Lys Ala Met Val Ser Ala Trp Ile Tyr Ser
    450                 455                 460
Asn Pro Glu Val Gly Leu Pro Leu Ala Gly Arg His Pro Phe Asn Ser
465                 470                 475                 480
Pro Ser Leu Lys Ser Val Ala Gln Gly Tyr Tyr Trp Leu Ala Met Ser
                485                 490                 495
Ala Lys Ser Ser Pro Asp Lys Thr Leu Ala Ser Ile Tyr Leu Ala Ile
            500                 505                 510
Ser Asp Lys Thr Gln Asn Glu Ser Thr Ala Ile Phe Gly Glu Thr Ile
        515                 520                 525
Thr Pro Ala Ser Leu Pro Gln Gly Phe Tyr Ala Phe Asn Gly Gly Ala
    530                 535                 540
Phe Gly Ile His Arg Trp Gln Asp Lys Met Val Thr Leu Lys Ala Tyr
545                 550                 555                 560
Asn Thr Asn Val Trp Ser Ser Glu Ile Tyr Asn Lys Asp Asn Arg Tyr
                565                 570                 575
Gly Arg Tyr Gln Ser His Gly Val Ala Gln Ile Val Ser Asn Gly Ser
            580                 585                 590
Gln Leu Ser Gln Gly Tyr Gln Gln Glu Gly Trp Asp Trp Asn Arg Met
        595                 600                 605
Glu Gly Ala Thr Thr Ile His Leu Pro Leu Lys Asp Leu Asp Ser Pro
    610                 615                 620
```

```
Lys Pro His Thr Leu Met Gly Arg Gly Glu Arg Gly Phe Ser Gly Thr
625                 630                 635                 640

Ser Ser Leu Glu Gly Gly Tyr Gly Met Met Ala Phe Asn Leu Ile Tyr
            645                 650                 655

Pro Ala Asn Leu Glu Arg Phe Asp Pro Asn Phe Thr Ala Lys Lys Ser
                660                 665                 670

Val Leu Ala Ala Asp Asn His Leu Ile Phe Ile Gly Ser Asn Ile Asn
            675                 680                 685

Ser Ser Asp Lys Asn Lys Asn Val Glu Thr Thr Leu Phe Gln His Ala
690                 695                 700

Ile Thr Pro Thr Leu Asn Thr Leu Trp Ile Asn Gly Gln Lys Ile Glu
705                 710                 715                 720

Asn Met Pro Tyr Gln Thr Thr Leu Gln Gln Gly Asp Trp Leu Ile Asp
                725                 730                 735

Ser Asn Gly Asn Gly Tyr Leu Ile Thr Gln Ala Glu Lys Val Asn Val
            740                 745                 750

Ser Arg Gln His Gln Val Ser Ala Glu Asn Lys Asn Arg Gln Pro Thr
            755                 760                 765

Glu Gly Asn Phe Ser Ser Ala Trp Ile Asp His Ser Thr Arg Pro Lys
770                 775                 780

Asp Ala Ser Tyr Glu Tyr Met Val Phe Leu Asp Ala Thr Pro Glu Lys
785                 790                 795                 800

Met Gly Glu Met Ala Gly Lys Phe Arg Glu Asn Asn Gly Leu Tyr Gln
                805                 810                 815

Val Leu Arg Lys Asp Lys Asp Val His Ile Ile Leu Asp Lys Leu Ser
            820                 825                 830

Asn Val Thr Gly Tyr Ala Phe Tyr Gln Pro Ala Ser Ile Glu Asp Lys
            835                 840                 845

Trp Ile Lys Lys Val Asn Lys Pro Ala Ile Val Met Thr His Arg Gln
850                 855                 860

Lys Asp Thr Leu Ile Val Ser Ala Val Thr Pro Asp Leu Asn Met Thr
865                 870                 875                 880

Arg Gly Lys Ala Ala Thr Pro Val Thr Ile Asn Val Thr Ile Asn Gly
                885                 890                 895

Lys Trp Gln Ser Ala Asp Lys Asn Ser Glu Val Lys Tyr Gln Val Ser
            900                 905                 910

Gly Asp Asn Thr Glu Leu Thr Phe Thr Ser Tyr Phe Gly Ile Pro Gly
            915                 920                 925

Glu Ile Lys Leu Ser Pro Leu Pro
930                 935
```

<210> SEQ ID NO 17
<211> LENGTH: 858
<212> TYPE: PRT
<213> ORGANISM: Proteus vulgaris

<400> SEQUENCE: 17

```
Phe Thr Leu His Lys Lys Leu Ile Val Pro Thr Asp Lys Glu Ala Ser
1               5                   10                  15

Lys Ala Trp Gly Arg Ser Ser Thr Pro Val Phe Ser Phe Trp Leu Tyr
            20                  25                  30

Asn Glu Lys Pro Ile Asp Gly Tyr Leu Thr Ile Asp Phe Gly Glu Lys
        35                  40                  45

Leu Ile Ser Thr Ser Glu Ala Gln Ala Gly Phe Lys Val Lys Leu Asp
    50                  55                  60
```

```
Phe Thr Gly Trp Arg Ala Val Gly Val Ser Leu Asn Asn Asp Leu Glu
 65                  70                  75                  80

Asn Arg Glu Met Thr Leu Asn Ala Thr Asn Thr Ser Ser Asp Gly Thr
                 85                  90                  95

Gly Asp Ser Ile Gly Arg Ser Leu Gly Ala Lys Val Asp Ser Ile Arg
            100                 105                 110

Phe Lys Ala Pro Ser Asn Val Ser Gln Gly Glu Ile Tyr Ile Asp Arg
        115                 120                 125

Ile Met Phe Ser Val Asp Asp Ala Arg Tyr Gln Trp Ser Asp Tyr Gln
    130                 135                 140

Val Lys Thr Arg Leu Ser Glu Pro Glu Ile Gly Phe His Asn Val Lys
145                 150                 155                 160

Pro Gly Leu Pro Val Thr Pro Glu Asn Leu Ala Ala Ile Asp Leu Ile
                165                 170                 175

Arg Gln Arg Leu Ile Asn Glu Phe Val Gly Gly Lys Glu Thr Asn
            180                 185                 190

Leu Ala Leu Glu Glu Asn Ile Ser Lys Leu Lys Ser Asp Phe Asp Ala
        195                 200                 205

Leu Asn Ile His Thr Leu Ala Asn Gly Gly Thr Gln Gly Arg His Leu
    210                 215                 220

Ile Thr Asp Lys Gln Ile Ile Tyr Gln Pro Glu Asn Leu Asn Ser
225                 230                 235                 240

Gly Asp Lys Gly Leu Phe Asp Asn Tyr Val Ile Leu Gly Asn Tyr Thr
                245                 250                 255

Thr Leu Met Phe Asn Ile Ser Arg Ala Tyr Val Leu Glu Lys Asp Pro
            260                 265                 270

Thr Gln Lys Ala Gln Leu Lys Gln Met Tyr Leu Leu Met Thr Lys His
        275                 280                 285

Leu Leu Asp Gly Gly Phe Val Lys Gly Ser Ala Leu Val Thr Thr His
    290                 295                 300

His Trp Gly Tyr Ser Ser Arg Trp Trp Tyr Ile Ser Thr Leu Leu Met
305                 310                 315                 320

Ser Asp Ala Leu Lys Glu Ala Asn Leu Gln Thr Gln Val Tyr Asp Ser
                325                 330                 335

Leu Leu Trp Tyr Ser Arg Glu Phe Lys Ser Ser Phe Asp Met Lys Val
            340                 345                 350

Ser Ala Asp Ser Ser Asp Leu Asp Tyr Phe Asn Thr Leu Ser Arg Gln
        355                 360                 365

His Leu Ala Leu Leu Leu Glu Pro Asp Asp Gly Lys Arg Ile Asn
    370                 375                 380

Leu Tyr Asn Thr Phe Ser His Tyr Ile Thr Gly Ala Leu Thr Gly Val
385                 390                 395                 400

Pro Pro Gly Gly Lys Asp Gly Leu Arg Pro Asp Gly Thr Ala Trp Arg
                405                 410                 415

His Glu Gly Asn Tyr Pro Gly Tyr Ser Phe Pro Ala Phe Lys Asn Ala
            420                 425                 430

Ser Gln Leu Ile Tyr Leu Leu Arg Asp Thr Pro Phe Ser Val Gly Glu
        435                 440                 445

Ser Gly Trp Asn Asn Ile Lys Lys Ala Met Val Ser Ala Trp Ile Tyr
    450                 455                 460

Ser Asn Pro Glu Val Gly Leu Pro Leu Ala Gly Arg His Pro Phe Asn
465                 470                 475                 480

Ser Pro Ser Leu Lys Ser Val Ala Gln Gly Tyr Tyr Trp Leu Ala Met
                485                 490                 495
```

```
Ser Ala Lys Ser Ser Pro Asp Lys Thr Leu Ala Ser Ile Tyr Leu Ala
            500                 505                 510

Ile Ser Asp Lys Thr Gln Asn Glu Ser Thr Ala Ile Phe Gly Glu Thr
            515                 520                 525

Ile Thr Pro Ala Ser Leu Pro Gln Gly Phe Tyr Ala Phe Asn Gly Gly
            530                 535                 540

Ala Phe Gly Ile His Arg Trp Gln Asp Lys Met Val Thr Leu Lys Ala
545                 550                 555                 560

Tyr Asn Thr Asn Val Trp Ser Ser Glu Ile Tyr Asn Lys Asp Asn Arg
                565                 570                 575

Tyr Gly Arg Tyr Gln Ser His Gly Val Ala Gln Ile Val Ser Asn Gly
                580                 585                 590

Ser Gln Leu Ser Gln Gly Tyr Gln Gln Glu Gly Trp Asp Trp Asn Arg
            595                 600                 605

Met Glu Gly Ala Thr Thr Ile His Leu Pro Leu Lys Asp Leu Asp Ser
            610                 615                 620

Pro Lys Pro His Thr Leu Met Gly Arg Gly Glu Arg Gly Phe Ser Gly
625                 630                 635                 640

Thr Ser Ser Leu Glu Gly Gly Tyr Gly Met Met Ala Phe Asn Leu Ile
                645                 650                 655

Tyr Pro Ala Asn Leu Glu Arg Phe Asp Pro Asn Phe Thr Ala Lys Lys
                660                 665                 670

Ser Val Leu Ala Ala Asp Asn His Leu Ile Phe Ile Gly Ser Asn Ile
            675                 680                 685

Asn Ser Ser Asp Lys Asn Lys Asn Val Glu Thr Thr Leu Phe Gln His
            690                 695                 700

Ala Ile Thr Pro Thr Leu Asn Thr Leu Trp Ile Asn Gly Gln Lys Ile
705                 710                 715                 720

Glu Asn Met Pro Tyr Gln Thr Thr Leu Gln Gln Gly Asp Trp Leu Ile
                725                 730                 735

Asp Ser Asn Gly Asn Gly Tyr Leu Ile Thr Gln Ala Glu Lys Val Asn
            740                 745                 750

Val Ser Arg Gln His Gln Val Ser Ala Glu Asn Lys Asn Arg Gln Pro
            755                 760                 765

Thr Glu Gly Asn Phe Ser Ser Ala Trp Ile Asp His Ser Thr Arg Pro
            770                 775                 780

Lys Asp Ala Ser Tyr Glu Tyr Met Val Phe Leu Asp Ala Thr Pro Glu
785                 790                 795                 800

Lys Met Gly Glu Met Ala Gln Lys Phe Arg Glu Asn Asn Gly Leu Tyr
                805                 810                 815

Gln Val Leu Arg Lys Asp Lys Asp Val His Ile Ile Leu Asp Lys Leu
            820                 825                 830

Ser Asn Val Thr Gly Tyr Ala Phe Tyr Gln Pro Ala Ser Ile Glu Asp
            835                 840                 845

Lys Trp Ile Lys Lys Val Asn Lys Pro Ala
850                 855

<210> SEQ ID NO 18
<211> LENGTH: 994
<212> TYPE: PRT
<213> ORGANISM: Proteus vulgaris

<400> SEQUENCE: 18

Gly Arg Lys Lys Arg Arg Gly Arg Arg Pro Pro Gln Cys Ala Gly
1               5                   10                  15
```

Asn Asn Pro Leu Ala Asp Phe Ser Ser Asp Lys Asn Ser Ile Leu Thr
            20                  25                  30

Leu Ser Asp Lys Arg Ser Ile Met Gly Asn Gly Ser Leu Leu Trp Lys
        35                  40                  45

Trp Lys Gly Gly Ser Ser Phe Thr Leu His Lys Lys Leu Ile Val Pro
    50                  55                  60

Thr Asp Lys Glu Ala Ser Lys Ala Trp Gly Arg Ser Ser Thr Pro Val
65                  70                  75                  80

Phe Ser Phe Trp Leu Tyr Asn Glu Lys Pro Ile Asp Gly Tyr Leu Thr
                85                  90                  95

Ile Asp Phe Gly Glu Lys Leu Ile Ser Thr Ser Glu Ala Gly Ala Gly
                100                 105                 110

Phe Lys Val Lys Leu Asp Phe Thr Gly Trp Arg Thr Val Gly Val Ser
            115                 120                 125

Leu Asn Asn Asp Leu Glu Asn Arg Glu Met Thr Leu Asn Ala Thr Asn
        130                 135                 140

Thr Ser Ser Asp Gly Thr Gly Asp Ser Ile Gly Arg Ser Leu Gly Ala
145                 150                 155                 160

Lys Val Asp Ser Ile Arg Phe Leu Cys Ala Pro Ser Asn Val Ser Gly
                165                 170                 175

Gly Glu Ile Tyr Ile Asp Arg Ile Met Phe Ser Val Asp Asp Ala Arg
                180                 185                 190

Tyr Gly Trp Ser Asp Tyr Gln Val Lys Thr Arg Leu Ser Glu Pro Glu
            195                 200                 205

Ile Gln Phe His Asn Val Lys Pro Gln Leu Pro Val Thr Pro Glu Asn
        210                 215                 220

Leu Ala Ala Ile Asp Leu Ile Arg Gln Arg Leu Ile Asn Glu Phe Val
225                 230                 235                 240

Gly Gly Glu Lys Glu Thr Asn Leu Ala Leu Glu Glu Asn Ile Ser Lys
                245                 250                 255

Leu Lys Ser Asp Phe Asp Ala Leu Asn Thr His Thr Leu Ala Asn Gly
            260                 265                 270

Gly Thr Gly Gly Arg His Leu Ile Thr Asp Lys Gly Ile Ile Ile Tyr
        275                 280                 285

Gly Pro Glu Asn Leu Asn Ser Gln Asp Lys Gln Leu Phe Asp Asn Tyr
    290                 295                 300

Val Ile Leu Gly Asn Tyr Thr Thr Leu Met Phe Asn Ile Ser Arg Ala
305                 310                 315                 320

Tyr Val Leu Glu Lys Asp Pro Thr Gln Lys Ala Gln Leu Lys Gln Met
                325                 330                 335

Tyr Leu Leu Met Thr Leu Cys His Leu Leu Asp Gln Gly Phe Val Lys
            340                 345                 350

Gly Ser Ala Leu Val Thr Thr His His Trp Gly Tyr Ser Ser Arg Trp
        355                 360                 365

Trp Tyr Ile Ser Thr Leu Leu Met Ser Asp Ala Leu Lys Glu Ala Asn
    370                 375                 380

Leu Gly Thr Gly Val Tyr Asp Ser Leu Leu Trp Tyr Ser Arg Glu Phe
385                 390                 395                 400

Lys Ser Ser Phe Asp Met Lys Val Ser Ala Asp Ser Ser Asp Leu Asp
                405                 410                 415

Tyr Phe Asn Thr Leu Ser Arg Gln His Leu Ala Leu Leu Leu Leu Glu
            420                 425                 430

Pro Asp Asp Gln Lys Arg Ile Asn Leu Val Asn Thr Phe Ser His Tyr

```
            435                 440                 445
Ile Thr Gly Ala Leu Thr Gly Val Pro Pro Gly Gly Lys Asp Gly Leu
    450                 455                 460

Arg Pro Asp Gly Thr Ala Trp Arg His Glu Gly Asn Tyr Pro Gly Tyr
465                 470                 475                 480

Ser Phe Pro Ala Phe Lys Asn Ala Ser Gly Leu Ile Tyr Leu Leu Tyr
                485                 490                 495

Asp Thr Pro Phe Ser Val Gly Glu Ser Gly Trp Asn Ser Leu Lys Lys
                500                 505                 510

Ala Met Val Ser Ala Trp Ile Tyr Ser Asn Pro Glu Val Gly Leu Pro
            515                 520                 525

Leu Ala Gly Arg His Pro Leu Asn Ser Pro Ser Leu Lys Ser Val Ala
        530                 535                 540

Gly Gly Tyr Tyr Trp Leu Ala Met Ser Ala Lys Ser Ser Pro Asp Lys
545                 550                 555                 560

Thr Leu Ala Ser Ile Tyr Leu Ala Ile Ser Asp Lys Thr Gly Asn Glu
                565                 570                 575

Ser Thr Ala Ile Phe Gly Glu Thr Ile Thr Pro Ala Ser Leu Pro Gly
                580                 585                 590

Gly Phe Tyr Ala Phe Asn Gly Ala Phe Gly Ile His Arg Trp Gln
            595                 600                 605

Asp Lys Met Val Thr Leu Lys Ala Tyr Asn Thr Asn Val Trp Ser Ser
    610                 615                 620

Glu Ile Tyr Asn Lys Asp Asn Arg Tyr Gly Arg Tyr Gly Ser His Gly
625                 630                 635                 640

Val Ala Gly Ile Val Ser Asn Gly Ser Gln Leu Ser Gln Gly Tyr Gln
                645                 650                 655

Gln Glu Gly Trp Asp Trp Asn Arg Met Pro Gly Ala Thr Thr Ile His
                660                 665                 670

Leu Pro Leu Lys Asp Leu Asp Ser Pro Lys Pro His Thr Leu Met Gln
            675                 680                 685

Arg Gly Glu Arg Gly Phe Ser Gly Thr Ser Ser Leu Glu Gly Gly Tyr
        690                 695                 700

Gly Met Met Ala Phe Asp Leu Ile Tyr Pro Ala Asn Leu Glu Arg Phe
705                 710                 715                 720

Asp Pro Asn Phe Thr Ala Lys Lys Ser Val Leu Ala Ala Asp Asn His
                725                 730                 735

Leu Ile Phe Ile Gly Ser Asn Ile Asn Ser Ser Asp Lys Asn Lys Asn
                740                 745                 750

Val Glu Thr Thr Leu Phe Gly His Ala Ile Thr Pro Thr Leu Asn Thr
            755                 760                 765

Leu Trp Ile Asn Gly Gln Lys Ile Glu Asn Met Pro Tyr Gly Thr Thr
        770                 775                 780

Leu Gly Gln Gly Asp Trp Leu Ile Asp Ser Asn Gly Asn Gly Tyr Leu
785                 790                 795                 800

Ile Thr Gln Ala Glu Lys Val Asn Val Ser Arg Gln His Gln Val Ser
                805                 810                 815

Ala Glu Asn Lys Asn Arg Gln Pro Thr Glu Gly Asn Phe Ser Ser Ala
                820                 825                 830

Trp Ile Asp His Ser Thr Arg Pro Lys Asp Ala Ser Tyr Glu Tyr Ile
            835                 840                 845

Asn Val Phe Leu Asp Ala Thr Pro Glu Lys Met Gly Glu Met Ala Gly
        850                 855                 860
```

Lys Phe Arg Glu Asn Asn Gly Leu Tyr Gly Val Leu Arg Lys Asp Lys
865                 870                 875                 880

Asp Val His Ile Ile Leu Asp Lys Leu Ser Asn Val Thr Gly Tyr Ala
            885                 890                 895

Phe Tyr Gly Pro Ala Ser Ile Glu Asp Lys Trp Ile Lys Lys Val Asn
                900                 905                 910

Lys Pro Ala Ile Val Met Thr His Arg Gln Lys Asp Thr Leu Ile Val
            915                 920                 925

Ser Ala Val Thr Pro Asp Leu Asn Met Thr Arg Gln Lys Ala Ala Thr
930                 935                 940

Pro Val Thr Ile Asn Val Thr Ile Asn Gly Lys Trp Gln Ser Ala Asp
945                 950                 955                 960

Lys Asn Ser Glu Val Lys Tyr Gln Val Ser Gly Asp Asn Thr Glu Leu
            965                 970                 975

Thr Phe Thr Ser Tyr Phe Gly Ile Pro Gln Glu Ile Lys Leu Ser Pro
            980                 985                 990

Leu Pro

<210> SEQ ID NO 19
<211> LENGTH: 951
<212> TYPE: PRT
<213> ORGANISM: Proteus vulgaris

<400> SEQUENCE: 19

Gly Arg Lys Lys Arg Gly Arg Arg Pro Pro Gly Cys Phe Thr
1               5                   10                  15

Leu His Lys Lys Leu Ile Val Pro Thr Asp Lys Glu Ala Ser Lys Ala
            20                  25                  30

Trp Gly Arg Ser Ser Thr Pro Val Phe Ser Phe Trp Leu Tyr Asn Glu
        35                  40                  45

Lys Pro Ile Asp Gly Tyr Leu Thr Ile Asp Phe Gly Glu Lys Leu Ile
    50                  55                  60

Ser Thr Ser Glu Ala Gln Ala Gly Phe Lys Val Lys Leu Asp Phe Thr
65                  70                  75                  80

Gly Trp Arg Thr Val Gly Val Ser Leu Asn Asn Asp Leu Glu Asn Arg
                85                  90                  95

Glu Met Thr Leu Asn Ala Thr Asn Thr Ser Ser Asp Gly Thr Gly Asp
            100                 105                 110

Ser Ile Gly Arg Ser Leu Gly Ala Lys Val Asp Ser Ile Arg Phe Leu
        115                 120                 125

Cys Ala Pro Ser Asn Val Ser Gly Gly Glu Ile Tyr Ile Asp Arg Ile
    130                 135                 140

Met Phe Ser Val Asp Asp Ala Arg Tyr Gln Trp Ser Asp Tyr Gln Val
145                 150                 155                 160

Lys Thr Arg Leu Ser Glu Pro Glu Ile Gln Phe His Asn Val Lys Pro
                165                 170                 175

Gly Leu Pro Val Thr Pro Glu Asn Leu Ala Ala Ile Asp Leu Ile Arg
            180                 185                 190

Gly Arg Leu Ile Asn Glu Phe Val Gly Gly Glu Lys Glu Thr Asn Leu
        195                 200                 205

Ala Leu Glu Glu Asn Ile Ser Lys Leu Lys Ser Asp Phe Asp Ala Leu
    210                 215                 220

Asn Thr His Thr Leu Ala Asn Gly Gly Thr Gln Gly Arg His Leu Ile
225                 230                 235                 240

Thr Asp Lys Gln Ile Ile Ile Tyr Gln Pro Glu Asn Leu Asn Ser Gln

```
                    245                 250                 255
Asp Lys Gln Leu Phe Asp Asn Tyr Val Ile Leu Gly Asn Tyr Thr Thr
            260                 265                 270

His Asn Phe Asn Ile Ser Arg Ala Tyr Val Leu Glu Lys Asp Pro Thr
            275                 280                 285

Gly Lys Ala Gly Leu Lys Gln Met Tyr Leu Leu Met Thr Lys His Leu
            290                 295                 300

Leu Asp Gln Gly Phe Val Lys Gly Ser Ala Leu Val Thr Thr His His
305                 310                 315                 320

Trp Gly Tyr Ser Ser Arg Trp Trp Tyr Ile Ser Thr Leu Leu Met Ser
                325                 330                 335

Asp Ala Leu Lys Glu Ala Asn Leu Gln Thr Gln Val Tyr Asp Ser Leu
            340                 345                 350

Leu Trp Tyr Ser Arg Glu Phe Lys Ser Ser Phe Asp Met Lys Val Ser
            355                 360                 365

Ala Asp Ser Ser Asp Leu Asp Tyr Phe Asn Thr Leu Ser Arg Gly His
            370                 375                 380

Leu Ala Leu Leu Leu Glu Pro Asp Asp Gly Lys Arg Ile Asn Leu
385                 390                 395                 400

Val Asn Thr Phe Ser His Tyr Ile Thr Gly Ala Leu Thr Gln Val Pro
                405                 410                 415

Pro Gly Gly Lys Asp Gly Leu Arg Pro Asp Gly Thr Ala Trp Arg His
            420                 425                 430

Glu Gly Asn Tyr Pro Gly Tyr Ser Phe Pro Ala Phe Lys Asn Ala Ser
            435                 440                 445

Gly Leu Ile Tyr Leu Leu Tyr Asp Thr Pro Phe Ser Val Gly Glu Ser
            450                 455                 460

Gly Trp Asn Ser Leu Lys Lys Ala Met Val Ser Ala Trp Ile Tyr Ser
465                 470                 475                 480

Asn Pro Glu Val Gly Pro Leu Ala Gly Arg His Pro Leu Asn Ser Pro
                485                 490                 495

Ser Leu Lys Ser Val Ala Gly Gly Tyr Tyr Trp Leu Ala Met Ser Ala
            500                 505                 510

Lys Ser Ser Pro Asp Lys Thr Leu Ala Ser Ile Tyr Leu Ala Ile Ser
            515                 520                 525

Asp Lys Thr Gly Asn Glu Ser Thr Ala Ile Phe Gly Glu Thr Ile Thr
            530                 535                 540

Pro Ala Ser Leu Pro Gly Gly Phe Tyr Ala Phe Asn Gly Gly Ala Phe
545                 550                 555                 560

Gly Ile His Arg Trp Gln Asp Lys Met Val Thr Leu Lys Ala Tyr Asn
                565                 570                 575

Thr Asn Val Trp Ser Ser Glu Ile Tyr Asn Lys Asp Asn Arg Tyr Gly
            580                 585                 590

Arg Tyr Gln Ser His Gly Val Ala Gln Ile Val Ser Asn Gly Ser Gln
            595                 600                 605

Leu Ser Gly Gly Tyr Gly Gln Glu Gly Trp Asp Trp Asn Arg Met Pro
            610                 615                 620

Gly Ala Thr Thr Ile His Leu Pro Leu Lys Asp Leu Asp Ser Pro Lys
625                 630                 635                 640

Pro His Thr Leu Met Gln Arg Gly Glu Arg Gly Phe Ser Gly Thr Ser
                645                 650                 655

Ser Leu Glu Gly Gln Tyr Gly Met Met Ala Phe Asp Leu Ile Tyr Pro
            660                 665                 670
```

```
Ala Asn Leu Glu Arg Phe Asp Pro Asn Phe Thr Ala Lys Lys Ser Val
        675                 680                 685

Leu Ala Ala Asp Asn His Leu Ile Phe Ile Gly Ser Asn Ile Asn Ser
690                 695                 700

Ser Asp Lys Asn Lys Asn Val Glu Thr Thr Leu Phe Gly His Ala Ile
705                 710                 715                 720

Thr Pro Thr Leu Asn Thr Leu Trp Ile Asn Gly Lys Ile Glu Asn
                725                 730                 735

Met Pro Tyr Gly Thr Thr Leu Gln Gln Gly Asp Trp Leu Ile Asp Ser
                740                 745                 750

Asn Gly Asn Gly Tyr Leu Ile Thr Gln Ala Glu Lys Val Asn Val Ser
        755                 760                 765

Arg Gln His Gln Val Ser Ala Glu Asn Lys Asn Arg Gly Pro Thr Glu
770                 775                 780

Gly Asn Phe Ser Ser Ala Trp Ile Asp His Ser Thr Arg Pro Lys Asp
785                 790                 795                 800

Ala Ser Tyr Glu Tyr Met Val Phe Leu Asp Ala Thr Pro Glu Lys Met
                805                 810                 815

Gly Glu Met Ala Gly Lys Phe Arg Glu Asn Asn Gly Leu Tyr Gly Val
                820                 825                 830

Leu Arg Lys Asp Lys Asp Val His Ile Ile Leu Asp Lys Leu Ser Asn
        835                 840                 845

Val Thr Gly Tyr Ala Phe Tyr Gln Pro Ala Ser Ile Glu Asp Lys Trp
850                 855                 860

Ile Lys Lys Val Asn Lys Pro Ala Ile Val Met Thr His Arg Gly Lys
865                 870                 875                 880

Asp Thr Leu Ile Val Ser Ala Val Thr Pro Asp Leu Asn Met Thr Arg
                885                 890                 895

Gly Lys Ala Ala Thr Pro Val Thr Ile Asn Val Thr Ile Asn Gly Lys
                900                 905                 910

Trp Gln Ser Ala Asp Lys Asn Ser Glu Val Lys Tyr Gln Val Ser Gly
        915                 920                 925

Asp Asn Thr Glu Leu Thr Phe Thr Ser Tyr Phe Gly Ile Pro Gln Glu
930                 935                 940

Ile Lys Leu Ser Pro Leu Pro
945                 950

<210> SEQ ID NO 20
<211> LENGTH: 1011
<212> TYPE: PRT
<213> ORGANISM: Proteus vulgaris

<400> SEQUENCE: 20

Ala Thr Ser Asn Pro Ala Phe Asp Pro Lys Asn Leu Met Gly Ser Glu
1               5                   10                  15

Ile Tyr His Phe Ala Gly Asn Asn Pro Leu Ala Asp Phe Ser Ser Asp
                20                  25                  30

Lys Asn Ser Ile Leu Thr Leu Ser Asp Lys Arg Ser Ile Met Gly Asn
        35                  40                  45

Gly Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95
```

-continued

```
Ile Asp Gly Tyr Leu Thr Ile Asp Phe Gly Glu Lys Leu Ile Ser Thr
            100                 105                 110

Ser Glu Ala Gly Ala Gly Phe Lys Val Lys Leu Asp Phe Thr Gly Trp
            115                 120                 125

Arg Thr Val Gly Val Ser Leu Asn Asn Asp Leu Glu Asn Arg Glu Met
130                 135                 140

Thr Leu Asn Ala Thr Asn Thr Ser Ser Asp Gly Thr Gly Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gly Gly Glu Ile Tyr Ile Asp Arg Ile Met Phe Ser
            180                 185                 190

Val Asp Asp Ala Arg Tyr Gly Trp Ser Asp Tyr Gln Val Lys Thr Arg
            195                 200                 205

Leu Ser Glu Pro Glu Ile Gln Thr His Asn Val Lys Pro Gln Leu Pro
        210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gly Gly Arg His Leu Ile Thr Asp Lys
        275                 280                 285

Gly Ile Ile Ile Tyr Gln Pro Glu Asn Leu Asn Ser Gln Asp Lys Gln
290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gly
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
370                 375                 380

Lys Glu Ala Asn Leu Gly Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gly Lys Arg Ile Asn Leu Val Asn Thr
        435                 440                 445

Phe Ser His Tyr Ile Thr Gly Ala Leu Thr Gly Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gly Leu Ile
                485                 490                 495

Tyr Leu Leu Tyr Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525
```

```
Val Gly Leu Pro Leu Ala Gly Arg His Pro Leu Asn Ser Pro Ser Leu
    530                 535                 540

Lys Ser Val Ala Gly Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gly Asn Glu Ser Thr Ala Ile Phe Gly Glu Thr Ile Thr Pro Ala
            580                 585                 590

Ser Leu Pro Gly Gly Phe Tyr Ala Phe Asn Gly Gly Ala Phe Gly Ile
        595                 600                 605

His Arg Trp Gly Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gly Ser His Gly Val Ala Gly Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gly Arg Gly Glu Arg Gly Phe Ser Gly Thr Ser Ser Leu
    690                 695                 700

Glu Gly Gly Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gly Thr Thr Leu Gly Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gly Lys Phe Arg Glu Asn Asn Gly Leu Tyr Gly Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gly
```

```
                                945                 950                 955                 960
Ser Ala Asp Lys Asn Ser Glu Val Lys Tyr Gly Val Ser Gly Asp Asn
                965                 970                 975

Thr Glu Leu Thr Phe Thr Ser Tyr Phe Gly Ile Pro Gly Glu Ile Lys
            980                 985                 990

Leu Ser Pro Leu Pro Gly Arg Lys  Lys Arg Arg Gln Arg  Arg Arg Pro
        995                 1000                1005

Pro Gln Cys
    1010

<210> SEQ ID NO 21
<211> LENGTH: 1018
<212> TYPE: PRT
<213> ORGANISM: Proteus vulgaris

<400> SEQUENCE: 21

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
            20                  25                  30

Pro Lys Asn Leu Met Gln Ser Glu Ile Tyr His Phe Ala Gln Asn Asn
        35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Val Gly Val Ser Leu Asn Asn
145                 150                 155                 160

Asp Leu Glu Asn Arg Glu Met Thr Leu Asn Ala Thr Asn Thr Ser Ser
                165                 170                 175

Asp Gly Thr Gln Asp Ser Ile Gly Arg Ser Leu Gly Ala Lys Val Asp
            180                 185                 190

Ser Ile Arg Phe Lys Ala Pro Ser Asn Val Ser Gln Gly Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
```

```
              305                 310                 315                 320
Asn Leu Asn Ser Gln Asp Lys Gln Leu Phe Asp Asn Tyr Val Ile Leu
                    325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
                355                 360                 365

Met Thr Lys His Leu Leu Asp Gln Gly Phe Val Lys Gly Ser Ala Leu
        370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
            405                 410                 415

Val Tyr Asp Ser Leu Leu Trp Tyr Ser Arg Glu Phe Lys Ser Ser Phe
                420                 425                 430

Asp Met Lys Val Ser Ala Asp Ser Ser Asp Leu Asp Tyr Phe Asn Thr
            435                 440                 445

Leu Ser Arg Gln His Leu Ala Leu Leu Leu Glu Pro Asp Asp Gln
450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
                500                 505                 510

Phe Lys Asn Ala Ser Gln Leu Ile Tyr Leu Leu Arg Asp Thr Pro Phe
                515                 520                 525

Ser Val Gly Glu Ser Gly Trp Asn Asn Leu Lys Lys Ala Met Val Ser
            530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
            595                 600                 605

Phe Gly Glu Thr Ile Thr Pro Ala Ser Leu Pro Gln Gly Phe Tyr Ala
        610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
                660                 665                 670

Val Ser Asn Gly Ser Gln Leu Ser Gln Gly Tyr Gln Gln Glu Gly Trp
            675                 680                 685

Asp Trp Asn Arg Met Gln Gly Ala Thr Thr Ile His Leu Pro Leu Lys
        690                 695                 700

Asp Leu Asp Ser Pro Lys Pro His Thr Leu Met Gln Arg Gly Glu Arg
705                 710                 715                 720

Gly Phe Ser Gly Thr Ser Leu Glu Gly Gln Tyr Gly Met Met Ala Phe
                725                 730                 735
```

```
Asp Leu Ile Tyr Pro Ala Asn Leu Glu Arg Phe Asp Pro Asn Phe Thr
            740                 745                 750

Ala Lys Lys Ser Val Leu Ala Ala Asp Asn His Leu Ile Phe Ile Gly
        755                 760                 765

Ser Asn Ile Asn Ser Ser Asp Lys Asn Lys Asn Val Glu Thr Thr Leu
    770                 775                 780

Phe Gln His Ala Ile Thr Pro Thr Leu Asn Thr Leu Trp Ile Asn Gly
785                 790                 795                 800

Gln Lys Ile Glu Asn Met Pro Tyr Gln Thr Thr Leu Gln Gln Gly Asp
                805                 810                 815

Trp Leu Ile Asp Ser Asn Gly Asn Gly Tyr Leu Ile Thr Gln Ala Glu
            820                 825                 830

Lys Val Asn Val Ser Arg Gln His Gln Val Ser Ala Glu Asn Lys Asn
        835                 840                 845

Arg Gln Pro Thr Glu Gly Asn Phe Ser Ser Ala Trp Ile Asp His Ser
    850                 855                 860

Thr Arg Pro Lys Asp Ala Ser Tyr Glu Tyr Met Val Phe Leu Asp Ala
865                 870                 875                 880

Thr Pro Glu Lys Met Gly Glu Met Ala Gln Lys Phe Arg Glu Asn Asn
                885                 890                 895

Gly Leu Tyr Gln Val Leu Arg Lys Asp Val His Ile Ile Leu Asp Lys
            900                 905                 910

Leu Ser Asn Val Thr Gly Tyr Ala Phe Tyr Gln Pro Ala Ser Ile Glu
        915                 920                 925

Asp Lys Trp Ile Lys Lys Val Asn Lys Pro Ala Ile Val Met Thr His
    930                 935                 940

Arg Gln Lys Asp Thr Leu Ile Val Ser Ala Val Thr Pro Asp Leu Asn
945                 950                 955                 960

Met Thr Arg Gln Lys Ala Ala Thr Pro Val Thr Ile Asn Val Thr Ile
                965                 970                 975

Asn Gly Lys Trp Gln Ser Ala Asp Lys Asn Ser Glu Val Lys Tyr Gln
            980                 985                 990

Val Ser Gly Asp Asn Thr Glu Leu  Thr Phe Thr Ser Tyr  Phe Gly Ile
        995                1000                1005

Pro Gln  Glu Ile Lys Leu Ser  Pro Leu Pro
    1010                1015

<210> SEQ ID NO 22
<211> LENGTH: 998
<212> TYPE: PRT
<213> ORGANISM: Proteus vulgaris

<400> SEQUENCE: 22

Met Ala Thr Ser Asn Pro Ala Phe Asp Pro Lys Asn Leu Met Gln Ser
1               5                  10                  15

Glu Ile Tyr His Phe Ala Gln Asn Asn Pro Leu Ala Asp Phe Ser Ser
            20                  25                  30

Asp Lys Asn Ser Ile Leu Thr Leu Ser Asp Lys Arg Ser Ile Met Gly
        35                  40                  45

Asn Gln Ser Leu Leu Trp Lys Trp Lys Gly Gly Ser Ser Phe Thr Leu
    50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95
```

```
Pro Ile Asp Gly Tyr Leu Thr Ile Asp Phe Gly Glu Lys Leu Ile Ser
            100                 105                 110
Thr Ser Glu Ala Gln Ala Gly Phe Lys Val Lys Leu Asp Phe Thr Gly
        115                 120                 125
Trp Arg Ala Val Gly Val Ser Leu Asn Asp Leu Glu Asn Arg Glu
130                 135                 140
Met Thr Leu Asn Ala Thr Asn Thr Ser Ser Asp Gly Thr Gln Asp Ser
145                 150                 155                 160
Ile Gly Arg Ser Leu Gly Ala Lys Val Asp Ser Ile Arg Phe Lys Ala
                165                 170                 175
Pro Ser Asn Val Ser Gln Gly Glu Ile Tyr Ile Asp Arg Ile Met Phe
            180                 185                 190
Ser Val Asp Asp Ala Arg Tyr Gln Trp Ser Asp Tyr Gln Val Lys Thr
        195                 200                 205
Arg Leu Ser Glu Pro Glu Ile Gln Phe His Asn Val Lys Pro Gln Leu
210                 215                 220
Pro Val Thr Pro Glu Asn Leu Ala Ala Ile Asp Leu Ile Arg Gln Arg
225                 230                 235                 240
Leu Ile Asn Glu Phe Val Gly Gly Glu Lys Glu Thr Asn Leu Ala Leu
                245                 250                 255
Glu Glu Asn Ile Ser Lys Leu Lys Ser Asp Phe Asp Ala Leu Asn Ile
            260                 265                 270
His Thr Leu Ala Asn Gly Gly Thr Gln Gly Arg His Leu Ile Thr Asp
        275                 280                 285
Lys Gln Ile Ile Ile Tyr Gln Pro Glu Asn Leu Asn Ser Gln Asp Lys
290                 295                 300
Gln Leu Phe Asp Asn Tyr Val Ile Leu Gly Asn Tyr Thr Thr Leu Met
305                 310                 315                 320
Phe Asn Ile Ser Arg Ala Tyr Val Leu Glu Lys Asp Pro Thr Gln Lys
                325                 330                 335
Ala Gln Leu Lys Gln Met Tyr Leu Leu Met Thr Lys His Leu Leu Asp
            340                 345                 350
Gln Gly Phe Val Lys Gly Ser Ala Leu Val Thr Thr His His Trp Gly
        355                 360                 365
Tyr Ser Ser Arg Trp Trp Tyr Ile Ser Thr Leu Leu Met Ser Asp Ala
370                 375                 380
Leu Lys Glu Ala Asn Leu Gln Thr Gln Val Tyr Asp Ser Leu Leu Trp
385                 390                 395                 400
Tyr Ser Arg Glu Phe Lys Ser Ser Phe Asp Met Lys Val Ser Ala Asp
                405                 410                 415
Ser Ser Asp Leu Asp Tyr Phe Asn Thr Leu Ser Arg Gln His Leu Ala
            420                 425                 430
Leu Leu Leu Leu Glu Pro Asp Asp Gln Lys Arg Ile Asn Leu Val Asn
        435                 440                 445
Thr Phe Ser His Tyr Ile Thr Gly Ala Leu Thr Gln Val Pro Pro Gly
450                 455                 460
Gly Lys Asp Gly Leu Arg Pro Asp Gly Thr Ala Trp Arg His Glu Gly
465                 470                 475                 480
Asn Tyr Pro Gly Tyr Ser Phe Pro Ala Phe Lys Asn Ala Ser Gln Leu
                485                 490                 495
Ile Tyr Leu Leu Arg Asp Thr Pro Phe Ser Val Gly Glu Ser Gly Trp
            500                 505                 510
Asn Asn Leu Lys Lys Ala Met Val Ser Ala Trp Ile Tyr Ser Asn Pro
        515                 520                 525
```

```
Glu Val Gly Leu Pro Leu Ala Gly Arg His Pro Phe Asn Ser Pro Ser
    530                 535                 540
Leu Lys Ser Val Ala Gln Gly Tyr Tyr Trp Leu Ala Met Ser Ala Lys
545                 550                 555                 560
Ser Ser Pro Asp Lys Thr Leu Ala Ser Ile Tyr Leu Ala Ile Ser Asp
                565                 570                 575
Lys Thr Gln Asn Glu Ser Thr Ala Ile Phe Gly Glu Thr Ile Thr Pro
            580                 585                 590
Ala Ser Leu Pro Gln Gly Phe Tyr Ala Phe Asn Gly Gly Ala Phe Gly
        595                 600                 605
Ile His Arg Trp Gln Asp Lys Met Val Thr Leu Lys Ala Tyr Asn Thr
    610                 615                 620
Asn Val Trp Ser Ser Glu Ile Tyr Asn Lys Asp Asn Arg Tyr Gly Arg
625                 630                 635                 640
Tyr Gln Ser His Gly Val Ala Gln Ile Val Ser Asn Gly Ser Gln Leu
                645                 650                 655
Ser Gln Gly Tyr Gln Gln Glu Gly Trp Asp Trp Asn Arg Met Gln Gly
            660                 665                 670
Ala Thr Thr Ile His Leu Pro Leu Lys Asp Leu Asp Ser Pro Lys Pro
        675                 680                 685
His Thr Leu Met Gln Arg Gly Glu Arg Gly Phe Ser Gly Thr Ser Ser
    690                 695                 700
Leu Glu Gly Gln Tyr Gly Met Met Ala Phe Asp Leu Ile Tyr Pro Ala
705                 710                 715                 720
Asn Leu Glu Arg Phe Asp Pro Asn Phe Thr Ala Lys Lys Ser Val Leu
                725                 730                 735
Ala Ala Asp Asn His Leu Ile Phe Ile Gly Ser Asn Ile Asn Ser Ser
            740                 745                 750
Asp Lys Asn Lys Asn Val Glu Thr Thr Leu Phe Gln His Ala Ile Thr
        755                 760                 765
Pro Thr Leu Asn Thr Leu Trp Ile Asn Gly Gln Lys Ile Glu Asn Met
    770                 775                 780
Pro Tyr Gln Thr Thr Leu Gln Gln Gly Asp Trp Leu Ile Asp Ser Asn
785                 790                 795                 800
Gly Asn Gly Tyr Leu Ile Thr Gln Ala Glu Lys Val Asn Val Ser Arg
                805                 810                 815
Gln His Gln Val Ser Ala Glu Asn Lys Asn Arg Gln Pro Thr Glu Gly
            820                 825                 830
Asn Phe Ser Ser Ala Trp Ile Asp His Ser Thr Arg Pro Lys Asp Ala
        835                 840                 845
Ser Tyr Glu Tyr Met Val Phe Leu Asp Ala Thr Pro Glu Lys Met Gly
    850                 855                 860
Glu Met Ala Gln Lys Phe Arg Glu Asn Asn Gly Leu Tyr Gln Val Leu
865                 870                 875                 880
Arg Lys Asp Lys Asp Val His Ile Ile Leu Asp Lys Leu Ser Asn Val
                885                 890                 895
Thr Gly Tyr Ala Phe Tyr Gln Pro Ala Ser Ile Glu Asp Lys Trp Ile
            900                 905                 910
Lys Lys Val Asn Lys Pro Ala Ile Val Met Thr His Arg Gln Lys Asp
        915                 920                 925
Thr Leu Ile Val Ser Ala Val Thr Pro Asp Leu Asn Met Thr Arg Gln
    930                 935                 940
Lys Ala Ala Thr Pro Val Thr Ile Asn Val Thr Ile Asn Gly Lys Trp
```

```
                        945                 950                 955                 960

Gln Ser Ala Asp Lys Asn Ser Glu Val Lys Tyr Gln Val Ser Gly Asp
                        965                 970                 975

Asn Thr Glu Leu Thr Phe Thr Ser Tyr Phe Gly Ile Pro Gln Glu Ile
                        980                 985                 990

Lys Leu Ser Pro Leu Pro
                        995

<210> SEQ ID NO 23
<211> LENGTH: 1021
<212> TYPE: PRT
<213> ORGANISM: Proteus vulgaris

<400> SEQUENCE: 23

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
                20                  25                  30

Pro Lys Asn Leu Met Gln Ser Glu Ile Tyr His Phe Ala Gln Asn Asn
            35                  40                  45

Pro Leu Ala Asp Phe Ser Ser Asp Lys Asn Ser Ile Leu Thr Leu Ser
        50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
            180                 185                 190

Asp Ser Ile Arg Phe Lys Ala Pro Ser Asn Val Ser Gln Gly Glu Ile
        195                 200                 205

Tyr Ile Asp Arg Ile Met Phe Ser Val Asp Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Tyr Gln Pro Glu
305                 310                 315                 320

Asn Leu Asn Ser Gln Asp Lys Gln Leu Phe Asp Asn Tyr Val Ile Leu
```

-continued

```
                325                 330                 335
Gly Asn Tyr Thr Thr Leu Met Phe Asn Ile Ser Arg Ala Tyr Val Leu
            340                 345                 350
Glu Lys Asp Pro Thr Gln Lys Ala Gln Leu Lys Gln Met Tyr Leu Leu
            355                 360                 365
Met Thr Lys His Leu Leu Asp Gln Gly Phe Val Lys Gly Ser Ala Leu
        370                 375                 380
Val Thr Thr His His Trp Gly Tyr Ser Ser Arg Trp Trp Tyr Ile Ser
385                 390                 395                 400
Thr Leu Leu Met Ser Asp Ala Leu Lys Glu Ala Asn Leu Gln Thr Gln
                405                 410                 415
Val Tyr Asp Ser Leu Leu Trp Tyr Ser Arg Glu Phe Lys Ser Ser Phe
            420                 425                 430
Asp Met Lys Val Ser Ala Asp Ser Asp Leu Asp Tyr Phe Asn Thr
            435                 440                 445
Leu Ser Arg Gln His Leu Ala Leu Leu Leu Glu Pro Asp Asp Gln
        450                 455                 460
Lys Arg Ile Asn Leu Val Asn Thr Phe Ser His Tyr Ile Thr Gly Ala
465                 470                 475                 480
Leu Thr Gln Val Pro Pro Gly Gly Lys Asp Gly Leu Arg Pro Asp Gly
                485                 490                 495
Thr Ala Trp Arg His Glu Gly Asn Tyr Pro Gly Tyr Ser Phe Pro Ala
            500                 505                 510
Phe Lys Asn Ala Ser Gln Leu Ile Tyr Leu Leu Arg Asp Thr Pro Phe
            515                 520                 525
Ser Val Gly Glu Ser Gly Trp Asn Asn Leu Lys Lys Ala Met Val Ser
        530                 535                 540
Ala Trp Ile Tyr Ser Asn Pro Glu Val Gly Leu Pro Leu Ala Gly Arg
545                 550                 555                 560
His Pro Phe Asn Ser Pro Ser Leu Lys Ser Val Ala Gln Gly Tyr Tyr
                565                 570                 575
Trp Leu Ala Met Ser Ala Lys Ser Ser Pro Asp Lys Thr Leu Ala Ser
            580                 585                 590
Ile Tyr Leu Ala Ile Ser Asp Lys Thr Gln Asn Glu Ser Thr Ala Ile
        595                 600                 605
Phe Gly Glu Thr Ile Thr Pro Ala Ser Leu Pro Gln Gly Phe Tyr Ala
        610                 615                 620
Phe Asn Gly Gly Ala Phe Gly Ile His Arg Trp Gln Asp Lys Met Val
625                 630                 635                 640
Thr Leu Lys Ala Tyr Asn Thr Asn Val Trp Ser Ser Glu Ile Tyr Asn
                645                 650                 655
Lys Asp Asn Arg Tyr Gly Arg Tyr Gln Ser His Gly Val Ala Gln Ile
            660                 665                 670
Val Ser Asn Gly Ser Gln Leu Ser Gln Gly Tyr Gln Gln Glu Gly Trp
        675                 680                 685
Asp Trp Asn Arg Met Glu Gly Ala Thr Thr Ile His Leu Pro Leu Lys
        690                 695                 700
Asp Leu Asp Ser Pro Lys Pro His Thr Leu Met Gln Arg Gly Glu Arg
705                 710                 715                 720
Gly Phe Ser Gly Thr Ser Ser Leu Glu Gly Gln Tyr Gly Met Met Ala
                725                 730                 735
Phe Asn Leu Ile Tyr Pro Ala Asn Leu Glu Arg Phe Asp Pro Asn Phe
            740                 745                 750
```

```
        Thr Ala Lys Lys Ser Val Leu Ala Ala Asp Asn His Leu Ile Phe Ile
            755                 760                 765

Gly Ser Asn Ile Asn Ser Ser Asp Lys Asn Lys Asn Val Glu Thr Thr
            770                 775                 780

Leu Phe Gln His Ala Ile Thr Pro Thr Leu Asn Thr Leu Trp Ile Asn
        785                 790                 795                 800

Gly Gln Lys Ile Glu Asn Met Pro Tyr Gln Thr Thr Leu Gln Gln Gly
                        805                 810                 815

Asp Trp Leu Ile Asp Ser Asn Gly Asn Gly Tyr Leu Ile Thr Gln Ala
                    820                 825                 830

Glu Lys Val Asn Val Ser Arg Gln His Gln Val Ser Ala Glu Asn Lys
                835                 840                 845

Asn Arg Gln Pro Thr Glu Gly Asn Phe Ser Ser Ala Trp Ile Asp His
            850                 855                 860

Ser Thr Arg Pro Lys Asp Ala Ser Tyr Glu Tyr Met Val Phe Leu Asp
        865                 870                 875                 880

Ala Thr Pro Glu Lys Met Gly Glu Met Ala Gln Lys Phe Arg Glu Asn
                        885                 890                 895

Asn Gly Leu Tyr Gln Val Leu Arg Lys Asp Lys Asp Val His Ile Ile
                    900                 905                 910

Leu Asp Lys Leu Ser Asn Val Thr Gly Tyr Ala Phe Tyr Gln Pro Ala
                915                 920                 925

Ser Ile Glu Asp Lys Trp Ile Lys Lys Val Asn Lys Pro Ala Ile Val
            930                 935                 940

Met Thr His Arg Gln Lys Asp Thr Leu Ile Val Ser Ala Val Thr Pro
        945                 950                 955                 960

Asp Leu Asn Met Thr Arg Gln Lys Ala Ala Thr Pro Val Thr Ile Asn
                        965                 970                 975

Val Thr Ile Asn Gly Lys Trp Gln Ser Ala Asp Lys Asn Ser Glu Val
                    980                 985                 990

Lys Tyr Gln Val Ser Gly Asp Asn  Thr Glu Leu Thr Phe  Thr Ser Tyr
                995                 1000                1005

Phe Gly  Ile Pro Gln Glu Ile  Lys Leu Ser Pro Leu  Pro
            1010                1015                1020

<210> SEQ ID NO 24
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 24
catatgccga tatttcgttt tactgca                                          27

<210> SEQ ID NO 25
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 25
catatgccca ccagcaatcc tgcatttg                                         28

<210> SEQ ID NO 26
<211> LENGTH: 33
<212> TYPE: DNA
<213> ORGANISM: Artificial sequence
```

```
<220> FEATURE:
<223> OTHER INFORMATION: Synthetic oligonucleotide

<400> SEQUENCE: 26
ggatcctcga gtcaagggag tggcgagagt ttg                                33

<210> SEQ ID NO 27
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 27
actggctggc gtgctgtggg agtctct                                       27

<210> SEQ ID NO 28
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 28
agagactccc acagcacgcc agccagt                                       27

<210> SEQ ID NO 29
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 29
ggaacgcaag gcagacatct gatcactgat aaacaaatc                          39

<210> SEQ ID NO 30
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 30
gatttgttta tcagtgatca gatgtctgcc ttgcgttcc                          39

<210> SEQ ID NO 31
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 31
caaccagaga atcttaactc tcaagataaa caactatttg                         40

<210> SEQ ID NO 32
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 32
caaatagttg tttatcttga gagttaagat tctctggttg                         40
```

```
<210> SEQ ID NO 33
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 33
ggttgggatt ggaatagaat gcaaggggca accact                          36

<210> SEQ ID NO 34
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 34
agtggttgcc ccttgcattc tattccaatc ccaacc                          36

<210> SEQ ID NO 35
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 35
tgatggtaca gcatggcgag ctgaaggcaa ctatccgggc ta                   42

<210> SEQ ID NO 36
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 36
tagcccggat agttgccttc agctcgccat gctgtaccat ca                   42

<210> SEQ ID NO 37
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 37
ggcaactatc cgggcgcctc tttcccagcc                                 30

<210> SEQ ID NO 38
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 38
ggctgggaaa gaggcgcccg gatagttgcc                                 30

<210> SEQ ID NO 39
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 39
```
ccgcttgcag gagcacaccc ttttaactca ccttcg        36

<210> SEQ ID NO 40
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 40
cgaaggtgag ttaaaagggt gtgctcctgc aagcgg        36

<210> SEQ ID NO 41
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 41
caccaatgtt tggtcatctg caatttataa caaagataac cgt        43

<210> SEQ ID NO 42
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 42
acggttatct ttgttataaa ttgcagatga ccaaacattg gtg        43

<210> SEQ ID NO 43
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 43
ccgcttgcag gaagagcccc ttttaactca ccttcg        36

<210> SEQ ID NO 44
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 44
cgaaggtgag ttaaaagggg ctcttcctgc aagcgg        36

<210> SEQ ID NO 45
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 45
gacagtccta aacctgctac cttaatgcaa cgtggagag        39

<210> SEQ ID NO 46
<211> LENGTH: 39
<212> TYPE: DNA
<213> ORGANISM: Artificial sequence

```
<220> FEATURE:
<223> OTHER INFORMATION: Synthetic oligonucleotide

<400> SEQUENCE: 46
ctctccacgt tgcattaagg tagcaggttt aggactgtc                              39

<210> SEQ ID NO 47
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 47
cctgatggta cagcatgggc acatgaaggc aactatccgg gc                         42

<210> SEQ ID NO 48
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 48
gcccggatag ttgccttcat gtgcccatgc tgtaccatca gg                         42

<210> SEQ ID NO 49
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 49
actggctggc gtgctgtggg agtctct                                          27

<210> SEQ ID NO 50
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 50
agagactccc acagcacgcc agccagt                                          27

<210> SEQ ID NO 51
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 51
ggaacgcaag gcagacatct gatcactgat aaacaaatc                             39

<210> SEQ ID NO 52
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 52
gatttgttta tcagtgatca gatgtctgcc ttgcgttcc                             39
```

```
<210> SEQ ID NO 53
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 53
caaccagaga atcttaactc tcaagataaa caactatttg                                40

<210> SEQ ID NO 54
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 54
caaatagttg tttatcttga gagttaagat tctctggttg                                40

<210> SEQ ID NO 55
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 55
ggttgggatt ggaatagaat gcaaggggca accact                                    36

<210> SEQ ID NO 56
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 56
agtggttgcc ccttgcattc tattccaatc ccaacc                                    36

<210> SEQ ID NO 57
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 57
tgatggtaca gcatggcgag ctgaaggcaa ctatccgggc ta                             42

<210> SEQ ID NO 58
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 58
tagcccggat agttgccttc agctcgccat gctgtaccat ca                             42

<210> SEQ ID NO 59
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 59
```
ggcaactatc cgggcgcctc tttcccagcc    30

<210> SEQ ID NO 60
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 60
ggctgggaaa gaggcgcccg gatagttgcc    30

<210> SEQ ID NO 61
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 61
ccgcttgcag gagcacaccc ttttaactca ccttcg    36

<210> SEQ ID NO 62
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 62
cgaaggtgag ttaaaagggt gtgctcctgc aagcgg    36

<210> SEQ ID NO 63
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 63
caccaatgtt tggtcatctg caatttataa caaagataac cgt    43

<210> SEQ ID NO 64
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 64
acggttatct ttgttataaa ttgcagatga ccaaacattg gtg    43

<210> SEQ ID NO 65
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 65
cctgatggta cagcatgggc acatgaaggc aactatccgg gc    42

<210> SEQ ID NO 66
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 66
gcccggatag ttgccttcat gtgcccatgc tgtaccatca gg         42

<210> SEQ ID NO 67
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 67
ggtacagcat ggcgaaagga aggcaactat ccgggc         36

<210> SEQ ID NO 68
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 68
gcccggatag ttgccttcct ttcgccatgc tgtacc         36

<210> SEQ ID NO 69
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 69
acagcatggc gacgtgaagg caactatccg ggc         33

<210> SEQ ID NO 70
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 70
gcccggatag ttgccttcac gtcgccatgc tgt         33

<210> SEQ ID NO 71
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 71
aactatccgg gcttctcttt cccagcc         27

<210> SEQ ID NO 72
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 72
ggctgggaaa gagaagcccg gatagtt         27

```
<210> SEQ ID NO 73
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 73
caatgtttgg tcatctgata tttataacaa agataaccgt tatgg            45

<210> SEQ ID NO 74
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 74
ccataacggt tatctttgtt ataaatatca gatgaccaaa cattg             45

<210> SEQ ID NO 75
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 75
caatgtttgg tcatctcaaa tttataacaa agataaccgt tatgg             45

<210> SEQ ID NO 76
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 76
ccataacggt tatctttgtt ataaatttga gatgaccaaa cattg             45

<210> SEQ ID NO 77
<211> LENGTH: 997
<212> TYPE: PRT
<213> ORGANISM: Proteus vulgaris

<400> SEQUENCE: 77

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Thr Pro Val Phe Ser Phe Trp Leu Tyr Asn Glu Lys Pro
                85                  90                  95
```

```
Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
            115                 120                 125

Arg Ala Val Gly Val Ser Leu Asn Asn Asp Leu Glu Asn Arg Glu Met
130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
            195                 200                 205

Leu Ser Glu Pro Glu Ile Gln Phe His Asn Val Lys Pro Gln Leu Pro
            210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Ile His
            260                 265                 270

Thr Leu Ala Asn Gly Gly Thr Gln Gly Arg His Leu Ile Thr Asp Lys
            275                 280                 285

Gln Ile Ile Ile Tyr Gln Pro Glu Asn Leu Asn Ser Gln Asp Lys Gln
            290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
            355                 360                 365

Ser Ser Arg Trp Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
            435                 440                 445

Phe Ser His Tyr Ile Thr Gly Ala Leu Thr Gln Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
            515                 520                 525
```

-continued

```
Val Gly Leu Pro Leu Ala Gly Arg His Pro Phe Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Gln Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
```

```
                945              950              955              960
Ser Ala Asp Lys Asn Ser Glu Val Lys Tyr Gln Val Ser Gly Asp Asn
                965                      970              975

Thr Glu Leu Thr Phe Thr Ser Tyr Phe Gly Ile Pro Gln Glu Ile Lys
            980                  985              990

Leu Ser Pro Leu Pro
            995
```